(12) United States Patent
Gokhale et al.

(10) Patent No.: US 12,215,102 B2
(45) Date of Patent: Feb. 4, 2025

(54) COMPOSITIONS AND METHODS FOR MAKING AND USING SMALL MOLECULES FOR TUBULIN-TARGETED THERAPY IN THE TREATMENT OF CANCERS AND RELATED CONDITIONS

(71) Applicant: Reglagene, Inc., Tucson, AZ (US)

(72) Inventors: Vijay Gokhale, Tucson, AZ (US); Teri C. Suzuki, Tucson, AZ (US)

(73) Assignee: REGLAGENE, INC., Tucson, AZ (US)

( * ) Notice: Subject to any disclaimer, the term of this patent is extended or adjusted under 35 U.S.C. 154(b) by 0 days.

(21) Appl. No.: 18/590,806

(22) Filed: Feb. 28, 2024

(65) Prior Publication Data
US 2024/0327398 A1 Oct. 3, 2024

Related U.S. Application Data

(60) Provisional application No. 63/555,767, filed on Feb. 20, 2024, provisional application No. 63/591,709, (Continued)

(51) Int. Cl.
*C07D 417/14* (2006.01)
*A61K 31/506* (2006.01)
(Continued)

(52) U.S. Cl.
CPC .......... *C07D 417/14* (2013.01); *A61K 31/506* (2013.01); *A61K 31/5377* (2013.01); *A61P 35/00* (2018.01); *C07D 417/12* (2013.01)

(58) Field of Classification Search
CPC .. C07D 417/14; C07D 417/12; A61K 31/506; A61K 31/5377; A61P 35/00
See application file for complete search history.

(56) References Cited

U.S. PATENT DOCUMENTS 7,144,911 B2   12/2006   Flynn et al.
7,342,037 B2    3/2008   Flynn et al.
(Continued)

FOREIGN PATENT DOCUMENTS

EP    2055697 A1    5/2009
WO   2005075435 A1    8/2005
(Continued)

OTHER PUBLICATIONS

Waterbeemd et al., Estimation of Blood-Brain Barrier Crossing of Drugs Using Molecular Size and Shape, and H-Bonding Descriptors, Journal of Drug Targeting, vol. 6, No. 2, 151-165, 1998 (Year: 1998).*

(Continued)

*Primary Examiner* — Sarah Pihonak
*Assistant Examiner* — Padmaja S Rao
(74) *Attorney, Agent, or Firm* — NGUYEN TARBET IP LAW

(57) ABSTRACT

The novel compounds, compositions and methods disclosed herein are effective for treating a subject having or suspected of developing a health condition, for example, cancer (i.e. brain cancer or a cancer metastasizing to the brain). The method of treating cancer can include administering a pharmaceutical composition to a subject, the composition including at least one of the novel compounds disclosed herein, and optionally, one or more additional anti-cancer therapies. The compounds, compositions and methods can be further used for drug screening and other methods of detection and isolation.

11 Claims, 27 Drawing Sheets

Modified β-tubulin - N,N'-ethylene-bis(iodoacetamide) (EBI) selectively crosslinks β-tubulin at the colchicine-binding site
Control - GAPDH is loading control for this experiment (Western Blot)
EBI only lane - Negative control, β-tubulin is modified in the absence of drug.
EBI + 6024 lane - RGN6024 protects β-tubulin from modification.
EBI + Colchicine lane - Positive control, β-tubulin is protected from modification.

Related U.S. Application Data filed on Oct. 19, 2023, provisional application No. 63/448,964, filed on Feb. 28, 2023.

(51) Int. Cl.
*A61K 31/5377* (2006.01)
*A61P 35/00* (2006.01)
*C07D 417/12* (2006.01)

(56) References Cited

U.S. PATENT DOCUMENTS

| | | | |
|---|---|---|---|
| 7,968,536 | B2 | 6/2011 | Cossrow et al. |
| 8,017,629 | B2 | 9/2011 | Cheng et al. |
| 8,034,954 | B2 | 10/2011 | Pacofsky et al. |
| 8,080,567 | B2 | 12/2011 | Oxford et al. |
| 8,124,632 | B2 | 2/2012 | Rossignol et al. |
| 8,158,636 | B2 | 4/2012 | Ibrahim et al. |
| 8,431,605 | B2 | 8/2013 | Hadida Ruah et al. |
| 8,703,761 | B2 | 4/2014 | Forster et al. |
| 8,722,702 | B2 | 5/2014 | Zhang et al. |
| 8,802,657 | B2 | 8/2014 | Cossrow et al. |
| 8,822,513 | B2 | 9/2014 | Lu et al. |
| 8,921,576 | B2 | 12/2014 | Ogamino et al. |
| 9,115,120 | B2 | 8/2015 | Jones et al. |
| 9,334,242 | B2 | 5/2016 | Lu et al. |
| 9,447,049 | B2 | 9/2016 | Li et al. |
| 9,550,768 | B2 | 1/2017 | Zhang et al. |
| 11,028,061 | B2 | 6/2021 | Kelly et al. |
| 11,078,171 | B2 | 8/2021 | Shapiro et al. |
| 11,084,811 | B2 | 8/2021 | Li et al. |
| 11,149,033 | B2 | 10/2021 | Min et al. |
| 2009/0036467 | A1 | 2/2009 | Rossignol et al. |
| 2009/0069310 | A1 | 3/2009 | Flynn et al. |
| 2009/0136472 | A1 | 5/2009 | Westman et al. |
| 2010/0076029 | A1 | 3/2010 | Bartolozzi et al. |
| 2010/0081644 | A1 | 4/2010 | Bartolozzi et al. |
| 2010/0152162 | A1 | 6/2010 | Uesaka et al. |
| 2010/0331338 | A1 | 12/2010 | Burgdorf et al. |
| 2011/0312932 | A1 | 12/2011 | Bartolozzi et al. |
| 2012/0010184 | A1 | 1/2012 | Bartolozzi et al. |
| 2012/0071524 | A1 | 3/2012 | Lu et al. |
| 2012/0108576 | A1 | 5/2012 | Zhang et al. |
| 2020/0024270 | A1 | 1/2020 | Li et al. |
| 2021/0186022 | A1 | 6/2021 | Pouliot et al. |
| 2022/0024912 | A1 | 1/2022 | Li et al. |
| 2022/0089532 | A1 | 3/2022 | Nojima et al. |
| 2022/0298168 | A1 | 9/2022 | Le Bourdonnec et al. |
| 2023/0029266 | A1 | 1/2023 | Cevikbas et al. |

FOREIGN PATENT DOCUMENTS

| | | | |
|---|---|---|---|
| WO | 2006004636 | A2 | 5/2006 |
| WO | 2007010273 | A2 | 1/2007 |
| WO | 2006122011 | A2 | 5/2007 |
| WO | 2008065409 | A2 | 6/2008 |
| WO | 2008090327 | A1 | 7/2008 |
| WO | 2009085256 | A1 | 7/2009 |
| WO | 2009106203 | A1 | 9/2009 |
| WO | 2010036630 | A1 | 4/2010 |
| WO | 2010133312 | A1 | 11/2010 |
| WO | 2012103583 | A1 | 8/2012 |
| WO | 2013131018 | A1 | 9/2013 |
| WO | 2016160938 | A1 | 10/2016 |
| WO | 2017006282 | A1 | 1/2017 |
| WO | 2018069863 | A1 | 4/2018 |
| WO | 2018087160 | A1 | 5/2018 |
| WO | 2019183587 | A1 | 9/2019 |
| WO | 2020198026 | A1 | 10/2020 |
| WO | 2021092240 | A1 | 5/2021 |
| WO | 2021115375 | A1 | 6/2021 |
| WO | 2021163192 | A1 | 8/2021 |
| WO | 2021216656 | A1 | 10/2021 |
| WO | 2021216660 | A1 | 10/2021 |
| WO | 2021248231 | A1 | 12/2021 |
| WO | 2021252555 | A1 | 12/2021 |
| WO | 2022063152 | A1 | 3/2022 |
| WO | 2022174031 | A1 | 8/2022 |
| WO | 2023274251 | A1 | 1/2023 |
| WO | 2023028238 | A1 | 3/2023 |

OTHER PUBLICATIONS

Alavijeh et al., Drug Metabolism and Pharmacokinetics, the Blood-Brain Barrier, and Central Nervous System Drug Discovery, The American Society for Experimental NeuroTherapeutics, Inc, vol. 2, 554-571, Oct. 2005 (Year: 2005).*

Sun et al., Why 90% of clinical drug development fails and how to improve it?, Acta Pharmaceutica Sinica B, vol. 2, No. 7, 3049-3062, 2022 (Year: 2022).*

Patron et al. "Abstract A023: Brain penetrant small molecule for the treatment of glioblastoma." Cancer Research 84.5_Supplement_1 (2024): A023-A023.

Wager et al. "Moving beyond rules: the development of a central nervous system multiparameter optimization (CNS MPO) approach to enable alignment of druglike properties." ACS chemical neuroscience 1.6 (2010): 435-449.

* cited by examiner

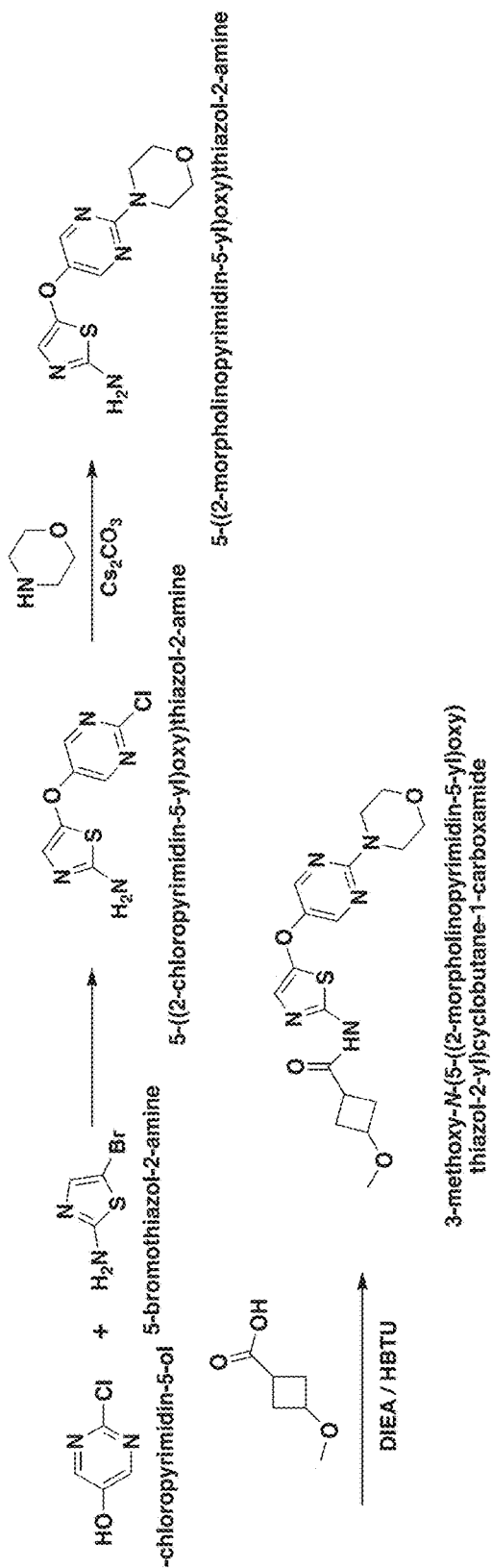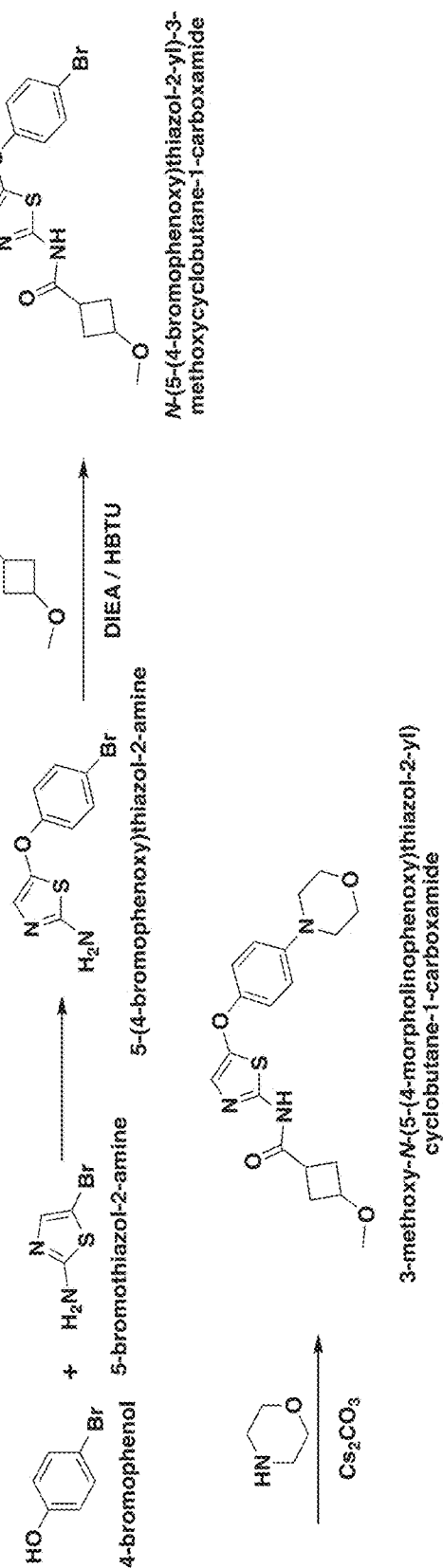

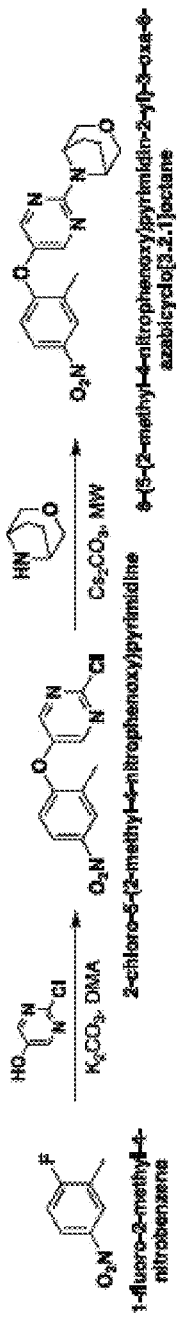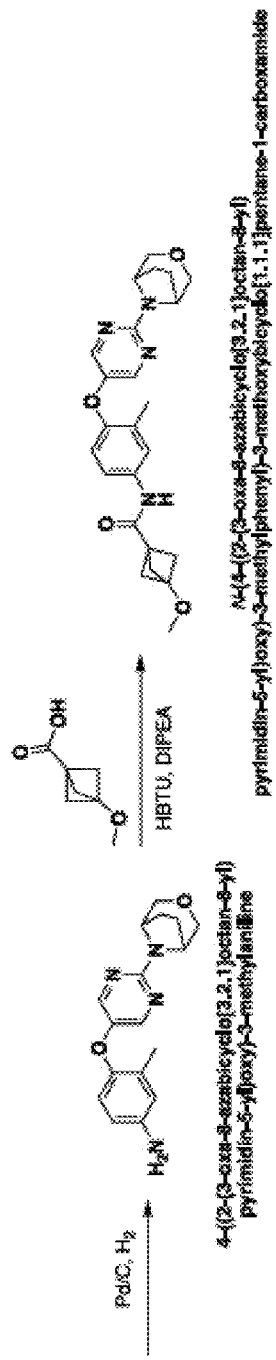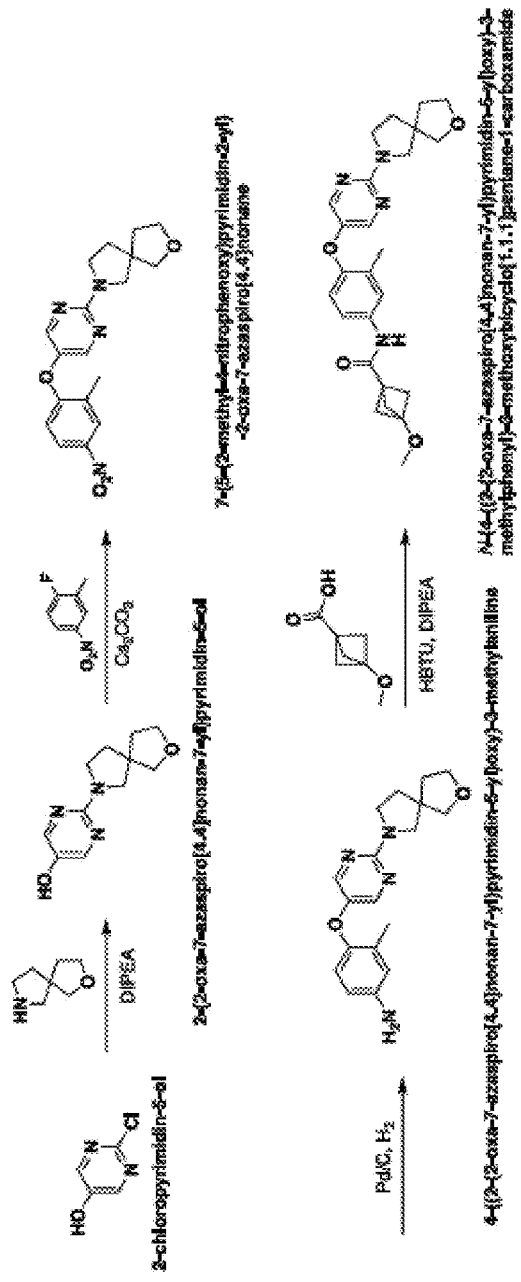
FIG. 17
FIG. 18

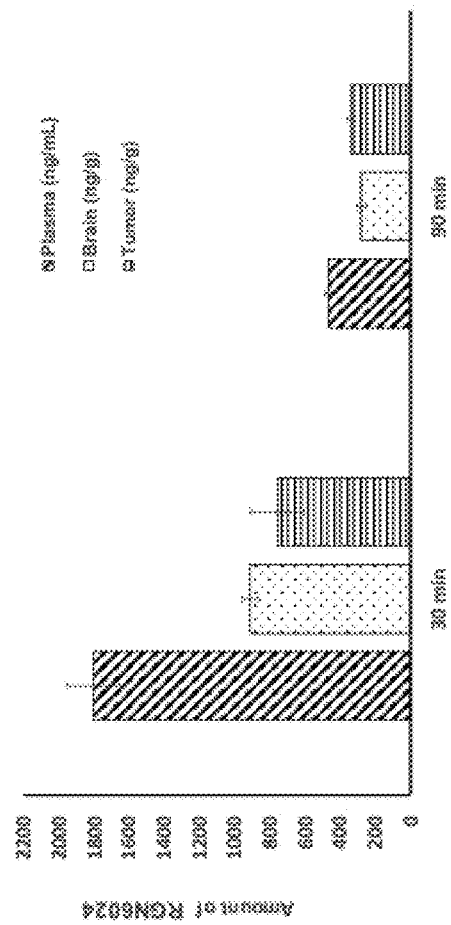
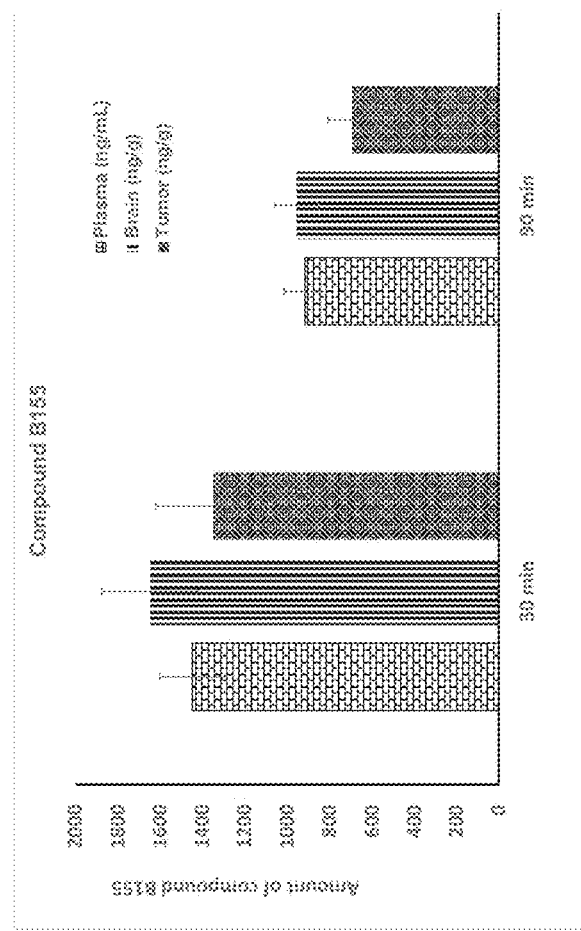
FIG. 26A
FIG. 26B

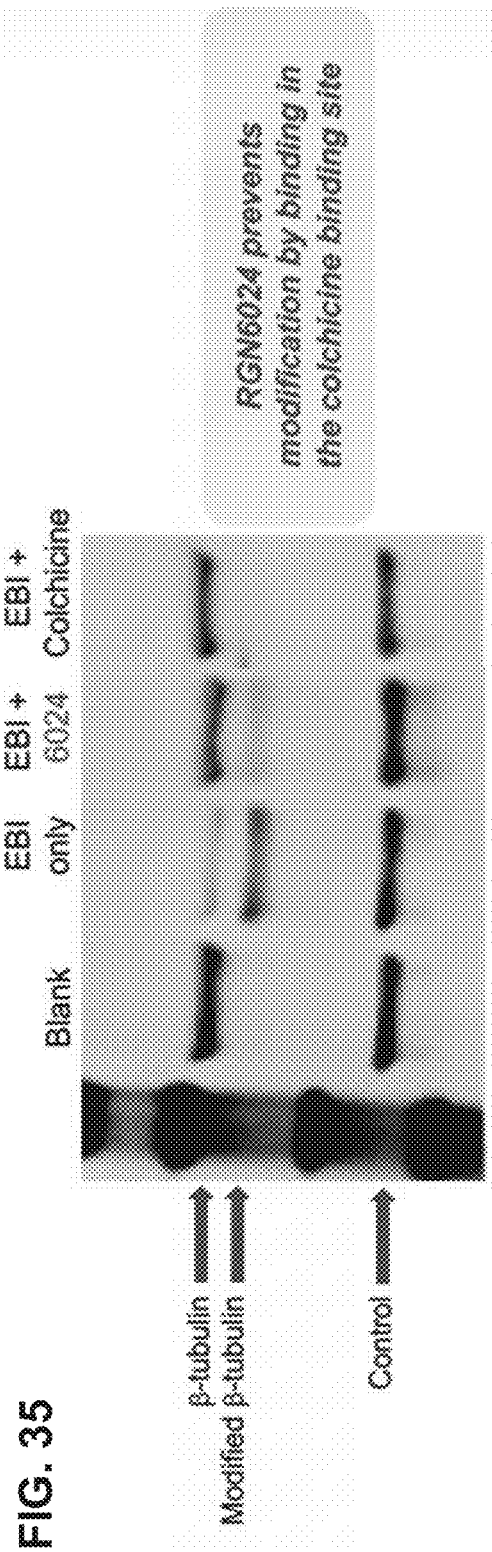

FIG. 35

Modified β-tubulin - N,N'-ethylene-bis(iodoacetamide) (EBI) selectively crosslinks β-tubulin at the colchicine-binding site
Control - GAPDH is loading control for this experiment (Western Blot)
EBi only lane - Negative control, β-tubulin is modified in the absence of drug.
EBi + 6024 lane - RGN6024 protects β-tubulin from modification.
EBi + Colchicine lane - Positive control, β-tubulin is protected from modification.

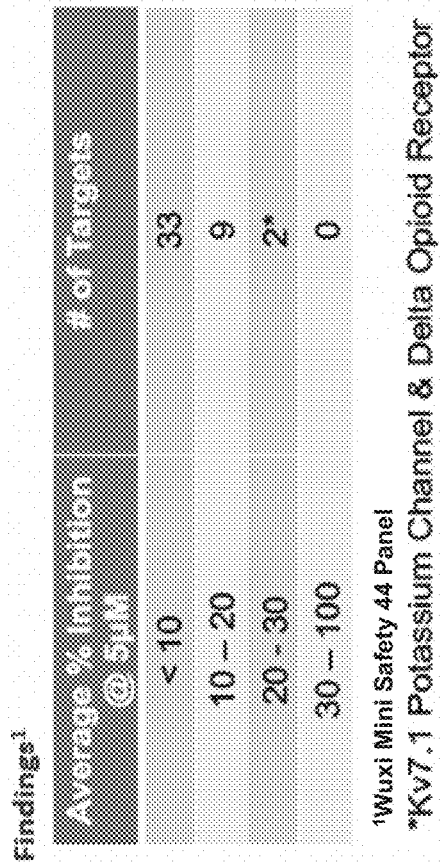

FIG. 36

Findings[1]

| Average % Inhibition @ 5 μM | # of Targets |
|---|---|
| <10 | 33 |
| 10 – 20 | 9 |
| 20 – 30 | 2* |
| 30 – 100 | 0 |

[1]Wuxi Mini Safety 44 Panel
*Kv7.1 Potassium Channel & Delta Opioid Receptor

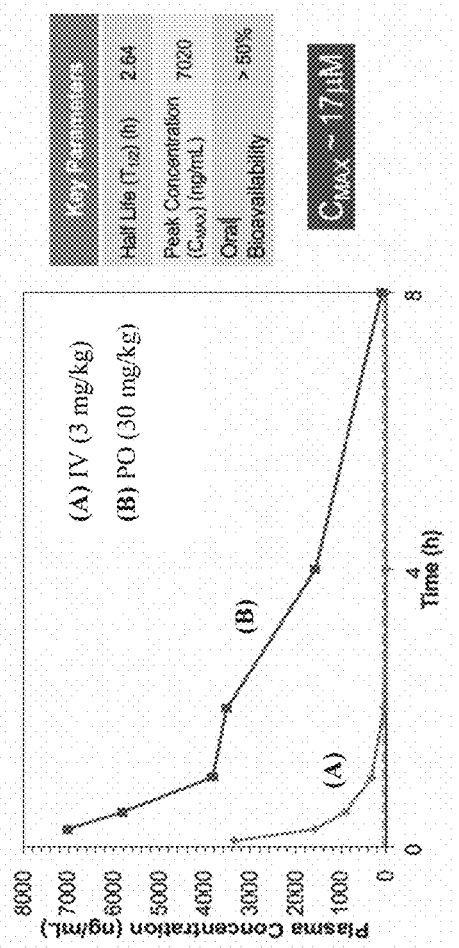
FIG. 37
FIG. 38
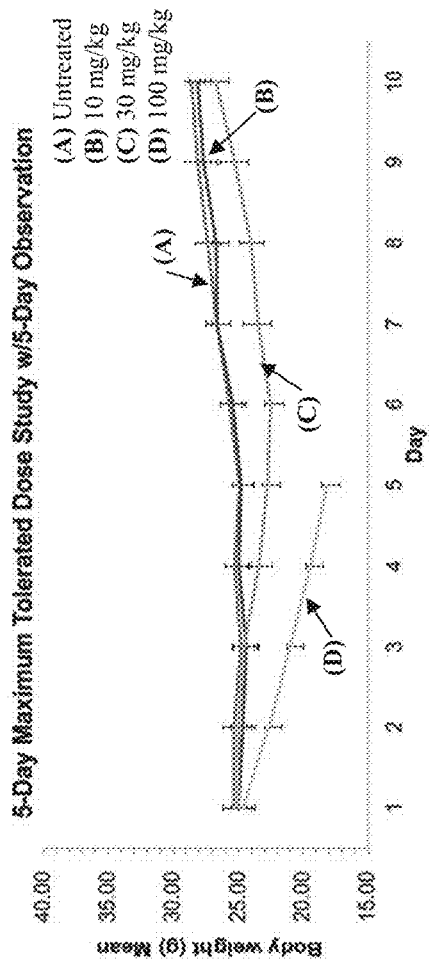
FIG. 39

FIG. 40

Physicochemical and ADME Properties of RGN6024

| Physicochemical Properties | |
|---|---|
| Molecular weight | 403.5 |
| Log D | 2.52 |
| MPO Score | 4.44 |

| Solubility | |
|---|---|
| Kinetic Solubility | 5.24 µM |

| Permeability | |
|---|---|
| Papp (x 10⁻⁶ cm/s) | 21.1 |
| Efflux Ratio | 1.0 |

- MPO score > 4.0 predicts good brain penetration.
- Water soluble in saline formulations
- Significant permeability (Papp > 10) leads to better diffusion.
- Efflux ratio < 2.0 : NOT MDR1 pump substrate.

FIG. 41

In Vitro ADME Properties of RGN6024

| Liver Microsomes (Clint) | | |
|---|---|---|
| Species | T1/2 (minutes) | Clint (µL min⁻¹ mg⁻¹) |
| Human | 131 | 13.3 |
| Mouse | 30 | 182 |
| Rat | 48 | 51.7 |

| Plasma Protein Binding (%) | |
|---|---|
| Human | 97.3 |
| Mouse | 98.8 |
| Rat | 88.9 |
| Dog | 88.1 |
| Monkey | 97.1 |

| Cytochrome P450 Inhibition | |
|---|---|
| 1A2 | No inhibition |
| 2C9 | 3.4 |
| 2C19 | 16.2 |
| 3A4 (M) | No inhibition |
| 3A4 (T) | No inhibition |
| 2D6 | No inhibition |

- Low clearance and high half-life leads to good plasma levels in humans.
- Moderate protein binding in humans for higher fraction of free drug.
- Mouse data is consistent with human data.
- No inhibition of cytochrome P450 avoids adverse drug interactions.

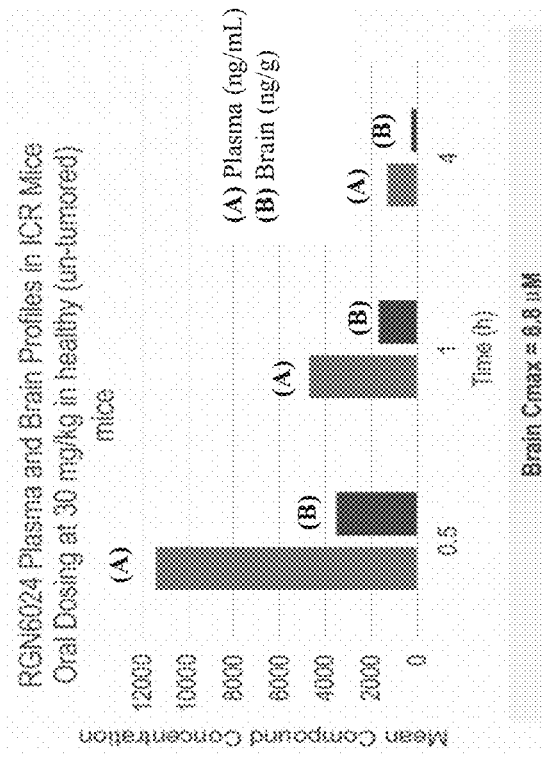
FIG. 43
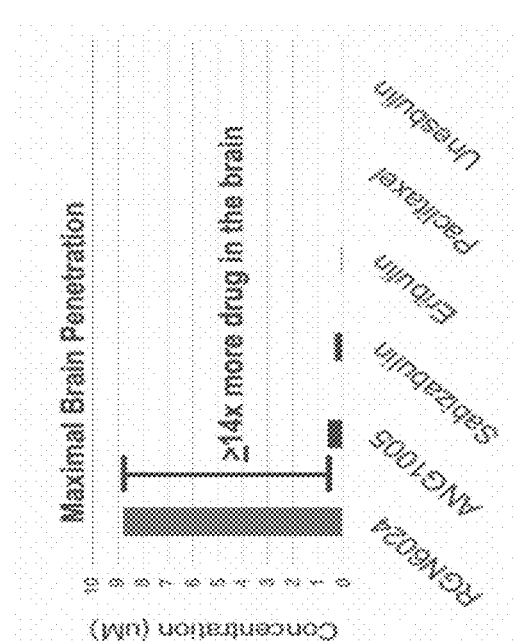
FIG. 42
FIG. 44

FIG. 46

Despite the Same Mechanism of Action and Target Affinity, Colchicine and Sabizabulin Produce Vastly Different Side Effect Profiles

| Adverse Events (Grade ≥ 3) | Colchicine | Sabizabulin |
|---|---|---|
| Neutropenia | HIGH | NO |
| Diarrhea | HIGH | LOW |
| Vomiting | HIGH | LOW |
| Peripheral Neuropathy | HIGH | NO |
| Reaches the brain | Very Low Level | Low Level |

FIG. 45

Safety Varies Markedly Among FDA Approved and Clinical Stage Colchicine-Binding Site Therapies – Colchicine and Sabizabulin Represent the Extremes

| Therapy | Maximum Oral Human Daily Dose | Maximum Plasma Concentration | Clinical Side Effects |
|---|---|---|---|
| Colchicine | 2.4 mg/day | 0.011 µM | GI toxicity, neuropathy, P-gp and drug-drug interactions |
| Sabizabulin | 63 mg/day | 0.39 µM | Fatigue, GI Toxicity* |

*Neurotoxicity and neutropenia are not observed. GI toxicity managed by taking temporary dosing "holidays"

Colchicine and Sabizabulin possess similar affinity for the tubulin protein yet vary widely in their safety profiles

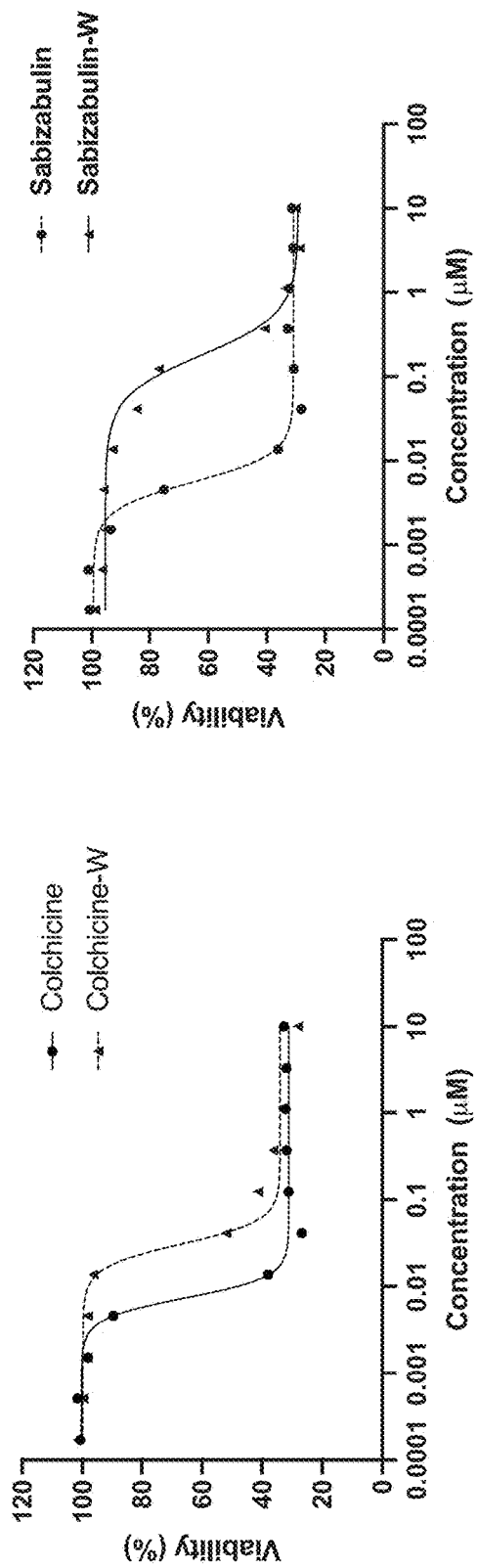
FIG. 47A
FIG. 47B
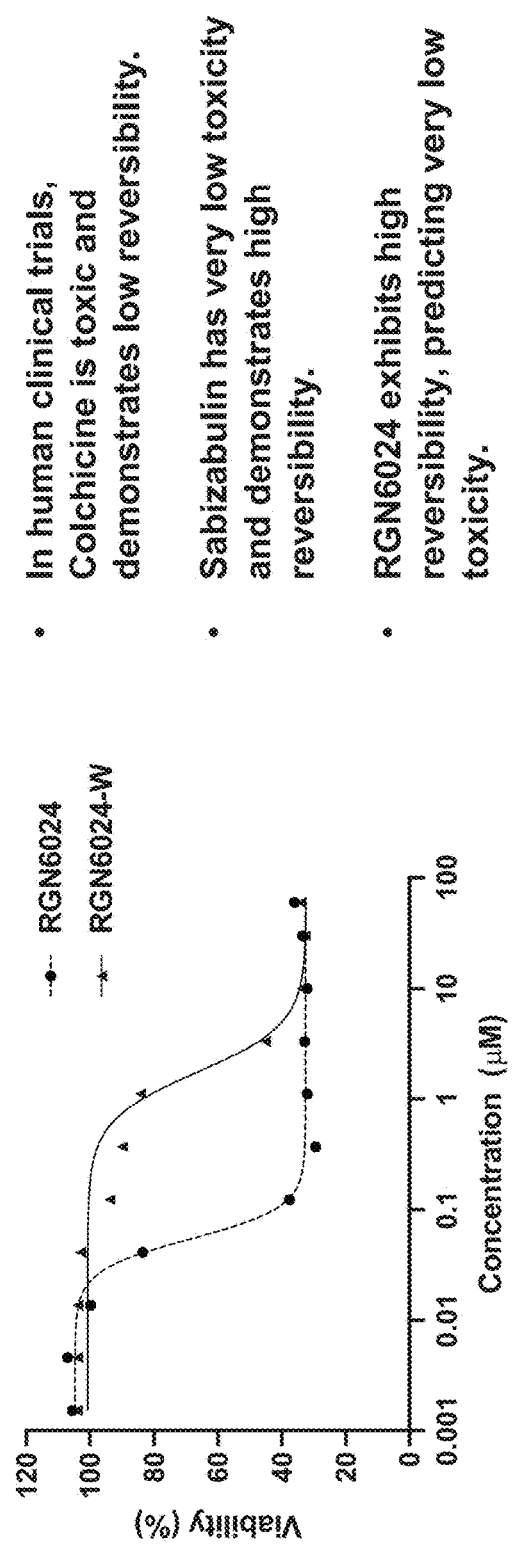
FIG. 47C
- In human clinical trials, Colchicine is toxic and demonstrates low reversibility.
- Sabizabulin has very low toxicity and demonstrates high reversibility.
- RGN6024 exhibits high reversibility, predicting very low toxicity.

COMPOSITIONS AND METHODS FOR MAKING AND USING SMALL MOLECULES FOR TUBULIN-TARGETED THERAPY IN THE TREATMENT OF CANCERS AND RELATED CONDITIONS

CROSS-REFERENCE TO RELATED APPLICATIONS

This application is a non-provisional and claims benefit of U.S. Provisional Application No. 63/555,767 filed Feb. 20, 2024, U.S. Provisional Application No. 63/591,709 filed Oct. 19, 2023, and U.S. Provisional Application No. 63/448,964 filed Feb. 28, 2023, the specifications of which are incorporated herein in their entirety by reference.

FIELD OF THE INVENTION

The present invention features compounds, compositions, and methods for making and using small molecules for treating health conditions. In some embodiments, the compositions include one or more novel compounds, tagged compounds, prodrugs, drug conjugates and metabolites, and intermediary compounds thereof. In other embodiments, the present invention features compounds, compositions and methods for treating and/or managing, and/or preemptively preventing, and/or reducing, and/or significantly decreasing cancers, including but not limited to, Glioblastoma, cancers that metastasize to the brain, and other brain cancers. In other embodiments, the compounds, compositions and methods relate to treating cancers, including, but not limited to, one or more of brain cancer, breast cancer, skin cancer, metastatic cancer, pancreatic cancer, lung cancer, kidney cancer, liver cancer, bladder cancer, bone sarcoma, ovarian cancer, rectal cancer, blood cancer, gastrointestinal cancer, or any combination thereof. In further embodiments, the compounds, compositions, and methods relate to drug screening and other methods for generating novel compounds.

BACKGROUND OF THE INVENTION

Despite advances in oncology treatment, cancer remains a leading cause of death due to its high morbidity and mortality. Small molecule therapy can be successful for treatment of some cancers; however, many have a narrow therapeutic index and are not highly selective causing unwanted drug toxicity in a subject. Poor penetrance into sanctuary sites (e.g., CNS) requires some small molecules to be administered at high concentrations which can further contribute to toxic side effects. Additionally, many cancers develop drug resistance to some small molecule therapies over time resulting in relapse of the disease. Therefore, a need exists for creating novel small molecules for more successful treatments for cancers and other health conditions.

BRIEF SUMMARY OF THE INVENTION

The present invention features compounds, compositions, and methods that allow for making and using small molecules for the treatment of health conditions. In some embodiments, the present disclosure provides novel compounds, compositions, and methods for treating cancer or cancers that metastasize to the brain in a subject in need thereof. In other embodiments, the compounds, compositions and methods relate to drug screening and other methods for the generation of novel compounds. Embodiments of the invention are given in the dependent claims. Embodiments of the present invention can be freely combined with each other if they are not mutually exclusive.

As will be discussed herein, the compounds, compositions and methods are effective for crossing the blood brain barrier (BBB) and acting as a tubulin-targeting therapy specific for brain cancer, significantly depolymerizing tubulin to stop cell division and kill cancer cells and resulting in reduced tumor growth.

Without wishing to limit the invention to any theory or mechanism, it is believed that the technical feature of the present invention advantageously provides for compounds and compositions with improved ability to cross the blood brain barrier compared to other known products in the market where many fail to cross into the brain and others cross the BBB at much lower success rates than observed herein. For example, some molecules of the instant application were designed to bind to a small cleft on the surface of the tubulin protein, which permits molecules of smaller size and affect and provides for improved brain penetration and avoidance of efflux pumps that would otherwise remove these molecules from the brain. In addition, it is believed that the present invention advantageously provides for a highly efficacious and potent treatment for cancer, including brain cancer (e.g. therapy-resistant glioblastoma) and cancers that metastasize to the brain, including but not limited to lung cancer, breast cancer and melanoma. None of the presently known prior art references have the unique inventive technical feature of the present invention.

Suitable methods and materials for the practice and/or testing of embodiments of the disclosure are described below. Such methods, materials and examples are illustrative only and are not intended to be limiting. Other methods and materials similar or equivalent to those described herein can be used. For example, conventional methods well known in the art to which the disclosure pertains are described in various general and more specific references.

In certain embodiments, the present disclosure provides for compounds for use to treat, prevent, or ameliorate a health condition in a subject or of use as combination therapies in treating, reducing onset, or ameliorating a health condition in a subject in need thereof.

In some embodiments, the present invention features a compound according to formula (I-D):

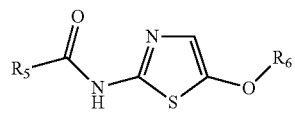

(I-D)

wherein $R_5$ is selected from:

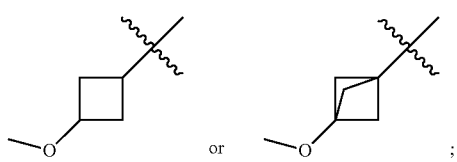

and $R_6$ is an aryl or a heteroaryl, wherein the aryl and the heteroaryl are each independently unsubstituted or are optionally each independently substituted with one or more of an alkyl, alkenyl, alkynyl, alkoxyl, alkylsulfo, alkylamino, halogen, thiol, hydroxyl, nitro, cyano, cycloalkyl, heterocyclyl, heterocyclic alkyl, aryl, heteroaryl, cycloalkoxyl, heterocyclic alkoxyl, cycloalkylthio, or heterocyclic alkylthio.

In other embodiments, $R_6$ is one of the following:

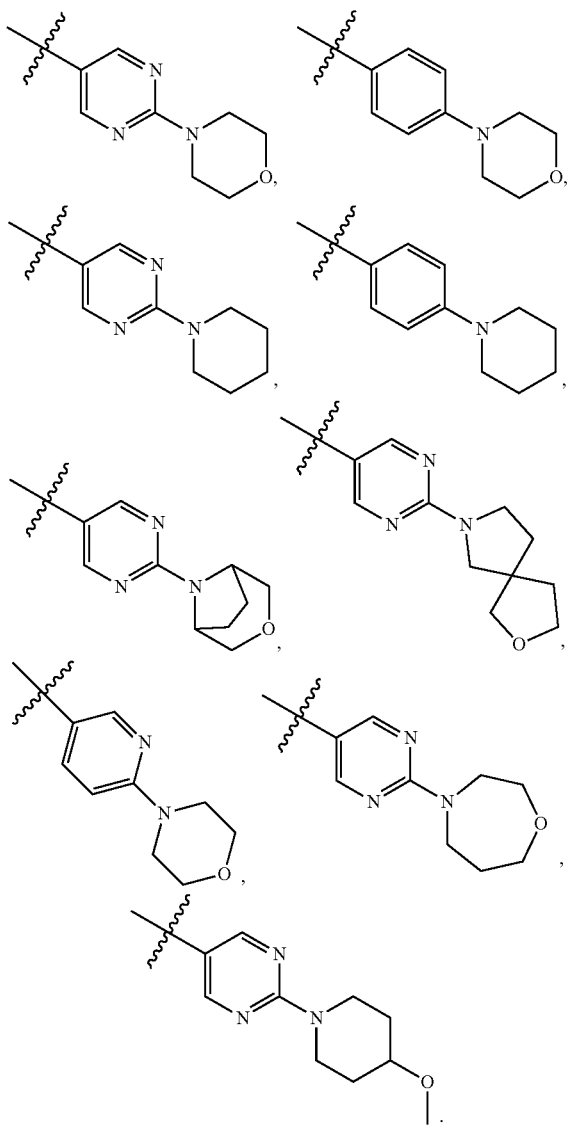

In certain embodiments, the compound is configured to cross the blood brain barrier (BBB) of a human or non-human subject. In certain embodiments, the present invention has a central nervous system multiparameter optimization (CNS MPO) score greater than or equal to 4.0, a Papp score greater than 10, or an efflux ratio of the compound is less than 2.0.

In certain embodiments, the compound is effective for treating a health condition, treating a cancer or metastasis, preventing cancer cells from dividing, inhibiting tubulin polymerization, destabilizing microtubules, arresting cell division in the G2/M phase, cytotoxicity against multiple cancer cell lines, targeting blood vessels and vasculature of a cancer or tumor, treating non-neoplastic conditions, treating gout, treating familial Mediterranean fever, treating nail fungus, targeting blood vessels or vasculature, or any combination thereof.

In certain embodiments, the present invention features a composition comprising a compound according to formula (I-D) and one or more of the following: a tag, an inactive moiety or a targeting moiety linked to the compound. In some embodiments, the tag is a fluorescent tag, radioactive tag, biotin, or any combination thereof. In some embodiments, the inactive moiety is an ester, carbamate, aminoacyl ester, or any combination thereof. In other embodiments, the targeting moiety is an antibody, polyethylene glycol (PEG) conjugate, or long chain polymer, peptide sequence, or any combination thereof.

In some preferred embodiments, the compound is RGN6024:

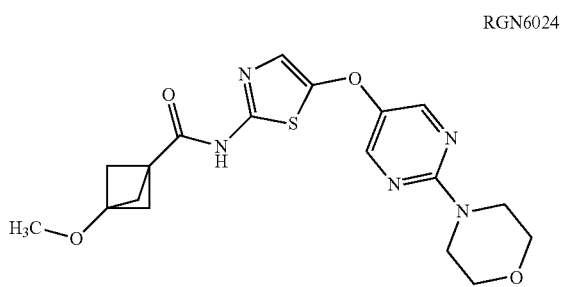 [SMILES: COC12CC(C(=O)Nc3ncc(Oc4cnc(N5CCOCC5)nc4)s3)(C1)C2]

In some embodiments, the present invention features a compound according to formula II-D:

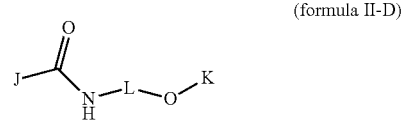

wherein J is:

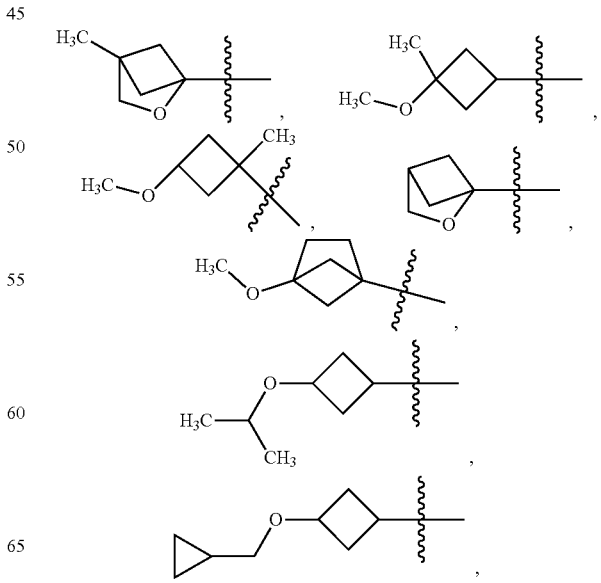

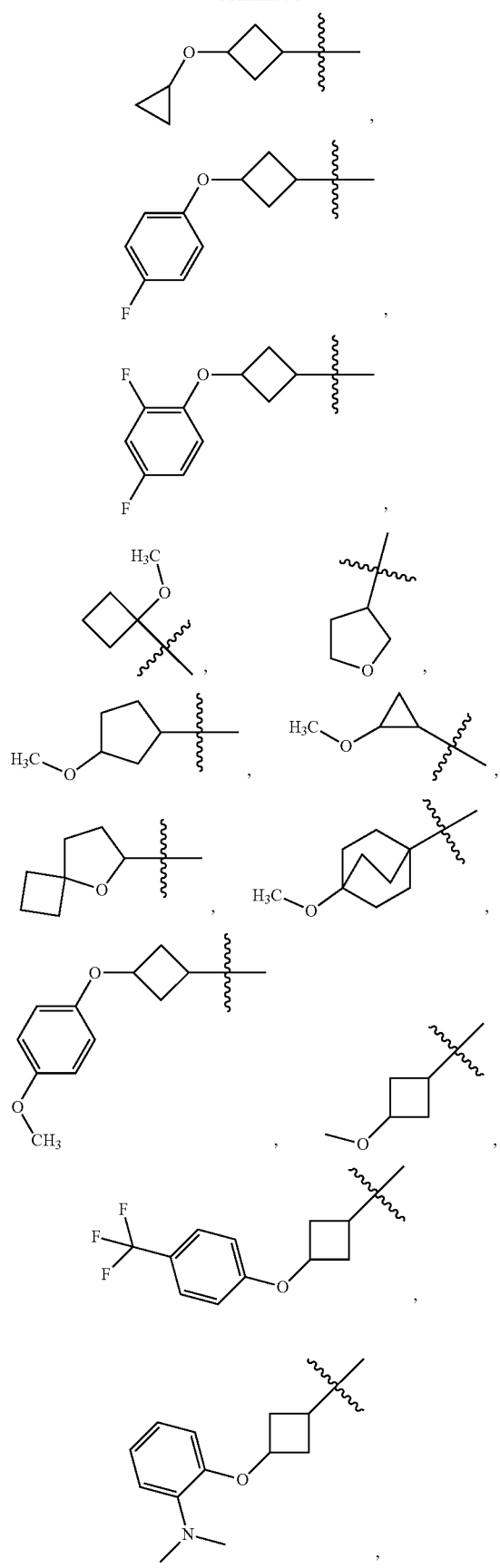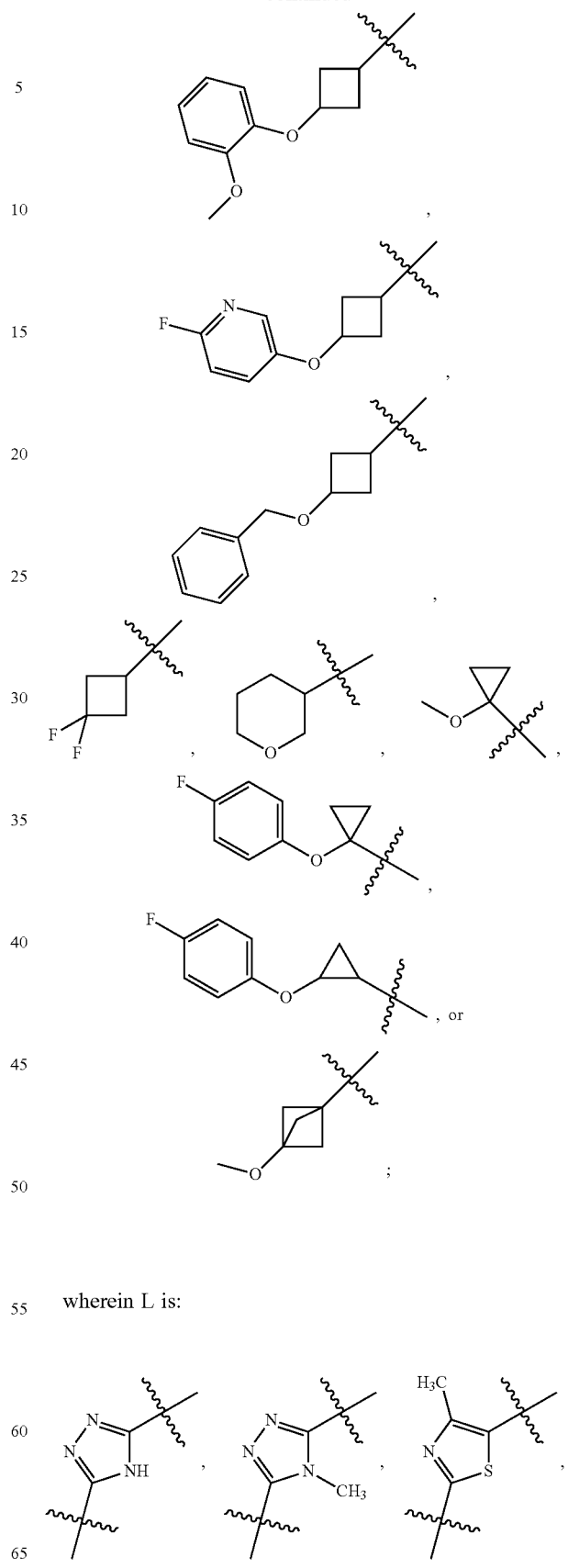
wherein L is:

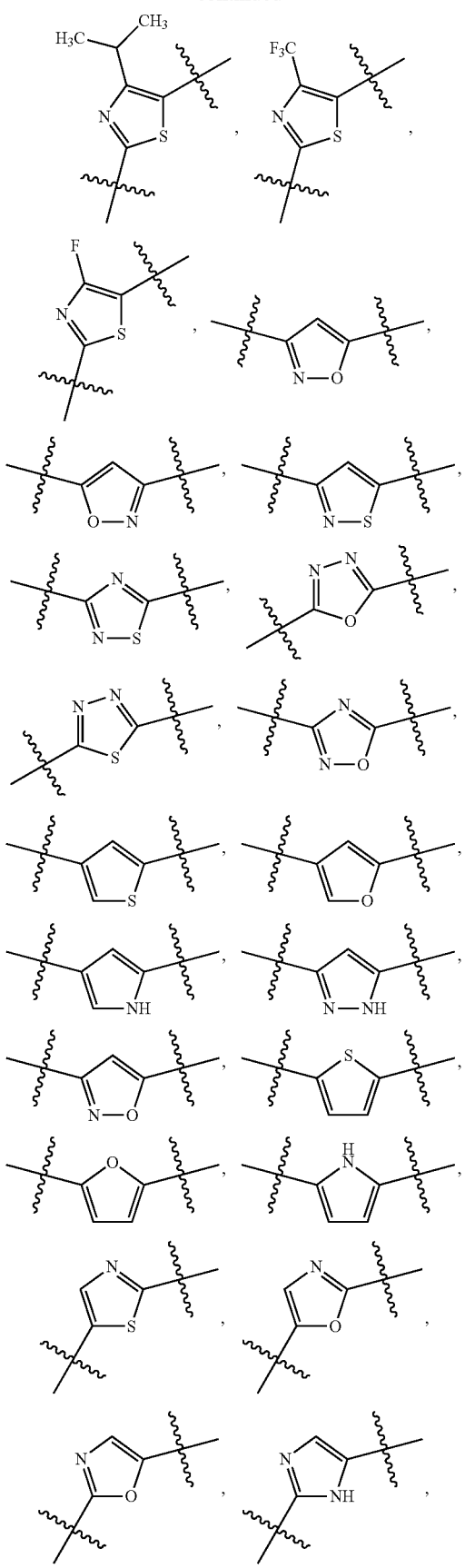

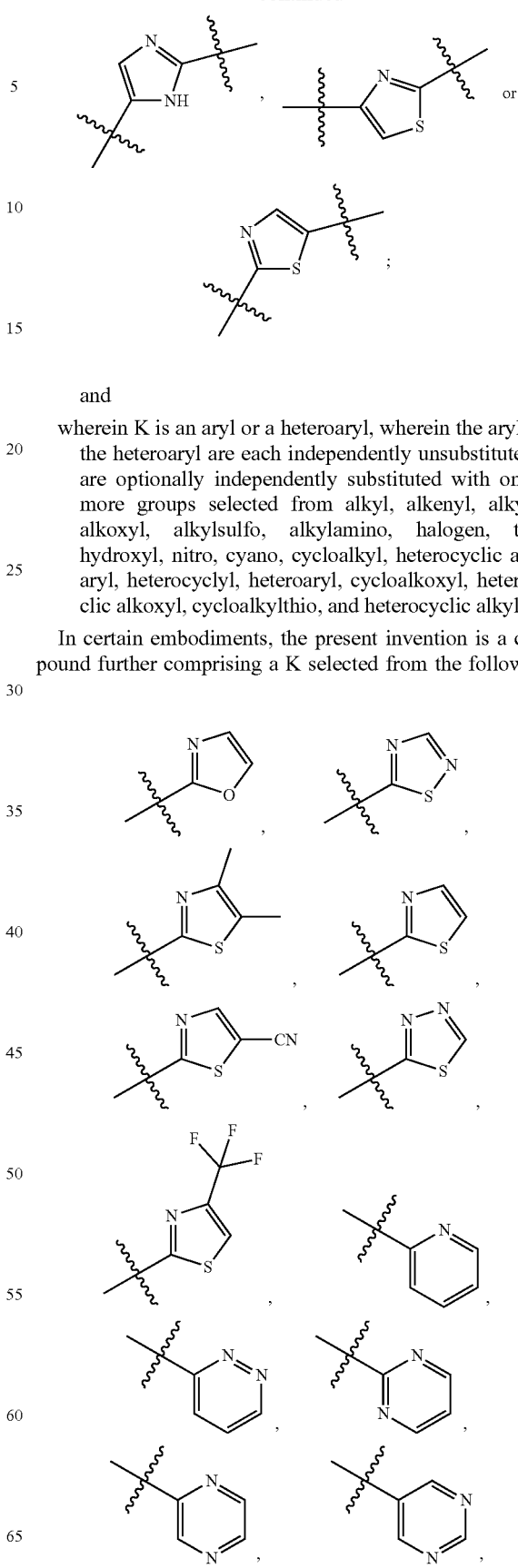

and wherein K is an aryl or a heteroaryl, wherein the aryl and the heteroaryl are each independently unsubstituted or are optionally independently substituted with one or more groups selected from alkyl, alkenyl, alkynyl, alkoxyl, alkylsulfo, alkylamino, halogen, thiol, hydroxyl, nitro, cyano, cycloalkyl, heterocyclic alkyl, aryl, heterocyclyl, heteroaryl, cycloalkoxyl, heterocyclic alkoxyl, cycloalkylthio, and heterocyclic alkylthio.

In certain embodiments, the present invention is a compound further comprising a K selected from the following:

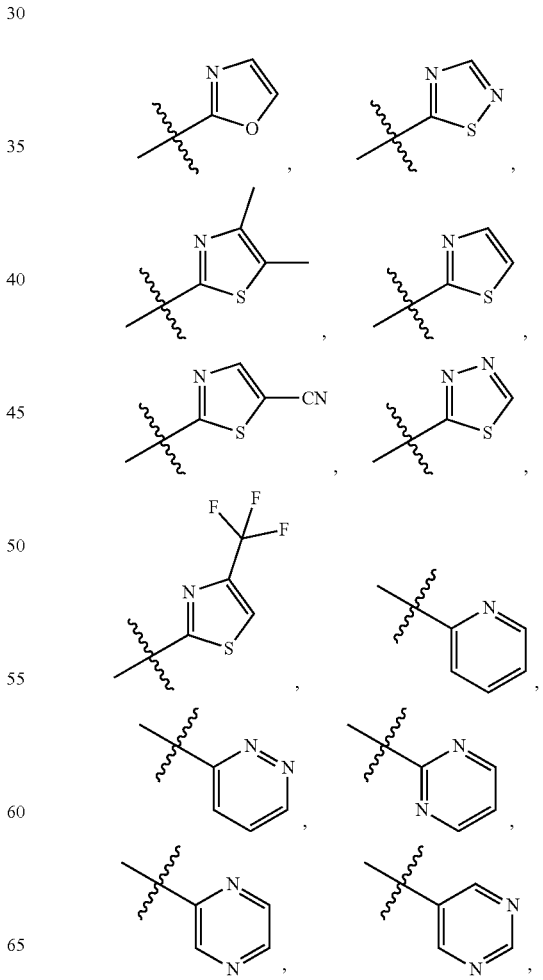

-continued
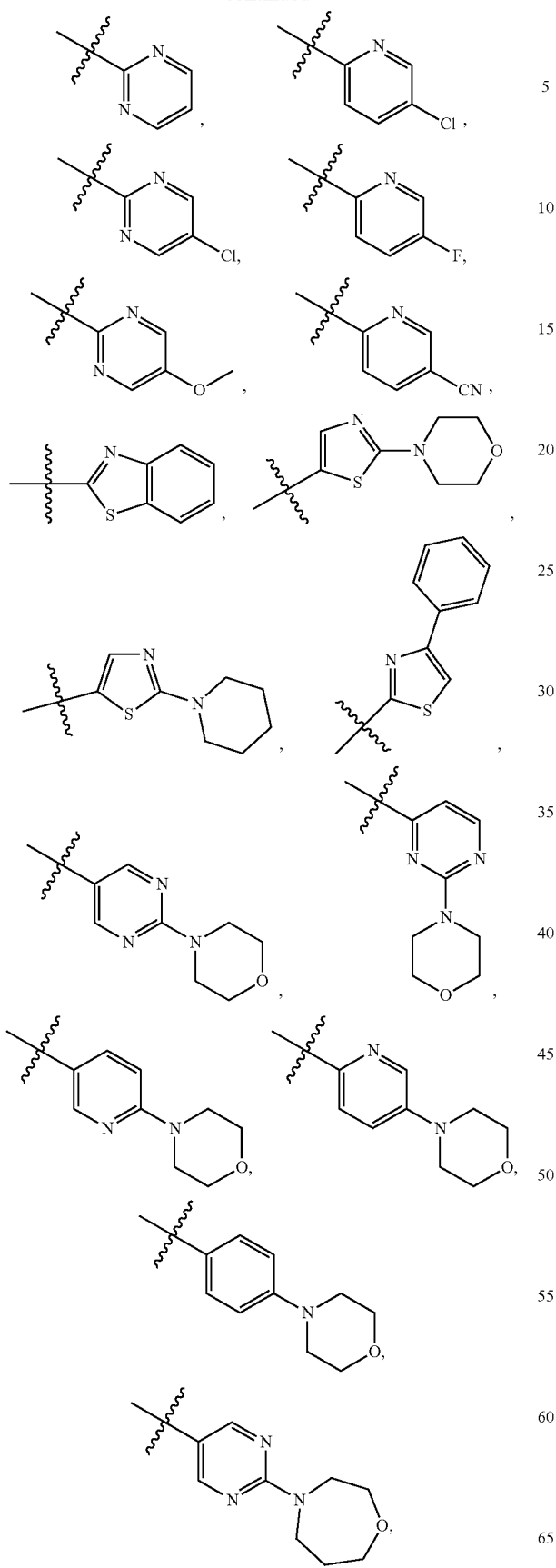
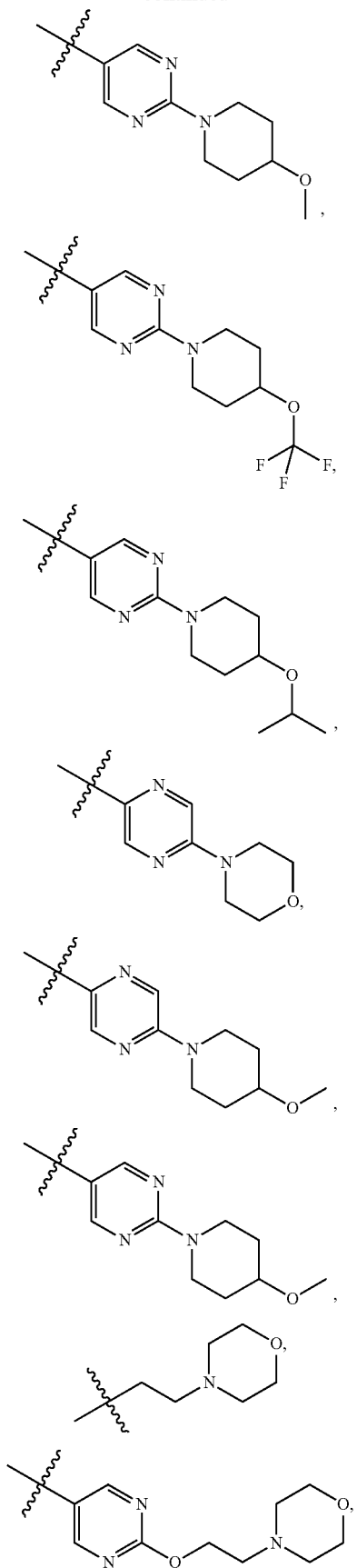

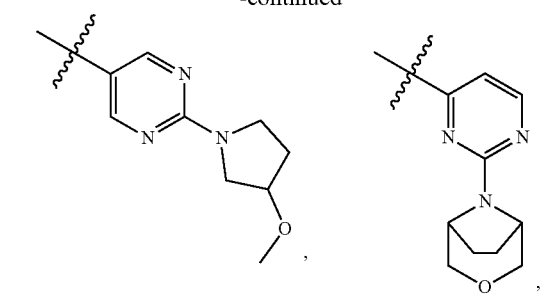
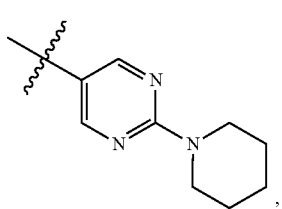
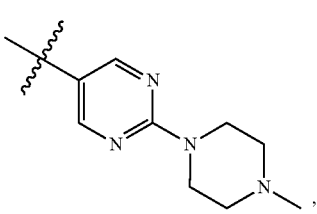
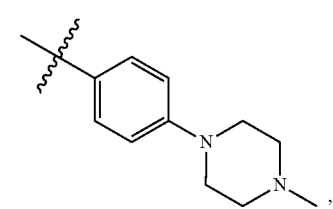
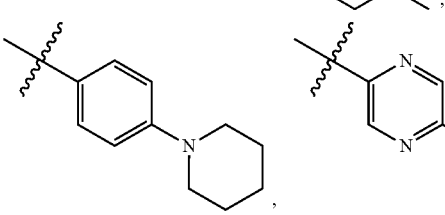
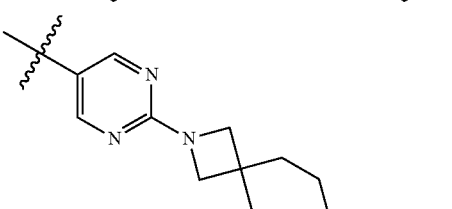
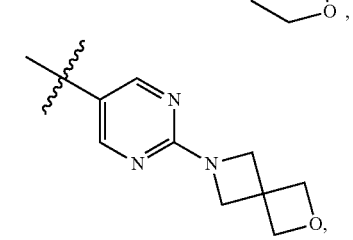
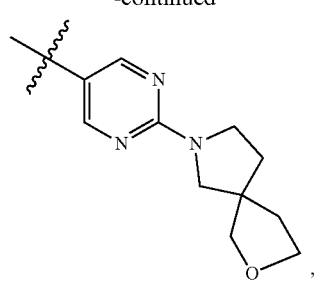
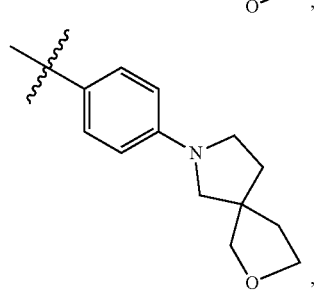
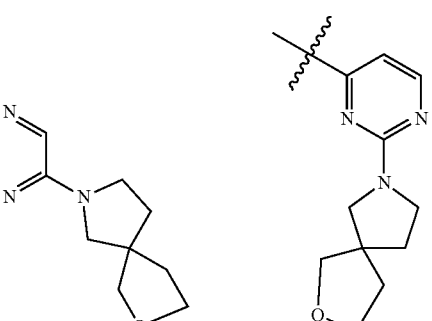
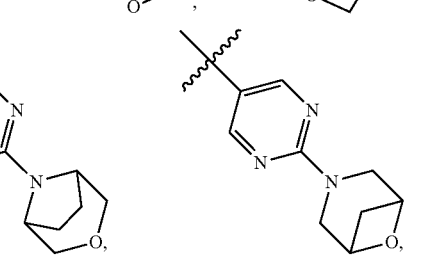
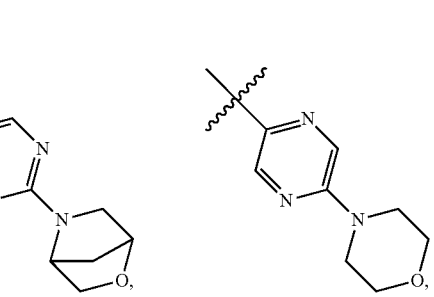
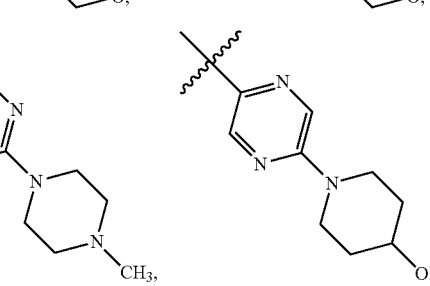

-continued

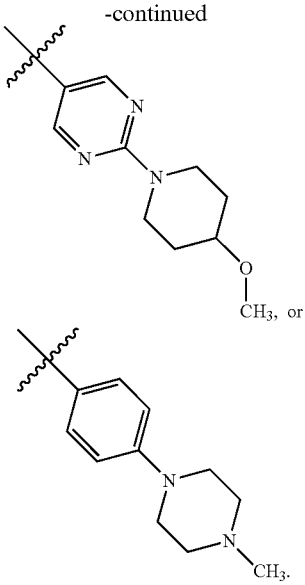

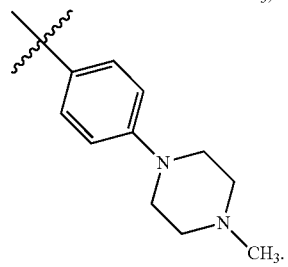

In certain embodiments, the compound is configured to cross the blood brain barrier (BBB) of a human or non-human subject. In other embodiments, the compound has a central nervous system multiparameter optimization (CNS MPO) score greater than or equal to 4.0, a Papp score greater than 10, or an efflux ratio of the compound is less than 2.0.

In some embodiments, the present invention features a composition comprising a compound according to formula (I-D) as disclosed herein. In other embodiments, the present invention features a composition comprising a compound according to formula (II-D) as disclosed herein.

In certain embodiments, the present invention features a compound according to one of the following compounds, or derivative thereof:

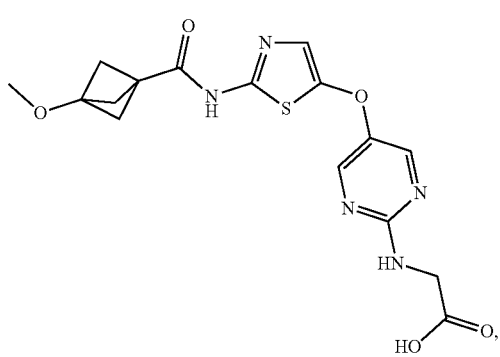

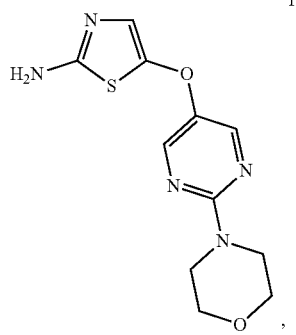

-continued

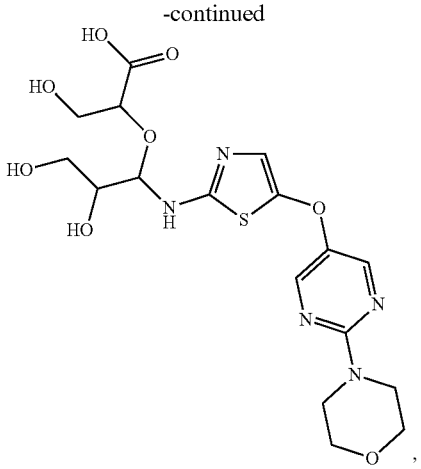

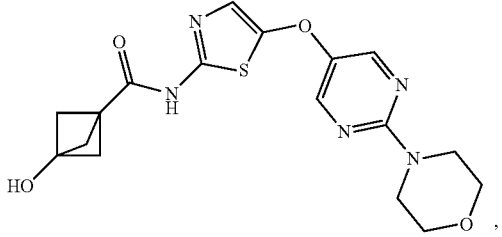

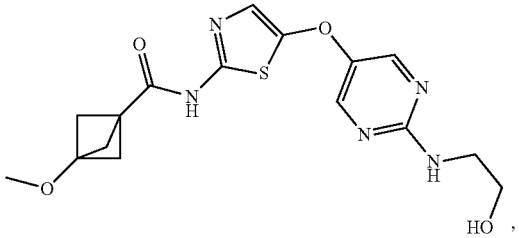

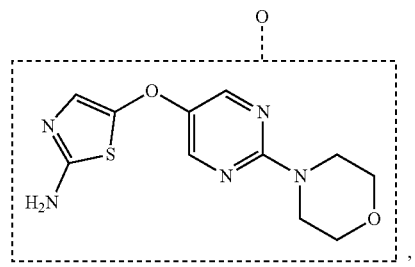

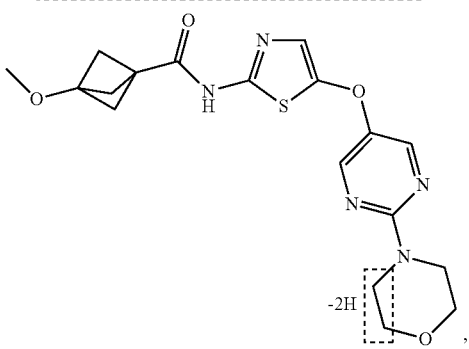

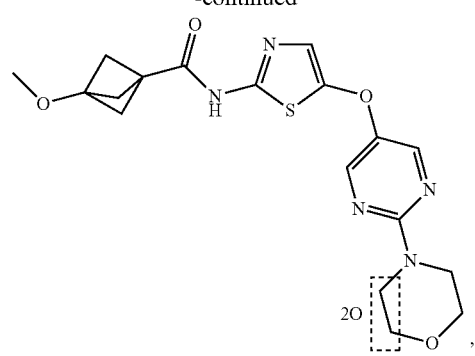
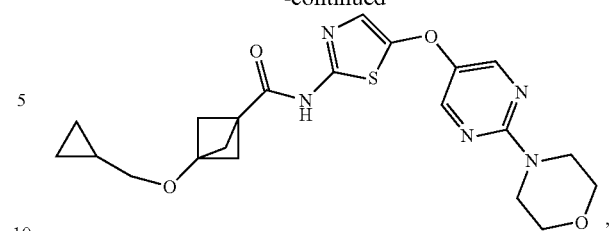
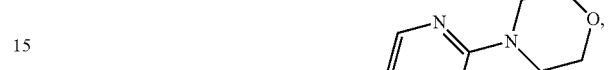
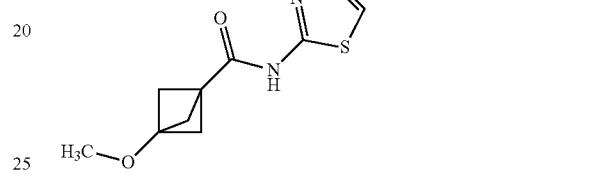
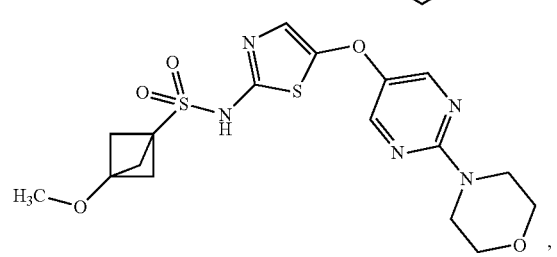
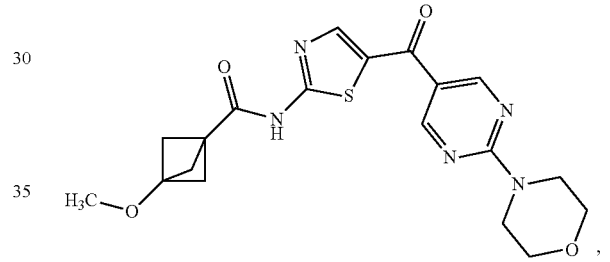
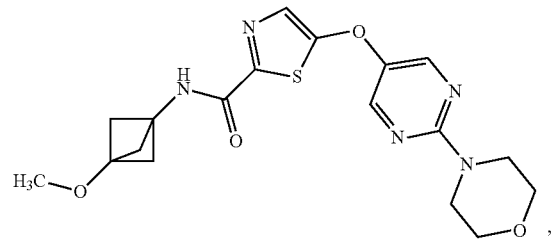
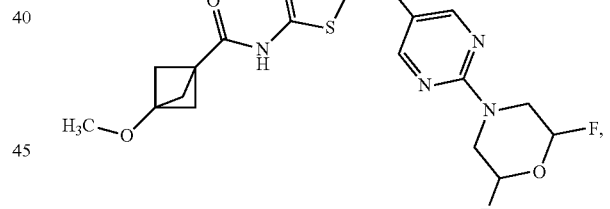
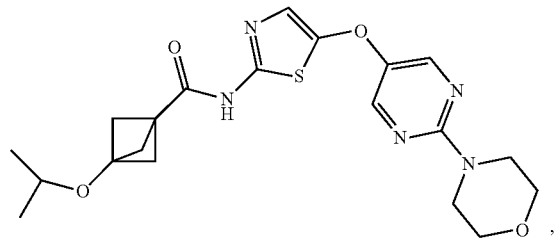
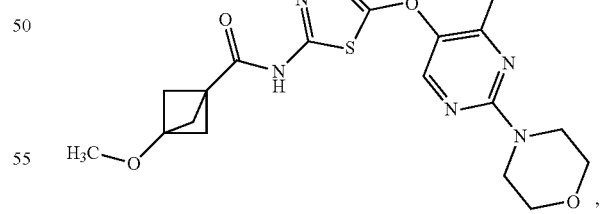

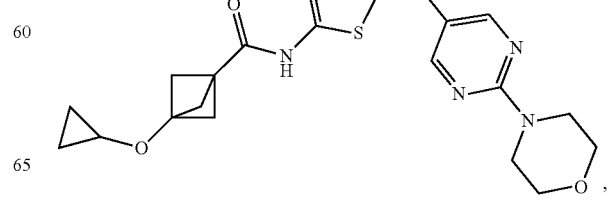

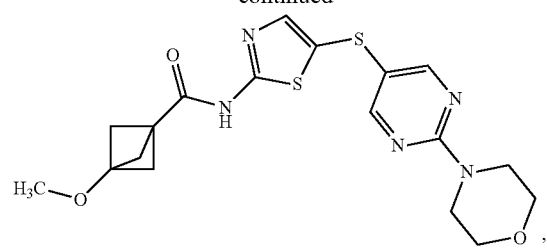
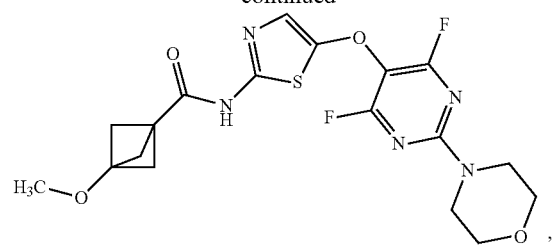
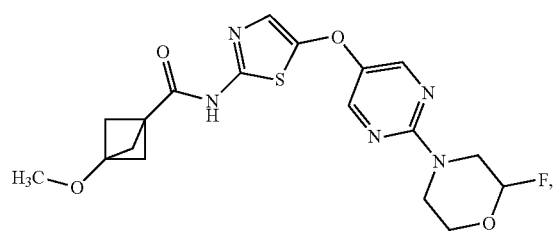
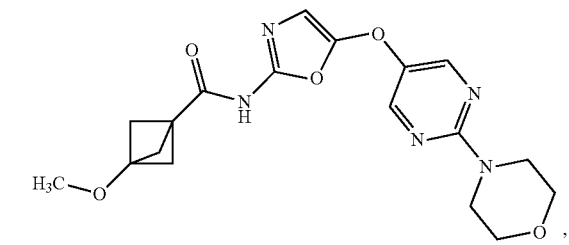
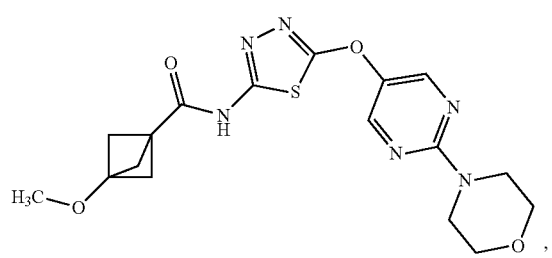
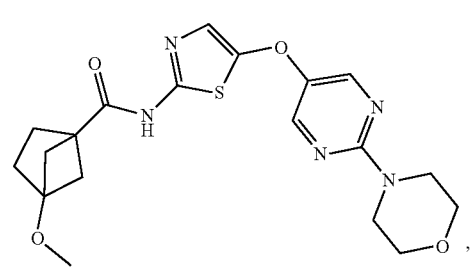
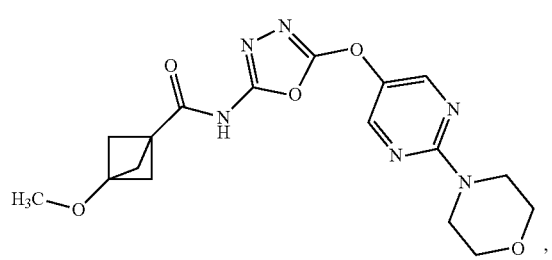
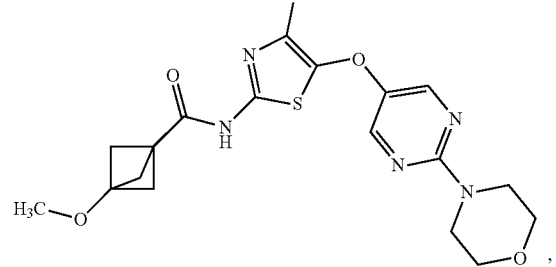
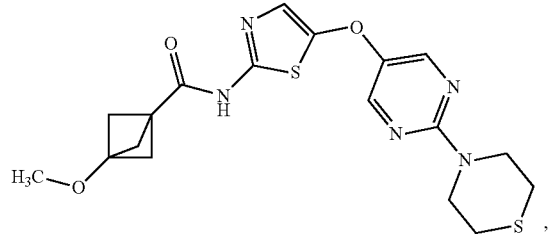
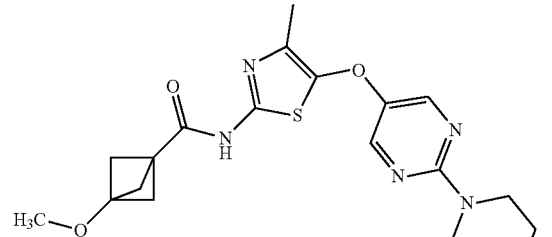
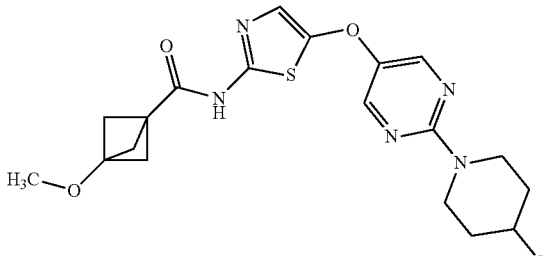
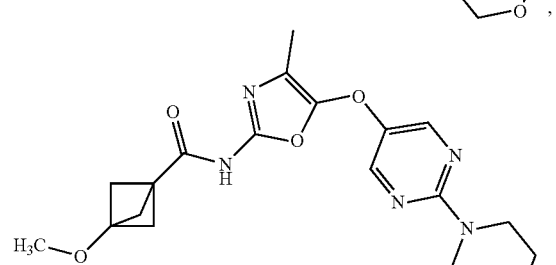

-continued

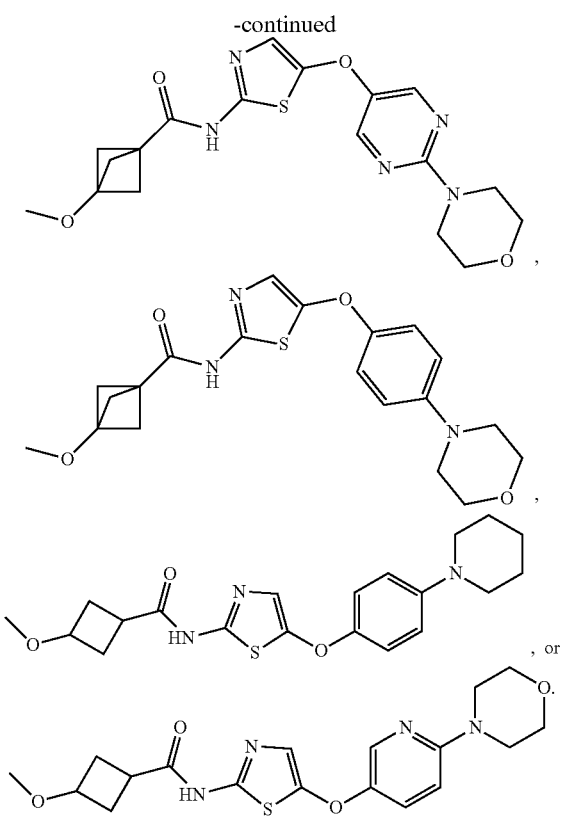

In certain embodiments, the present invention is configured to cross the blood brain barrier (BBB) of a human or non-human subject. In certain embodiments, the present invention has a central nervous system multiparameter optimization (CNS MPO) score greater than or equal to 4.0, a Papp score greater than 10, or an efflux ratio of the compound is less than 2.0.

In some other embodiments, the present invention is a composition comprising any of the compounds as disclosed herein.

Methods of Treatment

In some embodiments, the present invention features a method of preventing, delaying the onset of, or treating a health condition in a subject in need thereof, the method comprising the steps of: (a) identifying the subject presenting with the health condition; and (b) administering to the subject a therapeutically effective amount of a composition comprising one or more compounds as disclosed herein or a derivative thereof.

In certain embodiments, the present disclosure provides methods of treating a health condition in a subject having, having had, suspected of developing, or at risk of developing a health condition, the method including administering to the subject a therapeutically effective amount of at least one compound disclosed herein.

In some embodiments, the subject is a human or a non-human animal. In other embodiments, the non-human subject is a livestock, a companion animal, a lab animal, or a zoological, a wild animal, reptile, fish or bird.

In some embodiments, the health condition comprises one or more cancers. In certain embodiments, the health condition can be cancer such as prostate cancer, brain cancer, breast cancer, skin cancer, metastatic cancer, pancreatic cancer, lung cancer, kidney cancer, liver cancer, bladder cancer, bone sarcoma, ovarian cancer, rectal cancer, blood cancer, gastrointestinal cancer, medulloblastoma, or other solid organ, cellular or tissue cancer or any combination thereof. In some embodiments, the cancer can be Ewing sarcoma. In other embodiments, the cancer can be melanoma. In some embodiments, the health condition comprises brain cancer or a cancer capable of metastasizing to the brain. In some embodiments, the cancer is glioblastoma, high-grade glioma, other brain cancer, non-cell lung cancer (NSCLC) before or after metastasizing to the brain, a vascularized cancer, or any combination thereof.

In some embodiments, the health condition comprises a non-neoplastic condition. In some embodiments, the health condition comprises gout, familial Mediterranean fever, or nail fungus. In other embodiments, the health condition comprises vascular disease.

In some embodiments, the method further comprises administration of one or more of an anti-microbial agent, chemotherapeutic agent, other anti-cancer therapy, or antibody or fragment thereof. In some embodiments, the anti-microbial agent comprises one or more of an anti-viral, bactericidal agent, anti-fungal, or anti-bacterial agent or other anti-microbial agent. In further embodiments, the anti-microbial agent can be an anti-bacterial agent (antibiotic) such as doxycycline, tetracycline, or other antibiotics such as a generally applicable antibiotic.

In some embodiments, the chemotherapeutic agent comprises one or more of temozolomide, lomustine, belzutifan, cisplatin, carboplatin, nedaplatin, triplatin tetranitrate, phenanthriplatin, picoplatin, satraplatin, Doxorubicin, Melphalan, Roscovitine, Mitomycin C, Hydroxyurea, 5-Fluorouracil, AraC (cytarabine), 6-mercaptopurine, 6-thioguanine, Cisplatin, Ara-C, Etoposide, Gemcitabine, Bortezomib, Sunitinib, Sorafenib, Sodium Valproate, a HDAC Inhibitor, a DNA synthesis inhibitor, or Dacarbazine, FLT3 inhibitors, farnesyltransferase inhibitors, topoisomerase II inhibitors, P-glycoprotein modulators, hypomethylating agents, or a combination thereof.

In some embodiments, the anti-cancer therapy comprises one or more of chemotherapy, radiotherapy, immunotherapy, and/or surgery. In other embodiments, the anti-cancer therapy further comprises one or more anti-cancer therapeutic or treatment, e.g., one or more of chemotherapeutic agents, radiation therapies, small molecules, and an immunomodulatory agent. In some embodiments, anti-cancer therapeutics or treatments can be administered separately from a compound disclosed herein or a derivative thereof.

In other embodiments, the anti-microbial agent, a chemotherapeutic agent, other anti-cancer therapy, or antibody or fragment thereof, is administered before, during or after the administration of one or more compounds or compositions as disclosed herein or a derivative thereof.

In some embodiments, the health condition is cancer, and the one or more anti-cancer treatments comprises administration of one or more of temozolomide, lomustine, belzutifan, or any combination thereof before, during or after administering the composition. In other embodiments, the health condition is NSCLC, and the one or more anti-cancer treatments comprises administration of one or more of Crizotinib, Osimertinib, or any combination thereof before, during or after administering the composition.

In some embodiments, the composition is effective for preventing cancer cells from dividing. In some embodiments, the composition is effective for inhibiting tubulin polymerization. In other embodiments, the composition is effective for destabilizing microtubules.

In some embodiments, the therapeutically effective amount of the composition is determined based on the disorder treated and the mechanism of delivery. In some embodiments, the therapeutically effective dose in a human is in the range of 0.5-5 mg/kg twice daily. In other embodiments, the therapeutically effective dose in a mouse is in the range of 1-25 mg/kg.

In some embodiments, the route of administration is one or more of intravenous injection, oral administration, subcutaneous injection, intramuscular injection, intrasternal injection, intrathecal administration, intratumoral, intravascular, intracerebral injection, intracisternal, intracerebroventricular, intranasal or inhalation, parenteral, buccal, enteral, intraperitoneal, inhalable, infused, intramuscular, ophthalmic, intravitreal, otic, rectal, sublingual, topical, transdermal, intrapulmonary, intrauterine, vaginal, via ultrasound-mediated blood brain barrier disruption, implantable devices, infusion techniques, or nanoparticle-based delivery.

In some embodiments, the composition is in the form of a tablet, pill, coated tablet or coated pill. In some embodiments, the effective dose is administered to a subject before, during, or after at least one compound is administered at least once daily, every other day, every third day, twice weekly, weekly, every other week, twice monthly or monthly, every other month, every six months, or other suitable dosing regimen.

In some embodiments, the composition results in an 83% drug resistant glioblastoma (LN-18) tumor growth reduction in a mouse model versus placebo with oral daily dosing at less than 25% of a toxic dose. In other embodiments, the compound results in an 86% drug resistant glioblastoma (LN-18) tumor growth reduction in a mouse model versus Temozolomide (TMZ) with oral daily dosing at less than 25% of a toxic dose.

In other embodiments, methods can further include administering a therapeutically effective amount of one or more anti-cancer agents or treatments to a subject prior to, simultaneously, or after administering an effective amount of at least one compound or formulation disclosed herein to the subject. In accordance with these embodiments, the one or more anti-cancer treatments can include radiation therapy. In some embodiments, the cancer can be brain cancer, and the one or more anti-cancer agents include administering one or more of temozolomide, lomustine, belzutifan, or any combination thereof. In other embodiments, the cancer is NSCLC, and the one or more anti-cancer treatments includes administering one or more of Crizotinib, Osimertinib, or a combination thereof to the subject in addition to a compound or compound-containing formulation disclosed herein.

In certain embodiments, compounds and compositions and methods of use thereof relate to RGN6024. In accordance with these embodiments, compounds and compositions can include, but are not limited to, RGN6024 and mixtures and pharmaceutical compositions thereof. In other embodiments, methods for treating, reducing onset of, or preventing a health condition in a subject can include administering a compound or composition or formulation including, but not limited to, RGN6024 in a pharmaceutically acceptable formulation. In certain embodiments, the health condition is cancer. In some embodiments, the cancer is brain cancer. In some embodiments, a composition including, but not limited to RGN6024 can be used in a formulation and administered to a subject in need thereof; optionally, brain cancer.

Methods of Use

In some embodiments, the present invention is a method of modulating abnormal cell division, the method comprising the steps of: (a) identifying a cell with abnormal cell division; and (b) administering the compounds or compositions as disclosed herein or a derivative thereof.

In some embodiments, the present invention is a method of drug screening to identify a therapeutically effective drug candidate to treat a health condition in a subject in need thereof, the method comprising the steps of: (a) identifying an in vitro or in vivo model for a health condition; (b) administering the drug candidate and RGN6024 to the in vitro or in vivo model; (c) determining efficacy, toxicity, or side effects of the drug candidate and RGN6024; and (d) comparing the efficacy, toxicity, or side effects of the drug candidate and RGN6024 to identify the therapeutically effective drug candidate.

In some embodiments, the present invention is a method of detecting a target cell with abnormal cell division, the method comprising the steps of: (a) identifying a sample comprising the target cell with abnormal cell division; (b) performing an affinity-based assay using a small molecule conjugated with a tag to contact the target cell with abnormal cell division with the small molecule conjugated with the tag; and (c) determining whether the small molecule conjugated with a tag binds to the target cell with abnormal cell division. In some embodiments, the small molecule is RGN6024, or the compounds or compositions as disclosed herein or a derivative thereof. In further embodiments, the affinity-based assay is an immuno-based assay, receptor-based assay, antibody-based assay, nanoparticle-based assay, chemical assay, optical assay, or kinetic binding assay. In other embodiments, the affinity-based assay is a gel electrophoresis, enzyme-linked immunosorbent assay, immunoblot assay, fluorescence intensity assay, fluorescence anisotropy assay, fluorescence energy transfer assay, surface plasmon resonance (SPR) assay, light scattering assay, forward binding assay, dissociation assay, or reverse binding assay. In some embodiments, the affinity-based assay is a colchicine competitive binding assay.

In some embodiments, the present invention is a method of detecting a protein expressed by a target cell with abnormal cell division, wherein the method comprises the steps of: (a) identifying a sample comprising the protein expressed by the target cell with abnormal cell division; (b) performing an affinity-based assay using a small molecule conjugated with a tag to contact the protein expressed by the target cell with abnormal cell division with the small molecule conjugated with the tag; and (c) determining whether the small molecule conjugated with a tag binds to protein expressed by the target cell with abnormal cell division. In some embodiments, the small molecule is RGN6024, or the compounds or compositions as disclosed herein or a derivative thereof. In further embodiments, the affinity-based assay is an immuno-based assay, receptor-based assay, antibody-based assay, nanoparticle-based assay, chemical assay, optical assay, or kinetic binding assay. In other embodiments, the affinity-based assay is a gel electrophoresis, enzyme-linked immunosorbent assay, immunoblot assay, fluorescence intensity assay, fluorescence anisotropy assay, fluorescence energy transfer assay, surface plasmon resonance (SPR) assay, light scattering assay, forward binding assay, dissociation assay, or reverse binding assay. In some embodiments, the affinity-based assay is a colchicine competitive binding assay.

In some embodiments, the present invention is a method of detecting or isolating a target cell with abnormal cell division, wherein the method comprises the steps of: (a)

identifying a sample comprising the target cell with abnormal cell division; (b) performing an affinity-based pull-down assay using a small molecule conjugated with a tag to contact the target cell with abnormal cell division with the small molecule conjugated with the tag; and (c) selectively isolating the target cell with abnormal cell division. In some embodiments, the small molecule is RGN6024, or the compounds or compositions as disclosed herein or a derivative thereof.

In other embodiments, the method of detecting or isolating a protein expressed by a target cell with abnormal cell division, wherein the method comprises the steps of: (a) identifying a sample comprising the protein expressed by the target cell with abnormal cell division; (b) performing an affinity-based pull-down assay using a small molecule conjugated with a tag to contact the protein expressed by the target cell with abnormal cell division with the small molecule conjugated with the tag; and (c) selectively isolating the protein expressed by the target cell with abnormal cell division. In other embodiments, the small molecule is RGN6024, or the compounds or compositions as disclosed herein or a derivative thereof.

Kits

In some embodiments, the present invention is a kit for treating a cancer comprising: (a) a therapeutically effective dose of any one of the compositions as disclosed herein or a derivative thereof; (b) at least one container for storing the compositions; and (c) dosage and administration instructions.

In certain embodiments, the present disclosure provides kits for harboring or storing any of the compounds and/or compositions and for practicing any of the methods disclosed herein. In some embodiments, kits can include one or more compounds disclosed herein and/or one or more any-one pharmaceutically acceptable formulations disclosed herein and at least one container. In some embodiments, kits disclosed herein can be used to treat or prevent cancer in a subject.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The following drawings form part of the present specification and are included to further demonstrate certain embodiments of the present disclosure. Certain embodiments can be better understood by reference to one or more of these drawings in combination with the detailed description of specific embodiments presented herein.

FIG. 3 shows an exemplary experiment illustrating a chemical reaction equation for synthesis of 3-methoxy-N-(5-((2-morpholinopyrimidin-5-yl)oxy)thiazol-2-yl)cyclobutane-1-carboxamide (Compound B120) in accordance with certain embodiments of the present disclosure.

FIG. 4 shows an exemplary experiment illustrating a chemical reaction equation for synthesis of 3-methoxy-N-(5-(4-morpholinophenoxy)thiazol-2-yl)cyclobutane-1-carboxamide (Compound B121) in accordance with certain embodiments of the present disclosure.

Figure 15:
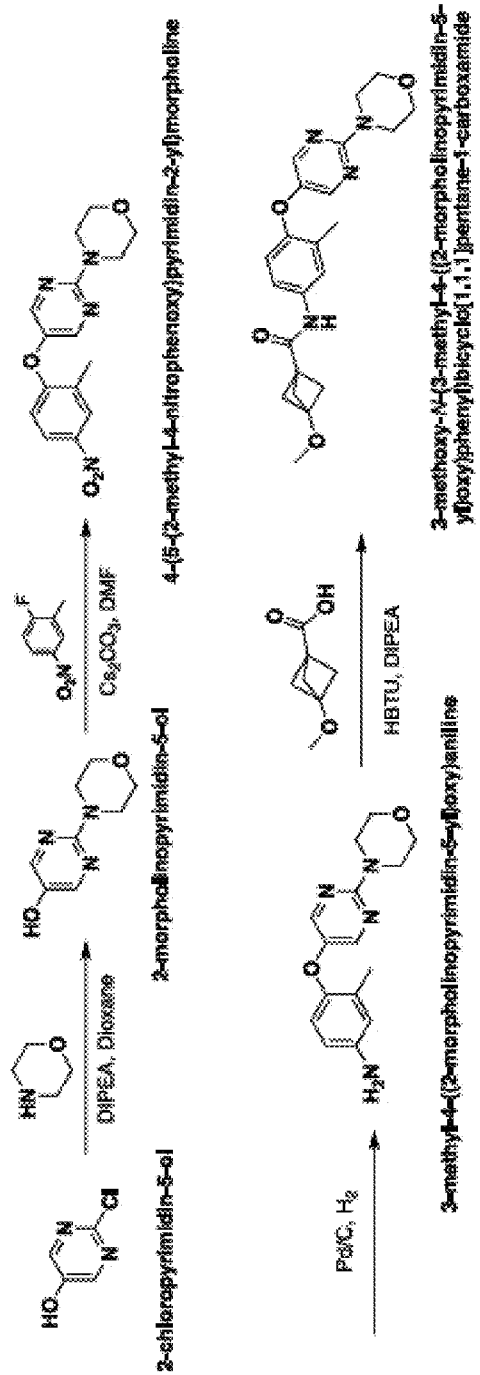

FIG. 15 shows an exemplary experiment illustrating a chemical reaction equation for synthesis of 3-methoxy-N-(3-methyl-4-((2-morpholinopyrimidin-5-yl)oxy)phenyl)bicyclo[1.1.1]pentane-1-carboxamide (Compound B89) in accordance with certain embodiments of the present disclosure.

Figure 16:
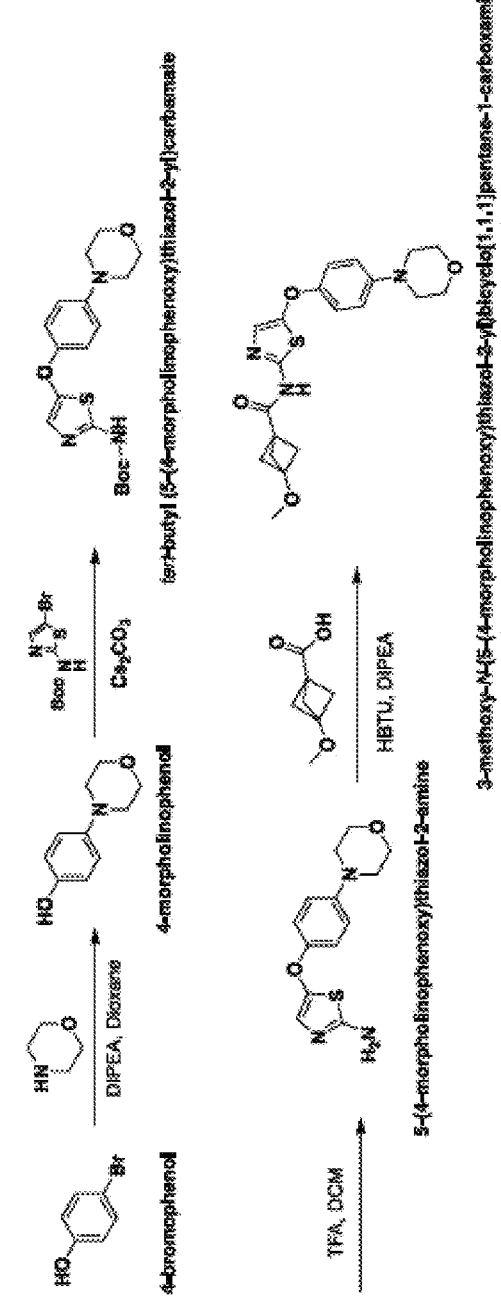

FIG. 16 shows an exemplary experiment illustrating a chemical reaction equation for synthesis of 3-methoxy-N-(5-(4-morpholinophenoxy)thiazol-2-yl)bicyclo[1.1.1]pentane-1-carboxamide (Compound B155) in accordance with certain embodiments of the present disclosure.

FIG. 17 shows an exemplary experiment illustrating a chemical reaction equation for synthesis of N-(4-((2-(3-oxa-8-azabicyclo[3.2.1]octan-8-yl)pyrimidin-5-yl)oxy)-3-methylphenyl)-3-methoxybicyclo[1.1.1]pentane-1-carboxamide (Compound B118) in accordance with certain embodiments of the present disclosure.

FIG. 18 shows an exemplary experiment illustrating a chemical reaction equation for synthesis of N-(4-((2-(2-oxa-7-azaspiro[4.4]nonan-7-yl)pyrimidin-5-yl)oxy)-3-methylphenyl)-3-methoxybicyclo[1.1.1]pentane-1-carboxamide (Compound B117) in accordance with certain embodiments of the present disclosure.

Figure 19A:
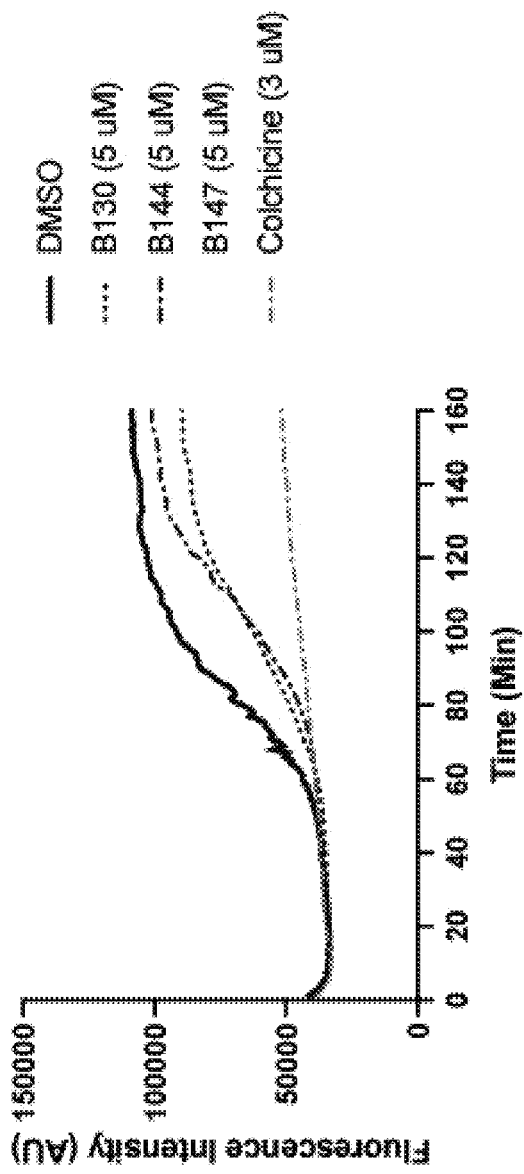

FIG. 19A shows an exemplary experiment illustrating inhibition of tubulin polymerization. The effects of compounds B130, B144, and B147 at 5 uM concentrations on tubulin polymerization are shown. Colchicine is a positive control.

Figure 19B:
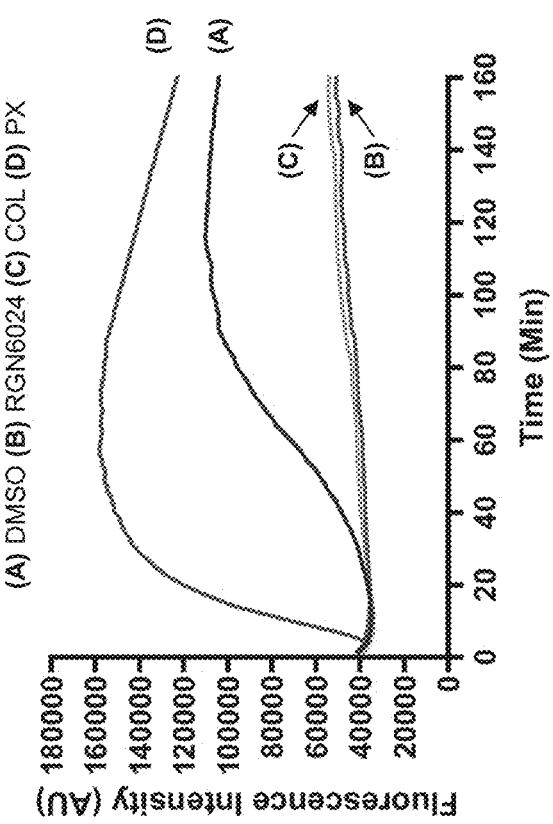

FIG. 19B shows an exemplary experiment illustrating inhibition of tubulin polymerization. The effects of RGN6024 at 5 uM concentrations on tubulin polymerization are shown. Colchicine (COL) is a positive control and PX is paclitaxel.

Figure 20A:
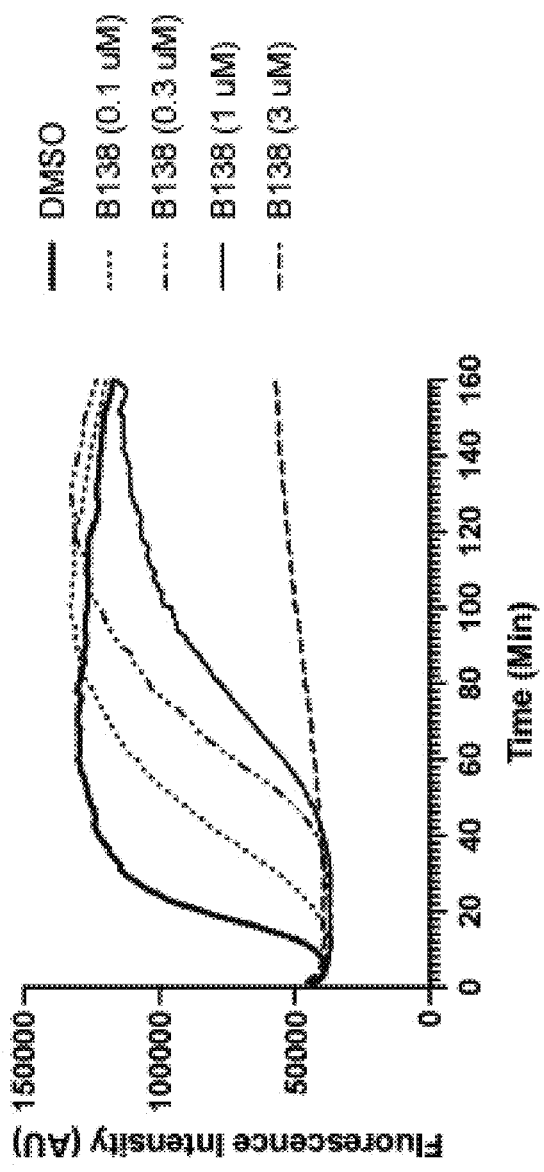

FIG. 20A shows an exemplary experiment illustrating inhibition of tubulin polymerization. The effects of compound B138 at 0.1, 0.3, 1, and 3 uM concentrations are shown.

Figure 20B:
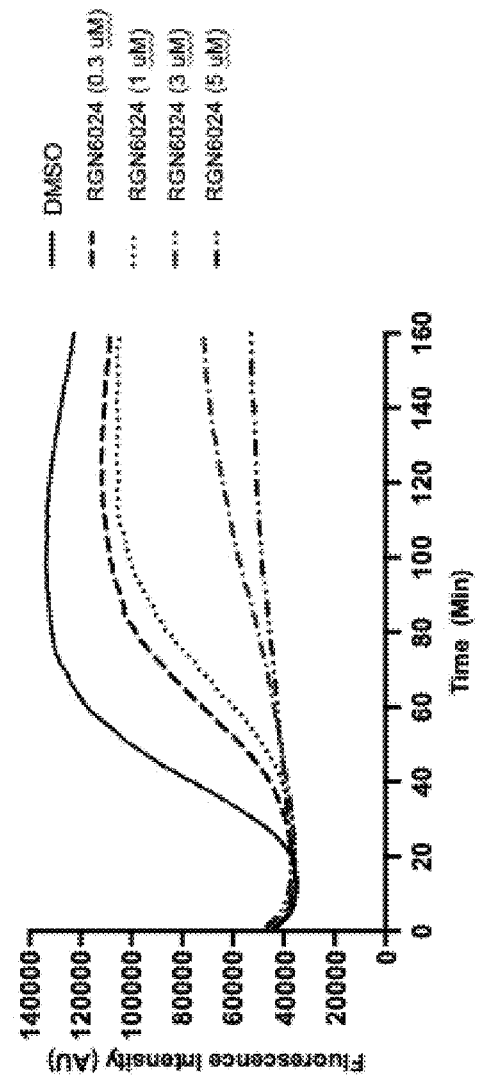

FIG. 20B shows an exemplary experiment illustrating inhibition of tubulin polymerization. The effects of RGN6024 at 0.3, 1, 3, and 5 uM concentrations are shown.

Figure 21:
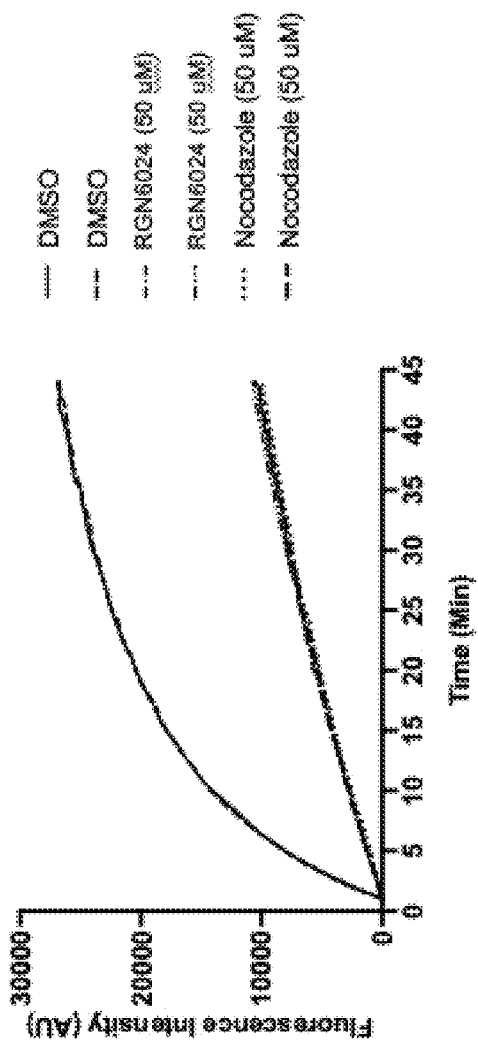

FIG. 21 shows fluorescence-based colchicine competitive binding assay with RGN6024 at 50 uM concentration in accordance with certain embodiments of the present disclosure. Nocodazole is positive control.

Figure 22:
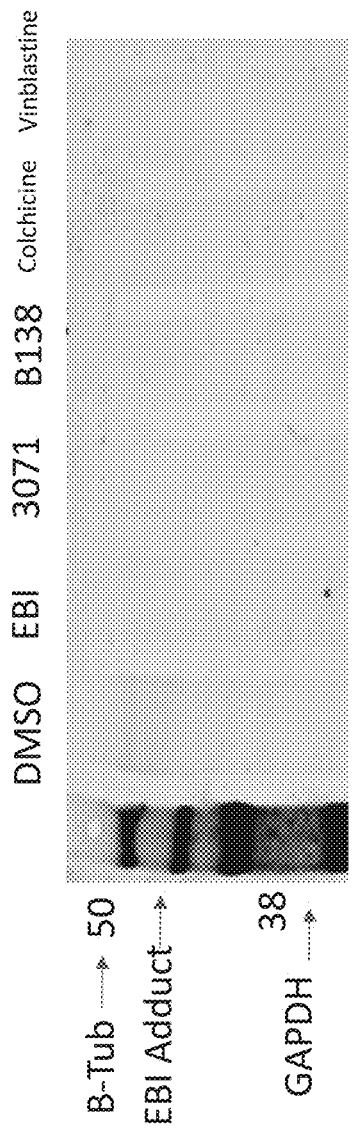

FIG. 22 shows N,N'-ethylene-bis(iodoacetamide) (EBI) competition assay with compound B138 in MCF7 cell lines showing binding of compounds in colchicine binding site in accordance with certain embodiments of the present disclosure. Colchicine is a positive control while vinblastine is a negative control. 3071 is an internal control compound.

Figure 23:
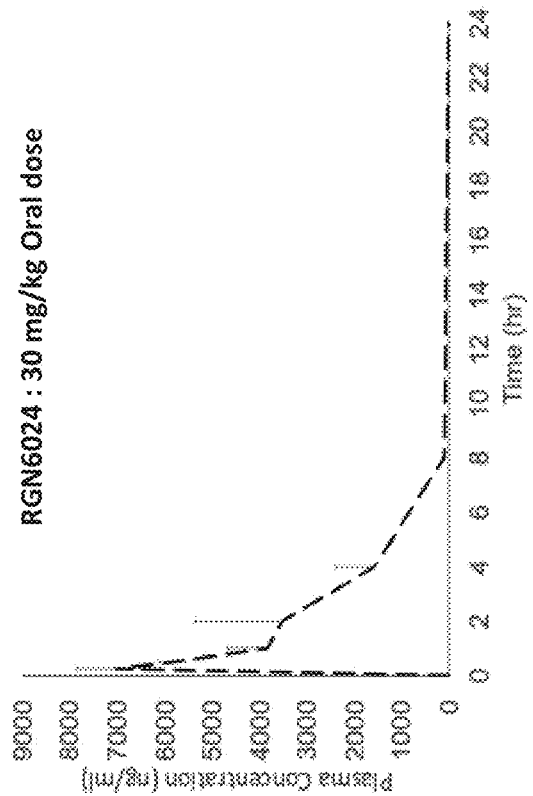

FIG. 23 shows an exemplary experiment illustrating concentrations of Compound B138 in plasma after oral administration to a rodent model at 30 mg/kg in accordance with certain embodiments of the present disclosure.

Figure 24:
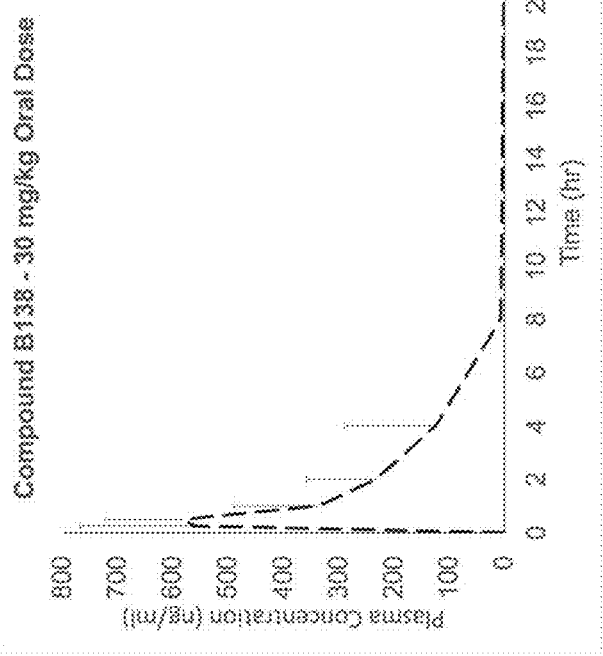

FIG. 24 shows an exemplary experiment illustrating concentrations of RGN6024 in plasma after oral administration to a rodent model at 30 mg/kg in accordance with certain embodiments of the present disclosure.

Figure 25:
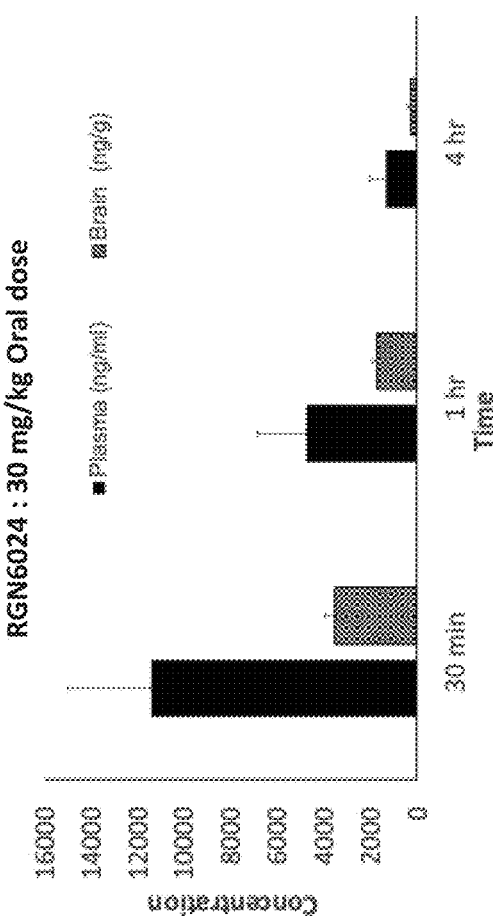

FIG. 25 shows an exemplary experiment illustrating concentrations of RGN6024 in plasma and brain tissue after oral administration to a rodent model at 30 mg/kg in accordance with certain embodiments of the present disclosure.

FIG. 26A shows the amount of RGN6024 in plasma, brain and tumor at end of the efficacy study using a subcutaneous mouse model of LN-18 cell line.

FIG. 26B shows the amount of compound B155 in plasma, brain and tumor at end of the efficacy study.

Figure 27:
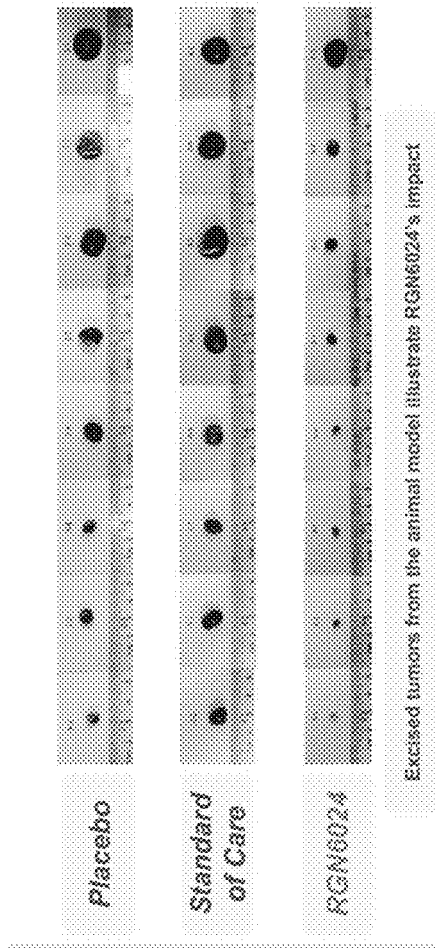

FIG. 27 shows RGN6024 in action with visible triumph against resistant tumors. FIG. 27 shows excised tumors from an animal model comparing placebo versus standard of care treatment Temozolomide (TMZ) versus RGN6024 and illustrating RGN6024's impact on tumor growth and size.

Figure 28:
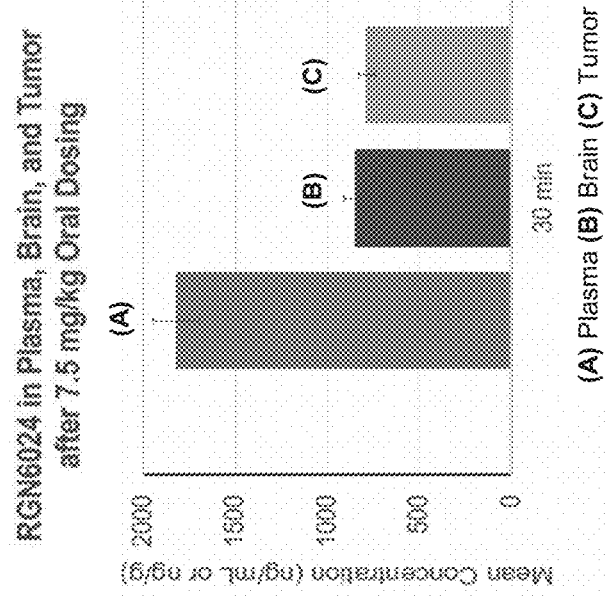

FIG. 28 shows RGN6024 reaches and permeates glioblastoma tumors in mouse brain tissue. It shows mean concentration of RGN6024 in plasma, brain and tumor after 7.5 mg/kg oral dosing. Samples harvested following the last dose of the tumor efficacy study.

Figure 29:
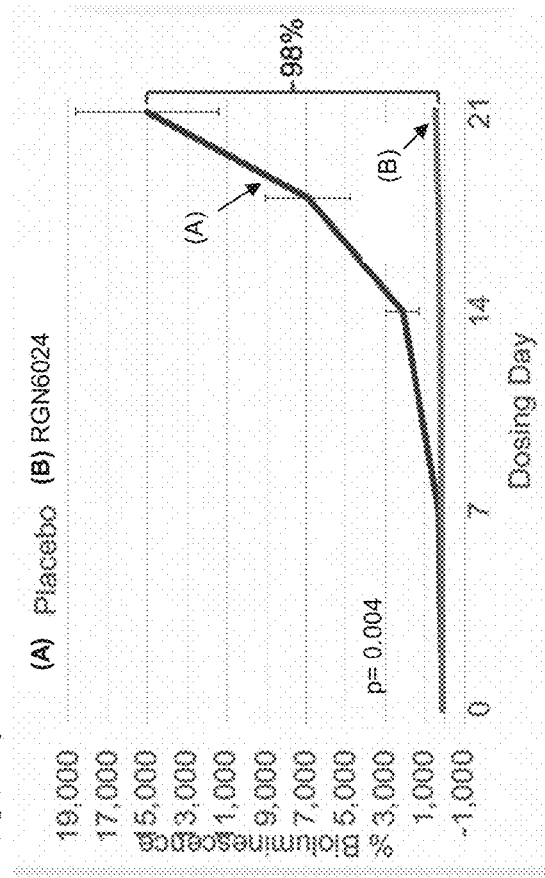

FIG. 29 shows RGN6024 reduces tumor growth by 98% in an intracranial model of Glioblastoma. BT-142 tumor (Glioblastoma) was implanted in the brain. RGN6024 versus placebo was dosed orally at 15 mg/kg twice per day. The bioluminescent signal observed was approximately proportional to the tumor size. Treated cells show only 2% of the bioluminescence signal observed in untreated cells.

Figure 30:
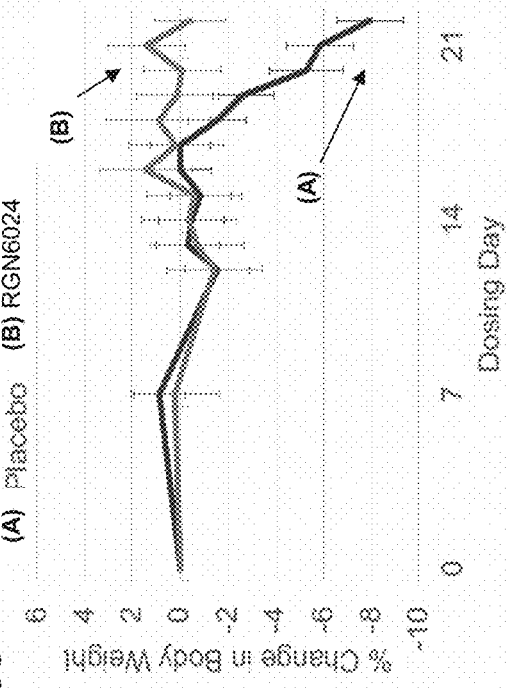

FIG. 30 shows body weight as a proxy for health in the intracranial model of Glioblastoma. Animals maintained body weight when treated with RGN6024 compared to animals receiving placebo, which in contrast experienced significant body weight loss and increased tumor signal. The placebo group shows increased weight loss relative to treated on dosing days 18-21.

Figure 31:
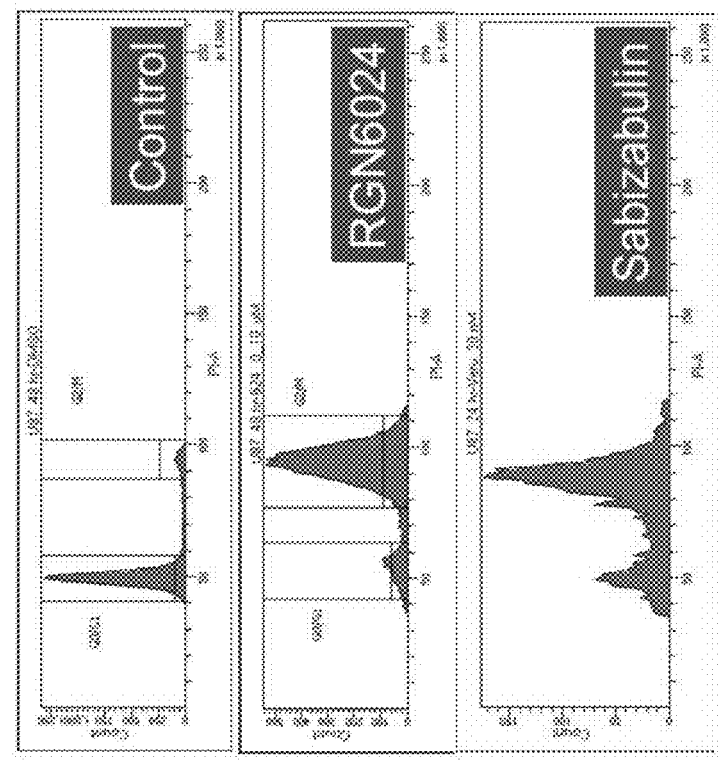

FIG. 31 shows RGN6024 induces G2/M cell cycle arrest compared to control (vehicle only) and Sabizabulin (clinical stage tubulin-targeting therapy with minimal brain penetrance). RGN6024 prevents brain cancer cells from dividing, pausing them in the G2/M phase. Literature indicates G2/M phase cells are more sensitive to radiation therapy.

Figure 32:
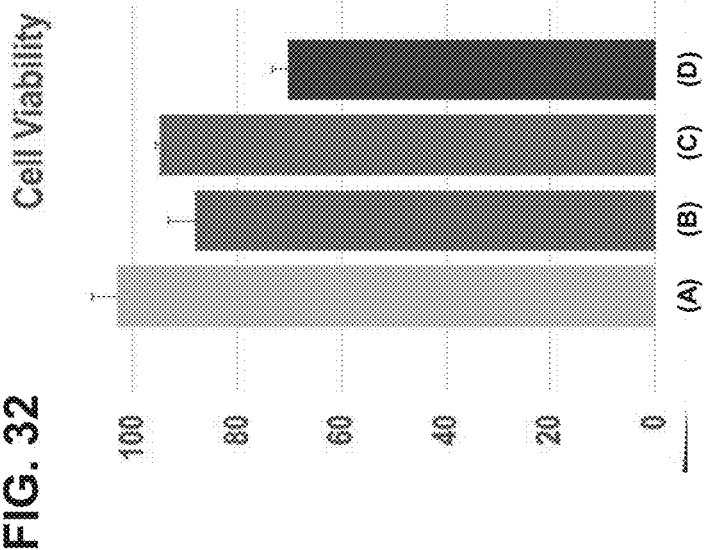

FIG. 32 shows prospects for RGN6024 combination therapy. Literature indicates radiation therapy targets cancer cells during the G2/M stage of cell division which is more sensitive to radiation therapy. Preliminary results show additive effects between radiation and RGN6024.

Figure 33:
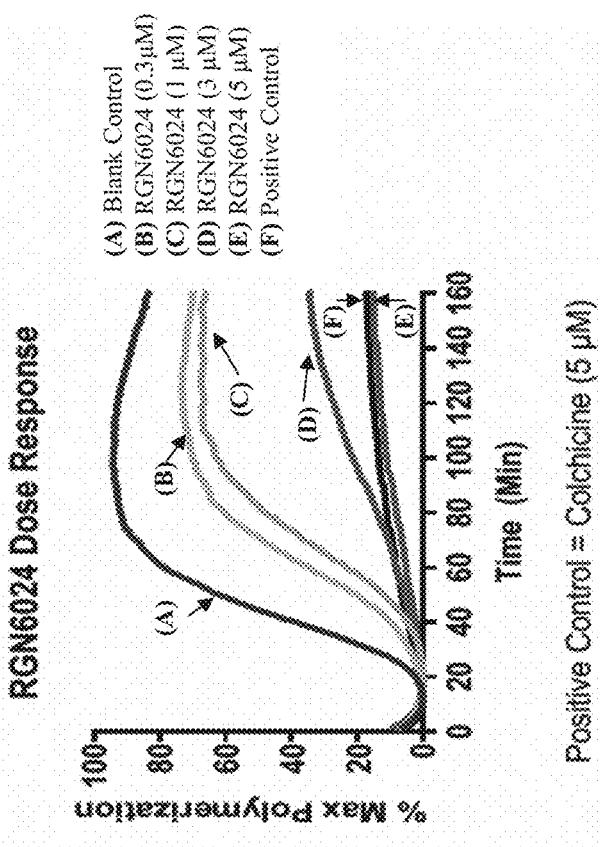

FIG. 33 shows RGN6024 demonstrates dose dependent tubulin polymerization inhibition in a biophysical assay. RGN6024's dose dependent effect on target shows (1) increasing dose results in increasing inhibition of tubulin polymerization consistent with binding to tubulin; and (2) RGN6024 (50 µM) achieves the same level of tubulin polymerization inhibition relative to Colchicine (positive control, 5 µM).

Figure 34:
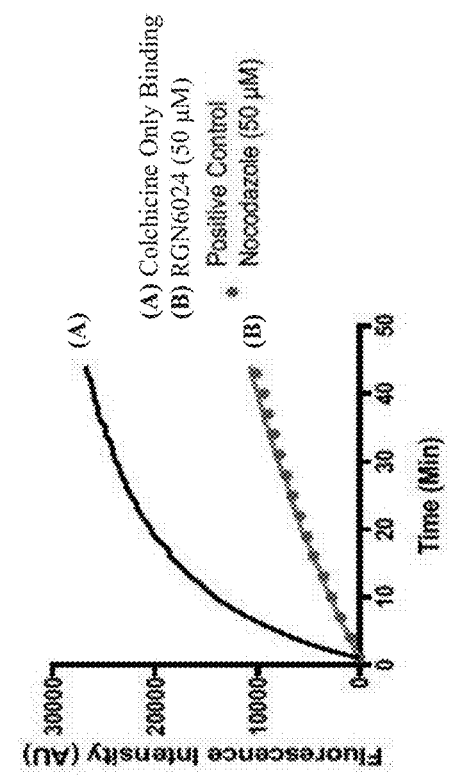

FIG. 34 shows validation that RGN6024 binds the Colchicine binding site. Colchicine binding in the Colchicine pocket produces fluorescence. RGN6024 competes with Colchicine at its binding pocket as shown by reduced fluorescence. This is consistent with RGN6024 targeting the Colchicine binding site.

FIG. 35 shows western blot target site engagement proof in living cells. RGN6024 prevents modification by binding in the Colchicine binding site. Modified b-tubulin-N,N'-ethylene-bis(iodoacetamide) (EBI) selectively crosslinks β-tubulin at the colchicine-binding site. GADPH (loading control). The EBI only lane (negative control) shows β-tubulin is modified in the absence of drug. The EBI+6024 lane shows RGN6024 reduces β-tubulin modification. The EBI+ Colchicine lane (positive control) shows β-tubulin is protected from modification.

FIG. 36 shows RGN6024 (5 uM concentration) is clean against the 44 drug targets with the most serious adverse drug reactions. No targets have inhibition >30%. RGN6024 is suitable for preclinical testing.

FIG. 37 shows RGN6024 potency in cancer cell lines (High Grade Glioma cell lines: BT142, LN-18, U-87, LN-229, U118, and T98G; and cell lines with the propensity for brain metastasis: SKMEL5, HCC1806, and NCI-H460).

FIG. 38 shows RGN6024 has oral availability in mice at a well-tolerated dose. FIG. 38 shows plasma concentration (ng/ml) in I.V. (3 mg/kg) versus PO (30 mg/kg) over time (8 hours). Half-life $(T_{1/2})(h)=2.64$. Peak concentration $(C_{MAX})$ (ng/mL)=7020. Oral bioavailability greater than 50% and proximately $C_{MAX}$~17 µM.

FIG. 39 shows a 5-day maximum tolerated dose study with 5-day observation of mice untreated versus treated with 10 mg/kg, 30 mg/kg or 100 mg/kg of RGN6024. RGN6024's oral maximum tolerated dose is between 30 mg/kg and 100 mg/kg. RGN6024 is water soluble in 30% 2-Hydroxypropyl-β-cyclodextrin in saline.

FIG. 40 shows physiochemical and ADME properties of RGN6024, including key brain penetrability properties (molecular weight, Log D, MPO score), key oral administration properties (kinetic solubility), and cellular permeability (MDR1-MDCK cells; Papp and efflux ratio). RGN6024 exhibits an MPO score>4.0 predicting good brain penetration, is water soluble in saline formulations, has significant permeability (Papp>10) leading to better diffusion, and has an efflux ratio<2.0, suggesting it is not a MDR1 pump substrate.

FIG. 41 shows in vitro ADME properties of RGN6024. RGN6024 exhibits low clearance and high half-life indicating the potential for good plasma levels in humans, moderate protein binding in humans, a higher fraction of free drug than mouse data, and no major inhibition of cytochrome P450 isoforms tested.

FIG. 42 shows maximal brain penetrance of tubulin-targeting therapies. RGN6024 has 14× more drug in the brain compared to tubulin-targeting therapies ANG1005, Sabizabulin, Eribulin, Paclitaxel, and Unesbulin.

FIG. 43 shows RGN6024 plasma and brain profiles in ICR mice with oral dosing at 30 mg/kg in healthy (untumored) mice. The mean compound concentration in plasma (ng/ml) and brain (ng/g) is compared over time (h). Brain Cmax=8.8 µM.

FIG. 44 shows RGN6024's in vitro efficacy is comparable to other colchicine-binding site therapies approved by the FDA or active in human clinical trials and far exceeds the field for brain penetration.

FIG. 45 shows the safety of FDA approved and clinical stage colchicine-binding site therapies including Colchicine and Sabizabulin. Colchicine and Sabizabulin possess similar affinity for the tubulin protein yet vary widely in their safety profiles.

FIG. 46 shows Colchicine and Sabizabulin side effect profiles. FIG. 46 shows despite the same mechanism of action and target affinity, Colchicine and Sabizabulin produce vastly different side effect profiles.

FIGS. 47A-47C show RGN6024's reversibility of binding to tubulin protein compared to Colchicine (high toxicity) and Sabizabulin (low toxicity) as evidenced from increased cellular viability after washout. FIG. 47A shows less increase in cellular viability after washout of Colchicine. FIG. 47B shows an increase in cellular viability after washout of Sabizabulin. FIG. 47C shows an increase in cellular viability after washout of RGN6024. RGN6024's reversibility of binding to tubulin suggests enhanced safety to humans and resembles the reversibility of binding to tubulin of Sabizabulin, consistent with low toxicity to humans.

Figure 48:
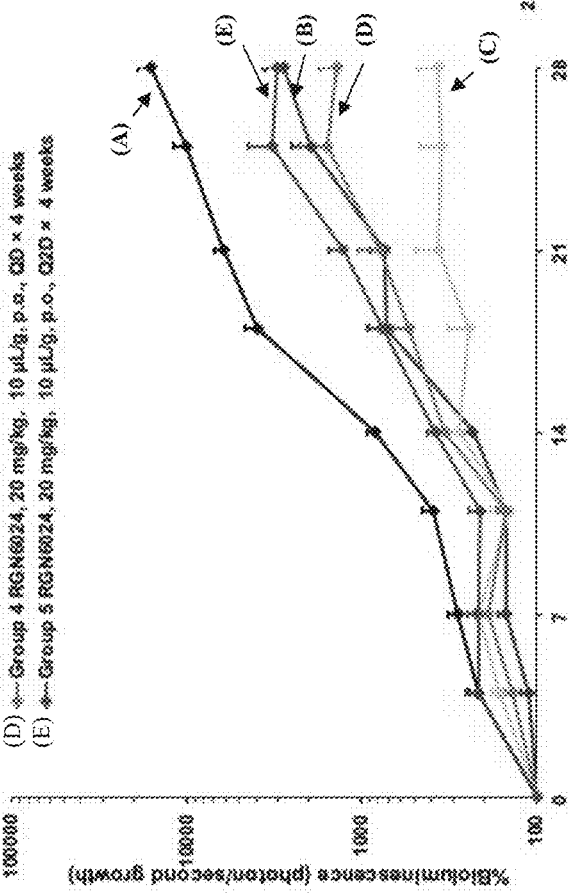

FIG. 48 shows tumor luminescence as a marker for tumor size. FIG. 48 shows RGN6024 reduces tumor size in an orthotopic mouse model using human GBM cell line BT-142 using tumor luminescence as a marker for tumor size.

Figure 49:
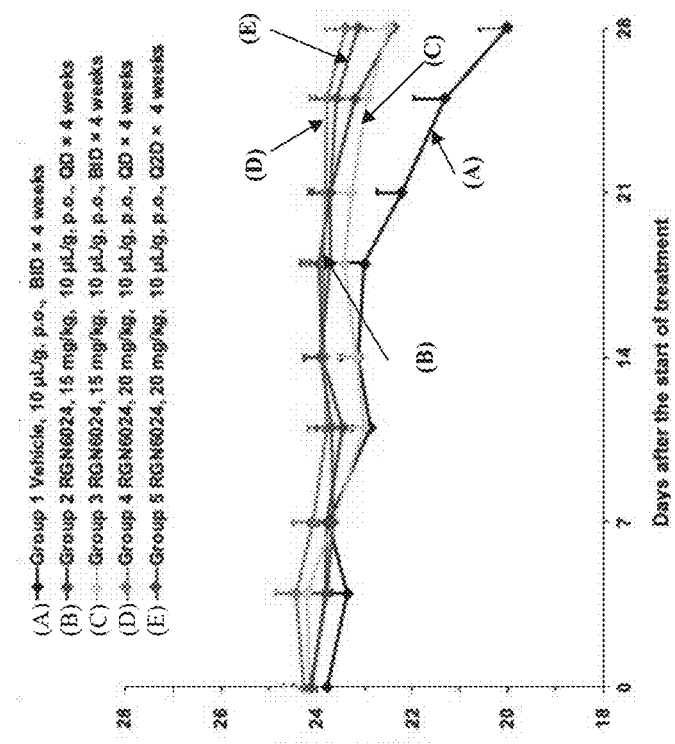

FIG. 49 shows mouse total body weight over days after the start of treatment with RGN6024. FIG. 49 shows vehicle (no drug) mice lose weight with tumor burden in the brain. Treated mice (with RGN6024) lose less weight compared to vehicle mice.

Figure 50:
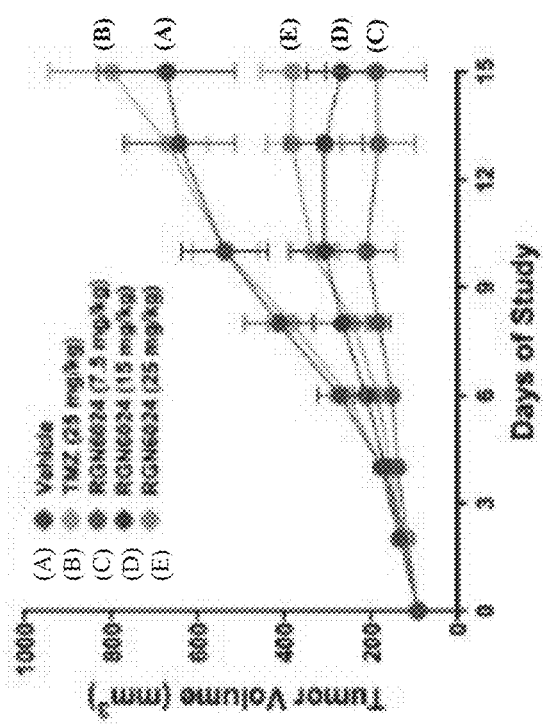

FIG. 50 shows RGN6024 inhibits tumor growth of LN-18 cells in mice. FIG. 50 shows Temozolomide (aka TMZ, standard of care drug) comparison data with RGN6024. Female CB17 SCID mice bearing LN-18 tumors (n=8 per group) were dosed QD orally for 15 days with vehicle, temozolomide (TMZ, 25 mg/kg), and RGN6024 (7.5, 15, and 25 mg/kg).

Figure 51:
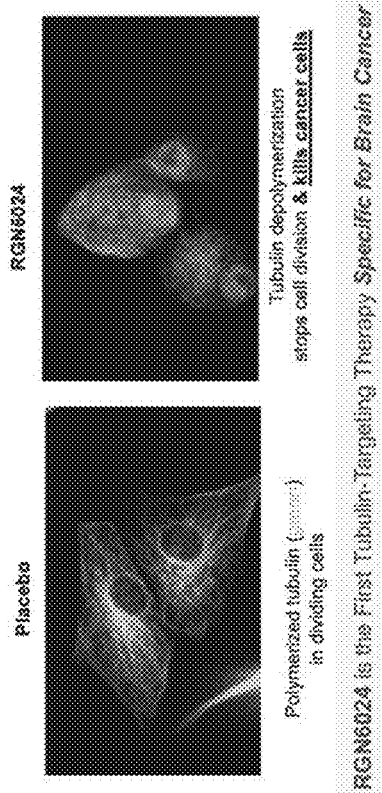

FIG. 51 shows RGN6024 can be used to treat health conditions such as cancer by targeting cell cycle elements and can induce cancer cell death. FIG. 51 shows that RGN6024 targets and binds to tubulin. U-87 cells were plated at a density of 4000 cells/well in black 96-well plates (PhenoPlate, Perkin Elmer) and grown overnight. These cells were treated with compounds for 24 h, then fixed with 4% paraformaldehyde for 20 min. The cells were washed with PBS, followed by permeabilization with FoxP3 perm buffer (BD Biosciences) for 10 min at room temperature. Cells were incubated with anti-TUBB3 (1:1000; Tuj1, STEMCELL Technologies) antibodies overnight, followed by incubation with secondary antibody for 1 h. The nuclear DNA was labeled with Hoechst. Representative images (40×) were obtained using an automated high content imaging microscope (Operetta, Perkin Elmer).

Figure 52:
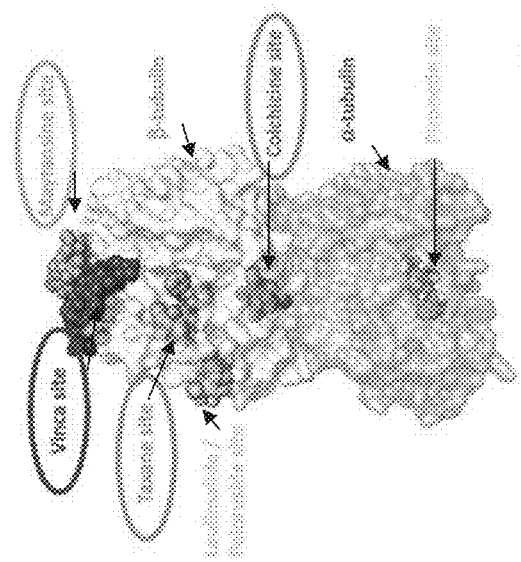

FIG. 52 shows current FDA approved therapies related to tubulin interactions bind to tubulin in large clefts on the surface of the protein, are too large for efficient brain penetration and are substrates of efflux pumps, and thus do not penetrate the brain. RGN6024 is smaller than the FDA approved therapies, can passively cross the blood brain barrier and does not act as an efflux pump substrate.

Figure 53:
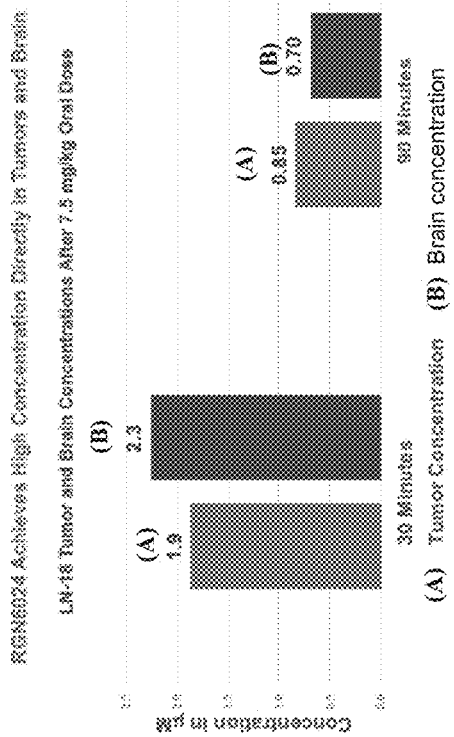

FIG. 53 shows LN-18 xenograft tumors and brains were excised from the mouse brain cancer model after dosing of RGN6024 at two time points: 30 minutes for half the mice and 90 minutes for the other half of the mice. The concentration of the target agent in the brain mirrored the concentration of the target agent in the tumor at both time points. FIG. 55 shows brain concentration of RGN6024 at 30 minutes exceeded the amount needed to shrink tumors in animals.

Figure 54:
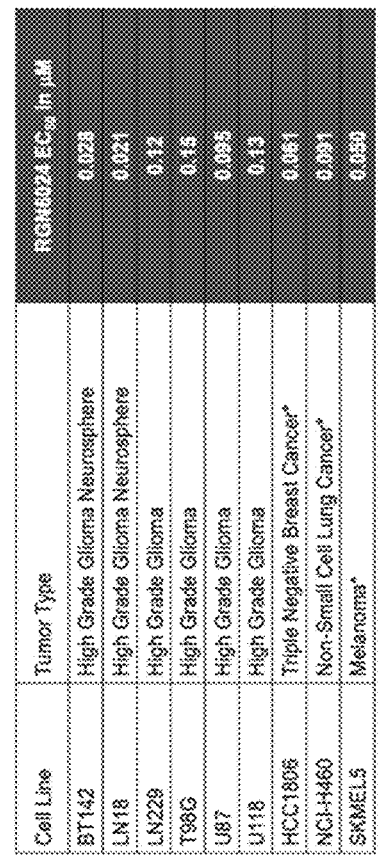

FIG. 54 shows RGN6024 was tested in a variety of high-grade glioma lines and breast, lung, and melanoma tumors with a propensity for brain metastasis. A 91 nM median potency was observed. Comparatively, RGN6024's brain penetration level is 25 times the concentration required to see an efficacious response in these cancer models in vitro.

DETAILED DESCRIPTION OF THE INVENTION

Terms

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise.

The term "comprising" means that other elements can also be present in addition to the defined elements presented. The use of "comprising" indicates inclusion rather than limitation. Stated another way, the term "comprising" means "including principally, but not necessarily solely". Furthermore, variation of the word "comprising", such as "comprise" and "comprises", have correspondingly the same meanings. In one respect, the technology described herein related to the herein described compositions, systems, methods, and respective component(s) thereof, as essential to the invention, yet open to the inclusion of unspecified elements, essential or not ("comprising").

In order to facilitate review of the various embodiments of the disclosure, the following explanations of specific terms are provided:

The term "about," as used herein, can mean relative to the recited value, e.g., amount, dose temperature, time, percentage, etc., ±10%, ±9%, ±8%, ±7%, ±6%, ±5%, ±4%, ±3%, ±2%, or ±1%.

As used herein, the terms "B137" or "Compound B137" or "C21" or "Compound C21" can be used interchangeably to refer to the compound according to the following formula: N-(5-((2-(2-oxa-7-azaspiro[4.4]nonan-7-yl)pyrimidin-5-yl)oxy) thiazol-2-yl)-3-methoxybicyclo[1.1.1]pentane-1-carboxamide, and having the structure:

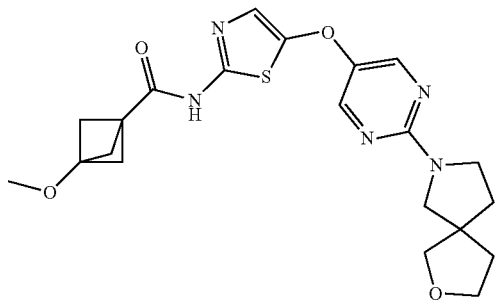 [SMILES: COC12CC(C(=O)Nc3ncc(Oc4cnc(N5CCC6(CCOC6)C5)nc4)s3)(C1)C2]

As used herein, the terms "B138" or "Compound B138" or "C18" or "Compound C18" can be used interchangeably to refer to the compound according to the following formula: N-(5-((2-(3-oxa-8-azabicyclo[3.2.1]octan-8-yl)pyrimidin-5-yl)oxy)thiazol-2-yl)-3-methoxybicyclo[1.1.1]pentane-1-carboxamide, and having the structure:

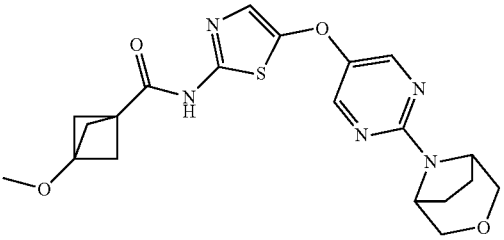 [SMILES: COC12CC(C(=O)Nc3ncc(Oc4cnc(N5C6CCC5COC6)nc4)s3)(C1)C2]

As used herein, the terms "RGN6024" or "Compound B139" or "B139" can be used interchangeably to refer to the compound according to the following formula: 3-Methoxy-N-(5-((2-morpholinopyrimidin-5-yl)oxy)thiazol-2-yl)bicyclo[1.1.1]pentane-1-carboxamide, and having the structure:

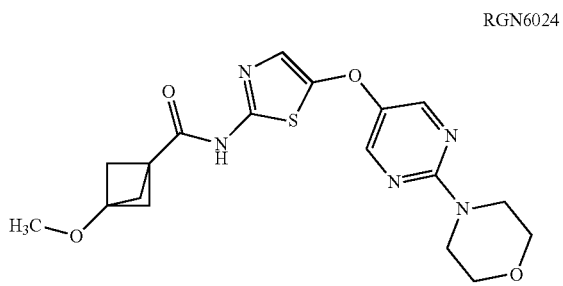 [SMILES: COC12CC(C(=O)Nc3ncc(Oc4cnc(N5CCOCC5)nc4)s3)(C1)C2]

As used herein, the terms "B141" or "Compound B141" or "C2" or "Compound C2" can be used interchangeably to refer to the compound according to the formula: 3-methoxy-3-methyl-N-(5-((2-morpholinopyrimidin-5-yl)oxy)thiazol-2-yl)cyclobutane-1-carboxamide, and having the structure:

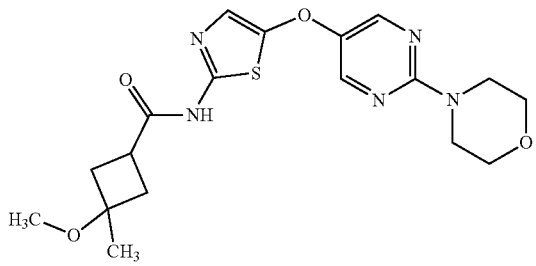

As used herein, the terms "B142" or "Compound B142" or "C7" or "Compound C7" can be used interchangeably to refer to the compound according to the formula: 3-(cyclopropylmethoxy)-N-(5-((2-morpholinopyrimidin-5-yl)oxy)thiazol-2-yl)cyclobutane-1-carboxamide, and having the structure:

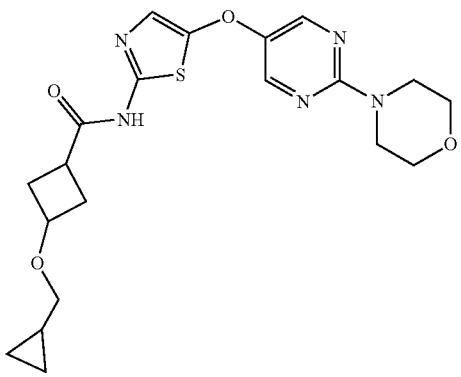 [SMILES: O=C(Nc1ncc(Oc2cnc(N3CCOCC3)nc2)s1)C1CC(OCC2CC2)C1]

As used herein, the terms "B144" or "Compound B144" or "C6" or "Compound C6" can be used interchangeably to refer to the compound according to the formula: 3-isopropoxy-N-(5-((2-morpholinopyrimidin-5-yl)oxy)thiazol-2-yl)cyclobutane-1-carboxamide, and having the structure:

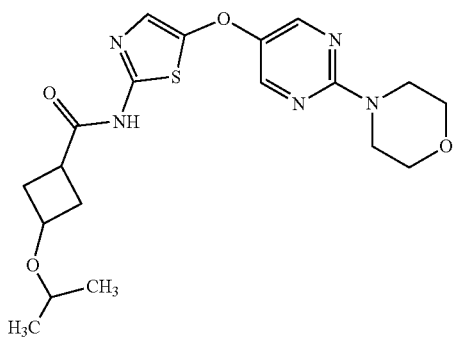 [SMILES: CC(C)OC1CC(C(=O)Nc2ncc(Oc3cnc(N4CCOCC4)nc3)s2)C1]

As used herein, the terms "B146" or "Compound 146" or "C3" or "Compound C3" can be used interchangeably to refer to the compound according to the formula: 3-methoxy-1-methyl-N-(5-((2-morpholino pyrimidin-5-yl)oxy)thiazol-2-yl)cyclobutane-1-carboxamide, and having the structure:

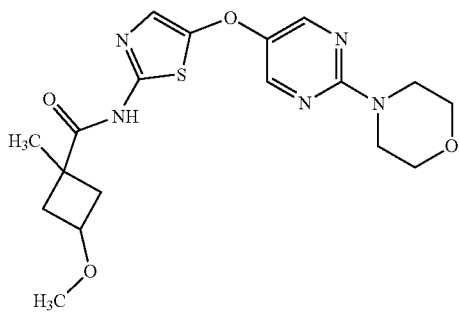 [SMILES: COC1CC(C)(C(=O)Nc2ncc(Oc3cnc(N4CCOCC4)nc3)s2)C1]

As used herein, the terms "B155" or "Compound 155" or "C27" or "Compound C27" or "C89" or "Compound C89" can be used interchangeably to refer to the compound according to the formula: 3-methoxy-N-(5-(4-morpholino phenoxy)thiazol-2-yl)bicycle [1.1.1]pentane-1-carboxamide, and having the structure:

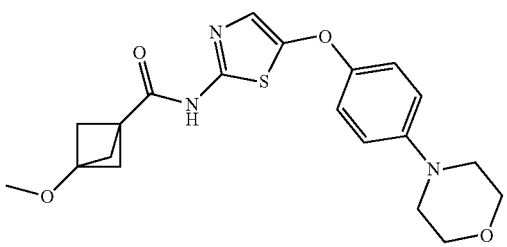 [SMILES: COC12CC(C(=O)Nc3ncc(Oc4ccc(N5CCOCC5)cc4)s3)(C1)C2]

As used herein, the terms "B156" or "Compound 156" or "C14" or "Compound C14" can be used interchangeably to refer to the compound according to the formula: 2-methoxy-N-(5-((2-morpholinopyrimidin-5-yl)oxy)thiazol-2-yl)cyclopropane-1-carboxamide, and having the structure:

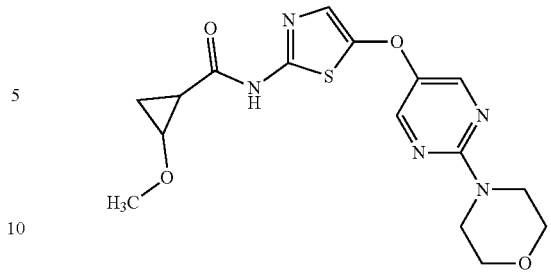

The term "analog," as used herein, refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The term "isomer," as used herein, refers to compounds having the same number and kind of atoms, and hence the same molecular weight, but differing in respect to the structural arrangement or configuration of the atoms.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present invention. Unless otherwise stated, all tautomeric forms of the compounds of the present invention are within the scope of the present invention. Unless otherwise stated, structures depicted herein are also meant to include compounds that differ only in the presence of one or more isotopically enriched atoms. For example, compounds having the present structures including replacement of hydrogen by deuterium or tritium, or the replacement of a carbon by a $^{13}C$- or $^{14}C$-enriched carbon are within the scope of the present invention. Such compounds are useful, for example, as analytical tools, as probes in biological assays, or as therapeutic agents in accordance with the present invention. In certain embodiments, a warhead moiety of a provided compound comprises one or more deuterium atoms.

The term "ester," as used herein, refers to a compound which is produced by modifying a functional group (e.g., hydroxyl, carboxyl, amino or the like group). Examples of an "ester" include "esters formed with a hydroxyl group" and "esters formed with a carboxyl group." The term "ester" can mean an ester whose ester residue is a "conventional protecting group" or a "protecting group removable in vivo by a biological method such as hydrolysis." In some embodiments, the term "conventional protecting group" can mean a protecting group removable by a chemical method such as hydrogenolysis, hydrolysis, electrolysis, or photolysis. In other embodiments, the term "protecting group removable in vivo by a biological method such as hydrolysis" can mean a protecting group removable in vivo after administration to a subject such as by hydrolysis to produce a free acid or its salt.

The term "salt," "pharmaceutically acceptable salt," as used herein, refers to those salts which are, within the scope of sound medical judgment, suitable for use in contact with the tissues of humans and lower animals without undue toxicity, irritation, and allergic response, commensurate with a reasonable benefit to risk ratio, and effective for their intended use. A "pharmacologically acceptable salt" can refer to a salt, which can be formed when a compound herein has an acidic group such as carboxyl or a basic group such as amino or imino. In some embodiments, a salt of a compound disclosed herein can be formed with an acidic group, can include, but is not limited to alkali metal salts such as a sodium salt, potassium salt or lithium salt, alkaline earth metal salts such as a calcium salt or magnesium salt, metal salts such as an aluminum salt or iron salt; amine salts, e.g., inorganic salts such as an ammonium salt and organic salts such as a t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt or tris(hydroxymethyl)aminomethane salt; and amino acid salts such as a glycine salt, lysine salt, arginine salt, ornithine salt, glutamate or aspartate. In some embodiments, a salt derivative of a compound disclosed herein formed with a basic group can include, but is not limited to, hydro-halides such as a hydrofluoride, hydrochloride, hydrobromide or hydroiodide, inorganic acid salts such as a nitrate, perchlorate, sulfate or phosphate; lower alkanesulfonates such as a methane sulfonate, trifluoromethanesulfonate or ethanesulfonate, arylsulfonates such as a benzenesulfonate or p-toluenesulfonate, organic acid salts such as an acetate, malate, fumarate, succinate, citrate, ascorbate, tartrate, oxalate or maleate; and amino acid salts such as a glycine salt, lysine salt, arginine salt, histidine salt, ornithine salt, glutamate or aspartate. In certain embodiments, when a pharmacologically acceptable salt of a compound disclosed herein remains exposed to the atmosphere or is recrystallized, it can absorb water to form a hydrate of use in formulations disclosed herein.

The term "active metabolite," "metabolite," as used herein, refers to a biomolecule that is involved in metabolism. The term "metabolite" may also refer to an intermediary or an end product of a metabolic reaction catalyzed by naturally occurring enzymes in cells. The term "metabolite" is used to describe a small molecule compound but can also be defined as endogenous compounds such as amino acids, lipids, sugars and organic acids. In addition to naturally occurring metabolites, metabolites can be artificially synthesized for industrial or pharmaceutical use.

The term "intermediary," "intermediary compound," as used herein, refers to a molecular entity (e.g. atom, ion, molecule, etc.) that is formed directly or indirectly from a reactant converted to a product in a multistep chemical reaction. A reactive intermediate may be reactive, short-lived, and high-energy and will typically react further to give a final product.

The term "tagged compound," as used herein, refers to a compound tagged or labelled with a probe to aid in the detection and/or tracking of a biomolecule. Examples of tags may include, but are not limited to biotin, fluorescent tags, radioisotopes, and hydrophobic tags.

The term "prodrug," as used herein, refers to a compound that is made more active in vivo through metabolism of a precursor drug. The compounds and compositions described herein can exist as prodrugs, as described in, for example, Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs described herein are structurally modified forms of the compound that readily undergo chemical changes under physiological conditions to provide the active compound. Additionally, prodrugs can be converted to the active compound by chemical or biochemical methods in an ex vivo environment.

The term "drug conjugate," as used herein, refers to covalently linking drugs or prodrugs to a natural or synthetic molecule carrier for a specific application. Conjugation of a drug can be used to control drug release, target drug delivery, improve drug stability (e.g., pharmacokinetics and pharmacodynamics), enhance drug solubility, and alter toxicity profiles. Drug conjugation can occur with polymers, proteins, antibodies, etc. Examples of drug conjugates include small molecule drug conjugates (SMDC's), nanoparticles, antibodies, and peptide sequences. SMDC's allow for targeted therapy and are composed of a low molecular weight, high affinity targeting ligand; a linker; and a drug payload.

The term "alkyl," as used herein, refers to a saturated aliphatic hydrocarbon group including $C_1$-$C_{20}$ straight chain and branched chain groups. Representative examples include, but are not limited to, methyl, ethyl, n-propyl, isopropyl, n-butyl, isobutyl, tert-butyl, sec-butyl, n-pentyl, 1,1-dimethyl propyl, 1,2-dimethyl propyl, 2,2-dimethyl propyl, I-ethyl propyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the isomers of branched chain thereof. An alkyl group can be a lower alkyl having 1 to 6 carbon atoms. Representative examples include, but are not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and etc. The alkyl group can be substituted or unsubstituted. When substituted, the substituent group(s) can have one or more groups independently selected from alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio, carbonyl, carboxy or carboxylic ester.

The term "alkylsulfo," as used herein, refers to esters of alkane sulfonic acids. The term "alkylamino," as used herein, refers to alkyl substitutes attached to an amino group. Representative examples include phenylalanino, threonine, tryptophano, tyrosine, valino, $N^2$-glutamino, $N^2$-histidino, $N^4$-asparagino, and the like.

The term "cycloalkyl," as used herein, refers to saturated and/or partially unsaturated monocyclic or polycyclic hydrocarbon group and have 3 to 20 carbon atoms. Representative examples of monocyclic cycloalkyl include, but are not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl etc. A polycyclic cycloalkyl can include the cycloalkyl having Spiro ring, fused ring, and bridged ring. Representative examples of polycyclic cycloalkyl include but not limited to bicyclo[1.1.1]pentyl, bicyclo[2.1.1]hexyl, bicyclo[2.2.2]octyl. Cycloalkyls herein can be substituted or unsubstituted. When substituted, the substituent group(s) can be one or more groups independently selected from of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio, carbonyl, carboxy or carboxylic ester. The term "cycloalkylthio," as used herein refers to a cycloalkyl ring attached to a sulfur group. The term "heterocyclic alkyl," as used herein, refers to a cycloalkyl group derived from a cycloalkane by removal of a hydrogen atom from a ring with atoms of at least two different elements as members of its ring(s). The term "heterocyclic alkylthio," as used herein refers to a cycloalkyl group derived from a cycloalkane by removal of a hydrogen atom from a ring with a sulfur atom as a member of its ring(s). Cycloalkyls, heterocyclic alkyls, and heterocyclic alkylthios herein can be substituted or unsubstituted. When substituted, the substituent group(s) can be one or more groups independently selected from of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio, carbonyl, carboxy or carboxylic ester.

The term "alkoxyl" as used herein, refers to an alkyl group which is singularly bonded to oxygen. Representative examples of alkoxyl groups include, but are not limited to, methoxyl, ethoxyl, and the like. The term "cycloalkoxyl" as used herein, refers to a cycloalkyl group bonded to an oxygen. Representative examples of cycloalkoxyl groups include, but are not limited to, cyclomethoxyl, cycloethoxyl, and the like.

The term "heterocyclic alkoxyl," as used herein, refers to a cycloalkoxyl group with atoms of at least two different elements as members of its ring(s). Cycloalkoxyls and heterocyclic alkoxyls herein can be substituted or unsubstituted. When substituted, the substituent group(s) can be one or more groups independently selected from of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio, carbonyl, carboxy or carboxylic ester.

The term "alkenyl," as used herein, refers to a fragment formed from an alkene, i.e. double bond, by the removal of one hydrogen atom from any carbon atom. Representative examples of alkenyl groups include, but are not limited to, allyl, isopropenyl, oleyl, phytyl, prenyl, vinyl, and the like. The term "alkynyl," as sued herein, refers to a fragment formed from an alkyne, i.e. triple bond, by the removal of one hydrogen atom from any carbon atom.

The term "aryl" as used herein, refers to an organic group derived from an aromatic ring where one hydrogen atom is removed from the ring. Representative examples of aryl groups are phenyl, naphthyl, tolyl, xylyl, and the like. The term "heteroaryl," as used herein, refers to an 5-14 membered aryl having 1 to 4 heteroatoms selected from O, S, and N as ring atoms, the remaining ring atoms being C. Examples of heteroaryl groups are furan, thiophene, pyridine, pyrrole, N-alkyl pyrrole, pyrimidine, pyrazine, imidazole, tetrazolyl, and the like. Heteroaryl herein can be fused to aryl, heterocyclic alkyl or cycloalkyl, wherein the ring connected with parent structure is heteroaryl.

Heteroaryls herein can be substituted or unsubstituted. When substituted, the substituent group(s) can be one or more groups independently selected from of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio, carbonyl, carboxy or carboxylic ester.

The term "hydroxyl," as used herein, refers to an —OH group. As used herein, "hydroxyalkyl" refers to -alkyl-OH, wherein alkyl as defined above. As used herein, "halo" or "halogen" refers to fluoro, chloro, bromo, or iodo. As used herein, "thiol" refers to an organosulfur compound according to the form R—SH, where R represents an alkyl or other organic substituent. As used herein, "carbonyl" refers to —C(=O)—. As used herein, "nitro" refers to —NO2. As used herein, "cyano" refers to —CN. As used herein, "amino" refers to —NH2. As used herein, "carboxy" refers to —C(=O)OH. As used herein, "carboxylic ester" refers to —C(=O)O-alky.

The term "heterocyclyl," as used herein, refers to a univalent group formed by removing a hydrogen atom from any ring atom of a heterocyclic compound. Representative examples of heterocyclyls include non-aromatic monocyclic, bicyclic, tricyclic, or spirocyclic ring systems comprising up to 7 atoms in each ring. Heterocyclyls herein can be substituted or unsubstituted. When substituted, the substituent group(s) can be one or more groups independently selected from of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio, carbonyl, carboxy or carboxylic ester.

The term "bicyclic," "bicyclic ring," as used herein, refers to a polycyclic molecule featuring two joined rings with at least two common atoms. Examples of bicyclic rings include fused bicyclic rings and bridged bicyclic rings. Non-limiting examples of fused bicyclic rings include, but are not limited to, bicyclo[4.3.0]nonane, bicyclo[3.3.0]octane, bicyclo[4.2.0]octane, and bicyclo[3.2.0]heptane. As used herein, the term "bridged bicyclic" or "bridged bicyclic ring" refers to a molecule featuring two rings that are joined sharing three or more atoms, with two bridgeheads separated by "bridges" containing at least one atom. Bicyclic compounds containing a bridge are typically in a rigid formation with little flexibility. Non-limiting examples of bridged bicyclic rings include, but are not limited to, bicyclo[1.1.1]pentane, bicyclo[2.1.1]hexane, bicyclo[2.2.2]octane, 5-oxaspiro[3.4]octane. Bicyclic rings herein can be substituted or unsubstituted. When substituted, the substituent group(s) can be one or more groups independently selected from of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio, carbonyl, carboxy or carboxylic ester.

The term "optionally substituted," as used herein, indicates that a group can be unsubstituted or can be substituted with one or more substituents as provided herein or known in the art. As used herein, "substituted" in reference to a group indicates that a hydrogen atom attached to a member atom within a group is replaced. It should be understood that the term "substituted" includes the provision that such substitution be in accordance with the permitted valence of the substituted atom and the substituent and that the substitution results in a stable compound (e.g. one that does not spontaneously undergo transformation such as by rearrangement, cyclization, or elimination). In certain embodiments, a single atom can be substituted with more than one substituent as long as such substitution is in accordance with the permitted valence of the atom. Suitable substituents are defined herein for each substituted or optionally substituted group.

The term "health condition," as used herein, refers to an illness, injury, impairment or physical or mental condition.

The term "therapeutically effective amount" may refer to an amount that is sufficient to achieve the desired therapeutic result or to have an effect on undesired symptoms but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days, weekly, twice weekly, etc. Guidance can be found in the literature for appropriate dosages for given classes of pharmaceutical products.

The exact amount of the compositions required will vary from subject to subject, depending on the species, age, weight, and general condition of the subject, the severity of the disorder being treated, the particular composition used, its mode of administration and the like. Thus, it is not possible to specify an exact amount for every composition. However, an appropriate amount can be determined by one of ordinary skill in the art using only routine experimentation given the teachings herein.

In some examples, the dosage can be administered to a subject once daily or in divided dosages throughout a day, depending on a subject's clinical response to the medication, as determined by methods known in the art. This dosage can be administered to a subject for one day, one a week, or a number of days, and then stopped if the subject responds immediately, or the dosage can be administered on a daily basis until a clinical response is noted. A person of skill can monitor a subject's clinical response to the administration of the composition and administer additional dosages as needed. It is contemplated that the composition can be administered to a subject on a daily basis, on an alternating daily basis, on a weekly basis, or at any interval in between.

In some examples, it may be advantageous to formulate the compositions in dosage units for case of administration and uniformity of dosage. Dosage units refer to physically discrete units suited as unitary dosages for the subject to be treated, each unit containing a predetermined quantity of the compound calculated to produce the desired therapeutic effect.

The dosage may vary within this range depending upon the dosage form employed and the route of administration utilized. A dose may be formulated in animal models to achieve a concentration range that includes the IC50 (i.e., the concentration of the test compound which achieves a half-maximal inhibition of symptoms) as determined in cell culture. Such information may be used to more accurately determine useful doses in humans.

The term "pharmaceutically acceptable," can refer to compounds, formulations, compositions, in any dosage form within the scope of sound medical judgment, suitable for use in contact with a human subject or tissues thereof and as appropriate, in animals without excessive toxicity, irritation, with reduced side effect or complication as a consumable or for administration thereof, commensurate with a reasonable benefit/risk ratio.

The term "individual," "subject," "host," "animal," and "patient," as used herein, can be used interchangeably and refer to any subject or any mammalian regarding diagnosis, treatment, prophylaxis or therapy as desired; for example, humans (e.g., adults, adolescents, toddlers, senior adults, children, infants and a fetus), companion animals (e.g., pets, horses), livestock, or other animals.

The term "treat," "treating," and "treatment," as used herein, can refer to both therapeutic treatment and prophylactic or preventative measures, with the objective of preventing, reducing, slowing down (lessen), inhibiting, or eliminating an undesired physiological change, symptom, disease, or disorder (e.g., cancer).

For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the subject or patient may be identified (e.g., diagnosed) as one suffering from the disease or condition prior to administration of the compositions of the invention. Subjects at risk for the disease or disorder can be identified by, for example, any or a combination of appropriate diagnostic or prognostic assays known in the art.

The term "administration," as used herein, refers to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), car, rectal, vaginal, by injection (e.g., intravenously, subcutaneously, intratumorally, intraperitoneally, etc.) and the like.

The term "co-administration" or "co-administering," as used herein, refers to administration of more than one active ingredient at the same time, just prior to, or just after the administration of one or more additional therapies. The compounds of the disclosure can be administered alone or can be co-administered to the subject along with another compound or a standard agent known in the art. Co-administration is meant to include simultaneous or sequential administration of the compounds individually or in combination. Dosage amounts and intervals can be adjusted individually to provide levels of the administered compound effective for the particular clinical indication being treated. This will provide a therapeutic regimen that is commensurate with the severity of the individual's disease state.

In one example, the compositions of the present invention can be administered by oral administration including, but not limited to, powders or granules, suspensions or solutions in water or non-aqueous media, pills, lozenges, capsules, sachets, or tablets. Thickeners, flavorings, diluents, emulsifiers, dispersing aids or binders may be desirable. A person of skill, monitoring a subject's clinical response, can adjust the frequency of administration and dosage of the medication according to methods known in the art.

In another example, the compositions of the present invention can be administered intranasally or administration by inhalant. As used herein, "intranasal administration" means delivery of the compositions into the nose and nasal passages through one or both of the nares and can comprise delivery by a spraying mechanism (device) or droplet mechanism (device), or through aerosolization of the composition, e.g., by using a nasal spray, atomizer, dropper, or syringe. Administration of the compositions by inhalant can be through the nose or mouth via delivery by a spraying or droplet mechanism. As used herein, "an inhaler" can be a spraying device or a droplet device for delivering the composition to the nasal passages and the upper and/or lower respiratory tracts of a subject. Delivery can also be directly to any area of the respiratory system (e.g., lungs) via intratracheal intubation. A person of skill, monitoring a subject's clinical response, can adjust the frequency of administration and dosage of the medication according to methods known in the art.

In another example, the compositions of the present invention can be administered by topical intranasal administration (intranasally) or administration by inhalant. As used herein, "topical intranasal administration" means delivery of the compositions into the nose and nasal passages through one or both of the nares and can comprise delivery by a spraying mechanism (device) or droplet mechanism (device), or through aerosolization of the composition. Administration of the compositions by inhalant can be through the nose or mouth via delivery by a spraying or droplet mechanism. As used herein, "an inhaler" can be a spraying device or a droplet device for delivering a composition, in a pharmaceutically acceptable carrier, to the nasal passages and the upper and/or lower respiratory tracts of a subject. Delivery can also be directly to any area of the respiratory system (e.g., lungs) via intratracheal intubation. The exact amount of the compositions required will vary from subject to subject, depending on the species, age, weight and general condition of the subject, the severity of the disorder being treated, the particular composition used, its mode of administration and the like. Thus, it is not possible to specify an exact amount for every composition. However, an appropriate amount can be determined by one of ordinary skill in the art using only routine experimentation given the teachings herein.

In one example, the compositions of the present invention can be administered by buccal delivery or by sublingual delivery. As used herein "buccal delivery" may refer to a method of administration in which the compound is delivered through the mucosal membranes lining the checks. In some embodiment, for a buccal delivery the composition is placed between the gum and the cheek of a patient. As used herein "sublingual delivery" may refer to a method of administration in which the composition is delivered through the mucosal membrane under the tongue. In some embodiment, for a sublingual delivery the composition is administered under the tongue of a patient.

In another example, the compositions of the present invention can be administered by Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

In another example, the compositions of the present invention can be administered to a subject intramuscularly, e.g., by using muscular injections or electroporation. A person of skill, monitoring a subject's clinical response, can adjust the frequency of administration and dosage of the medication according to methods known in the art.

In one example, the compositions of the present invention can be administered via pulmonary lavage procedures. As used herein "pulmonary lavage" or "whole lung lavage" is a procedure wherein a double lumen endotracheal tube isolates one lung, into which sufficient saline or other pharmaceutically acceptable carrier is instilled to fill the entire volume of one lung. Additionally, the pulmonary lavage can be used for delivering a composition in a pharmaceutically acceptable carrier to the lungs/lower respiratory tracts of a subject. The lung undergoing lavage may be drained and repeatedly filled with fluid, and finally suctioned as many times are necessary. The procedure is repeated on the alternate lung at another time. In some embodiments, administration of the composition via pulmonary lavage may be used in patients that are extremely sick and have been admitted to the intensive care unit (ICU).

In another example, the compositions of the present invention can be placed or stored in a container, bag, pack, or dispenser together with instructions for administration. For example, the instructions can include directions for administering the composition to the subject.

The following patents and applications are incorporated herein by reference in their entirety: U.S. Provisional Application No. 63/555,767 filed Feb. 20, 2024; U.S. Provisional Application No. 63/591,709 filed Oct. 19, 2023; U.S. Provisional Application No. 63/448,964 filed Feb. 28, 2023; and PCT/IB2022/062416 filed Dec. 16, 2022.

All publications, patent applications, patents, and other references mentioned herein are incorporated by reference in their entirety for all purposes. In case of conflict, the present specification, including explanations of terms, will control.

Briefly, the present invention features compounds and compositions for the treatment of health conditions. In some embodiments, the compositions include one or more novel compounds, tagged compounds, prodrugs, drug conjugates and metabolites and intermediary compounds thereof. The compounds and compositions herein are clinically and extraordinarily effective at crossing the blood brain barrier (BBB) and acting as a tubulin-targeting therapy specific for brain cancer, significantly depolymerizing tubulin to stop cell division and kill cancer cells and resulting in reduced tumor growth. Without wishing to limit the invention to any theory or mechanism, it is believed that the technical feature of the present invention advantageously provides for a highly efficacious and potent treatment for cancer, including brain cancer and cancers that metastasize to the brain, including but not limited to lung cancer, breast cancer and melanoma. None of the presently known prior art references have the unique inventive technical feature of the present invention.

The present invention also includes methods featuring administration of the compounds and compositions herein for treating and/or managing, and/or preemptively preventing, and/or reducing, and/or significantly decreasing cancers, including but not limited to, Glioblastoma and other brain cancers. In some embodiments, the compounds, compositions and methods relate to treating cancers, including, but not limited to cancers that metastasize to the brain. In other embodiments, the compounds, compositions and methods relate to treating cancers, including, but not limited to, one or more of brain cancer, breast cancer, skin cancer, metastatic cancer, pancreatic cancer, lung cancer, kidney cancer, liver cancer, bladder cancer, bone sarcoma, ovarian cancer, rectal cancer, blood cancer, gastrointestinal cancer, medulloblastoma, or any combination thereof.

The present invention further includes methods for modulating abnormal cell division. In other embodiments, the present invention relates to methods for isolating, detecting and screening for novel drugs.

Figure 1:
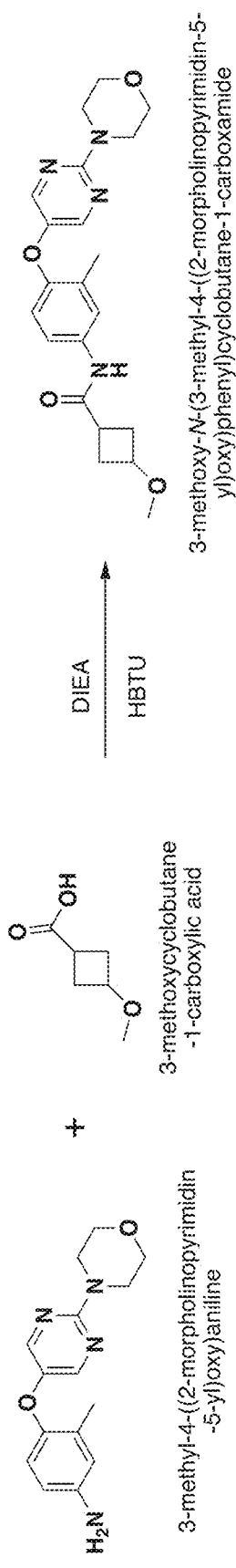
FIG. 1 shows an exemplary experiment illustrating a chemical reaction equation for synthesis of 3-methoxy-N-(3-methyl-4-((2-morpholinopyrimidin-5-yl)oxy)phenyl)cyclobutane-1-carboxamide (Compound B19) in accordance with certain embodiments of the present disclosure.

Referring now to FIGS. 1-54, the present invention features compounds, compositions and methods for making and using small molecules for the treatment of health conditions, including but not limited to cancer. In some embodiments, the compositions include one or more novel compounds, tagged compounds, prodrugs, drug conjugates and metabolites and intermediary compounds thereof. The present invention also features compounds, compositions and methods for treating and/or managing, and/or preemptively preventing, and/or reducing, and/or significantly decreasing cancers, including but not limited to, Glioblastoma and other brain cancers. In further embodiments, the compounds, compositions and methods relate to drug screening and other methods for the generation of novel compounds.

In the following sections, certain exemplary compositions and methods are described to detail certain embodiments of the invention. It will be obvious to one skilled in the art that practicing the certain embodiments does not require the employment of all or even some of the specific details outlined herein, but rather that concentrations, times, and other specific details can be modified through routine experimentation. In some cases, well known methods, or components have not been included in the description.

Embodiments disclosed herein relate to novel chemical compounds of use to treat or prevent a health condition. In certain embodiments, chemical compounds disclosed herein can target microtubules. In accordance with these embodiments, chemical compounds disclosed herein can target and destabilize microtubules. The microtubule destabilizing agents can be used in treating, preventing or reducing the risk of onset of a health condition. In certain embodiments, health condition can include cancer or other health condition.

Some embodiments disclosed herein concern agents, methods, and processes of use to prepare the disclosed compounds and compositions containing at least these compounds disclosed herein. It is understood that combinations, subsets, interactions, agents disclosed herein where specific reference of each individual and collective combinations and permutation of these compounds cannot be explicitly disclosed, each is contemplated. Additional embodiments of the disclosure are described below.

I. Compounds

In certain embodiments, the present disclosure provides compounds for use to treat, prevent, or ameliorate a health condition in a subject or of use as combination therapies in treating, reducing onset, or ameliorating a health condition in a subject in need thereof.

In certain embodiments, the present invention features compounds for use to treat, prevent or ameliorate a health condition in a subject or of use as combination therapies in treating, reducing onset, or ameliorating a health condition in a subject in need thereof.

For example, in some embodiments, the present invention features compounds having a formula as illustrated in formula (I-A), $$((A_m\text{-}B_n)_j\text{-}C\text{-}[L']_q)_k\text{-}E\text{-}L''_s\text{-}G_t \quad \text{(formula I-A)}$$

or analogs, isomers or pharmaceutically acceptable salts thereof;

wherein:

A is a H, alkyl, alkylcarbonyl, carboxyl, carboxylic ester, carboalkoxy, ester, heterocyclic alkyl, aryl, heteroaryl, halo alkyl, hydrocarbyl, alkenyl, alkynyl, phosphate, acetyl, or combination thereof;

m is 0 or 1;

B is a F, O, or S, wherein if B is F, then m=0;

n is 0, 1, or 2;

j is 0, 1, 2, or 3;

C is a 3-, 4-, 5-, or 6-membered cyclic or bicyclic moiety, optionally substituted by one or more heteroatoms or substituents, wherein C is bonded to A if n is 0;

L' is a linker comprising at least one thioester, ester, —CONH—, or —SO$_2$NH—, —NHCO—, or any combination thereof;

q is 0, 1, 2, 3 or 4;

k is 0, 1, 2, 3 or 4;

E is a 3-, 4-, 5-, or 6-membered cyclic or bicyclic moiety, optionally substituted by one or more heteroatoms or substituents, wherein E is bonded to C if q is 0;

L" is a linker, wherein L" is O, CH2, —S—, or —C—O;

s is 0 or 1;

G is:

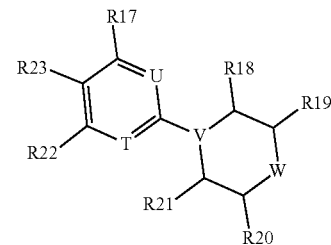

t is 0 or 1;

wherein L" is bonded to a carbon in one of the rings in G in place of any one of R17, R18, R19, R20, R21, R22, or R23;

wherein T, U, and V are each a CH or N;

wherein W is a O, S, —CH(R24) or —CH(OR25), wherein R24 and R25 are each independently selected from a group consisting of H, a substituted or unsubstituted alkyl, a substituted or unsubstituted aryl, a substituted or unsubstituted heteroaryl, a substituted or unsubstituted heterocyclic, and a substituted or unsubstituted cycloalkyl; and wherein R17, R18, R19, R20, R21, R22, R23 are each independently selected from the group consisting of H, F, Cl, I, Br, a linear or branched, substituted or unsubstituted alkyl, a substituted or unsubstituted aryl, a substituted or unsubstituted heteroaryl, and a substituted or unsubstituted heterocyclic.

In some preferred embodiments, L" is bonded to a carbon of G in place of any one of R17, R22, or R23.

In some embodiments, the present invention also features compounds having a formula as illustrated in formula (II-B):

(formula II-B)

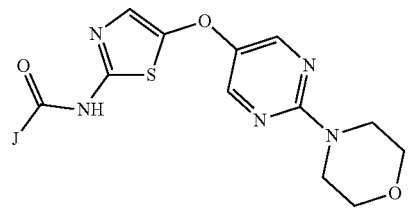

wherein J is any one of the following:

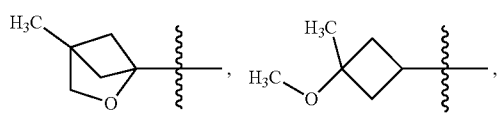

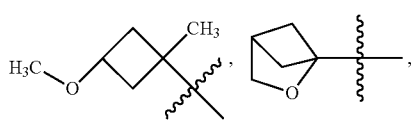

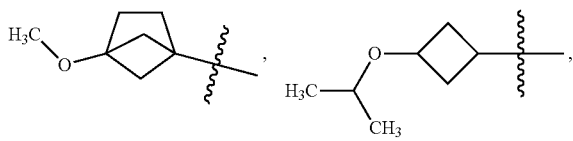

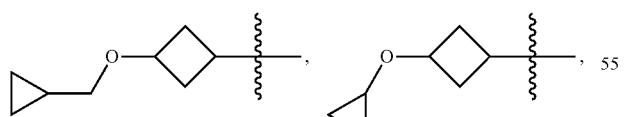

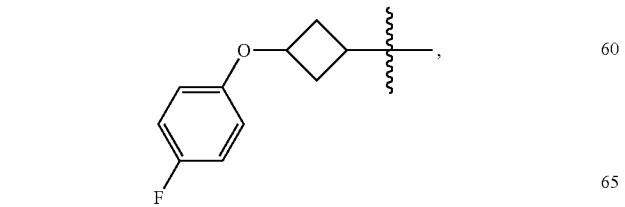

-continued

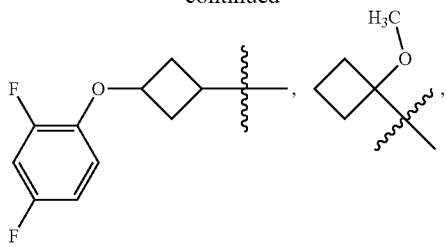

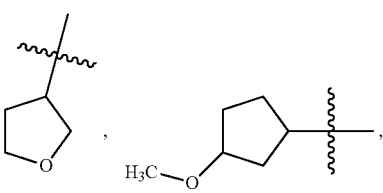

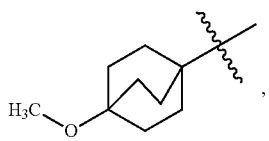

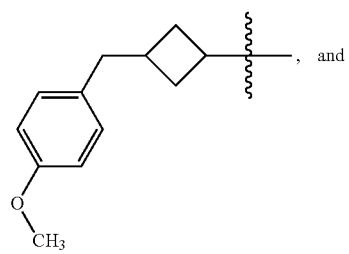

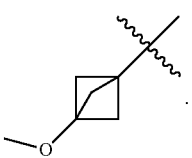

, and

In certain embodiments, compounds of the present disclosure can include any one of the compounds provided in Table 1.

TABLE 1

Compounds C1-C17, RGN6024

| Compound | Structure | "J" Group |
|---|---|---|
| C1 | 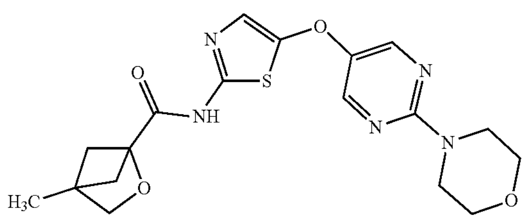 [SMILES: CC12COC(C(=O)Nc3ncc(Oc4cnc(N5CCOCC5)nc4)s3)(C1)C2] | |
| C2 (B141) | 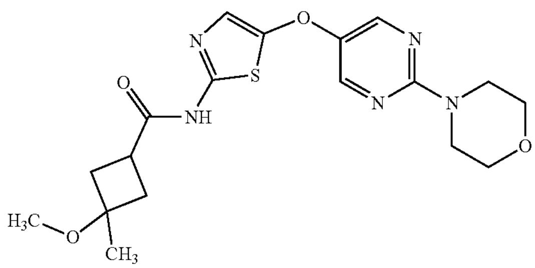 [SMILES: COC1(C)CC(C(=O)Nc2ncc(Oc3cnc(N4CCOCC4)nc3)s2)C1] | |
| C3 (B146) | 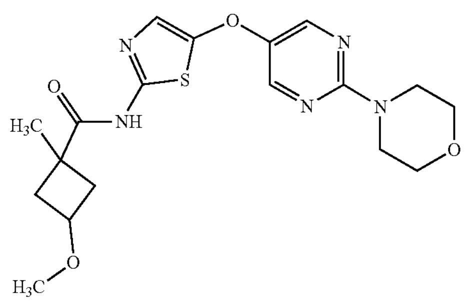 | |
| C4 | 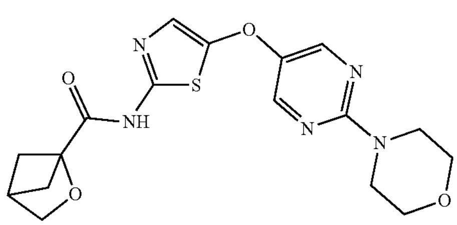 [SMILES: O=C(Nc1ncc(Oc2cnc(N3CCOCC3)nc2)s1)C12CC(CO1)C2] | |
| C5 | 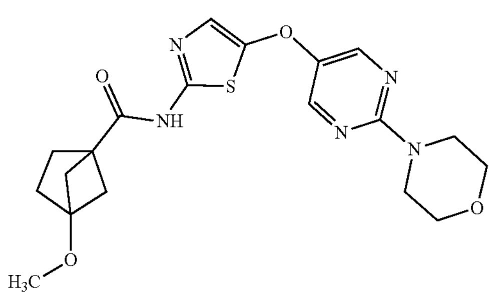 [SMILES: COC12CCC(C(=O)Nc3ncc(Oc4cnc(N5CCOCC5)nc4)s3)(C1)C2] | |

TABLE 1-continued
Compounds C1-C17, RGN6024
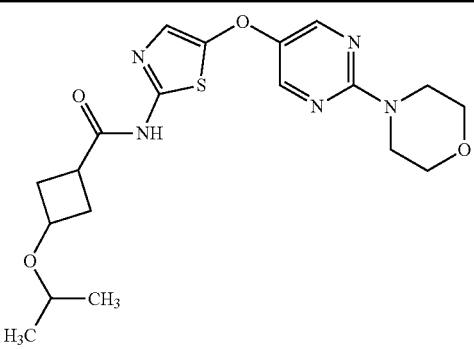
| Compound | Structure | "J" Group |
|---|---|---|
| C6 (B144) | 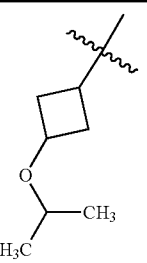 | 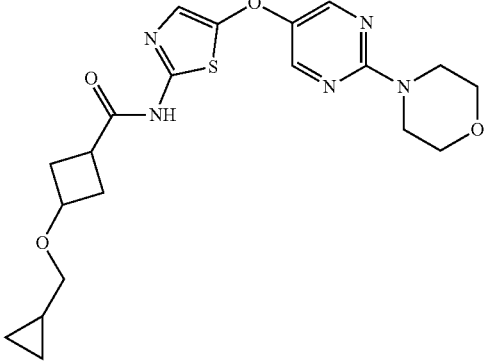 |
| C7 (B142) | 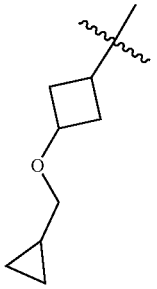 [SMILES: *C1CC(OCC2CC2)C1] | 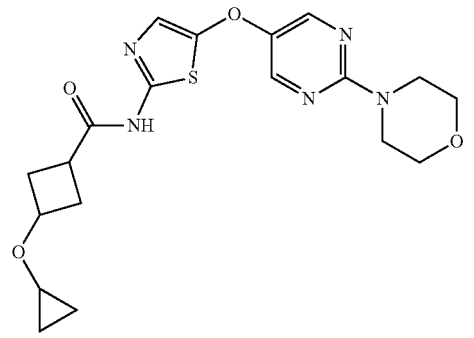 [SMILES: O=C(Nc1ncc(Oc2cnc(N3CCOCC3)nc2)s1)C1CC(OC2CC2)C1] |
| C8 | 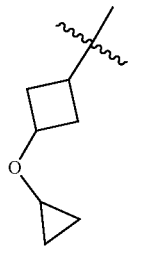 [SMILES: *C1CC(OC2CC2)C1] | |

TABLE 1-continued
Compounds C1-C17, RGN6024
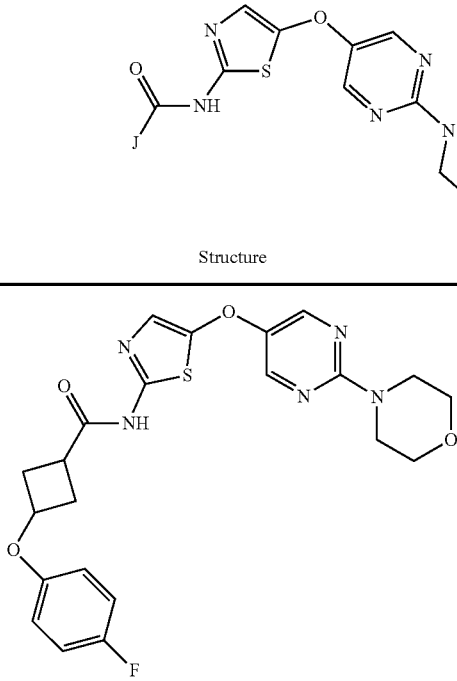
| Compound | Structure | "J" Group |
|---|---|---|
| C9 | 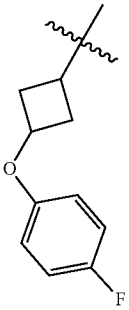 [SMILES: *C1CC(Oc2ccc(F)cc2)C1] | 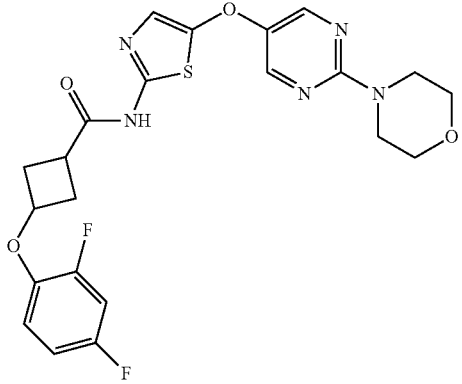 [SMILES: O=C(Nc1ncc(Oc2cnc(N3CCOCC3)nc2)s1)C1CC(Oc2ccc(F)cc2F)C1] |
| C10 | 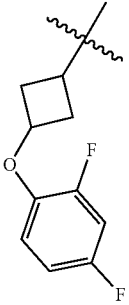 [SMILES: *C1CC(Oc2ccc(F)cc2F)C1] | 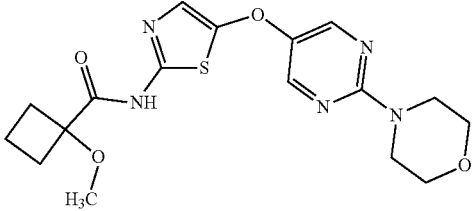 [SMILES: COC1(C(=O)Nc2ncc(Oc3cnc(N4CCOCC4)nc3)s2)CCC1] |
| C11 | 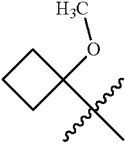 [SMILES: *C1(OC)CCC1] | 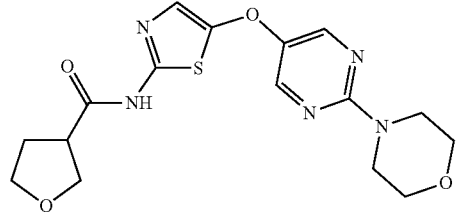 [SMILES: O=C(Nc1ncc(Oc2cnc(N3CCOCC3)nc2)s1)C1CCOC1] |
| C12 | 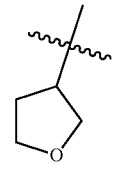 [SMILES: *C1CCOC1] | |

TABLE 1-continued

Compounds C1-C17, RGN6024

| Compound | Structure | "J" Group |
|---|---|---|
| C13 | [structure: methoxycyclopentyl-C(=O)-NH-thiazole-O-pyrimidine-morpholine] | [H₃C-O-cyclopentyl-] |
| C14 (B156) | [structure: methoxycyclopropyl-C(=O)-NH-thiazole-O-pyrimidine-morpholine] | [H₃C-O-cyclopropyl-] |
| C15 | [structure: 2-oxaspiro[3.4]octyl-C(=O)-NH-thiazole-O-pyrimidine-morpholine] | [oxaspiro[3.4]octyl-] |
| C16 | [structure: 4-methoxybicyclo[2.2.2]octyl-C(=O)-NH-thiazole-O-pyrimidine-morpholine] | [H₃C-O-bicyclo[2.2.2]octyl-] |

TABLE 1-continued
Compounds C1-C17, RGN6024
| Compound | Structure | "J" Group |
|---|---|---|
| C17 | 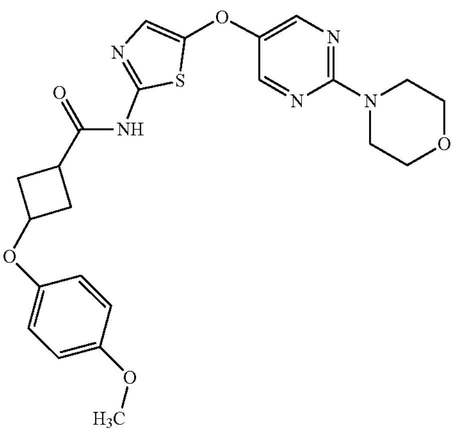 [SMILES: COc1ccc(OC2CC(C(=O)Nc3ncc(Oc4cnc(N5CCOCC5)nc4)s3)C2)cc1] | |
| RGN6024 | 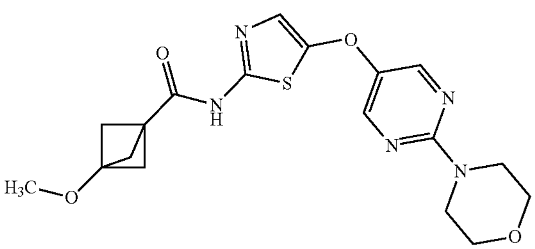 | |
The present invention features compounds according to formula (III-A):
(formula III-A)
wherein K is any one of the following:
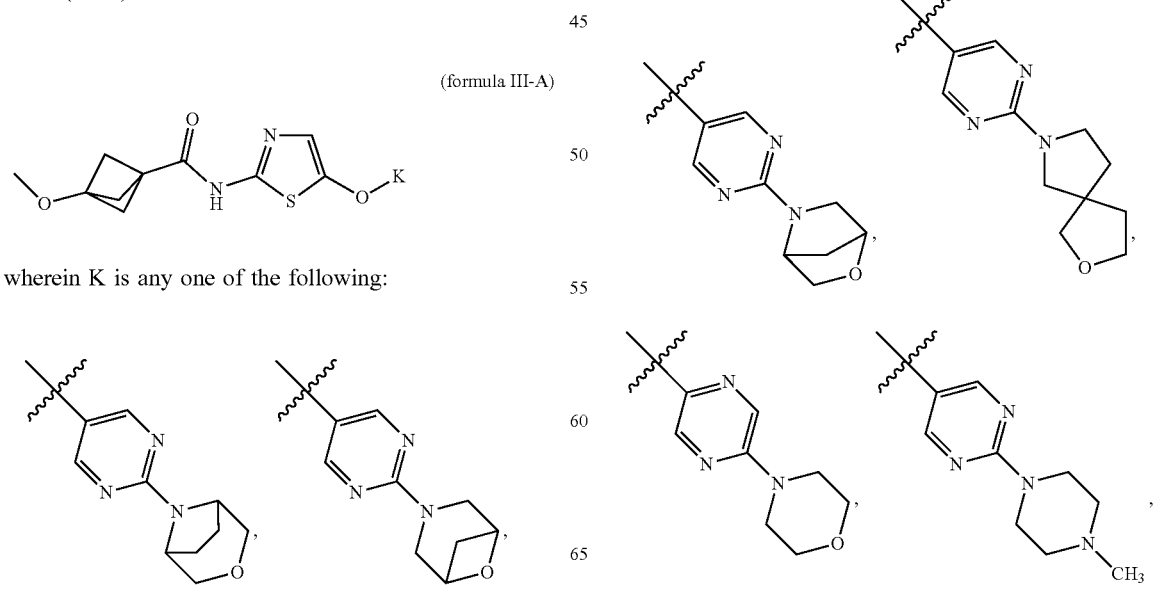

57
-continued
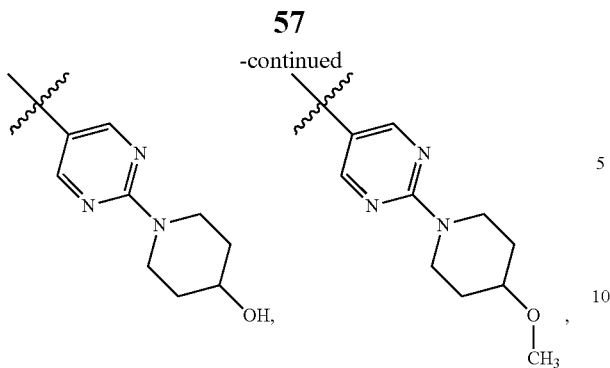
58
-continued
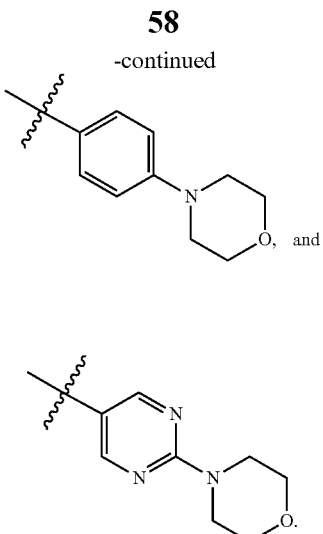
In certain embodiments, compounds of the present disclosure can include any one of the compounds provided in Table 2.
TABLE 2
Compounds C18-C27, RGN6024
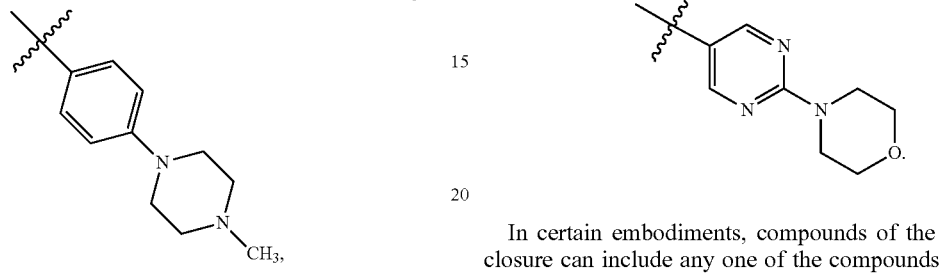
| Compound | Structure | "K" Group |
| --- | --- | --- |
| C18 (B138) | 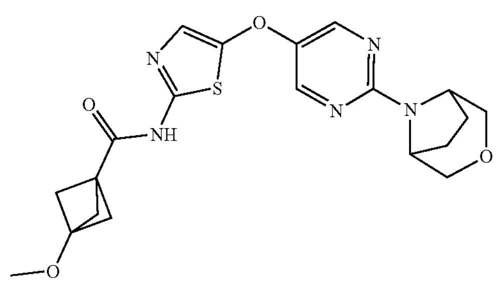 [SMILES: COC12CC(C(=O)Nc3ncc(Oc4cnc(N5C6CCC5COC6)nc4)s3)(C1)C2] | |
| C19 | 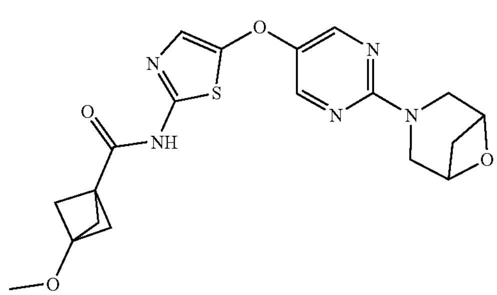 [SMILES: COC12CC(C(=O)Nc3ncc(Oc4cnc(N5CC6CC(C5)O6)nc4)s3)(C1)C2] | |

TABLE 2-continued
Compounds C18-C27, RGN6024
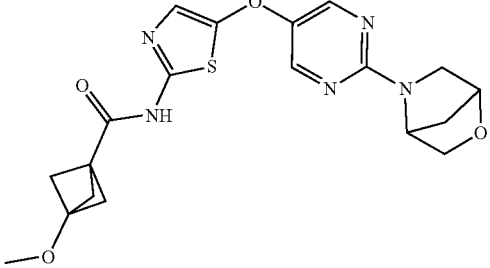
| Compound | Structure | "K" Group |
|---|---|---|
| C20 | 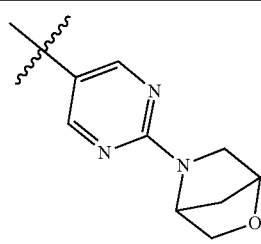 | 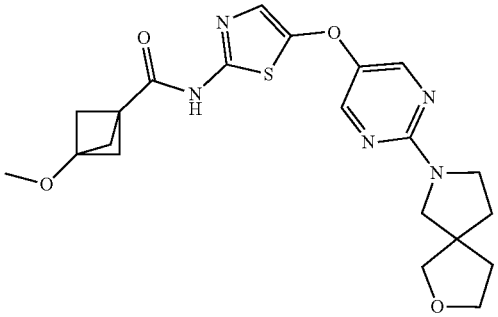 [SMILES: COC12CC(C(=O)Nc3ncc(Oc4cnc(N5CCC6(CCOC6)C5)nc4)s3)(C1)C2] |
| C21 (B137) | 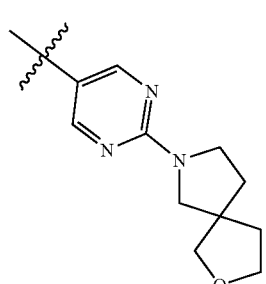 | 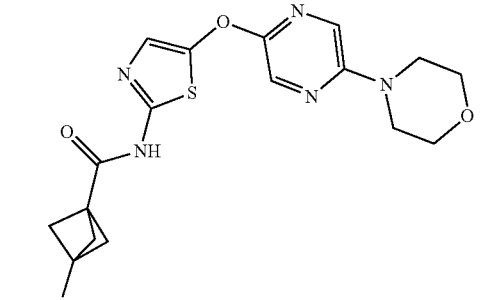 |
| C22 | 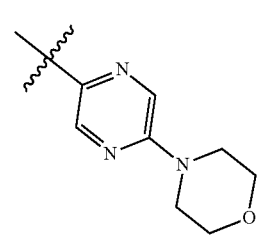 [SMILES: *c1cnc(N2CCOCC2)cn1] | 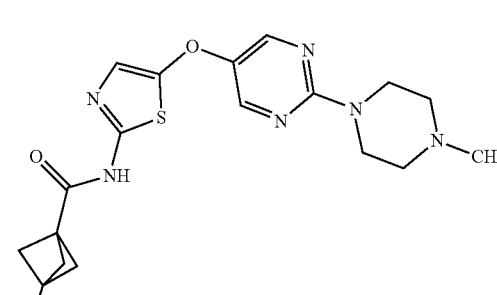 |
| C23 | 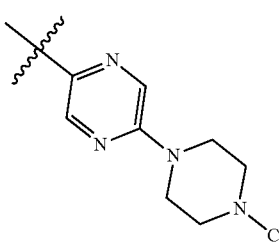 | |

TABLE 2-continued

Compounds C18-C27, RGN6024

| Compound | Structure | "K" Group |
|---|---|---|
| C24 | 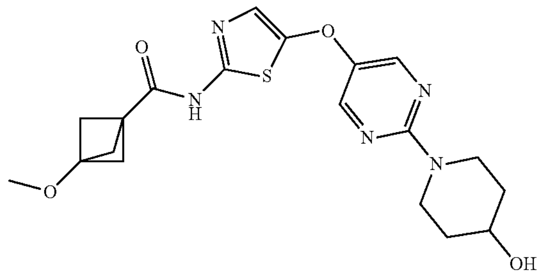 [SMILES: COC12CC(C(=O)Nc3ncc(Oc4cnc(N5CCC(O)CC5)nc4)s3)(C1)C2] | |
| C25 | 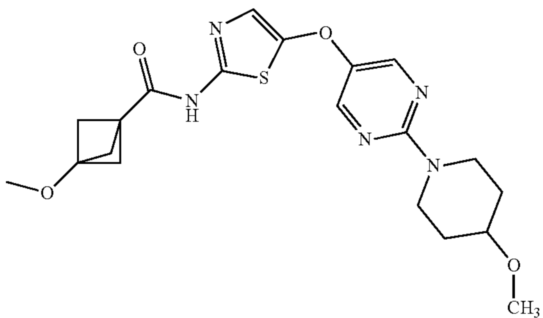 | |
| C26 | 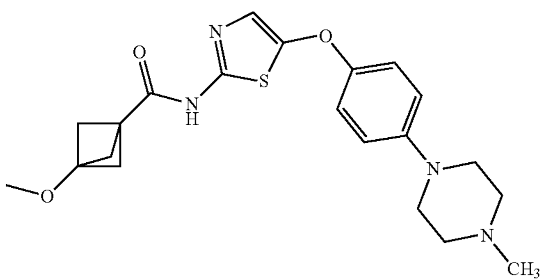 | |
| C27 (C89 and B155) | 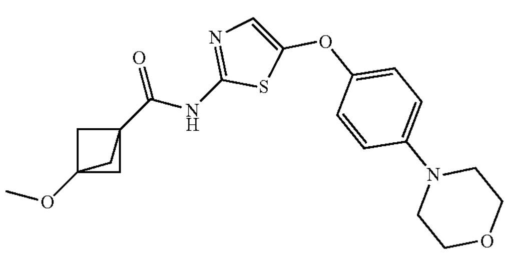 [SMILES: COC12CC(C(=O)Nc3ncc(Oc4ccc(N5CCOCC5)cc4)s3)(C1)C2] | |
| RGN6024 | 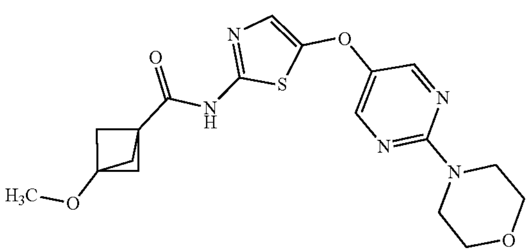 | |

The present invention features compounds according to formula (IV-A):
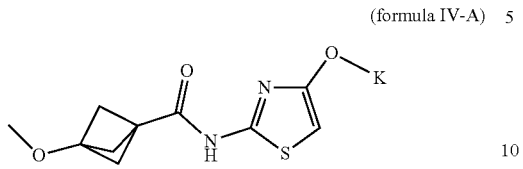
(formula IV-A)
wherein K is any one of the following:
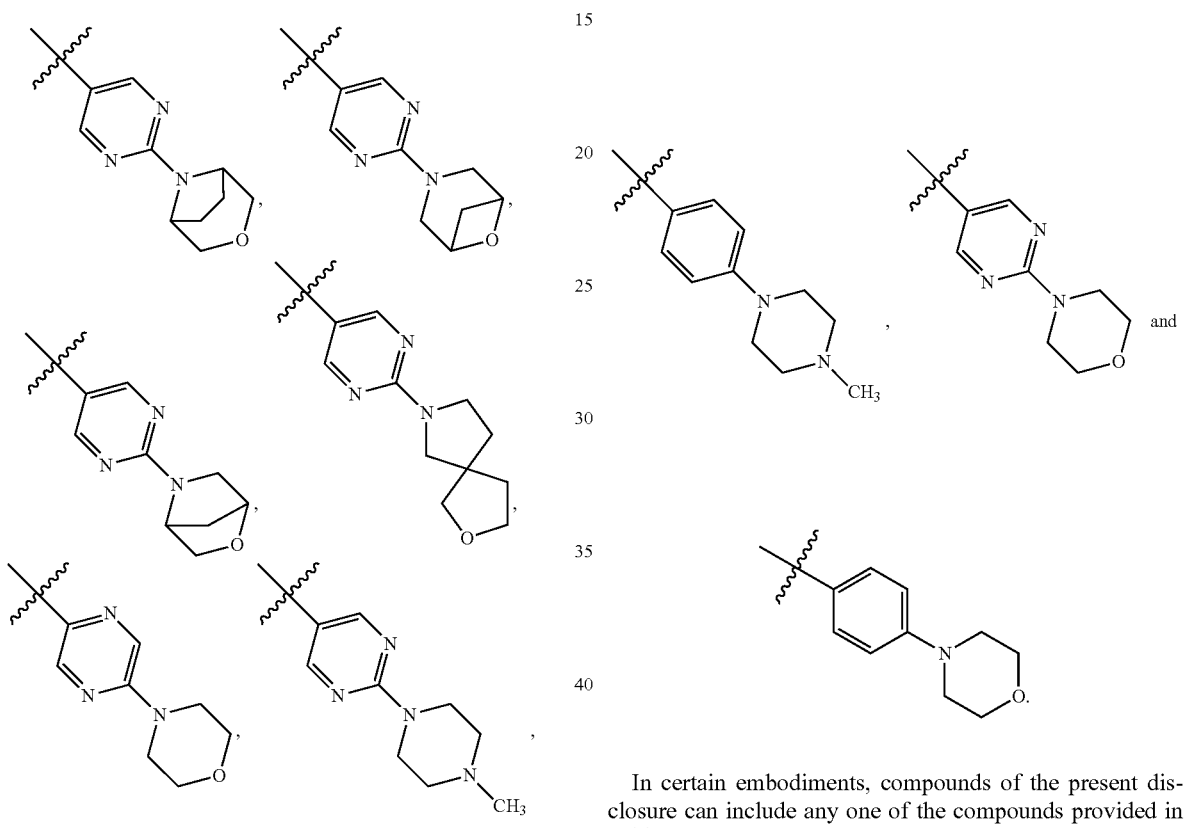
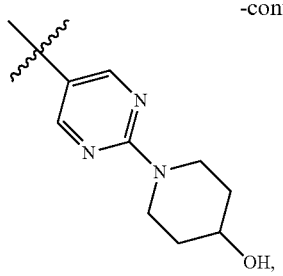
In certain embodiments, compounds of the present disclosure can include any one of the compounds provided in Table 3.
TABLE 3
Compounds C28-38
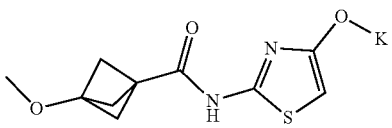
| Compound | Structure | "K" Group |
|---|---|---|
| C28 | 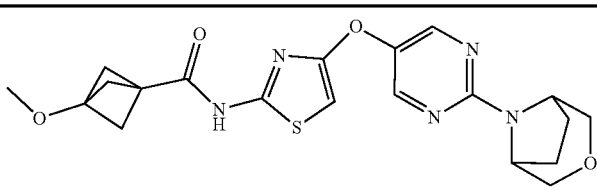 | 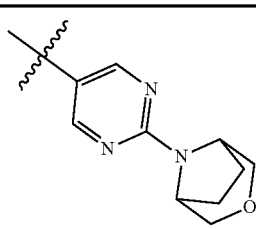 |

TABLE 3-continued

Compounds C28-38

| Compound | Structure | "K" Group |
|---|---|---|
| C29 | 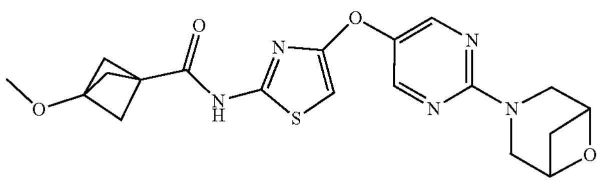 [SMILES: COC12CC(C(=O)Nc3nc(Oc4cnc(N5CC6CC(C5)O6)nc4)cs3)(C1)C2] | |
| C30 | 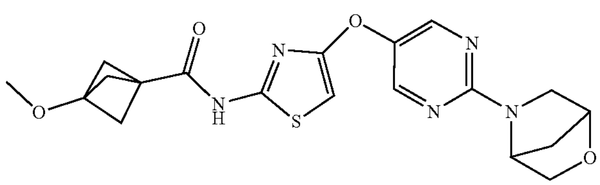 [SMILES: COC12CC(C(=O)Nc3nc(Oc4cnc(N5CC6CC5CO6)nc4)cs3)(C1)C2] | |
| C31 | 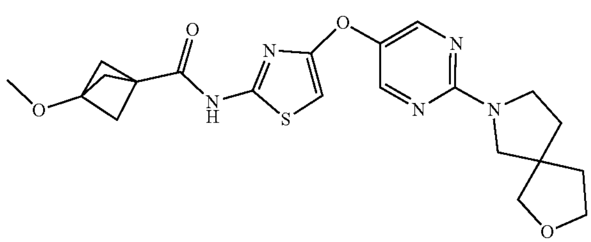 [SMILES: COC12CC(C(=O)Nc3nc(Oc4cnc(N5CCC6(CCOC6)C5)nc4)cs3)(C1)C2] | |
| C32 | 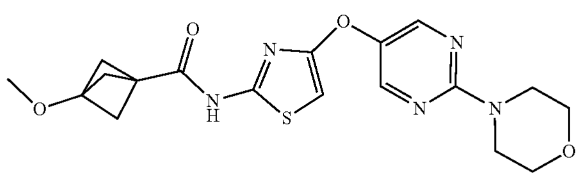 [SMILES: COC12CC(C(=O)Nc3nc(Oc4cnc(N5CCOCC5)nc4)cs3)(C1)C2] | |
| C33 | 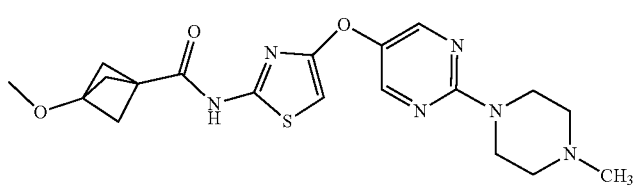 | |

TABLE 3-continued

Compounds C28-38

| Compound | Structure | "K" Group |
|---|---|---|
| C34 | 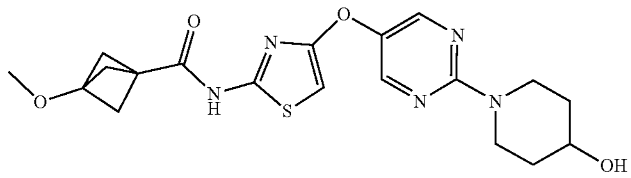 [SMILES: COC12CC(C(=O)Nc3nc(Oc4cnc(N5CCC(O)CC5)nc4)cs3)(C1)C2] | |
| C35 | 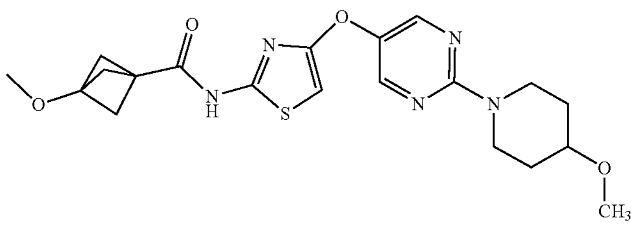 | |
| C36 | 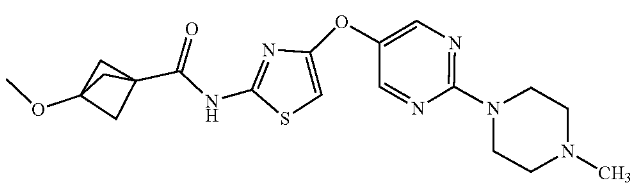 | |
| C37 | 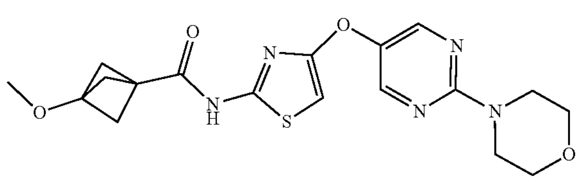 [SMILES: COC12CC(C(=O)Nc3nc(Oc4cnc(N5CCOCC5)nc4)cs3)(C1)C2] | |
| C38 | 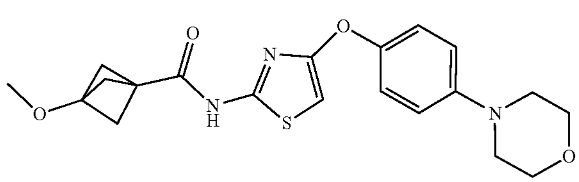 [SMILES: COC12CC(C(=O)Nc3nc(Oc4ccc(N5CCOCC5)cc4)cs3)(C1)C2] | |

The present invention also features compounds according to formula (V-A)
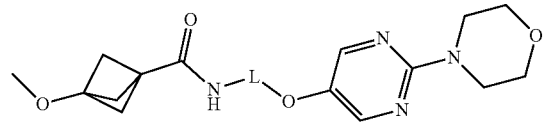
(formula V-A)
wherein L is any one of the following:
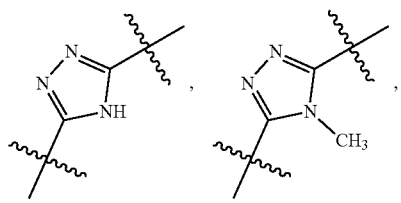
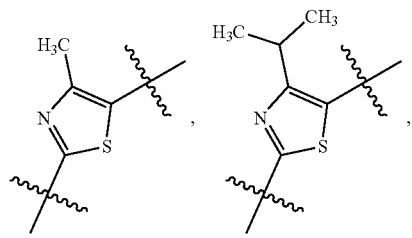
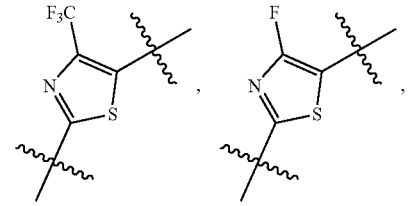
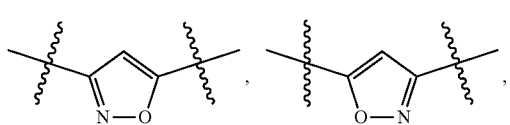
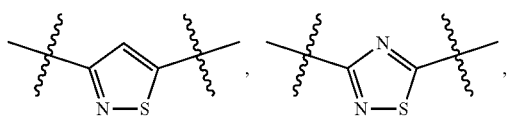
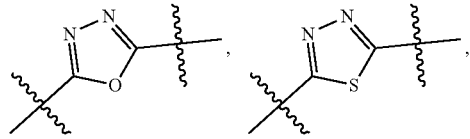
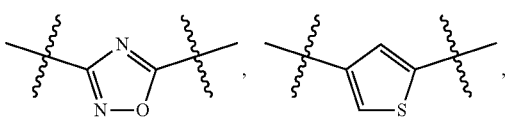
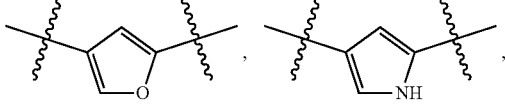
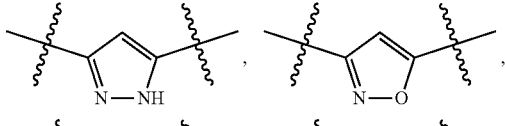
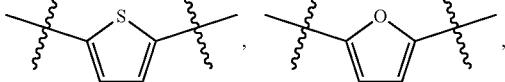
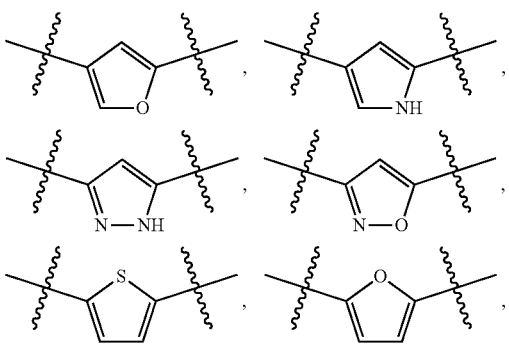
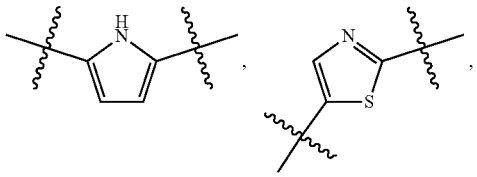
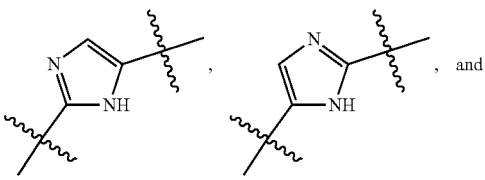, and
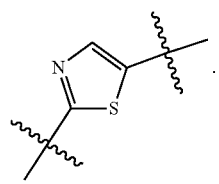.
In certain embodiments, compounds of the present disclosure can include any one of the compounds provided in Table 4.

TABLE 4
Compounds C39-C63, RGN6024
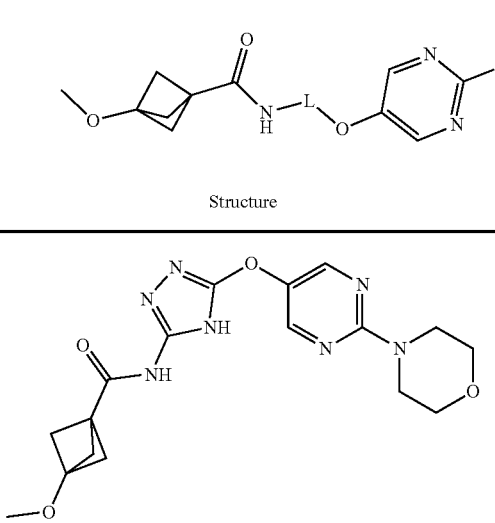
| Compound | Structure | "L" Group |
|---|---|---|
| C39 | 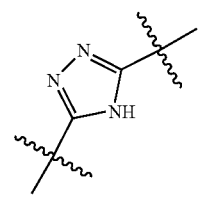 [SMILES: *c1nnc(*)[nH]1] | 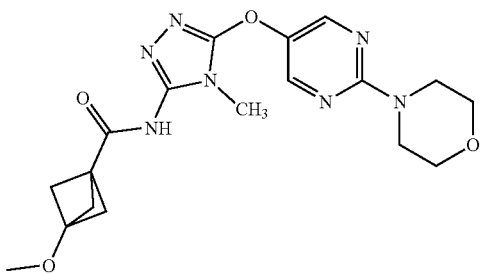 [SMILES: COC12CC(C(=O)Nc3nnc(Oc4cnc(N5CCOCC5)nc4)n3C)(C1)C2] |
| C40 | 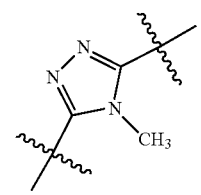 [SMILES: *c1nnc(*)n1C] | 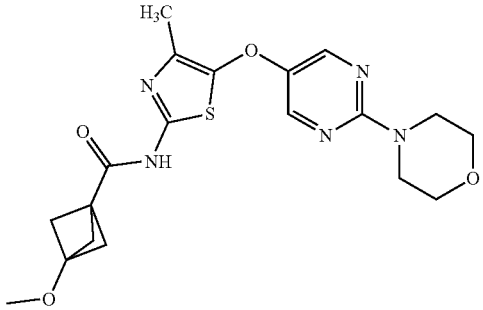 [SMILES: COC12CC(C(=O)Nc3nc(C)c(Oc4cnc(N5CCOCC5)nc4)s3)(C1)C2] |
| C41 | 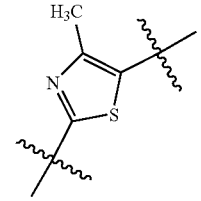 [SMILES: *c1nc(C)c(*)s1] | 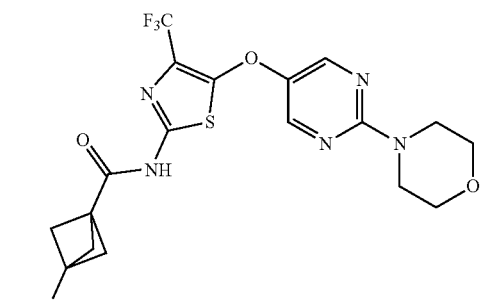 |
| C42 | 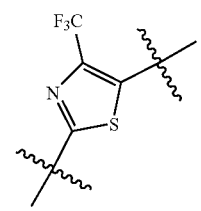 [SMILES: *c1nc(C(F)(F)F)c(*)s1] | |

TABLE 4-continued
Compounds C39-C63, RGN6024
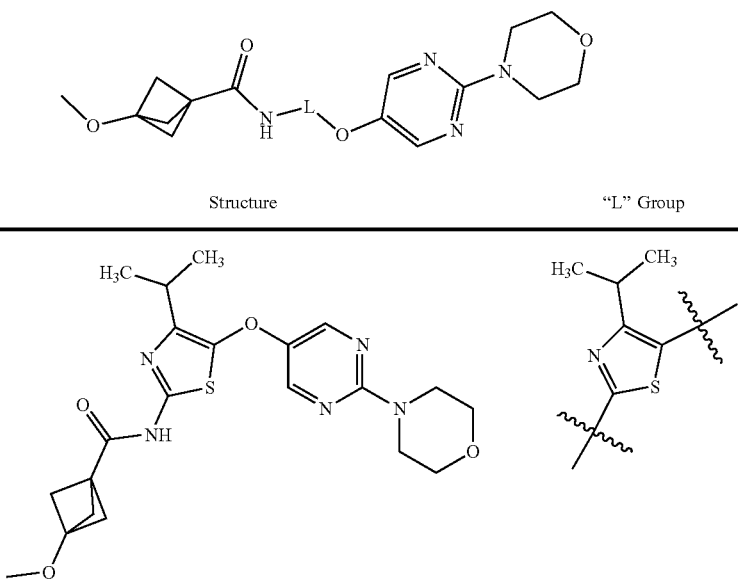
| Compound | Structure | "L" Group |
|---|---|---|
| C43 | 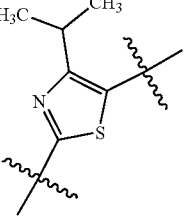 | 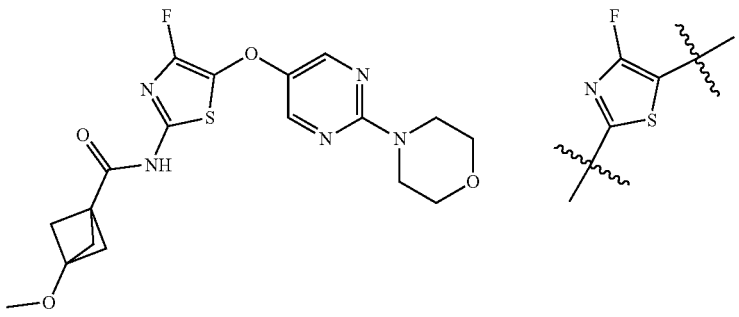 |
| C44 | 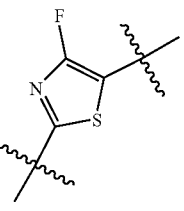 [SMILES: *c1nc(F)c(*)s1] | 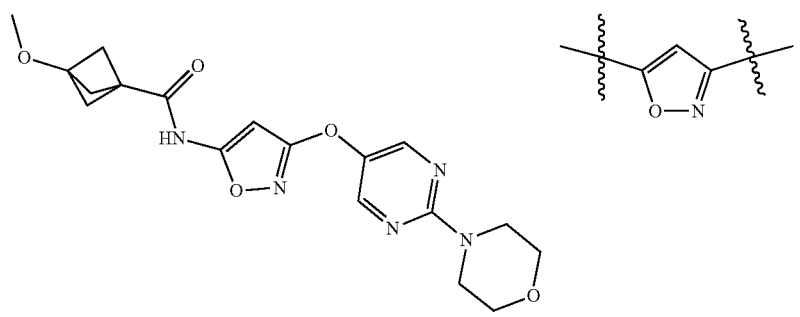 |
| C45 | 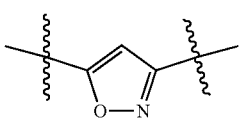 [SMILES: *c1cc(*)on1] | 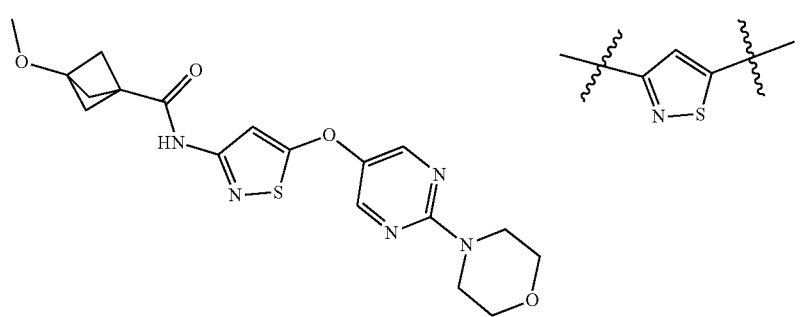 |
| C46 | 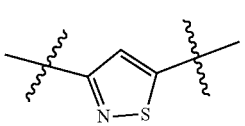 [SMILES: *c1cc(*)sn1] | |

TABLE 4-continued

Compounds C39-C63, RGN6024

| Compound | Structure | "L" Group |
|---|---|---|
| C47 | | 1,2,4-thiadiazole linker |
| C48 | | 1,3,4-oxadiazole linker |
| C49 | | 1,3,4-thiadiazole linker |
| C50 | | 1,2,4-oxadiazole linker |

TABLE 4-continued

Compounds C39-C63, RGN6024

| Compound | Structure | "L" Group |
|---|---|---|
| C51 | 4-amino-thiophen-2-yl linked structure with methoxy-bicyclopentyl carboxamide and 2-morpholinopyrimidin-5-yloxy | thiophene-2,4-diyl |
| C52 | corresponding furan analog | furan-2,4-diyl |
| C53 | corresponding pyrrole analog | 1H-pyrrole-2,4-diyl |
| C54 | corresponding pyrazole analog | 1H-pyrazole-3,5-diyl |

TABLE 4-continued

Compounds C39-C63, RGN6024

| Compound | Structure | "L" Group |
|---|---|---|
| C55 | | 3,5-isoxazolediyl |
| C56 | | 2,5-thiophenediyl |
| C57 | | 2,5-furandiyl |
| C58 | | 2,5-pyrroldiyl |

TABLE 4-continued

Compounds C39-C63, RGN6024

| Compound | Structure | "L" Group |
|---|---|---|
| C59 | 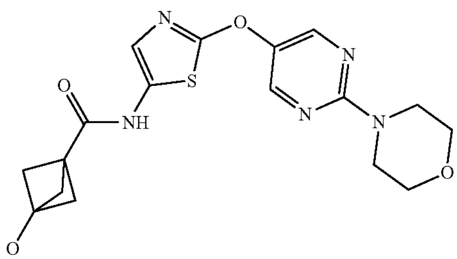 [SMILES: O=C(Nc1cnc(Oc2cnc(N3CCOCC3)nc2)s1)C12CC(O)(C1)C2] | thiazole (2,5-linked) |
| C60 | 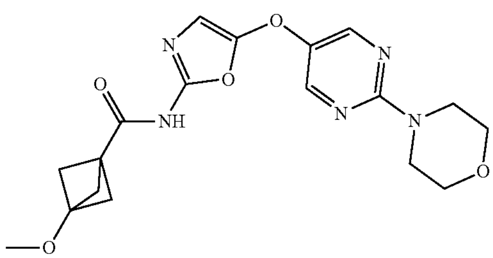 [SMILES: COC12CC(C(=O)Nc3ncc(Oc4cnc(N5CCOCC5)nc4)o3)(C1)C2] | oxazole (2,5-linked) |
| C61 | 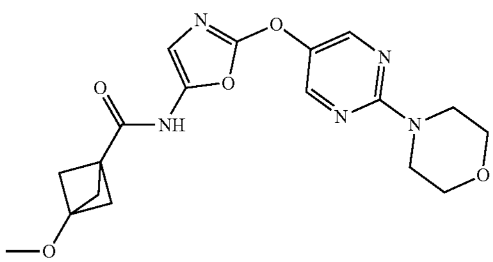 [SMILES: COC12CC(C(=O)Nc3cnc(Oc4cnc(N5CCOCC5)nc4)o3)(C1)C2] | oxazole (2,5-linked, alternate) |
| C62 | 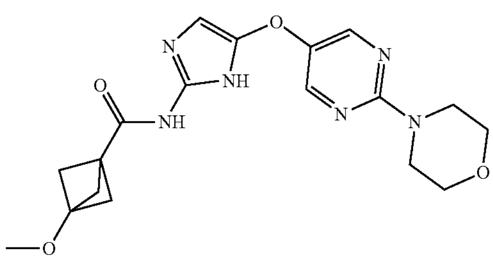 [SMILES: COC12CC(C(=O)Nc3ncc(Oc4cnc(N5CCOCC5)nc4)[nH]3)(C1)C2] | imidazole (2,5-linked) |
| C63 | 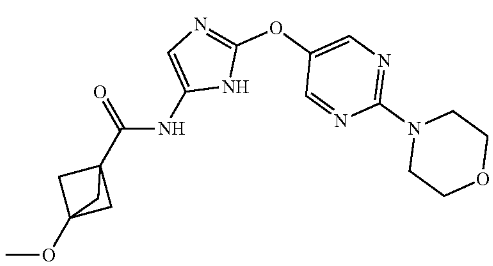 [SMILES: COC12CC(C(=O)Nc3cnc(Oc4cnc(N5CCOCC5)nc4)[nH]3)(C1)C2] | imidazole (2,5-linked, alternate) |

TABLE 4-continued
Compounds C39-C63, RGN6024
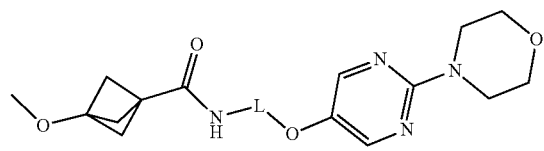
| Compound | Structure | "L" Group |
|---|---|---|
| RGN6024 | 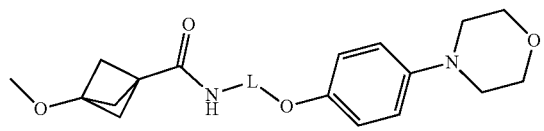 |  |
The present invention also features compounds according to formula (VI-A):
(formula VI-A)
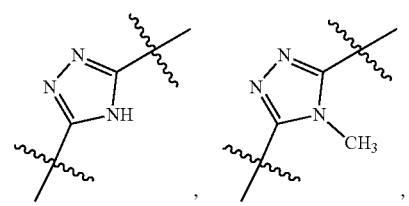
wherein L is any one of the following:
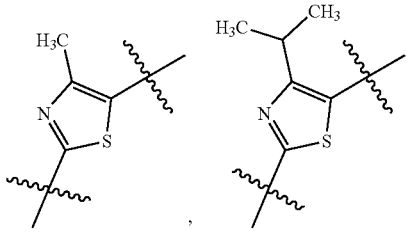
,
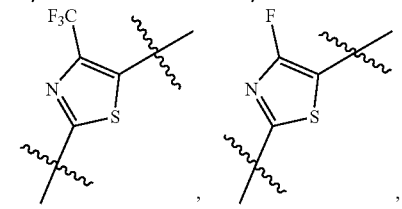
,
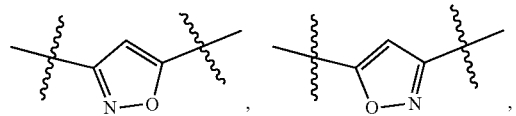
,
-continued
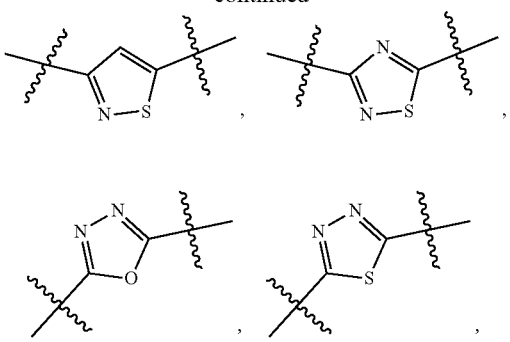
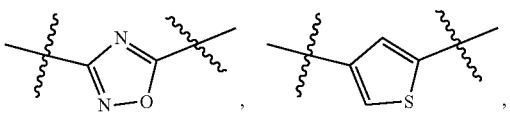
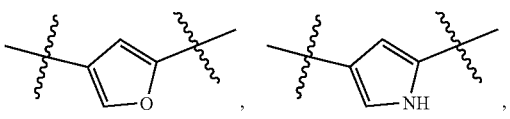
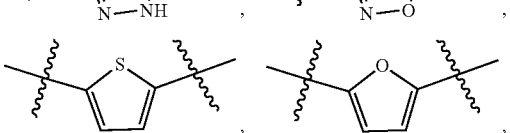
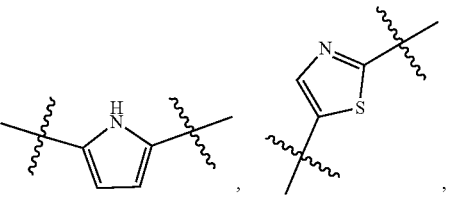
, -continued
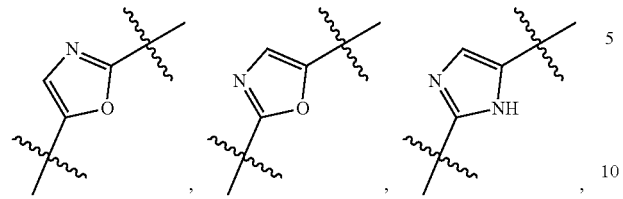
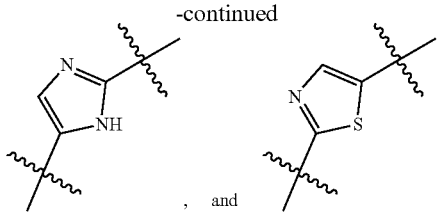
, and .
In certain embodiments, compounds of the present disclosure can include any one of the compounds provided in Table 5.
TABLE 5
Compounds C64-C89
| Compound | Structure | "L" Group |
|---|---|---|
| C64 | | |
| C65 | | |
| C66 | | |

TABLE 5-continued
Compounds C64-C89
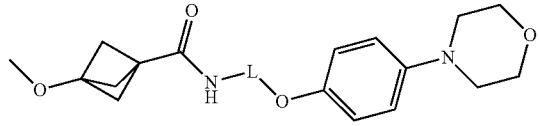
| Compound | Structure | "L" Group |
|---|---|---|
| C67 | 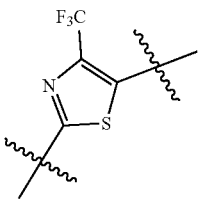 [SMILES: *c1nc(C(F)(F)F)c(*)s1] | 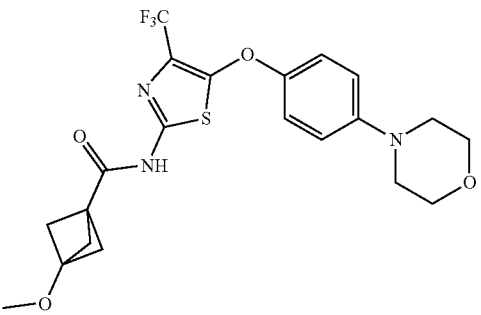 [SMILES: COC12CC(C(=O)Nc3nc(C(F)(F)F)c(Oc4ccc(N5CCOCC5)cc4)s3)(C1)C2] |
| C68 | 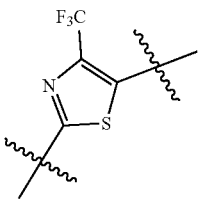 [SMILES: *c1nc(C(F)(F)F)c(*)s1] | 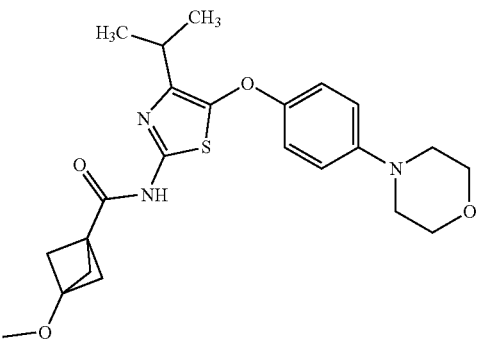 [SMILES: COC12CC(C(=O)Nc3nc(C(C)C)c(Oc4ccc(N5CCOCC5)cc4)s3)(C1)C2] |
| C69 | 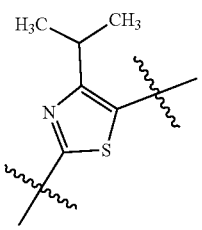 [SMILES: *c1nc(C(C)C)c(*)s1] | 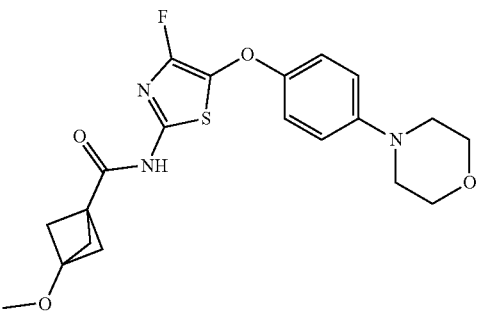 [SMILES: COC12CC(C(=O)Nc3nc(F)c(Oc4ccc(N5CCOCC5)cc4)s3)(C1)C2] |
| C70 | 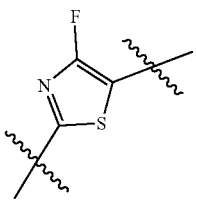 [SMILES: *c1nc(F)c(*)s1] | 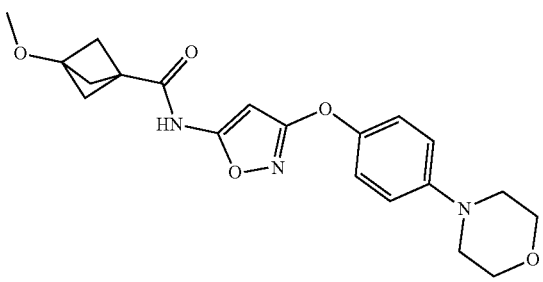 [SMILES: COC12CC(C(=O)Nc3cc(Oc4ccc(N5CCOCC5)cc4)no3)(C1)C2] |

TABLE 5-continued

Compounds C64-C89

| Compound | Structure | "L" Group |
|---|---|---|
| C71 | 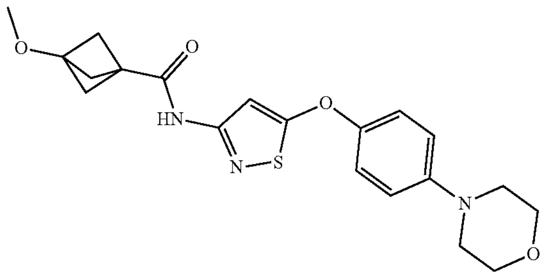 | isothiazole-3,5-diyl |
| C72 | 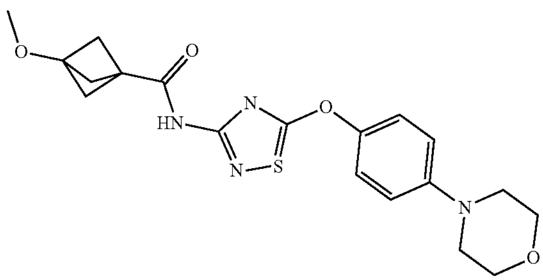 | 1,2,4-thiadiazole-3,5-diyl |
| C73 | 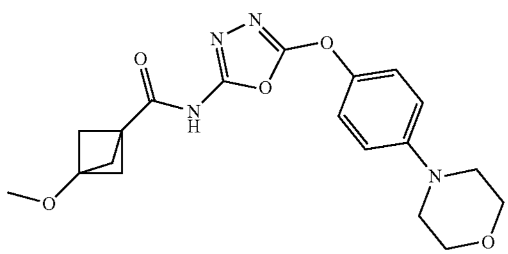 [SMILES: COC12CC(C(=O)Nc3nnc(Oc4ccc(N5CCOCC5)cc4)o3)(C1)C2] | 1,3,4-oxadiazole-2,5-diyl |
| C74 | 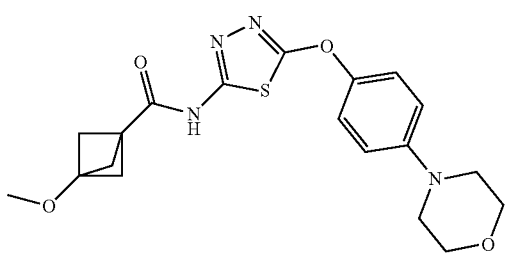 [SMILES: COC12CC(C(=O)Nc3nnc(Oc4ccc(N5CCOCC5)cc4)s3)(C1)C2] | 1,3,4-thiadiazole-2,5-diyl |
| C75 | 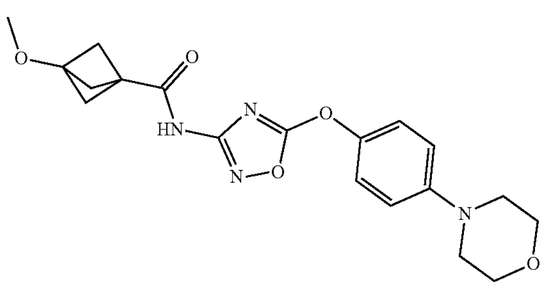 [SMILES: COC12CC(C(=O)Nc3noc(Oc4ccc(N5CCOCC5)cc4)n3)(C1)C2] | 1,2,4-oxadiazole-3,5-diyl |

TABLE 5-continued

Compounds C64-C89

| Compound | Structure | "L" Group |
|---|---|---|
| C76 | 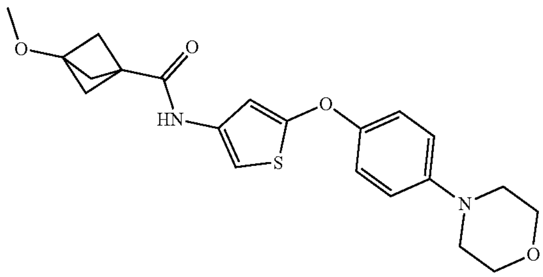 | thiophene-2,4-diyl |
| C77 | 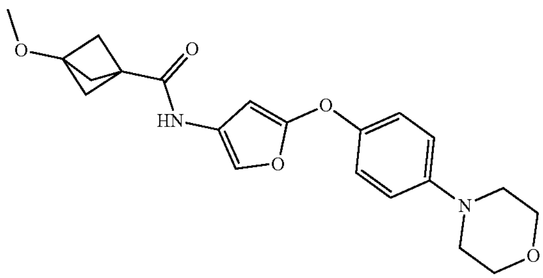 [SMILES: COC12CC(C(=O)Nc3coc(Oc4ccc(N5CCOCC5)cc4)c3)(C1)C2] | furan-2,4-diyl |
| C78 | 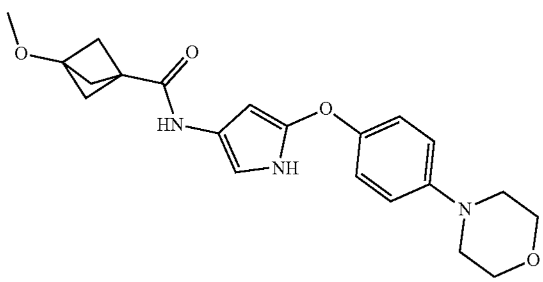 [SMILES: COC12CC(C(=O)Nc3c[nH]c(Oc4ccc(N5CCOCC5)cc4)c3)(C1)C2] | 1H-pyrrole-2,4-diyl |
| C79 | 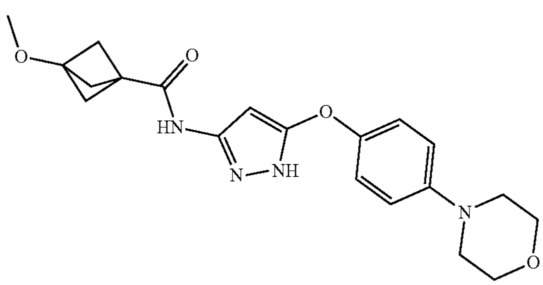 [SMILES: COC12CC(C(=O)Nc3cc(Oc4ccc(N5CCOCC5)cc4)[nH]n3)(C1)C2] | 1H-pyrazole-3,5-diyl |
| C80 | 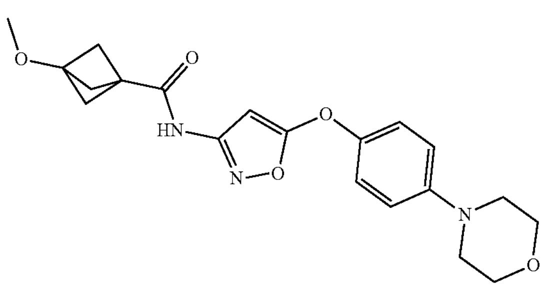 [SMILES: COC12CC(C(=O)Nc3cc(Oc4ccc(N5CCOCC5)cc4)on3)(C1)C2] | isoxazole-3,5-diyl |

TABLE 5-continued

Compounds C64-C89

| Compound | Structure | "L" Group |
|---|---|---|
| C81 | 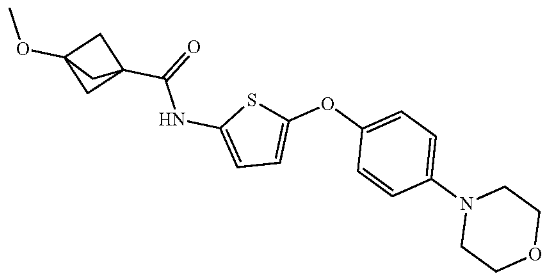 | thiophene-2,5-diyl |
| C82 | 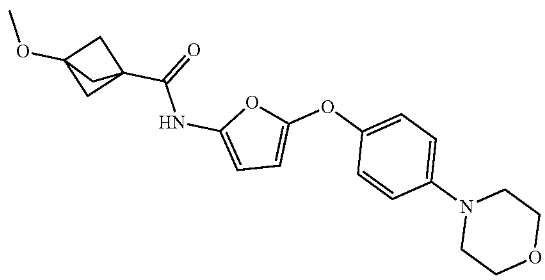 [SMILES: COC12CC(C(=O)Nc3ccc(Oc4ccc(N5CCOCC5)cc4)s3)(C1)C2] | furan-2,5-diyl |
| C83 | 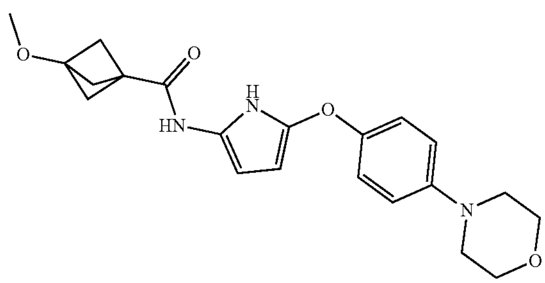 [SMILES: COC12CC(C(=O)Nc3ccc(Oc4ccc(N5CCOCC5)cc4)[nH]3)(C1)C2] | 1H-pyrrole-2,5-diyl |
| C84 | 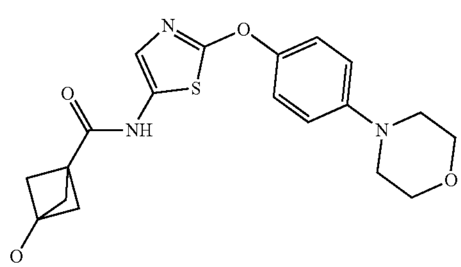 [SMILES: O=C(Nc1cnc(Oc2ccc(N3CCOCC3)cc2)s1)C12CC(O)(C1)C2] | thiazole-2,5-diyl |
| C85 | 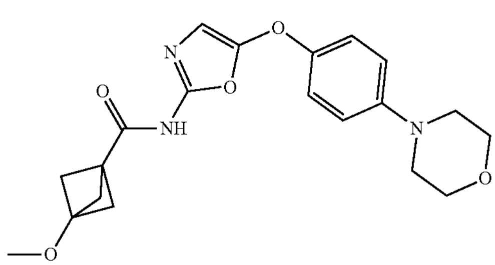 [SMILES: COC12CC(C(=O)Nc3ncc(Oc4ccc(N5CCOCC5)cc4)o3)(C1)C2] | oxazole-2,5-diyl |

TABLE 5-continued
Compounds C64-C89
| Compound | Structure | "L" Group |
|---|---|---|
| C86 | 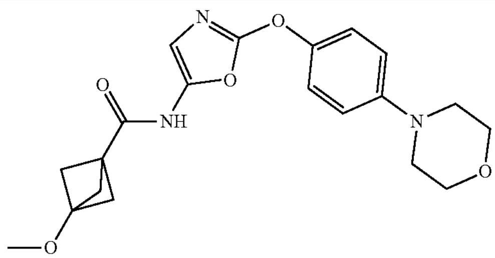 [SMILES: COC12CC(C(=O)Nc3cnc(Oc4ccc(N5CCOCC5)cc4)o3)(C1)C2] | |
| C87 | 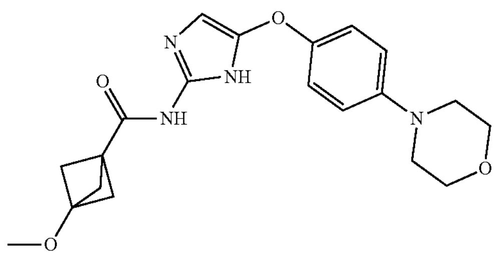 [SMILES: COC12CC(C(=O)Nc3ncc(Oc4ccc(N5CCOCC5)cc4)[nH]3)(C1)C2] | |
| C88 | 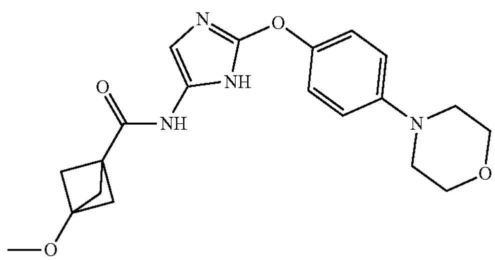 [SMILES: COC12CC(C(=O)Nc3cnc(Oc4ccc(N5CCOCC5)cc4)[nH]3)(C1)C2] | |
| C89 (C27 and B155) | 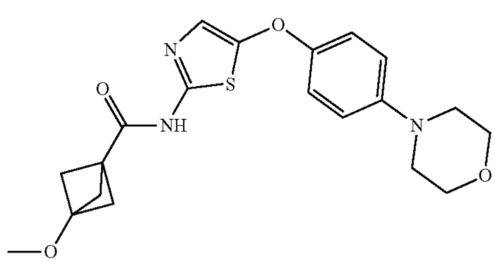 [SMILES: COC12CC(C(=O)Nc3ncc(Oc4ccc(N5CCOCC5)cc4)s3)(C1)C2] | |
The present invention features compounds according to formula (VII-A):
wherein L is any one of the following:
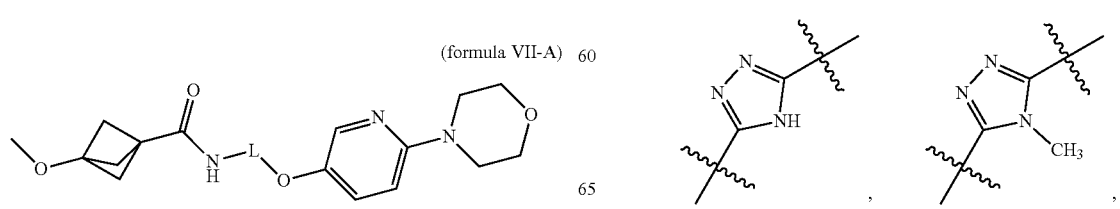

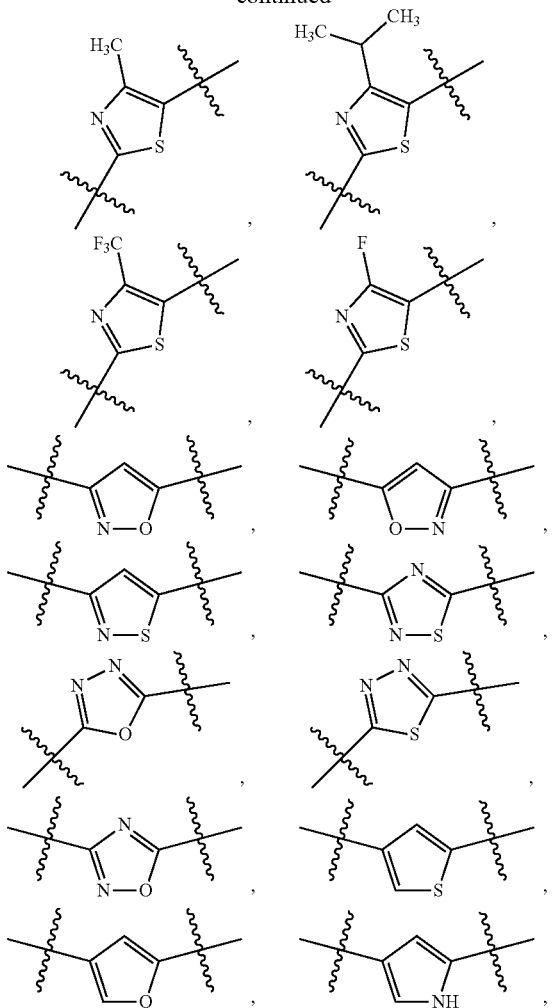
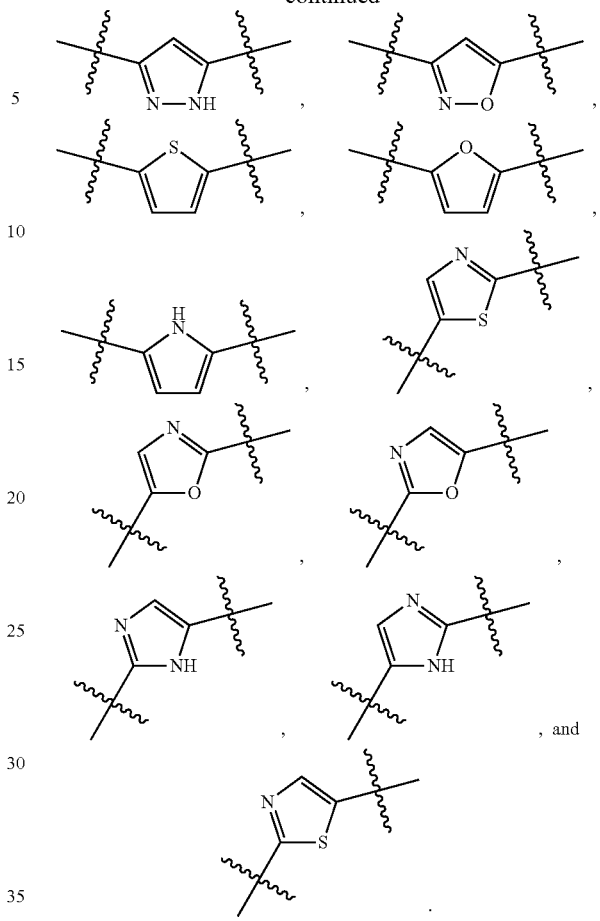
In certain embodiments, compounds of the present disclosure can include any one of the compounds provided in Table 6.
TABLE 6
Compounds C90-115
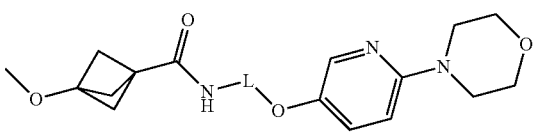
| Compound | Structure | "L" Group |
| --- | --- | --- |
| C90 | 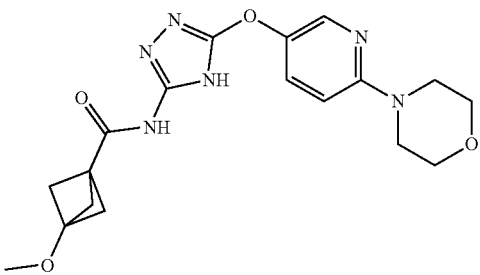 [SMILES: COC12CC(C(=O)Nc3nnc(Oc4ccc(N5CCOCC5)nc4)[nH]3)(C1)C2] | 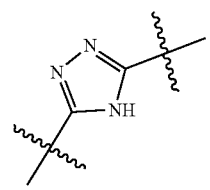 [SMILES: *c1nnc(*)[nH]1] |

TABLE 6-continued

Compounds C90-115

| Compound | Structure | "L" Group |
|---|---|---|
| C91 | 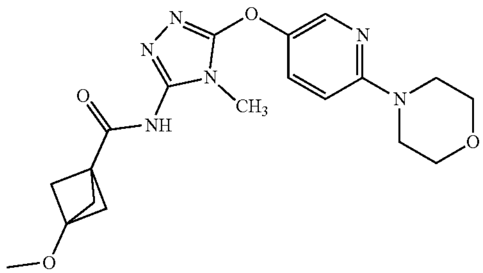 [SMILES: COC12CC(C(=O)Nc3nnc(Oc4ccc(N5CCOCC5)nc4)n3C)(C1)C2] | |
| C92 | 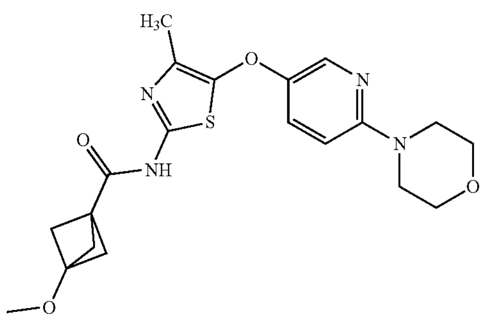 [SMILES: COC12CC(C(=O)Nc3nc(C)c(Oc4ccc(N5CCOCC5)nc4)s3)(C1)C2] | |
| C93 | 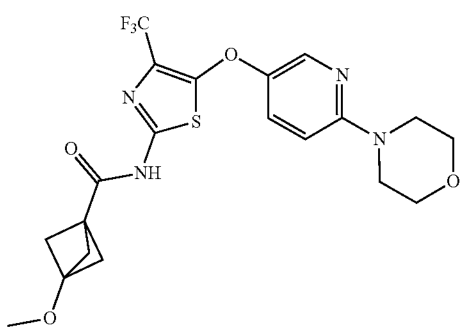 [SMILES: COC12CC(C(=O)Nc3nc(C(F)(F)F)c(Oc4ccc(N5CCOCC5)nc4)s3)(C1)C2] | |
| C94 | 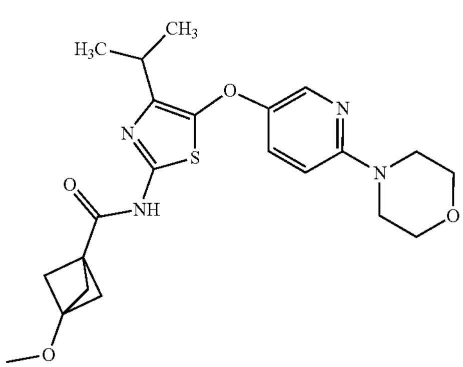 [SMILES: COC12CC(C(=O)Nc3nc(C(C)C)c(Oc4ccc(N5CCOCC5)nc4)s3)(C1)C2] | |

TABLE 6-continued
Compounds C90-115
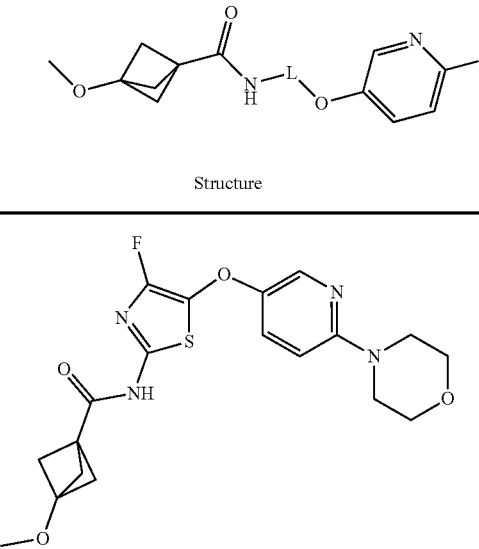
| Compound | Structure | "L" Group |
|---|---|---|
| C95 | 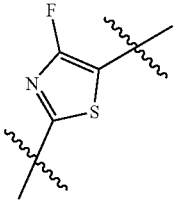 [SMILES: *c1nc(F)c(*)s1] | 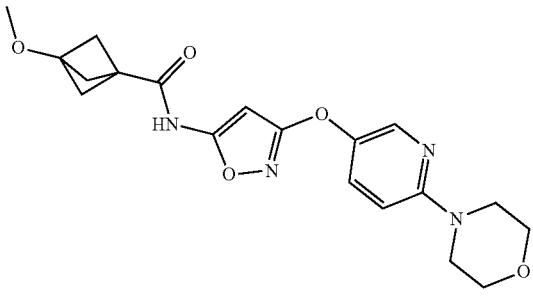 [SMILES: COC12CC(C(=O)Nc3cc(Oc4ccc(N5CCOCC5)nc4)no3)(C1)C2] |
| C96 | 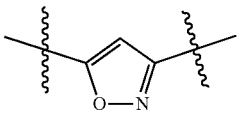 [SMILES: *c1cc(*)on1] | 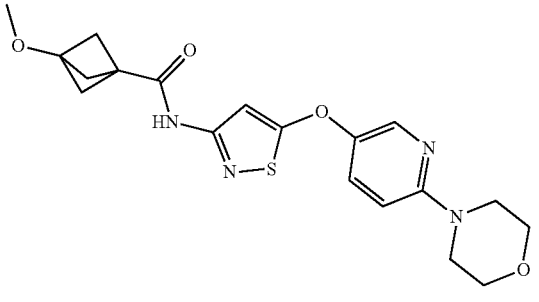 [SMILES: COC12CC(C(=O)Nc3cc(Oc4ccc(N5CCOCC5)nc4)sn3)(C1)C2] |
| C97 | 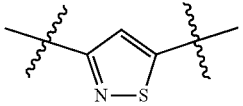 [SMILES: *c1cc(*)sn1] | 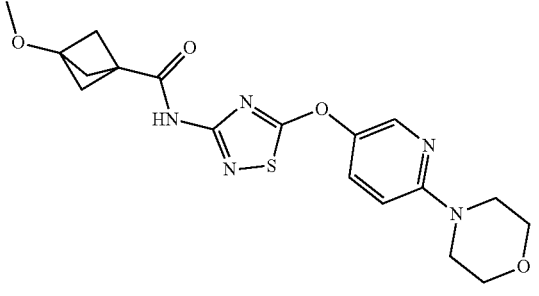 [SMILES: COC12CC(C(=O)Nc3nsc(Oc4ccc(N5CCOCC5)nc4)n3)(C1)C2] |
| C98 | 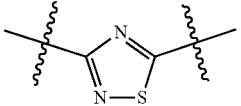 [SMILES: *c1nsc(*)n1] | |

TABLE 6-continued

Compounds C90-115

| Compound | Structure | "L" Group |
|---|---|---|
| C99 | 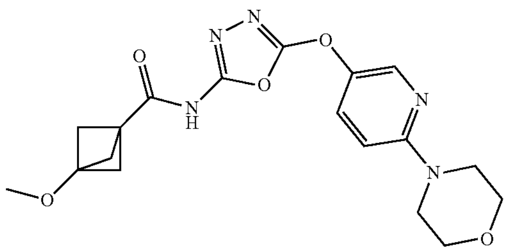 [SMILES: COC12CC(C(=O)Nc3nnc(Oc4ccc(N5CCOCC5)nc4)o3)(C1)C2] | 1,3,4-oxadiazole-2,5-diyl |
| C100 | 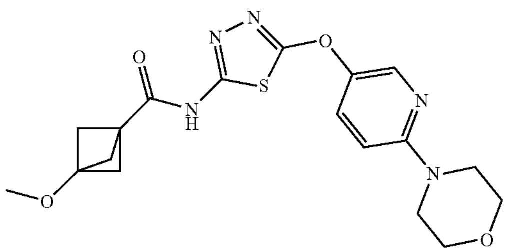 [SMILES: COC12CC(C(=O)Nc3nnc(Oc4ccc(N5CCOCC5)nc4)s3)(C1)C2] | 1,3,4-thiadiazole-2,5-diyl |
| C101 | 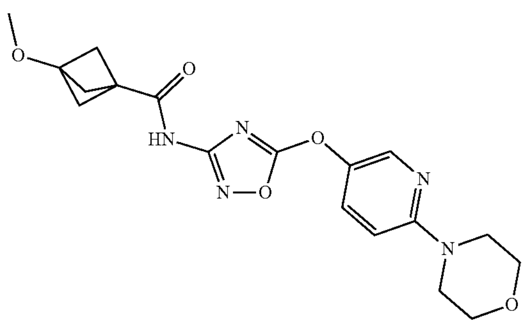 [SMILES: COC12CC(C(=O)Nc3noc(Oc4ccc(N5CCOCC5)nc4)n3)(C1)C2] | 1,2,4-oxadiazole-3,5-diyl |
| C102 | 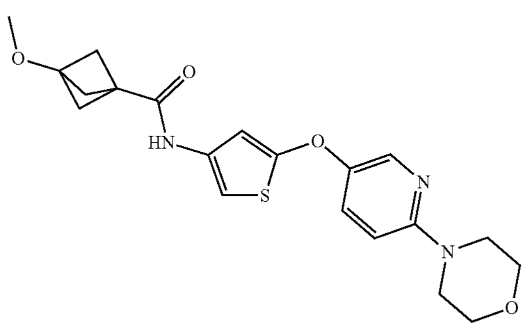 [SMILES: COC12CC(C(=O)Nc3csc(Oc4ccc(N5CCOCC5)nc4)c3)(C1)C2] | thiophene-2,4-diyl |

TABLE 6-continued
Compounds C90-115
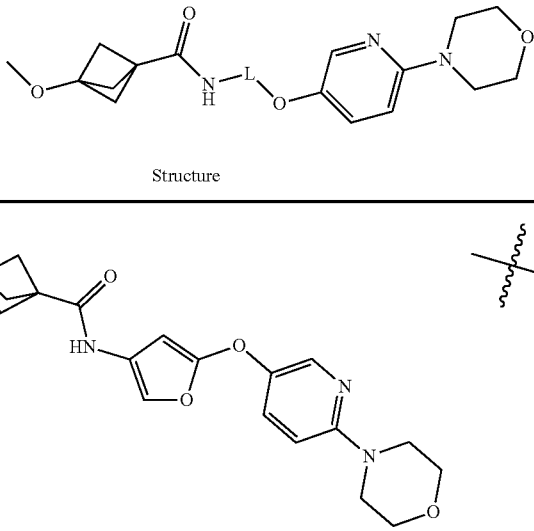
| Compound | Structure | "L" Group |
|---|---|---|
| C103 | 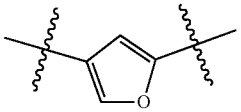 [SMILES: *c1coc(*)c1] | 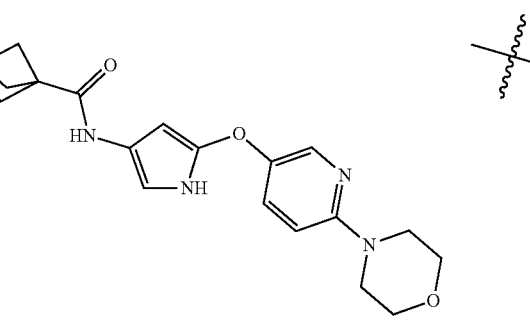 |
| C104 | 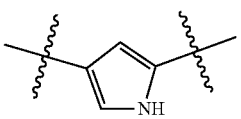 [SMILES: *c1c[nH]c(*)c1] | 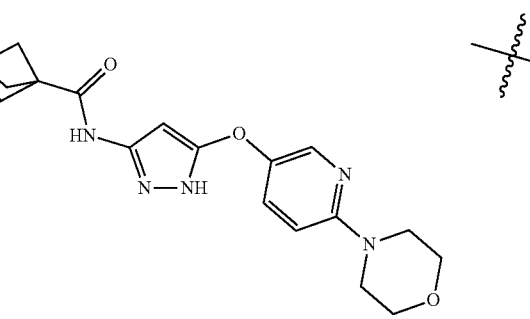 |
| C105 | 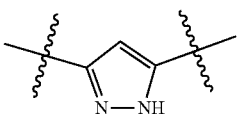 [SMILES: *c1cc(*)[nH]n1] | 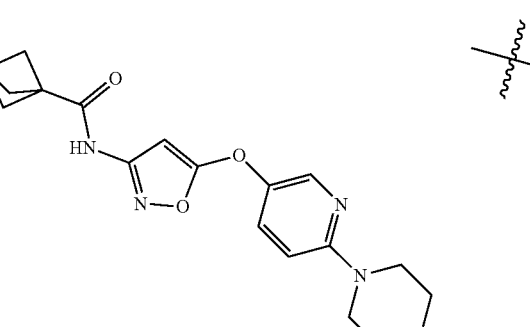 |
| C106 | 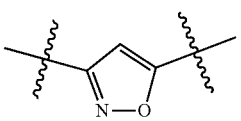 [SMILES: *c1cc(*)on1] | |

TABLE 6-continued

Compounds C90-115

| Compound | Structure | "L" Group |
|---|---|---|
| C107 | | thiophene-2,5-diyl |
| C108 | | furan-2,5-diyl |
| C109 | | 1H-pyrrole-2,5-diyl |
| C110 | | thiazole-2,5-diyl |

TABLE 6-continued

Compounds C90-115

| Compound | Structure | "L" Group |
|---|---|---|
| C111 | 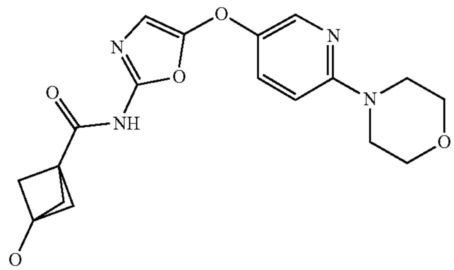 [SMILES: O=C(Nc1ncc(Oc2ccc(N3CCOCC3)nc2)o1)C12CC(O)(C1)C2] | |
| C112 | 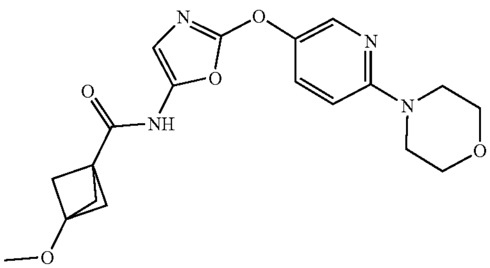 [SMILES: COC12CC(C(=O)Nc3cnc(Oc4ccc(N5CCOCC5)nc4)o3)(C1)C2] | |
| C113 | 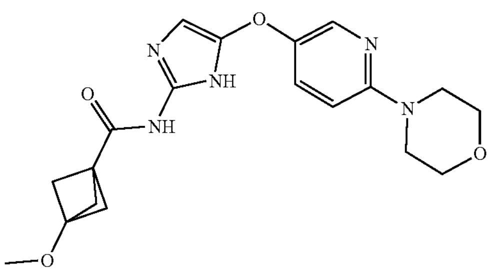 [SMILES: COC12CC(C(=O)Nc3ncc(Oc4ccc(N5CCOCC5)nc4)[nH]3)(C1)C2] | |
| C114 | 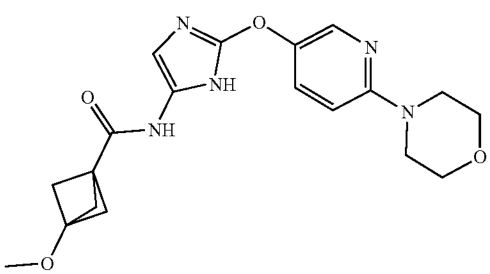 [SMILES: COC12CC(C(=O)Nc3cnc(Oc4ccc(N5CCOCC5)nc4)[nH]3)(C1)C2] | |
| C115 | 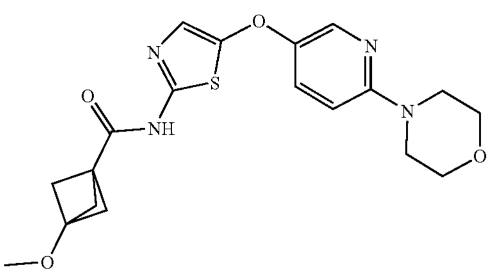 [SMILES: COC12CC(C(=O)Nc3ncc(Oc4ccc(N5CCOCC5)nc4)s3)(C1)C2] | |

In certain embodiments, the present invention features a compound according to any one of the compounds provided in Table 7, or a derivative thereof:

TABLE 7

Compounds C116-C125

| Compound | Structure |
|---|---|
| C116 | 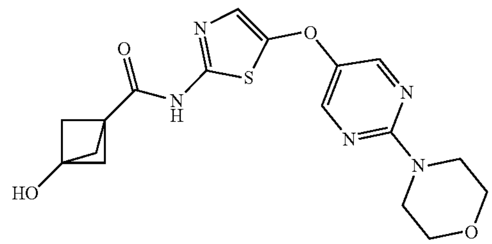 [SMILES: O=C(Nc1ncc(Oc2cnc(N3CCOCC3)nc2)s1)C12CC(O)(C1)C2] |
| C117 | 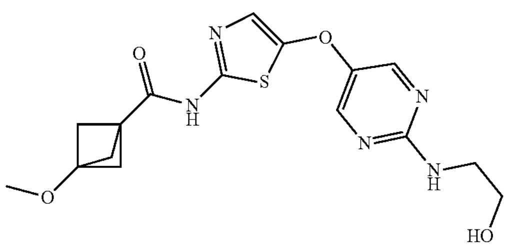 [SMILES: COC12CC(C(=O)Nc3ncc(Oc4cnc(NCCO)nc4)s3)(C1)C2] |
| C118 | 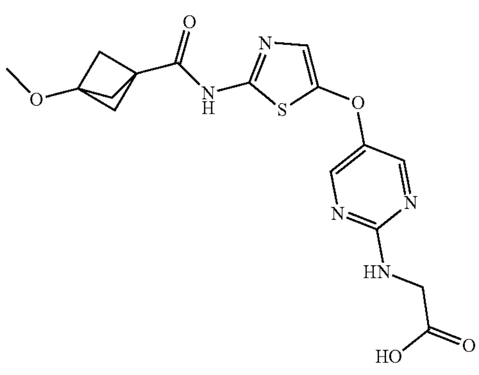 [SMILES: COC12CC(C(=O)Nc3ncc(Oc4cnc(NCC(=O)O)nc4)s3)(C1)C2] |
| C119 | 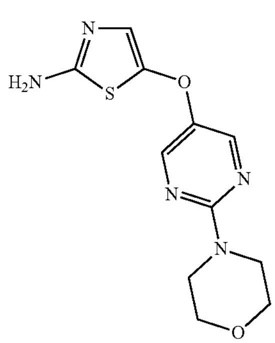 [SMILES: Nc1ncc(Oc2cnc(N3CCOCC3)nc2)s1] |
| C120 | |
| C121 | |
| C122 | |
| C123 | |

TABLE 7-continued

Compounds C116-C125

| Compound | Structure |
|---|---|
| C124 | 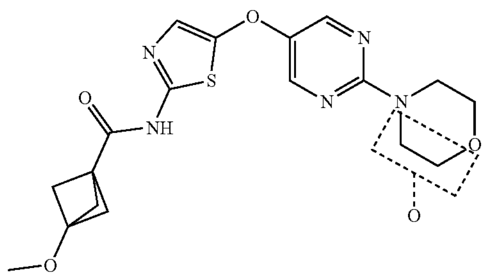 |
| C125 | 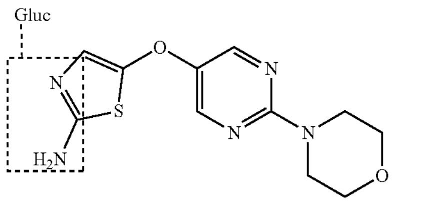 |

In some embodiments, the present invention is a compound or composition comprising RGN6024, or derivative thereof:

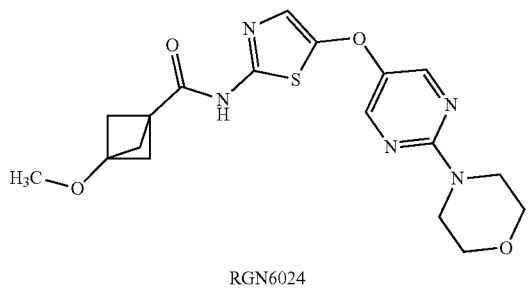 [SMILES: COC12CC(C(=O)Nc3ncc(Oc4cnc(N5CCOCC5)nc4)s3)(C1)C2]

RGN6024

In some embodiments, a compound can include a compound according to formula I-B:

A-B—C-L'-E-L"-G   (formula I-B)

wherein:

A is a straight chain or branched alkyl, cycloalkyl, or cycloalkyl methyl;

B is an O or S, wherein B is covalently bonded to any available atom on A;

C is a cycloalkyl or bicyclic alkyl, wherein any available atom on C is covalently bonded to B;

L' is a thioester, ester, —CONH—, or —SO$_2$NH—, —NHCO—, wherein any available atom on L' is covalently bonded to any available atom on C;

E is a thiazole, wherein any available atom on E is covalently bonded to any available atom on L';

L" is a linker selected from a group consisting of a O, CH$_2$, —S—, and —C=O, wherein L" is covalently bonded to any available atom on E; and G is $$\begin{array}{c}\text{R17} \\ \text{R23} \quad \text{U} \quad \text{R18} \\ \text{T} \quad \text{V} \quad \text{R19} \\ \text{R22} \quad \text{R21} \quad \text{W} \quad \text{R20}\end{array}$$

wherein any available atom on G is covalently bonded to L", wherein L" can bond to a carbon of one of the rings in G in place of any one of R17, R18, R19, R20, R21, R22, or R23, wherein in any position not bonded to L" can remain as designated, wherein T and U is a CH or N;

wherein V is a CH or N;

wherein W is a O, S, —CH(R24) or —CH(OR25), wherein R24 and R25 are each independently selected from a group consisting of H, a substituted or unsubstituted alkyl, a substituted or unsubstituted aryl, a substituted or unsubstituted heteroaryl, a substituted or unsubstituted heterocyclic, and a substituted or unsubstituted cycloalkyl; and wherein $R_{17}$, $R_{18}$, $R_{19}$, $R_{20}$, $R_{21}$, $R_{22}$, $R_{23}$ are each independently selected from the group consisting of H, F, Cl, I, Br, a linear or branched, substituted or unsubstituted alkyl, a substituted or unsubstituted aryl, a substituted or unsubstituted heteroaryl, and a substituted or unsubstituted heterocyclic.

In certain embodiments, compounds of formula (I-B) can include any one of the compounds provided in Table 8.

TABLE 8

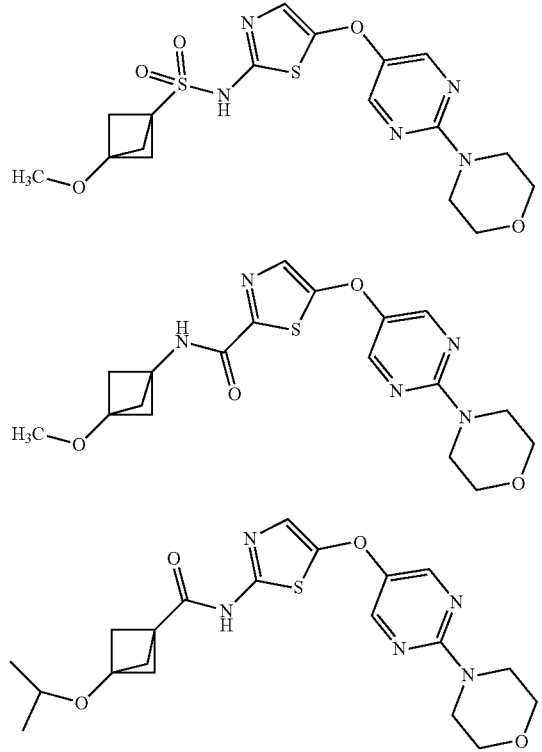

TABLE 8-continued

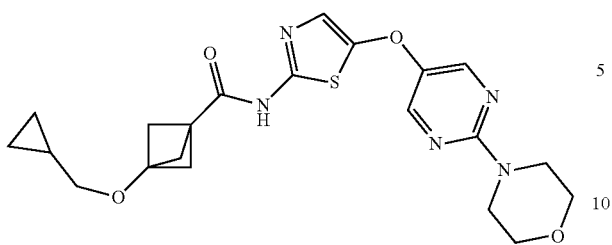

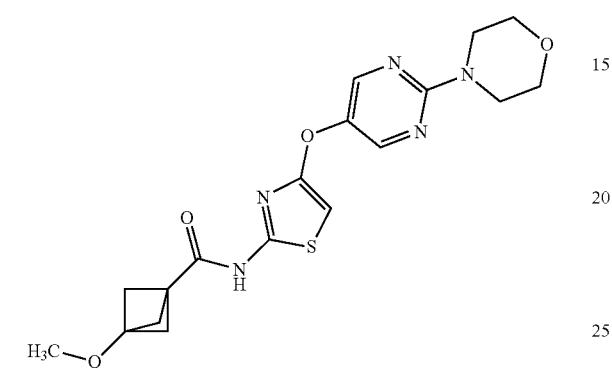

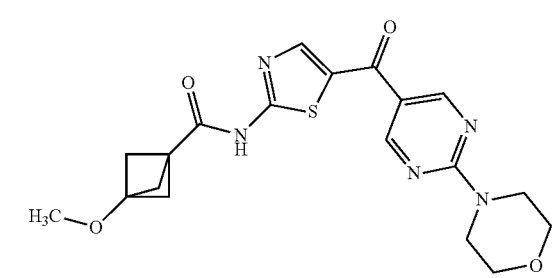 [SMILES: COC12CC(C(=O)Nc3ncc(C(=O)c4cnc(N5CCOCC5)nc4)s3)(C1)C2]

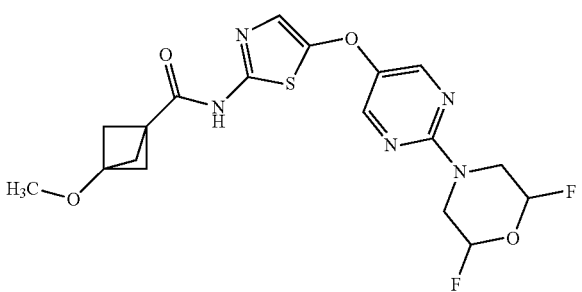 [SMILES: COC12CC(C(=O)Nc3ncc(Oc4cnc(N5CC(F)OC(F)C5)nc4)s3)(C1)C2]

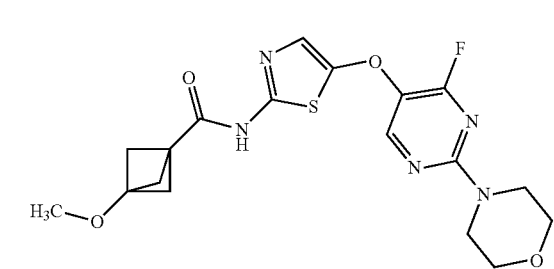 [SMILES: COC12CC(C(=O)Nc3ncc(Oc4cnc(N5CCOCC5)nc4F)s3)(C1)C2]

TABLE 8-continued

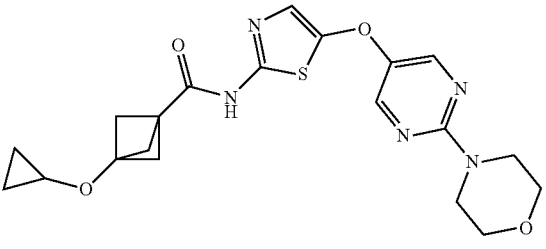 [SMILES: O=C(Nc1ncc(Oc2cnc(N3CCOCC3)nc2)s1)C12CC(OC3CC3)(C1)C2]

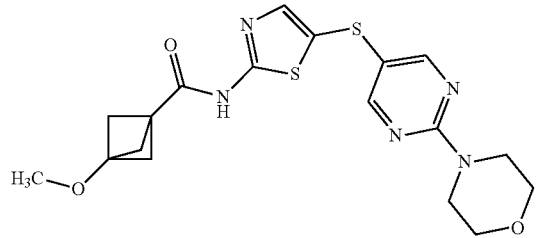 [SMILES: COC12CC(C(=O)Nc3ncc(Sc4cnc(N5CCOCC5)nc4)s3)(C1)C2]

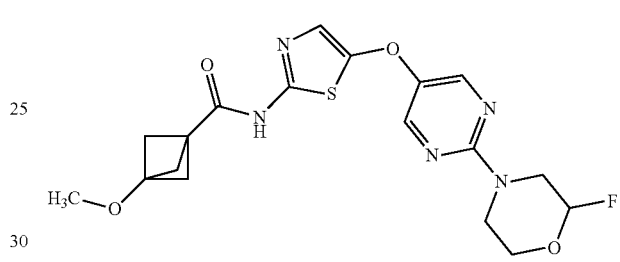

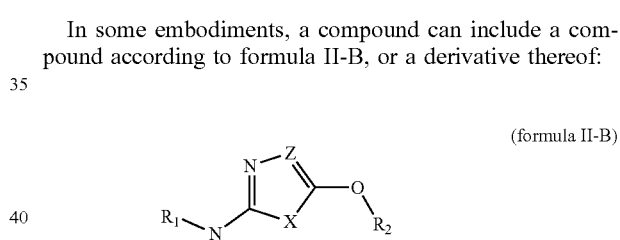

In some embodiments, a compound can include a compound according to formula II-B, or a derivative thereof:

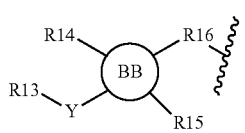

(formula II-B)

wherein X is selected from the group consisting of an O, S, or N(R26), wherein R26 is selected from a group consisting of a H, a substituted or unsubstituted alkyl, a substituted or unsubstituted aryl, a substituted or unsubstituted heteroaryl;

Z is selected from the group consisting of —CH or N;

R1 is wherein Y is selected from a group consisting of an O, S, —C=O, and halide, wherein if Y is a halide, R13 is not present;

wherein R13 is selected from the group consisting of H, a linear or branched, substituted or unsubstituted alkyl, a substituted or unsubstituted aryl, a substituted or unsubstituted heteroaryl, and a substituted or unsubstituted heterocyclic;

wherein BB is a bridged bicyclic moiety;
wherein R14 and R15 are each independently selected from the group consisting of H, F, Cl, I, Br, a linear or branched, substituted or unsubstituted alkyl, a substituted or unsubstituted aryl, a substituted or unsubstituted heteroaryl, and a substituted or unsubstituted heterocyclic;
wherein R16 is a —CO— or —SO₂—; and
R2 is

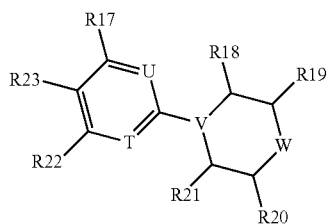

wherein the O of formula II-B is covalently bonded to a carbon of one of the rings in R2 in place of any one of R17, R18, R19, R20, R21, R22, or R23, wherein in any position not bonded to R2 can remain as designated,
wherein T and U is a CH or N;
wherein V is a CH or N;
wherein W is an O, S, —CH(R24) or —CH(OR25), wherein R24 and R25 are each independently selected from a group consisting of H, a substituted or unsubstituted alkyl, a substituted or unsubstituted aryl, a substituted or unsubstituted heteroaryl, a substituted or unsubstituted heterocyclic, and a substituted or unsubstituted cycloalkyl; and
wherein each one of R17, R18, R19, R20, R21, R22, and R23 are each independently selected from the group consisting of H, F, Cl, I, Br, a linear or branched, substituted or unsubstituted alkyl, a substituted or unsubstituted aryl, a substituted or unsubstituted heteroaryl, and a substituted or unsubstituted heterocyclic.

In certain embodiments, compounds of formula (II-B) can include any one of the compounds provided in Table 9.

TABLE 9

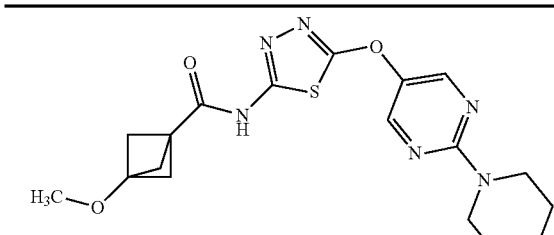

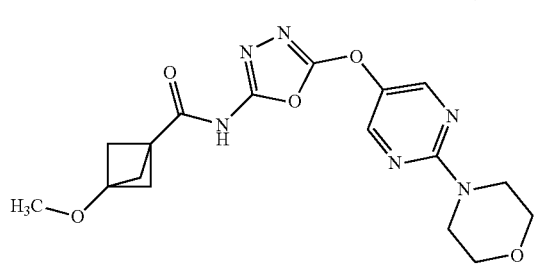 [SMILES: COC12CC(C(=O)Nc3nnc(Oc4cnc(N5CCOCC5)nc4)o3)(C1)C2]

TABLE 9-continued

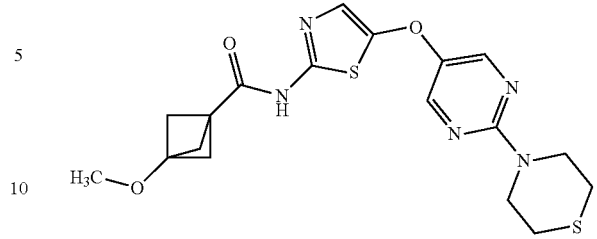

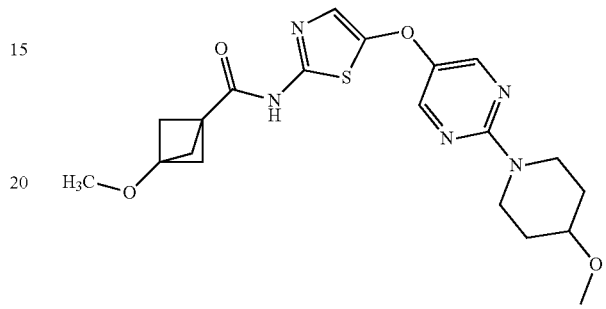

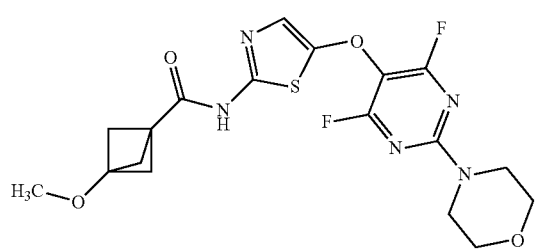 [SMILES: COC12CC(C(=O)Nc3ncc(Oc4c(F)nc(N5CCOCC5)nc4F)s3)(C1)C2]

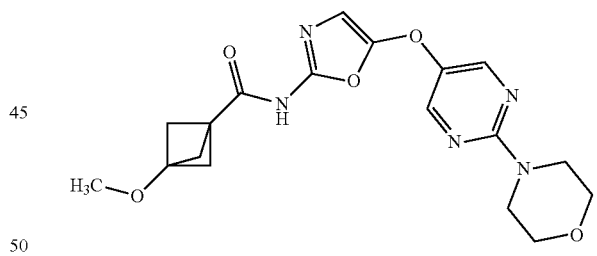

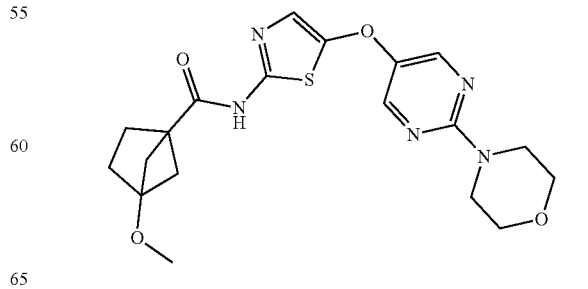

In some embodiments, a compound can include a compound according to formula III-B, or a derivative thereof:

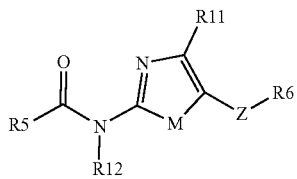
(formula III-B)

wherein:
R5 is

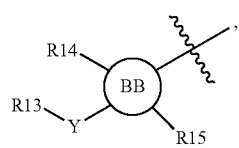

and
R<sub>6</sub> is

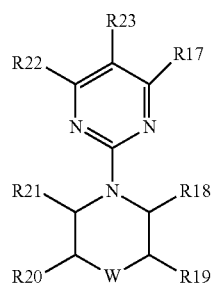

wherein the Z of formula III-B is covalently bonded to a carbon of one of the rings in R6 in place of any one of R17, R18, R19, R20, R21, R22, or R23, wherein in any position not bonded to R6 can remain as designated;
wherein R11, R14, R15, R17, R18, R19, R20, R21, R22, and R23 are each independently selected from the group consisting of H, F, Cl, I, Br, a linear or branched, substituted or unsubstituted alkyl, a substituted or unsubstituted aryl, a substituted or unsubstituted heteroaryl, and a substituted or unsubstituted heterocyclic;
R12 and R13 are each independently selected from the group consisting of H, a linear or branched, substituted or unsubstituted alkyl, a substituted or unsubstituted aryl, a substituted or unsubstituted heteroaryl, and a substituted or unsubstituted heterocyclic;
M is selected from the group consisting of an O, S, and N(R26), wherein R26 selected from a group consisting of H, a substituted or unsubstituted alkyl, a substituted or unsubstituted aryl, a substituted or unsubstituted heteroaryl;
Q is selected from the group consisting of an O, S, and halide, wherein if Z is a halide, R6 is not present;
Y is selected from a group consisting of O, S, —C=O, and halide, wherein if Y is a halide, R13 is not present;
BB is a bridged bicyclic moiety; and
W is selected from the group consisting of an O, S, —CH(R24) and —CH(OR25), wherein R24 and R25 are each independently selected from a group consisting of H, a substituted or unsubstituted alkyl, a substituted or unsubstituted aryl, a substituted or unsubstituted heteroaryl, a substituted or unsubstituted heterocyclic, and a substituted or unsubstituted cycloalkyl.

In certain embodiments, compounds of formula (III-B) can include any one of the compounds provided in Table 10.

TABLE 10

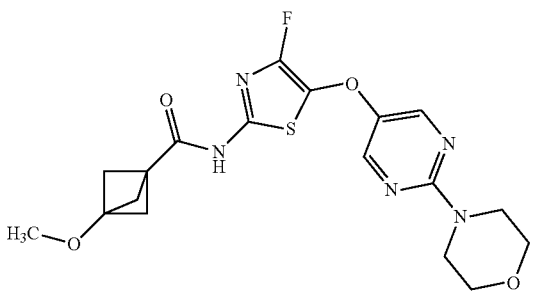

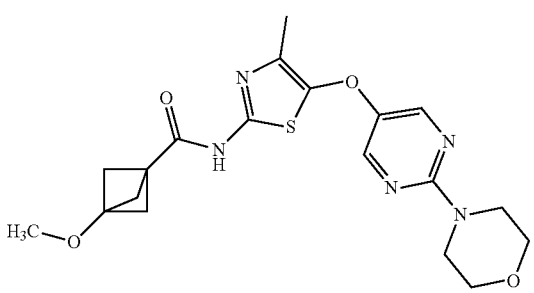

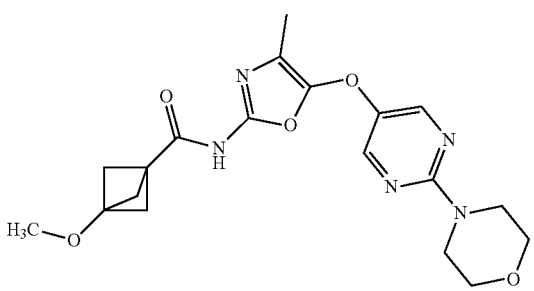 [SMILES: COC12CC(C(=O)Nc3nc(C)c(Oc4cnc(N5CCOCC5)nc4)o3)(C1)C2]

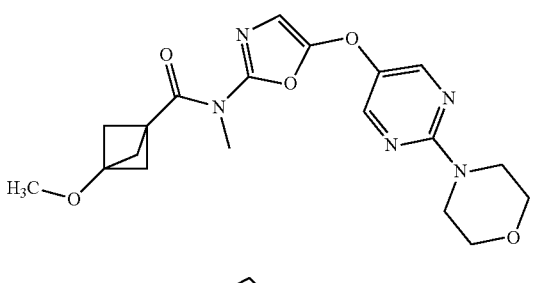

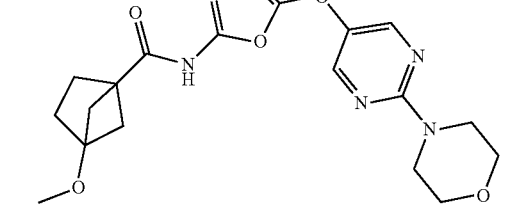

TABLE 10-continued
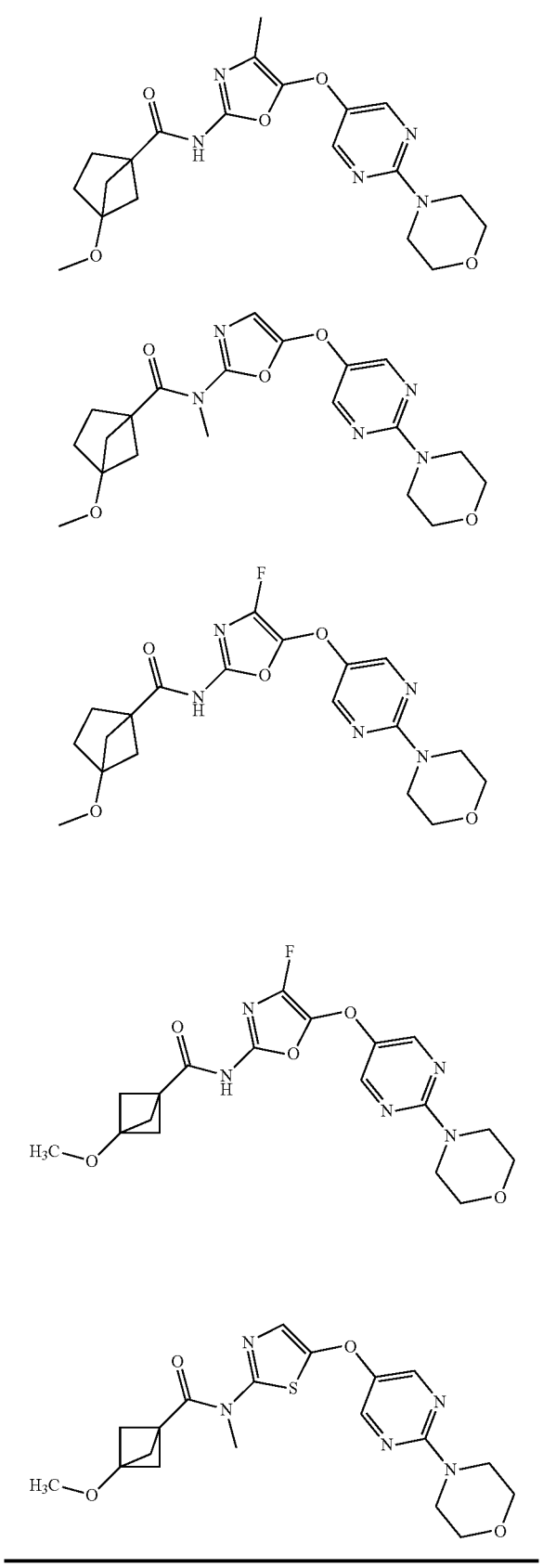
In some embodiments, the compound of the present invention may be any one of the following:
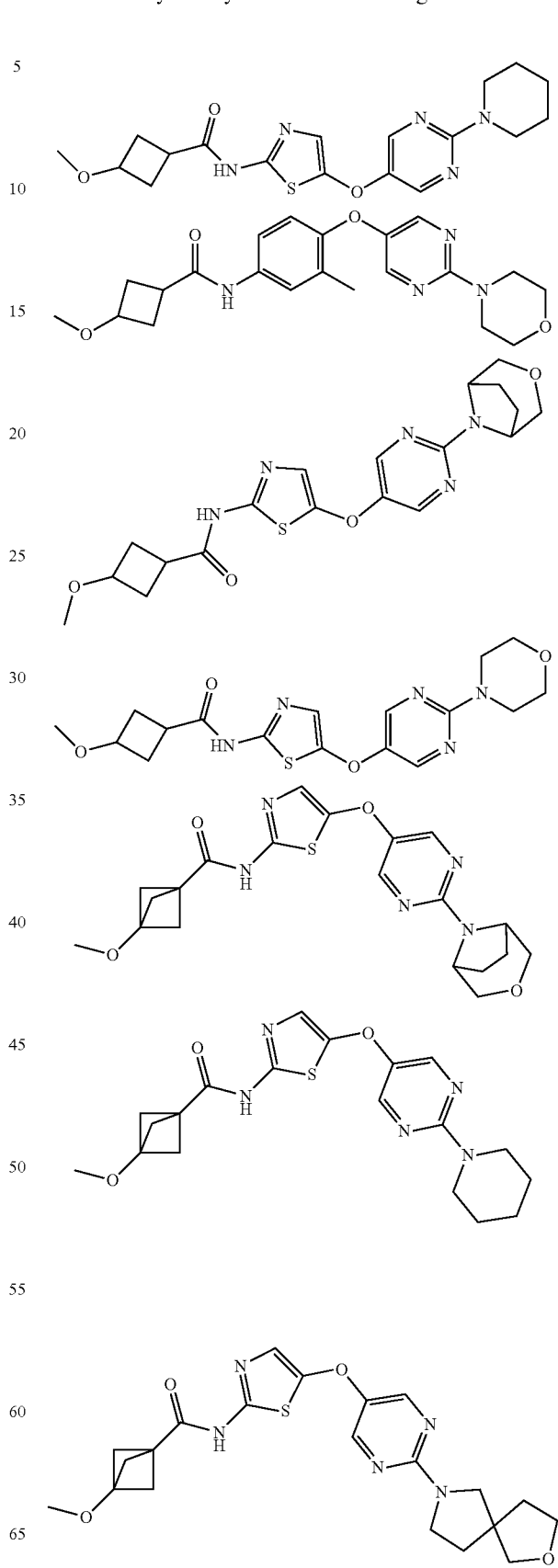

123
-continued
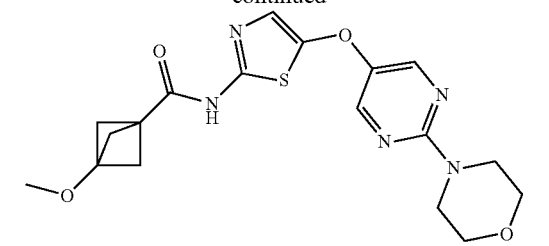
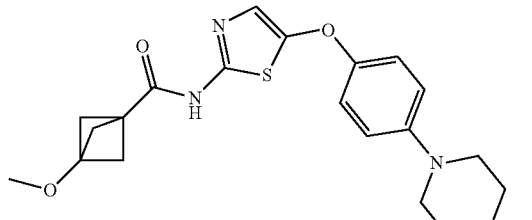
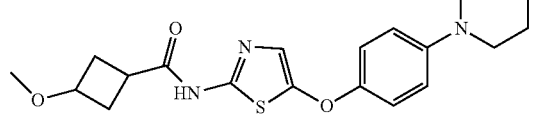
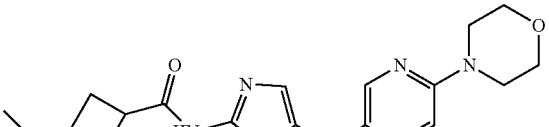
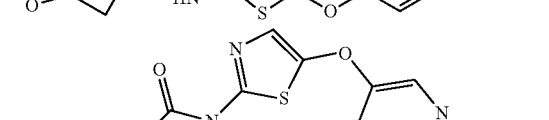
In some embodiments, a compound can include a compound according to formula (I-C),
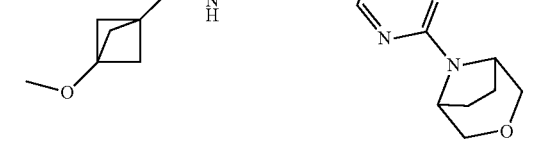
(I-C)
an analog, an isomer, a pharmaceutically acceptable salt, and/or a prodrug thereof, and/or formulation thereof;
wherein $R_1$ is selected from:
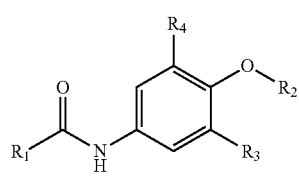
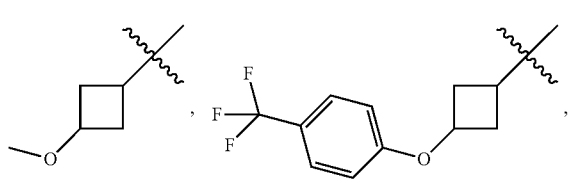
124
-continued
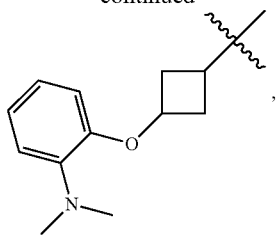
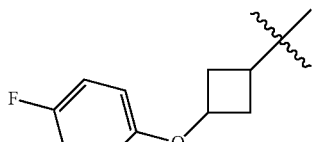
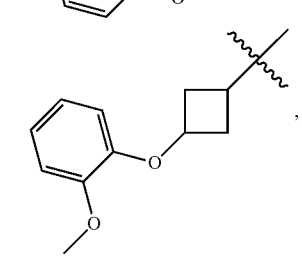
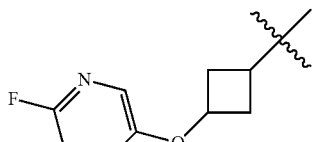
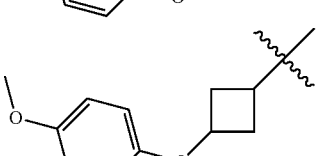
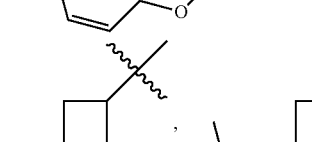
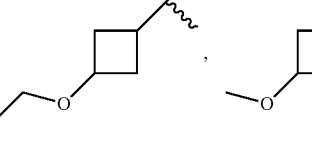
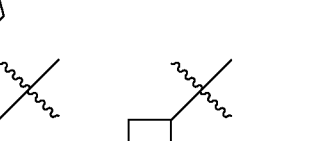
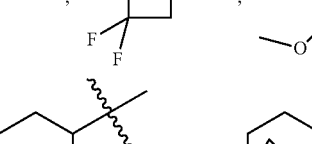

-continued

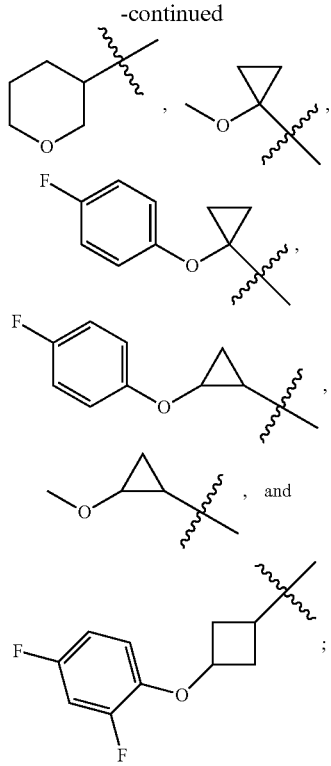

R$_2$, is an alkyl, an aryl, and a heteroaryl, wherein the aryl and the heteroaryl are each independently unsubstituted or are optionally independently substituted with one or more groups independently selected from alkyl, alkenyl, alkynyl, alkoxyl, alkylsulfo, alkylamino, halogen, thiol, hydroxyl, nitro, cyano, cycloalkyl, heterocyclyl, heterocyclic alkyl, aryl, heteroaryl, cycloalkoxyl, heterocyclic alkoxyl, cycloalkylthio, and heterocyclic alkylthio;

R$_3$ is selected from H, CH$_3$, or F; and R$_4$ is selected from H or F.

In some embodiments, R$_1$ of compounds of formula (I-C) disclosed herein is selected from:

-continued

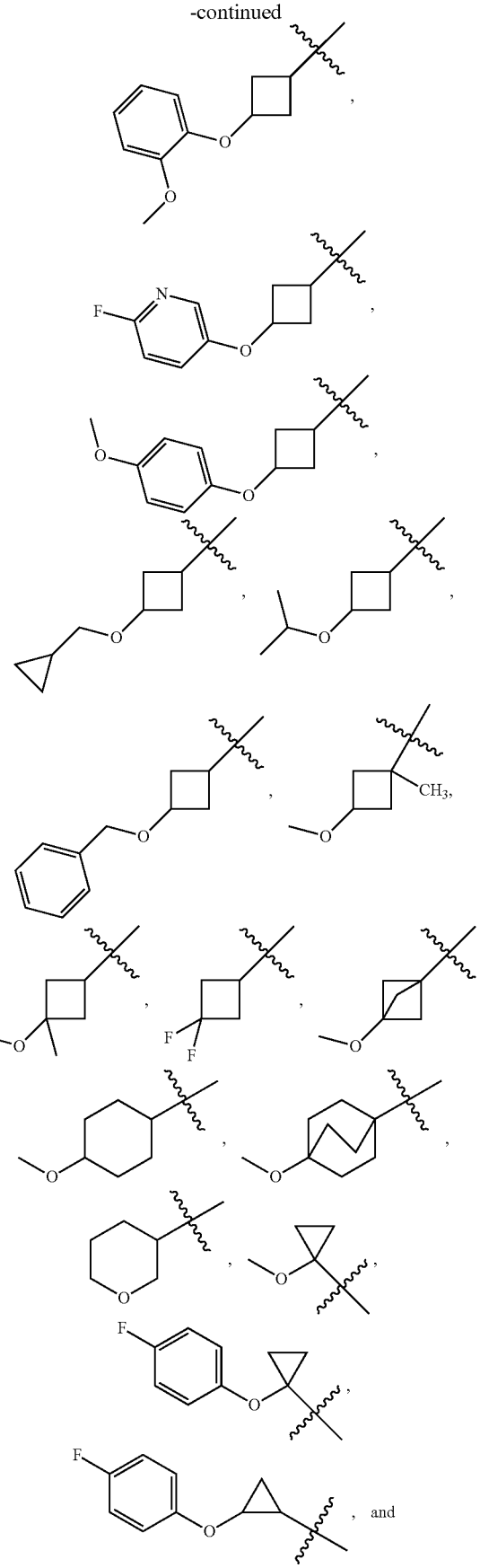

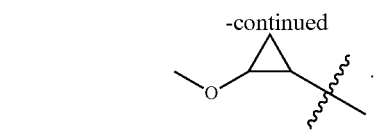
In some embodiments, R₁ of compounds of formula (I-C) disclosed herein is selected from:
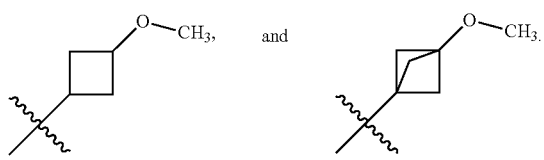 [SMILES: *C1CC(OC)C1 ; *C12CC(OC)(C1)C2]
In some embodiments, R₂ of compounds of formula (I-C) disclosed herein is selected from:
—CH₃,
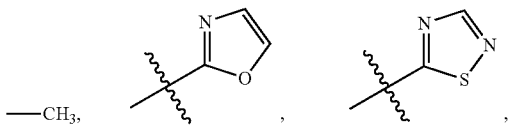
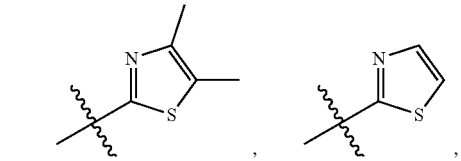
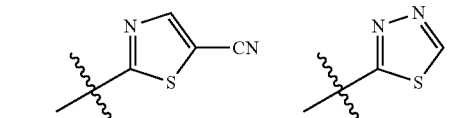
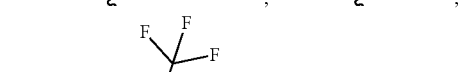
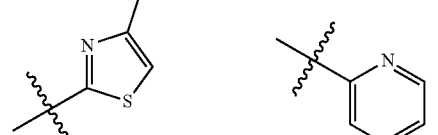
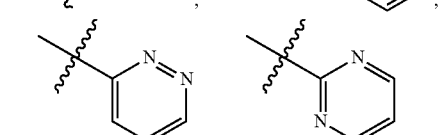
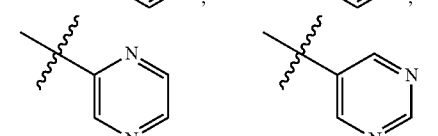
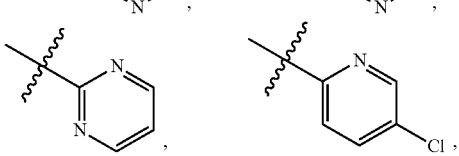
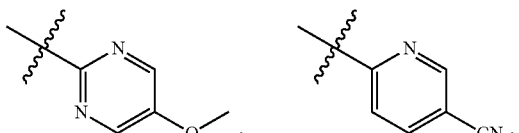
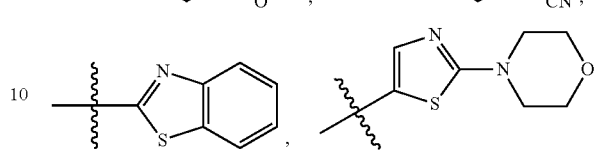
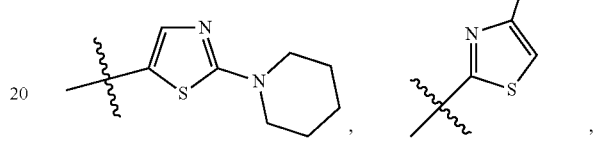
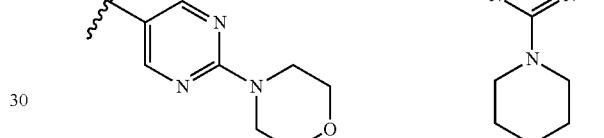
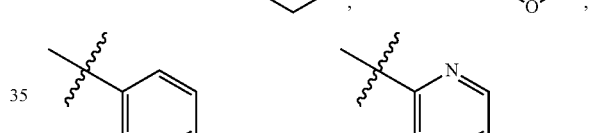
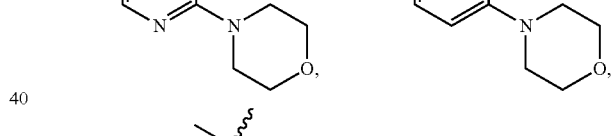
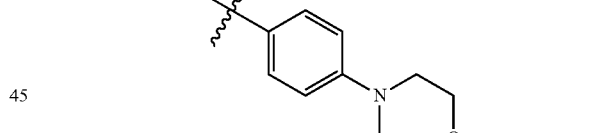
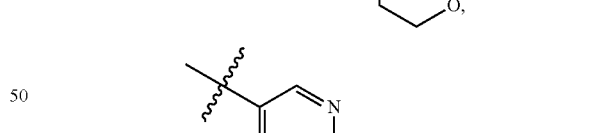
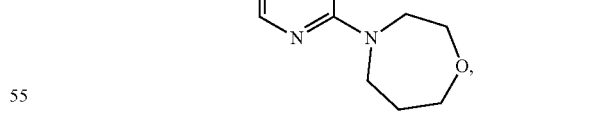
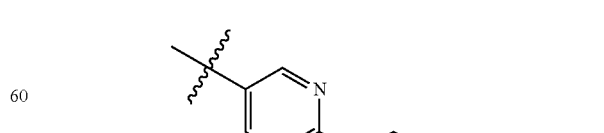
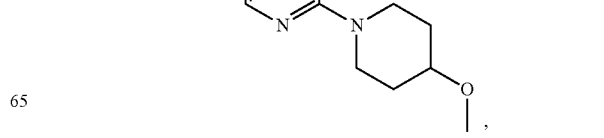

129
-continued
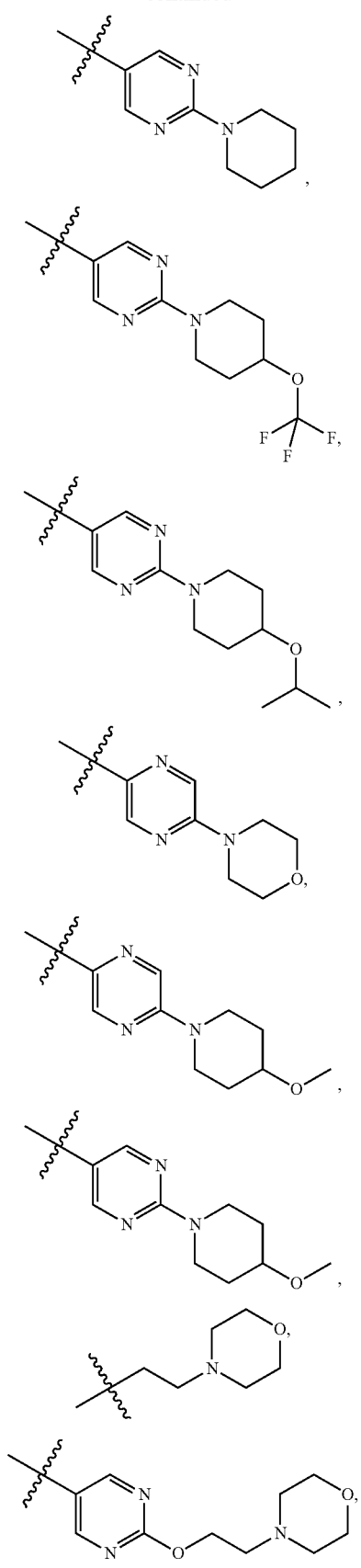
130
-continued
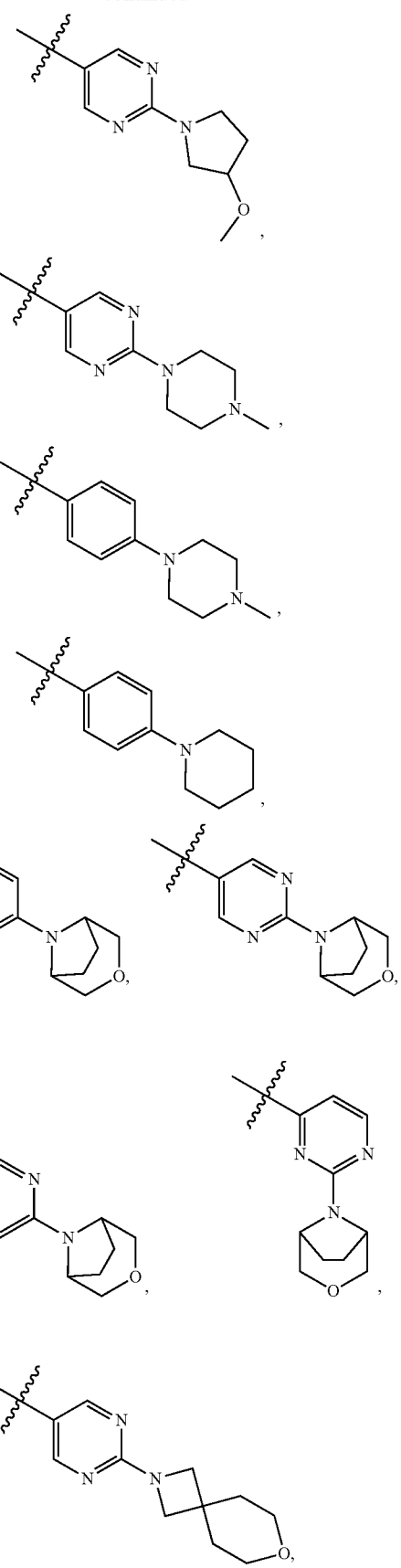

-continued
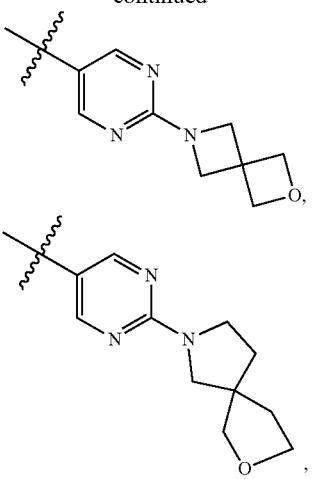
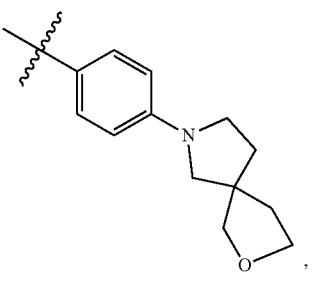
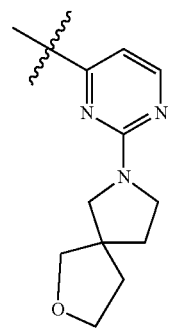, and 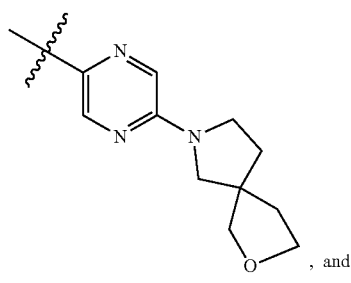
In some embodiments, R$_2$ of compounds of formula (I-C) disclosed herein is selected from:
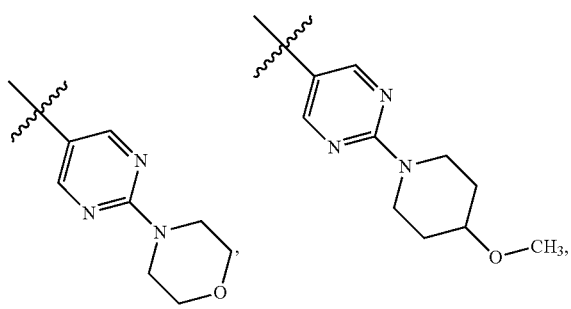
-continued
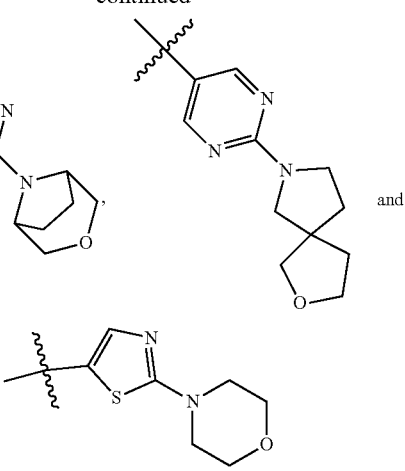
In some embodiments, a compound of the instant disclosure includes a compound of formula (I-C), an analog, an isomer, a pharmaceutically acceptable salt, and/or a prodrug thereof, wherein R$_1$ is selected from:
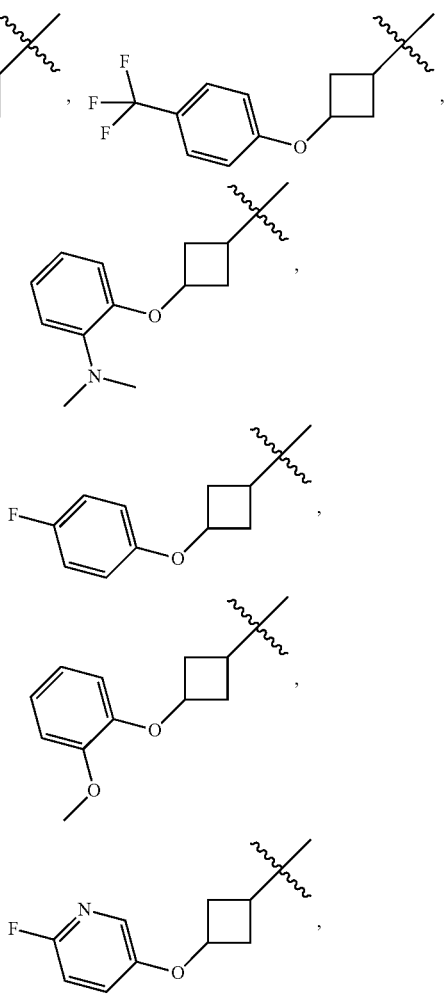

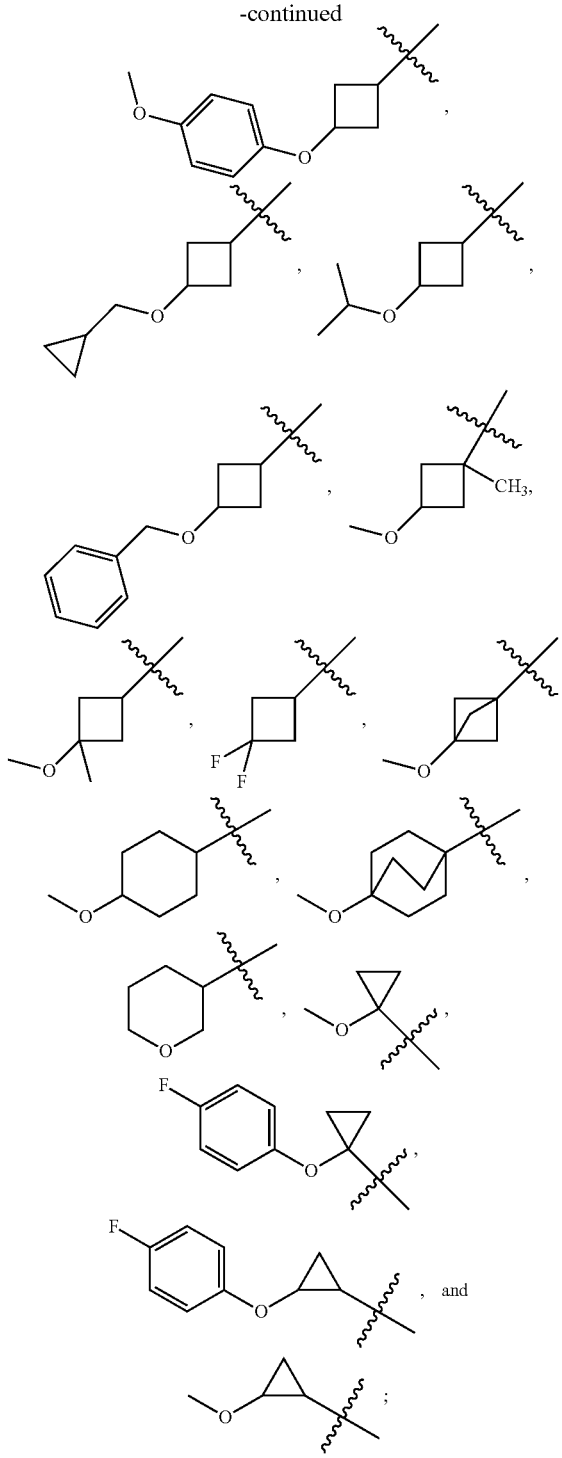
R is selected from:
—CH₃.
—CH₃, 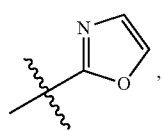, 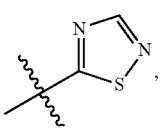,
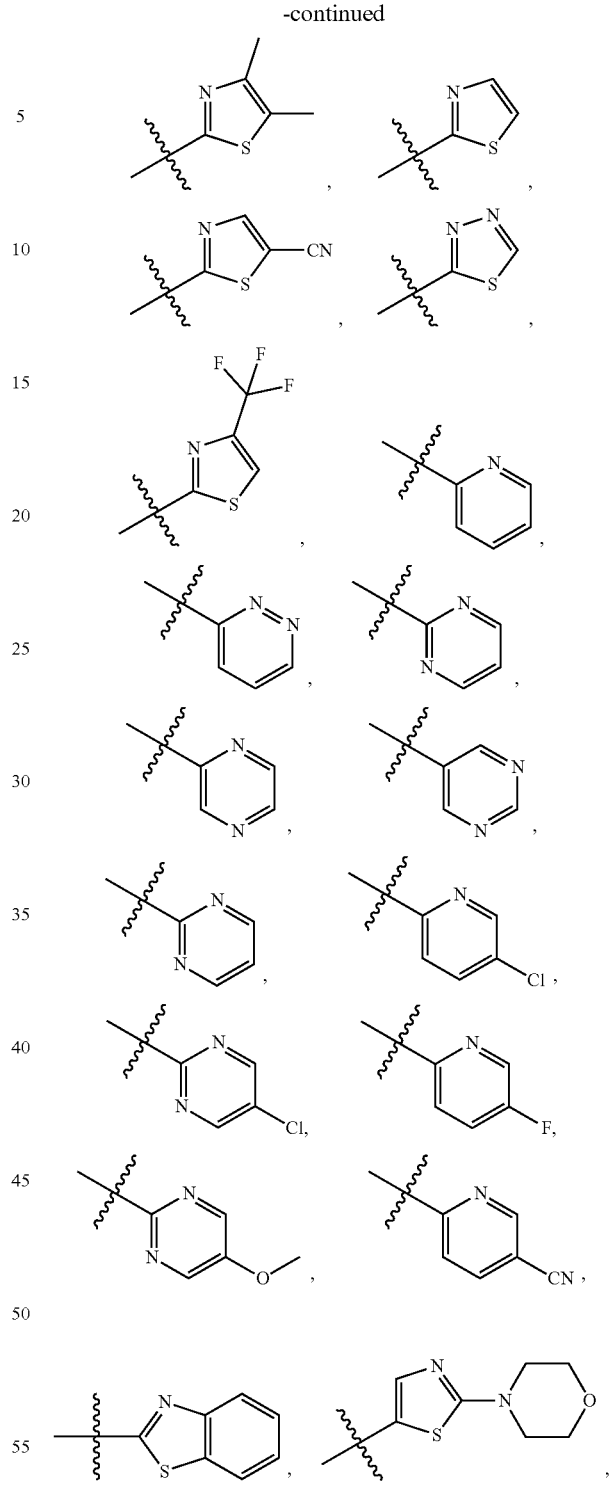
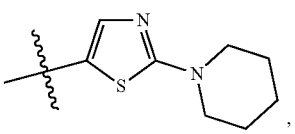, 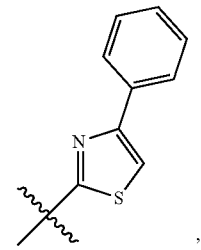

135
-continued
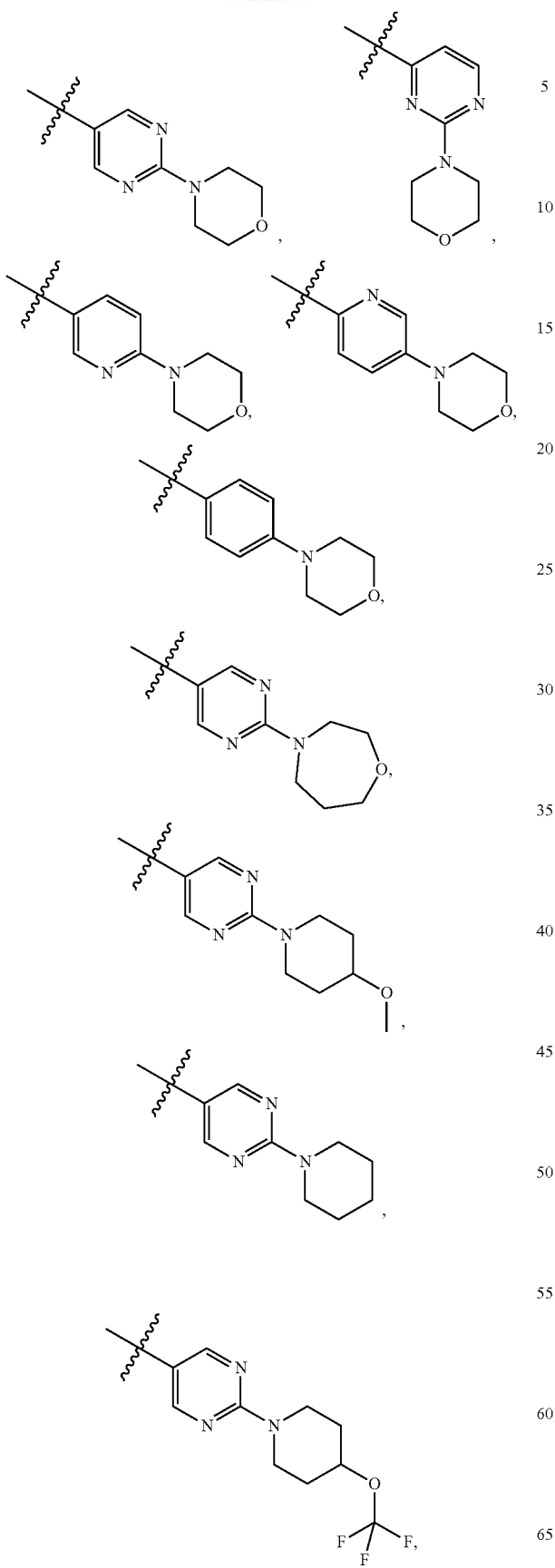
136
-continued
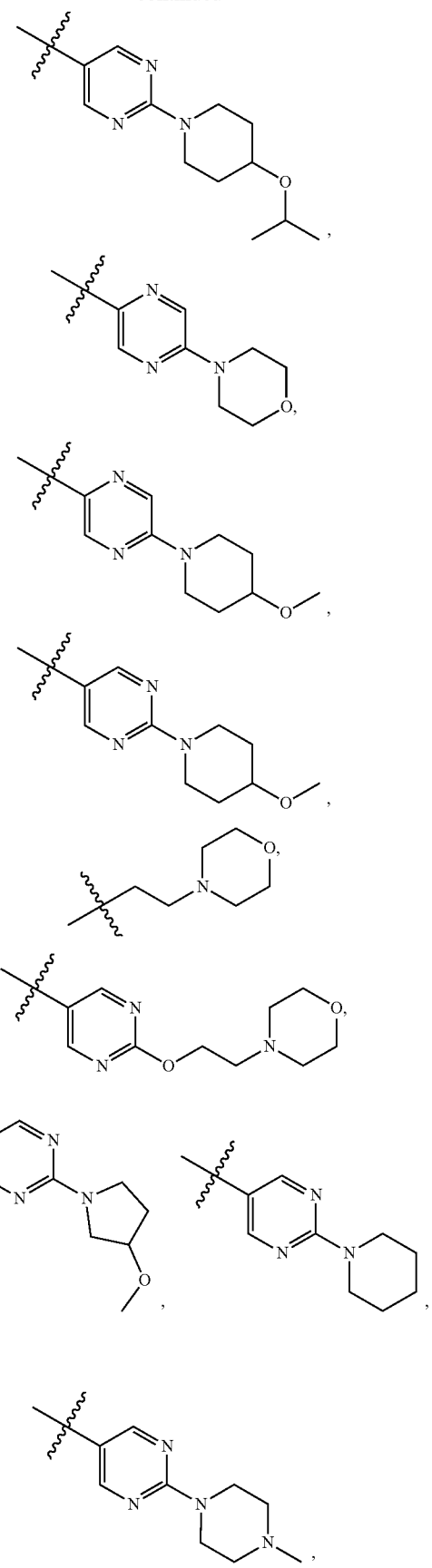

137
-continued

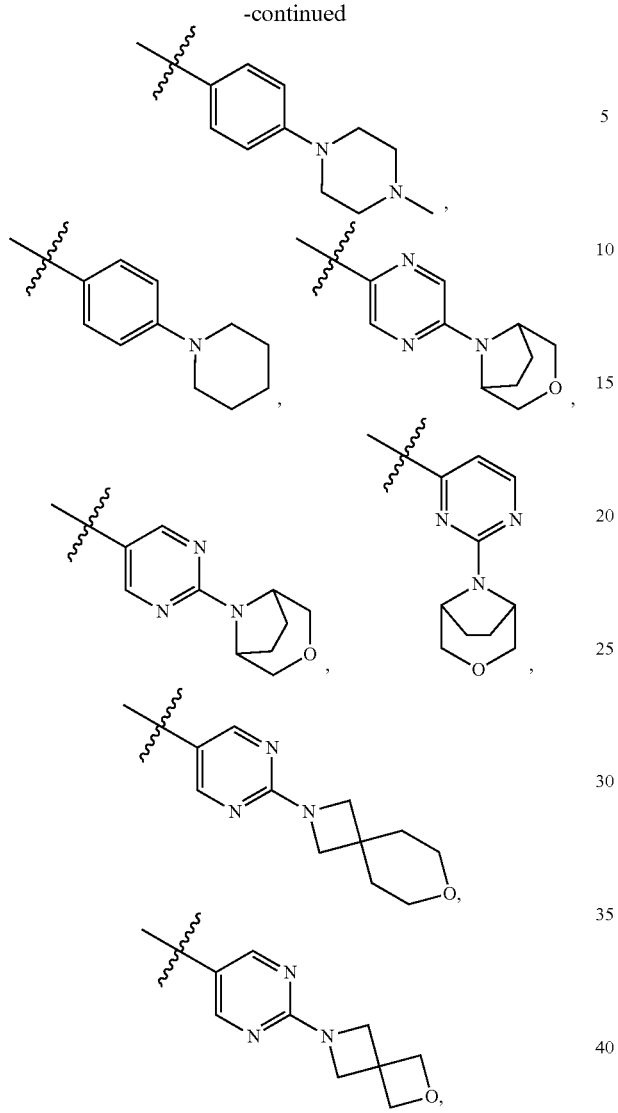

138
-continued

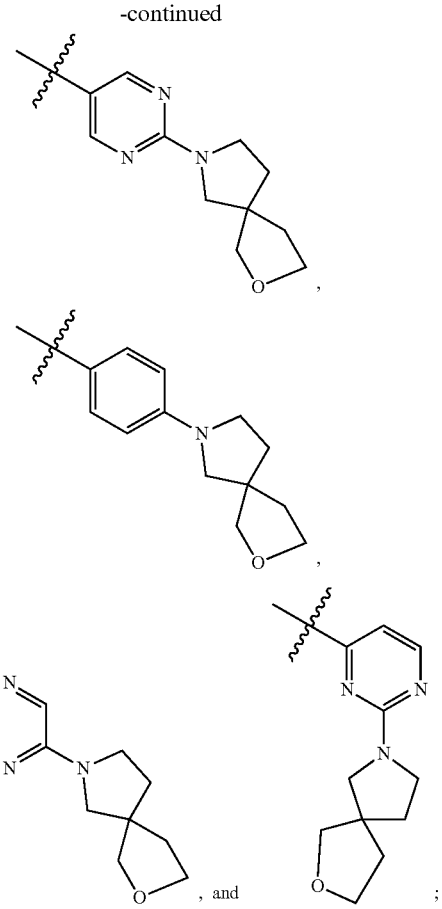

R₃ is selected from H and CH₃; and R₄ is selected from H and F.

In certain embodiments, compounds of formula (I-C) can have R₁, R₂, R₃, and/or R₄ as indicated in Table 11. In other embodiments, compounds of the present disclosure can include any one of the compounds provided in Table 11.

TABLE 11

Compounds B1-B118

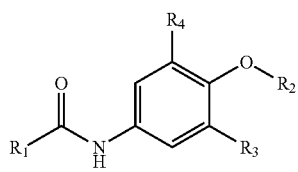

| Compound | R₁ | R₂ | R₃ | R₄ | Name |
|---|---|---|---|---|---|
| B1 | | | —F | —H | N-(4-((5-chloropyrimidin-2-yl)oxy)-3-fluorophenyl)-3-(4-(trifluoromethyl)phenoxy)cyclobutane-1-carboxamide |

TABLE 11-continued

Compounds B1-B118

| Compound | R1 | R2 | R3 | R4 | Name |
|---|---|---|---|---|---|
| B2 | 4-(trifluoromethyl)phenoxy-cyclobutyl | 5-chloropyrimidin-2-yl | —CH₃ | —H | N-(4-((5-chloropyrimidin-2-yl)oxy)-3-methylphenyl)-3-(4-(trifluoromethyl)phenoxy)cyclobutane-1-carboxamide |
| B3 | 2-(dimethylamino)phenoxy-cyclobutyl | 5-chloropyrimidin-2-yl | —CH₃ | —H | N-(4-((5-chloropyrimidin-2-yl)oxy)-3-methylphenyl)-3-(2-(dimethylamino)phenoxy)cyclobutane-1-carboxamide |
| B4 | 4-fluorophenoxy-cyclobutyl | thiazol-2-yl | —CH₃ | —H | 3-(4-fluorophenoxy)-N-(3-methyl-4-(thiazol-2-yloxy)phenyl)cyclobutane-1-carboxamide |
| B5 | 4-fluorophenoxy-cyclobutyl | 5-fluoropyridin-2-yl | —CH₃ | —H | 3-(4-fluorophenoxy)-N-(4-((5-fluoropyridin-2-yl)oxy)-3-methylphenyl)cyclobutane-1-carboxamide |
| B6 | 4-fluorophenoxy-cyclobutyl | 5-cyanopyridin-2-yl | —CH₃ | —H | N-(4-((5-cyanopyridin-2-yl)oxy)-3-methylphenyl)-3-(4-fluorophenoxy)cyclobutane-1-carboxamide |
| B7 | 4-fluorophenoxy-cyclobutyl | 5-chloropyrimidin-2-yl | —CH₃ | —H | N-(4-((5-chloropyrimidin-2-yl)oxy)-3-methylphenyl)-3-(4-fluorophenoxy)cyclobutane-1-carboxamide |
| B8 | 2-methoxyphenoxy-cyclobutyl | thiazol-2-yl | —CH₃ | —H | 3-(2-methoxyphenoxy)-N-(3-methyl-4-(thiazol-2-yloxy)phenyl)cyclobutane-1-carboxamide |

TABLE 11-continued

Compounds B1-B118

| Compound | R₁ | R₂ | R₃ | R₄ | Name |
|---|---|---|---|---|---|
| B9 | 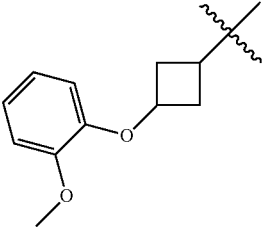 [SMILES: *C1CC(Oc2ccccc2OC)C1] | 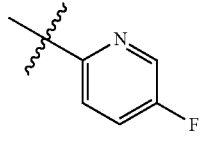 [SMILES: *c1ccc(F)cn1] | —CH₃ | —H | N-(4-((5-fluoropyridin-2-yl)oxy)-3-methylphenyl)-3-(2-methoxyphenoxy)cyclobutane-1-carboxamide |
| B10 | 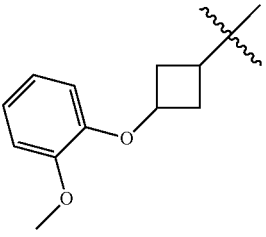 [SMILES: *C1CC(Oc2ccccc2OC)C1] | 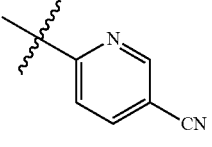 [SMILES: *c1ccc(C#N)cn1] | —CH₃ | —H | N-(4-((5-cyanopyridin-2-yl)oxy)-3-methylphenyl)-3-(2-methoxyphenoxy)cyclobutane-1-carboxamide |
| B11 | 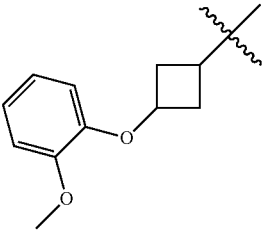 [SMILES: *C1CC(Oc2ccccc2OC)C1] | 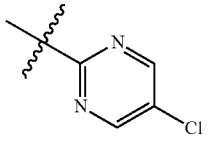 [SMILES: *c1ncc(Cl)cn1] | —CH₃ | —H | N-(4-((5-chloropyrimidin-2-yl)oxy)-3-methylphenyl)-3-(2-methoxyphenoxy)cyclobutane-1-carboxamide |
| B12 | 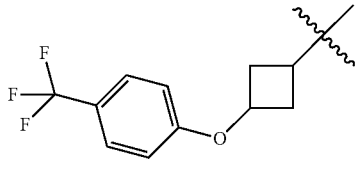 [SMILES: *C1CC(Oc2ccc(C(F)(F)F)cc2)C1] | 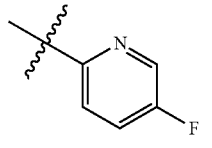 [SMILES: *c1ccc(F)cn1] | —CH₃ | —H | N-(4-((5-fluoropyridin-2-yl)oxy)-3-methylphenyl)-3-(4-(trifluoromethyl)phenoxy)cyclobutane-1-carboxamide |
| B13 | 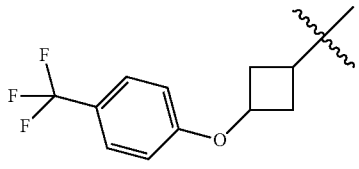 [SMILES: *C1CC(Oc2ccc(C(F)(F)F)cc2)C1] | 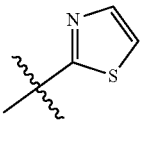 [SMILES: *c1nccs1] | —CH₃ | —H | N-(3-methyl-4-(thiazol-2-yloxy)phenyl)-3-(4-(trifluoromethyl)phenoxy)cyclobutane-1-carboxamide |
| B14 | 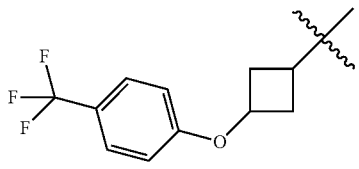 [SMILES: *C1CC(Oc2ccc(C(F)(F)F)cc2)C1] | 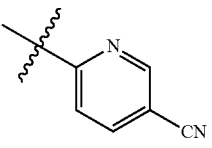 [SMILES: *c1ccc(C#N)cn1] | —CH₃ | —H | N-(4-((5-cyanopyridin-2-yl)oxy)-3-methylphenyl)-3-(4-(trifluoromethyl)phenoxy)cyclobutane-1-carboxamide |

TABLE 11-continued

Compounds B1-B118

| Compound | R₁ | R₂ | R₃ | R₄ | Name |
|---|---|---|---|---|---|
| B15 | 4-fluorophenoxy-cyclobutyl | benzo[d]thiazol-2-yl | —CH₃ | —H | N-(4-(benzo[d]thiazol-2-yloxy)-3-methylphenyl)-3-(4-fluorophenoxy)cyclobutane-1-carboxamide |
| B16 | 4-fluorophenoxy-cyclobutyl | 4-phenylthiazol-2-yl | —CH₃ | —H | 3-(4-fluorophenoxy)-N-(3-methyl-4-((4-phenylthiazol-2-yl)oxy)phenyl)cyclobutane-1-carboxamide |
| B17 | 4-fluorophenoxy-cyclobutyl | 5-cyanothiazol-2-yl | —CH₃ | —H | N-(4-((5-cyanothiazol-2-yl)oxy)-3-methylphenyl)-3-(4-fluorophenoxy)cyclobutane-1-carboxamide |
| B18 | 4-fluorophenoxy-cyclobutyl | 1,3,4-thiadiazol-2-yl | —CH₃ | —H | N-(4-((1,3,4-thiadiazol-2-yl)oxy)-3-methylphenyl)-3-(4-fluorophenoxy)cyclobutane-1-carboxamide |
| B19 | 3-methoxycyclobutyl | 2-morpholinopyrimidin-5-yl | —CH₃ | —H | 3-Methoxy-N-(3-methyl-4-((2-morpholinopyrimidin-5-yl)oxy)phenyl)cyclobutane-1-carboxamide |
| B20 | 3-methoxycyclobutyl | benzo[d]thiazol-2-yl | —CH₃ | —H | N-(4-(benzo[d]thiazol-2-yloxy)-3-methylphenyl)-3-methoxycyclobutane-1-carboxamide |

TABLE 11-continued

Compounds B1-B118

| Compound | R₁ | R₂ | R₃ | R₄ | Name |
|---|---|---|---|---|---|
| B21 | 4-fluorophenoxy-cyclobutyl | 4-(trifluoromethyl)thiazol-2-yl | —CH₃ | —H | 3-(4-fluorophenoxy)-N-(3-methyl-4-((4-(trifluoromethyl)thiazol-2-yl)oxy)phenyl)cyclobutane-1-carboxamide |
| B22 | 4-fluorophenoxy-cyclobutyl | pyrazin-2-yl | —CH₃ | —H | 3-(4-fluorophenoxy)-N-(3-methyl-4-(pyrazin-2-yloxy)phenyl)cyclobutane-1-carboxamide |
| B23 | 3-methoxycyclobutyl | 5-chloropyridin-2-yl | —CH₃ | —H | N-(4-((5-chloropyridin-2-yl)oxy)-3-methylphenyl)-3-methoxycyclobutane-1-carboxamide |
| B24 | 3-methoxycyclobutyl | 5-chloropyrimidin-2-yl | —CH₃ | —H | N-(4-((5-chloropyrimidin-2-yl)oxy)-3-methylphenyl)-3-methoxycyclobutane-1-carboxamide |
| B25 | 3-methoxycyclobutyl | 2-(2-oxa-6-azaspiro[3.3]heptan-6-yl)pyrimidin-5-yl | —CH₃ | —H | N-(4-((2-(2-oxa-6-azaspiro[3.3]heptan-6-yl)pyrimidin-5-yl)oxy)-3-methylphenyl)-3-methoxycyclobutane-1-carboxamide |
| B26 | 4-fluorophenoxy-cyclobutyl | 1,2,4-thiadiazol-5-yl | —CH₃ | —H | N-(4-((1,2,4-thiadiazol-5-yl)oxy)-3-methylphenyl)-3-(4-fluorophenoxy)cyclobutane-1-carboxamide |
| B27 | (6-fluoropyridin-3-yl)oxy-cyclobutyl | 1,3,4-thiadiazol-2-yl | —CH₃ | —H | N-(4-((1,3,4-thiadiazol-2-yl)oxy)-3-methylphenyl)-3-((6-fluoropyridin-3-yl)oxy)cyclobutane-1-carboxamide |

TABLE 11-continued

Compounds B1-B118

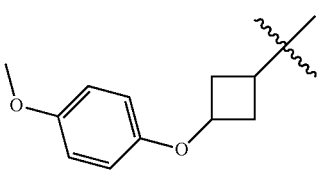 [SMILES: *C1CC(Oc2ccc(OC)cc2)C1]

| Compound | R₁ | R₂ | R₃ | R₄ | Name |
|---|---|---|---|---|---|
| B28 | 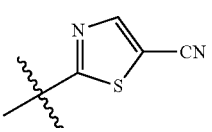 [SMILES: *c1ncc(C#N)s1] | 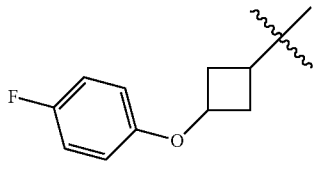 [SMILES: *C1CC(Oc2ccc(F)cc2)C1] | —CH₃ | —H | N-(4-((5-cyanothiazol-2-yl)oxy)-3-methylphenyl)-3-(4-methoxyphenoxy)cyclobutane-1-carboxamide |
| B29 | 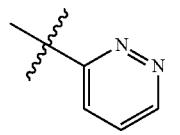 [SMILES: *c1cccnn1] | 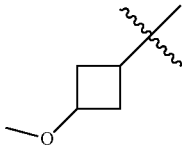 [SMILES: *C1CC(OC)C1] | —CH₃ | —H | 3-(4-fluorophenoxy)-N-(3-methyl-4-(pyridazin-3-yloxy)phenyl)cyclobutane-1-carboxamide |
| B30 | 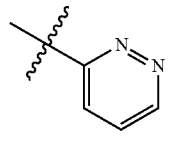 [SMILES: *c1cccnn1] | 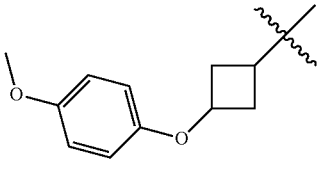 [SMILES: *C1CC(Oc2ccc(OC)cc2)C1] | —CH₃ | —H | 3-methoxy-N-(3-methyl-4-(pyridazin-3-yloxy)phenyl)cyclobutane-1-carboxamide |
| B31 | 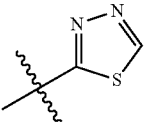 [SMILES: *c1nncs1] | 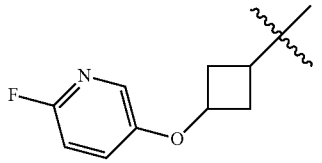 [SMILES: *C1CC(Oc2ccc(F)nc2)C1] | —CH₃ | —H | N-(4-((1,3,4-thiadiazol-2-yl)oxy)-3-methylphenyl)-3-(4-methoxyphenoxy)cyclobutane-1-carboxamide |
| B32 | 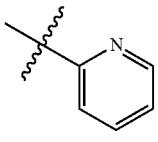 [SMILES: *c1ccccn1] | 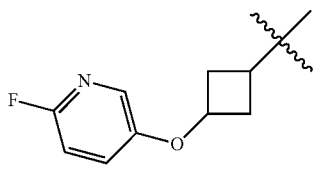 [SMILES: *C1CC(Oc2ccc(F)nc2)C1] | —CH₃ | —H | 3-((6-fluoropyridin-3-yl)oxy)-N-(3-methyl-4-(pyridin-2-yloxy)phenyl)cyclobutane-1-carboxamide |
| B33 | 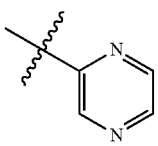 [SMILES: *c1cnccn1] | 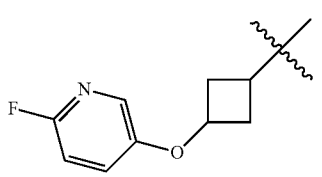 [SMILES: *C1CC(Oc2ccc(F)nc2)C1] | —CH₃ | —H | 3-((6-fluoropyridin-3-yl)oxy)-N-(3-methyl-4-(pyrazin-2-yloxy)phenyl)cyclobutane-1-carboxamide |
| B34 | 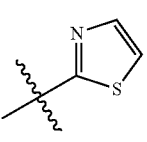 [SMILES: *c1nccs1] | | —CH₃ | —H | 3-((6-fluoropyridin-3-yl)oxy)-N-(3-methyl-4-(thiazol-2-yloxy)phenyl)cyclobutane-1-carboxamide |

TABLE 11-continued

Compounds B1-B118

| Compound | R1 | R2 | R3 | R4 | Name |
|---|---|---|---|---|---|
| B35 | 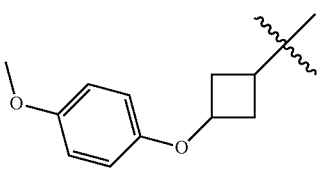 [SMILES: *C1CC(Oc2ccc(OC)cc2)C1] | 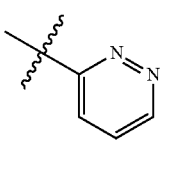 | —CH3 | —H | 3-(4-methoxyphenoxy)-N-(3-methyl-4-(pyridazin-3-yloxy)phenyl)cyclobutane-1-carboxamide |
| B36 | 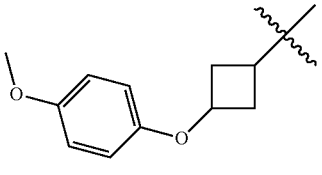 [SMILES: *C1CC(Oc2ccc(OC)cc2)C1] | 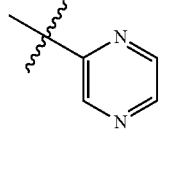 [SMILES: *c1cnccn1] | —CH3 | —H | 3-(4-methoxyphenoxy)-N-(3-methyl-4-(pyrazin-2-yloxy)phenyl)cyclobutane-1-carboxamide |
| B37 | 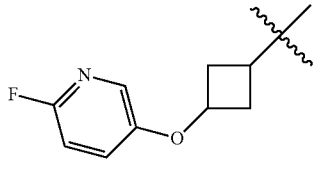 [SMILES: *C1CC(Oc2ccc(F)nc2)C1] | 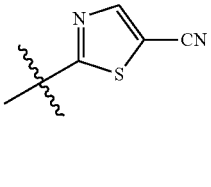 [SMILES: *c1ncc(C#N)s1] | —CH3 | —H | N-(4-((5-cyanothiazol-2-yl)oxy)-3-methylphenyl)-3-((6-fluoropyridin-3-yl)oxy)cyclobutane-1-carboxamide |
| B38 | 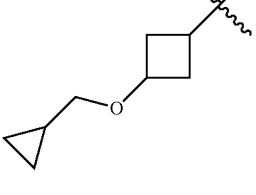 | 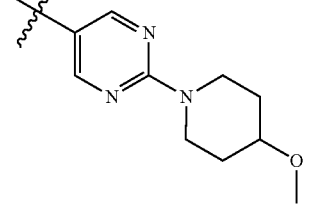 | —CH3 | —H | 3-(cyclopropylmethoxy)-N-(4-((2-(4-methoxypiperidin-1-yl)pyrimidin-5-yl)oxy)-3-methylphenyl)cyclobutane-1-carboxamide |
| B39 | 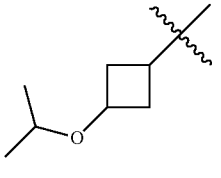 [SMILES: *C1CC(OC(C)C)C1] | 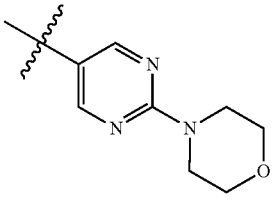 [SMILES: *c1cnc(N2CCOCC2)nc1] | —CH3 | —H | 3-isopropoxy-N-(3-methyl-4-((2-morpholinopyrimidin-5-yl)oxy)phenyl)cyclobutane-1-carboxamide |
| B40 | 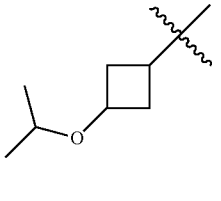 [SMILES: *C1CC(OC(C)C)C1] | 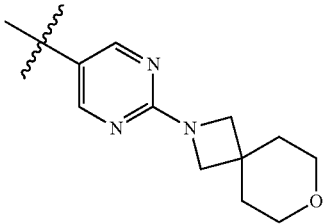 [SMILES: *c1cnc(N2CC3(CCOCC3)C2)nc1] | —CH3 | —H | N-(4-((2-(7-oxa-2-azaspiro[3.5]nonan-2-yl)pyrimidin-5-yl)oxy)-3-methylphenyl)-3-isopropoxycyclobutane-1-carboxamide |

TABLE 11-continued

Compounds B1-B118

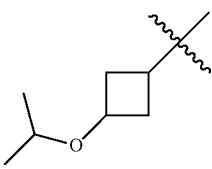 [SMILES: *C1CC(OC(C)C)C1]

| Compound | R₁ | R₂ | R₃ | R₄ | Name |
|---|---|---|---|---|---|
| B41 | 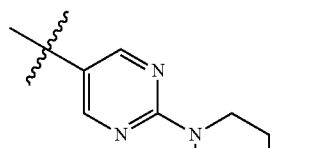 | 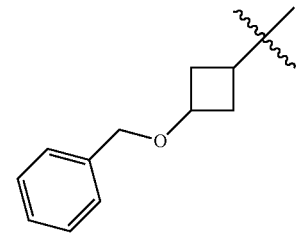 [SMILES: *C1CC(OCc2ccccc2)C1] | —CH₃ | —H | 3-isopropoxy-N-(4-((2-(4-methoxypiperidin-1-yl)pyrimidin-5-yl)oxy)-3-methylphenyl)cyclobutane-1-carboxamide |
| B42 | 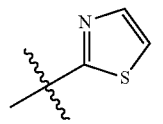 [SMILES: *c1nccs1] | 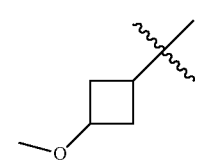 [SMILES: *C1CC(OC)C1] | —CH₃ | —H | 3-(benzyloxy)-N-(3-methyl-4-(thiazol-2-yloxy)phenyl)cyclobutane-1-carboxamide |
| B43 | 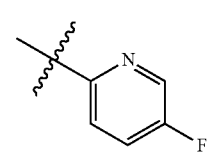 | 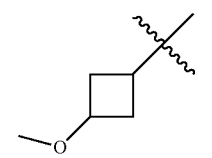 [SMILES: *C1CC(OC)C1] | —CH₃ | —H | N-(4-((5-fluoropyridin-2-yl)oxy)-3-methylphenyl)-3-methoxycyclobutane-1-carboxamide |
| B44 | 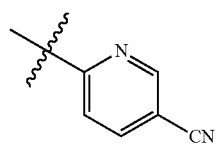 [SMILES: *c1ccc(C#N)cn1] | 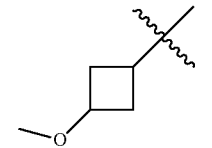 [SMILES: *C1CC(OC)C1] | —CH₃ | —H | N-(4-((5-cyanopyridin-2-yl)oxy)-3-methylphenyl)-3-methoxycyclobutane-1-carboxamide |
| B45 | 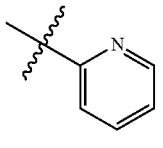 [SMILES: *c1ccccn1] | 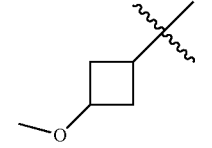 [SMILES: *C1CC(OC)C1] | —CH₃ | —H | 3-methoxy-N-(3-methyl-4-(pyridin-2-yloxy)phenyl)cyclobutane-1-carboxamide |
| B46 | 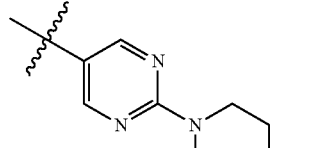 | | —CH₃ | —H | 3-methoxy-N-(4-((2-(4-methoxypiperidin-1-yl)pyrimidin-5-yl)oxy)-3-methylphenyl)cyclobutane-1-carboxamide |

TABLE 11-continued

Compounds B1-B118

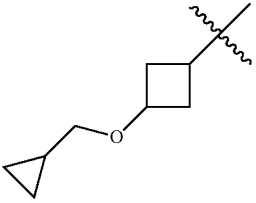 [SMILES: *C1CC(OCC2CC2)C1]

| Compound | R₁ | R₂ | R₃ | R₄ | Name |
|---|---|---|---|---|---|
| B47 | 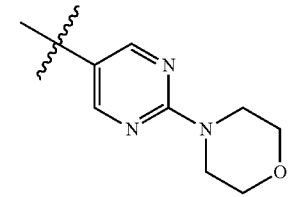 [SMILES: *c1cnc(N2CCOCC2)nc1] | 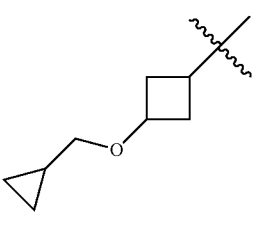 | —CH₃ | —H | 3-(cyclopropylmethoxy)-N-(3-methyl-4-((2-morpholino-pyrimidin-5-yl)oxy)phenyl)cyclobutane-1-carboxamide |
| B48 | 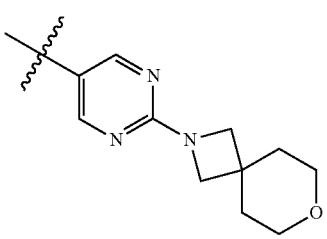 [SMILES: *c1cnc(N2CC3(CCOCC3)C2)nc1] | 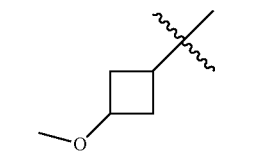 [SMILES: *C1CC(OC)C1] | —CH₃ | —H | N-(4-((2-(7-oxa-2-azaspiro[3.5]nonan-2-yl)pyrimidin-5-yl)oxy)-3-methylphenyl)-3-(cyclopropylmethoxy)cyclobutane-1-carboxamide |
| B49 | 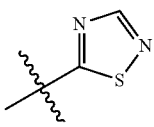 [SMILES: *c1ncns1] | 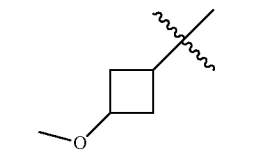 [SMILES: *C1CC(OC)C1] | —CH₃ | —H | N-(4-((1,2,4-thiadiazol-5-yl)oxy)-3-methylphenyl)-3-methoxycyclobutane-1-carboxamide |
| B50 | 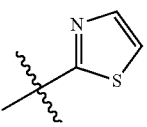 [SMILES: *c1nccs1] | 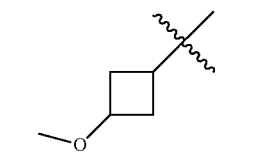 [SMILES: *C1CC(OC)C1] | —CH₃ | —H | 3-methoxy-N-(3-methyl-4-(thiazol-2-yloxy)phenyl)cyclobutane-1-carboxamide |
| B51 | 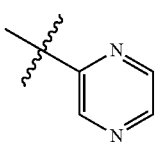 [SMILES: *c1cnccn1] | 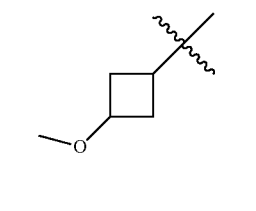 [SMILES: *C1CC(OC)C1] | —CH₃ | —H | 3-methoxy-N-(3-methyl-4-(pyrazin-2-yloxy)phenyl)cyclobutane-1-carboxamide |
| B52 | 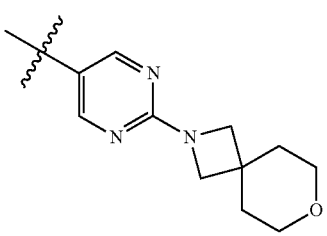 [SMILES: *c1cnc(N2CC3(CCOCC3)C2)nc1] | 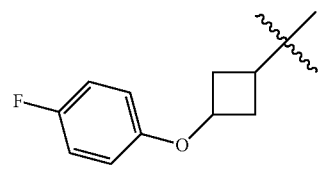 [SMILES: *C1CC(Oc2ccc(F)cc2)C1] | —CH₃ | —H | N-(4-((2-(7-oxa-2-azaspiro[3.5]nonan-2-yl)pyrimidin-5-yl)oxy)-3-methylphenyl)-3-methoxycyclobutane-1-carboxamide |
| B53 | 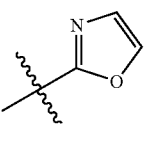 [SMILES: *c1ncco1] | | —CH₃ | —H | 3-(4-fluorophenoxy)-N-(3-methyl-4-(oxazol-2-yloxy)phenyl)cyclobutane-1-carboxamide |

TABLE 11-continued

Compounds B1-B118

| Compound | R₁ | R₂ | R₃ | R₄ | Name |
|---|---|---|---|---|---|
| B54 | 6-fluoropyridin-3-yloxy-cyclobutane | oxazol-2-yl | —CH₃ | —H | 3-((6-fluoropyridin-3-yl)oxy)-N-(3-methyl-4-(oxazol-2-yloxy)phenyl)cyclobutane-1-carboxamide |
| B55 | 3-methoxycyclobutane | 4,5-dimethylthiazol-2-yl | —CH₃ | —H | N-(4-((4,5-dimethylthiazol-2-yl)oxy)-3-methylphenyl)-3-methoxycyclobutane-1-carboxamide |
| B56 | 3-methoxycyclobutane | 5-(trifluoromethyl)thiazol-2-yl | —CH₃ | —H | 3-methoxy-N-(3-methyl-4-((5-(trifluoromethyl)thiazol-2-yl)oxy)phenyl)cyclobutane-1-carboxamide |
| B57 | 3-methoxycyclobutane | 5-cyanothiazol-2-yl | —CH₃ | —H | N-(4-((5-cyanothiazol-2-yl)oxy)-3-methylphenyl)-3-methoxycyclobutane-1-carboxamide |
| B58 | 3-methoxycyclobutane | 2-morpholinoethyl | —CH₃ | —H | 3-methoxy-N-(3-methyl-4-(2-morpholinoethoxy)phenyl)cyclobutane-1-carboxamide |
| B59 | 3-methoxycyclobutane | 4-morpholinophenyl | —CH₃ | —H | 3-methoxy-N-(3-methyl-4-(4-morpholinophenoxy)phenyl)cyclobutane-1-carboxamide |
| B60 | 3-methoxycyclobutane | 2-(2-morpholinoethoxy)pyrimidin-5-yl | —CH₃ | —H | 3-methoxy-N-(3-methyl-4-((2-(2-morpholinoethoxy)pyrimidin-5-yl)oxy)phenyl)cyclobutane-1-carboxamide |

TABLE 11-continued

Compounds B1-B118

| Compound | R₁ | R₂ | R₃ | R₄ | Name |
|---|---|---|---|---|---|
| B61 | (4-fluorophenoxy)cyclobutyl | 2-morpholinopyrimidin-5-yl | —CH₃ | —H | 3-(4-fluorophenoxy)-N-(3-methyl-4-((2-morpholinopyrimidin-5-yl)oxy)phenyl)cyclobutane-1-carboxamide |
| B62 | 3-methoxycyclobutyl | 2-(3-methoxypyrrolidin-1-yl)pyrimidin-5-yl | —CH₃ | —H | 3-methoxy-N-(4-((2-(3-methoxypyrrolidin-1-yl)pyrimidin-5-yl)oxy)-3-methylphenyl)cyclobutane-1-carboxamide |
| B63 | 3-methoxycyclobutyl | 5-morpholinopyridin-2-yl | —CH₃ | —H | 3-methoxy-N-(3-methyl-4-((5-morpholinopyridin-2-yl)oxy)phenyl)cyclobutane-1-carboxamide |
| B64 | 3-methoxycyclobutyl | 2-(piperidin-1-yl)pyrimidin-5-yl | —CH₃ | —H | 3-methoxy-N-(3-methyl-4-((2-(piperidin-1-yl)pyrimidin-5-yl)oxy)phenyl)cyclobutane-1-carboxamide |
| B65 | 3-methoxycyclobutyl | 5-morpholinopyrazin-2-yl | —CH₃ | —H | 3-methoxy-N-(3-methyl-4-((5-morpholinopyrazin-2-yl)oxy)phenyl)cyclobutane-1-carboxamide |
| B66 | 3-methoxycyclobutyl | 5-(4-methoxypiperidin-1-yl)pyrazin-2-yl | —CH₃ | —H | 3-methoxy-N-(4-((5-(4-methoxypiperidin-1-yl)pyrazin-2-yl)oxy)-3-methylphenyl)cyclobutane-1-carboxamide |

TABLE 11-continued

Compounds B1-B118

| Compound | R₁ | R₂ | R₃ | R₄ | Name |
|---|---|---|---|---|---|
| B67 | 4-fluorophenoxy-cyclobutyl | pyrimidin-5-yl | —CH₃ | —H | 3-(4-fluorophenoxy)-N-(3-methyl-4-(pyrimidin-5-yloxy)phenyl)cyclobutane-1-carboxamide |
| B68 | 2-methoxyphenoxy-cyclobutyl | pyrimidin-5-yl | —CH₃ | —H | 3-(2-methoxyphenoxy)-N-(3-methyl-4-(pyrimidin-5-yloxy)phenyl)cyclobutane-1-carboxamide |
| B69 | 3-methoxycyclobutyl | 5-methoxypyrimidin-2-yl | —CH₃ | —H | 3-methoxy-N-(4-((5-methoxypyrimidin-2-yl)oxy)-3-methylphenyl)cyclobutane-1-carboxamide |
| B70 | 3-methoxycyclobutyl | 5-(3-oxa-8-azabicyclo[3.2.1]octan-8-yl)pyrazin-2-yl | —CH₃ | —H | N-(4-((5-(3-oxa-8-azabicyclo[3.2.1]octan-8-yl)pyrazin-2-yl)oxy)-3-methylphenyl)-3-methoxycyclobutane-1-carboxamide |
| B71 | 3-methoxycyclobutyl | 2-morpholinothiazol-5-yl | —CH₃ | —H | 3-Methoxy-N-(3-methyl-4-((2-morpholinothiazol-5-yl)oxy)phenyl)cyclobutane-carboxamide |
| B72 | 3-methoxycyclobutyl | 2-(3-oxa-8-azabicyclo[3.2.1]octan-8-yl)pyrimidin-5-yl | —CH₃ | —H | N-(4-((2-(3-oxa-8-azabicyclo[3.2.1]octan-8-yl)pyrimidin-5-yl)oxy)-3-methylphenyl)-3-methoxycyclobutane-1-carboxamide |
| B73 | 4-fluorophenoxy-cyclobutyl | —CH₃ | —CH₃ | —H | 3-(4-fluorophenoxy)-N-(4-methoxy-3-methylphenyl)cyclobutane-1-carboxamide |

TABLE 11-continued

Compounds B1-B118

| Compound | R₁ | R₂ | R₃ | R₄ | Name |
|---|---|---|---|---|---|
| B74 | 3-methoxycyclobutyl | 5-(2-(2-oxa-7-azaspiro[4.4]nonan-7-yl)pyrimidinyl) | —CH₃ | —H | N-(4-((2-(2-oxa-7-azaspiro[4.4]nonan-7-yl)pyrimidin-5-yl)oxy)-3-methylphenyl)-3-methoxycyclobutane-1-carboxamide |
| B75 | 3-methoxycyclobutyl | 5-(2-(1,4-oxazepan-4-yl)pyrimidinyl) | —CH₃ | —H | N-(4-((2-(1,4-oxazepan-4-yl)pyrimidin-5-yl)oxy)-3-methylphenyl)-3-methoxycyclobutane-1-carboxamide |
| B76 | 3-methoxycyclobutyl | 4-(2-oxa-7-azaspiro[4.4]nonan-7-yl)phenyl | —CH₃ | —H | N-(4-(4-(2-oxa-7-azaspiro[4.4]nonan-7-yl)phenoxy)-3-methylphenyl)-3-methoxycyclobutane-1-carboxamide |
| B77 | 3-methoxycyclobutyl | 5-(2-(4-(trifluoromethoxy)piperidin-1-yl)pyrimidinyl) | —CH₃ | —H | 3-methoxy-N-(3-methyl-4-((2-(4-(trifluoromethoxy)piperidin-1-yl)pyrimidin-5-yl)oxy)phenyl)cyclobutane-1-carboxamide |
| B78 | 3-methoxycyclobutyl | 5-(2-(4-isopropoxypiperidin-1-yl)pyrimidinyl) | —CH₃ | —H | N-(4-((2-(4-isopropoxypiperidin-1-yl)pyrimidin-5-yl)oxy)-3-methylphenyl)-3-methoxycyclobutane-1-carboxamide |

TABLE 11-continued

Compounds B1-B118

| Compound | R₁ | R₂ | R₃ | R₄ | Name |
|---|---|---|---|---|---|
| B79 | methoxycyclobutyl | 5-(2-oxa-7-azaspiro[4.4]nonan-7-yl)pyrazin-2-yl | —CH₃ | —H | N-(4-((5-(2-oxa-7-azaspiro[4.4]nonan-7-yl)pyrazin-2-yl)oxy)-3-methylphenyl)-3-methoxycyclobutane-1-carboxamide |
| B80 | methoxycyclobutyl | 2-morpholinopyrimidin-4-yl | —CH₃ | —H | 3-methoxy-N-(3-methyl-4-((2-morpholinopyrimidin-4-yl)oxy)phenyl)cyclobutane-1-carboxamide |
| B81 | methoxycyclobutyl | 2-((1R,5S)-3-oxa-8-azabicyclo[3.2.1]octan-8-yl)pyrimidin-4-yl | —CH₃ | —H | N-(4-((2-((1R,5S)-3-oxa-8-azabicyclo[3.2.1]octan-8-yl)pyrimidin-4-yl)oxy)-3-methylphenyl)-3-methoxycyclobutane-1-carboxamide |
| B82 | methoxycyclobutyl | 2-(2-oxa-7-azaspiro[4.4]nonan-7-yl)pyrimidin-4-yl | —CH₃ | —H | N-(4-((2-(2-oxa-7-azaspiro[4.4]nonan-7-yl)pyrimidin-4-yl)oxy)-3-methylphenyl)-3-methoxycyclobutane-1-carboxamide |
| B83 | methoxycyclobutyl | 2-(piperidin-1-yl)pyrimidin-5-yl | —CH₃ | —F | N-(3-fluoro-5-methyl-4-((2-(piperidin-1-yl)pyrimidin-5-yl)oxy)phenyl)-3-methoxycyclobutane-1-carboxamide |

TABLE 11-continued

Compounds B1-B118

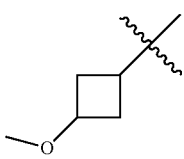 [SMILES: *C1CC(OC)C1]

| Compound | R1 | R2 | R3 | R4 | Name |
|---|---|---|---|---|---|
| B84 | 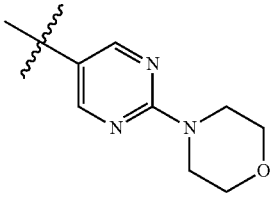 [SMILES: *c1cnc(N2CCOCC2)nc1] | 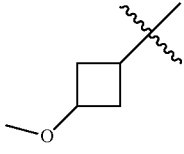 [SMILES: *C1CC(OC)C1] | —CH3 | —F | N-(3-fluoro-5-methyl-4-((2-morpholinopyrimidin-5-yl)oxy)phenyl)-3-methoxycyclobutane-1-carboxamide |
| B85 | 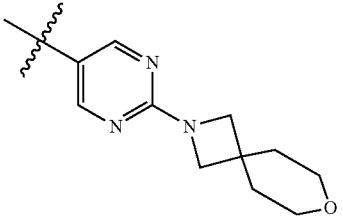 [SMILES: *c1cnc(N2CC3(CCOCC3)C2)nc1] | 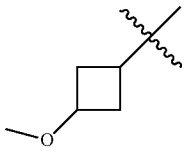 [SMILES: *C1CC(OC)C1] | —CH3 | —F | N-(4-((2-(7-oxa-2-azaspiro[3.5]nonan-2-yl)pyrimidin-5-yl)oxy)-3-fluoro-5-methylphenyl)-3-methoxycyclobutane-1-carboxamide |
| B86 | 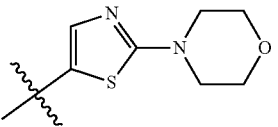 | 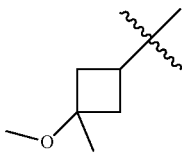 [SMILES: *C1CC(C)(OC)C1] | —CH3 | —F | N-(3-fluoro-5-methyl-4-((5-morpholinothiazol-2-yl)oxy)phenyl)-3-methoxycyclobutane-1-carboxamide |
| B87 | 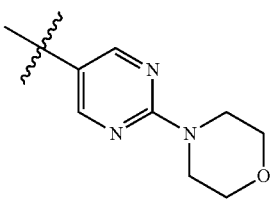 [SMILES: *c1cnc(N2CCOCC2)nc1] | 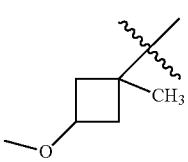 | —CH3 | —H | 3-methoxy-3-methyl-N-(3-methyl-4-((2-morpholinopyrimidin-5-yl)oxy)phenyl)cyclobutane-1-carboxamide |
| B88 | 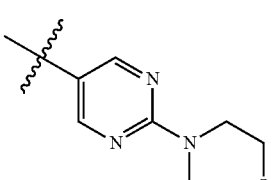 | 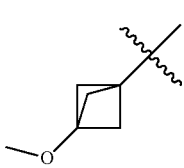 [SMILES: *C12CC(OC)(C1)C2] | —CH3 | —H | 3-methoxy-1-methyl-N-(3-methyl-4-((2-morpholinopyrimidin-5-yl)oxy)phenyl)cyclobutane-1-carboxamide |
| B89 | 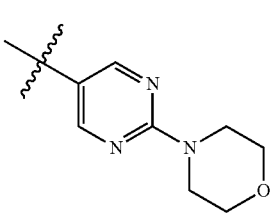 [SMILES: *c1cnc(N2CCOCC2)nc1] | 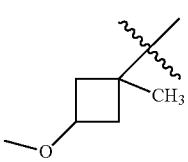 | —CH3 | —H | 3-Methoxy-N-(3-methyl-4-((2-morpholinopyrimidin-5-yl)oxy)phenyl)bicyclo[1.1.1]pentane-1-carboxamide |

TABLE 11-continued

Compounds B1-B118

| Compound | R₁ | R₂ | R₃ | R₄ | Name |
|---|---|---|---|---|---|
| B90 | methoxybicyclo[1.1.1]pentanyl | 2-morpholinopyrimidin-5-yl | —H | —F | N-(3-fluoro-4-((2-morpholino-pyrimidin-5-yl)oxy)phenyl)-3-methoxybicyclo[1.1.1]pentane-1-carboxamide |
| B91 | methoxybicyclo[1.1.1]pentanyl | 2-morpholinothiazol-5-yl | —CH₃ | —H | 3-methoxy-N-(3-methyl-4-((2-morpholinothiazol-5-yl)oxy)phenyl)bicyclo[1.1.1]pentane-1-carboxamide |
| B92 | 4-methoxycyclohexyl | thiazol-2-yl | —CH₃ | —H | 4-methoxy-N-(3-methyl-4-(thiazol-2-yloxy)phenyl)cyclohexane-1-carboxamide |
| B93 | 3,3-difluorocyclobutyl | 2-(4-methoxypiperidin-1-yl)pyrimidin-5-yl | —CH₃ | —H | 3,3-difluoro-N-(4-((2-(4-methoxypiperidin-1-yl)pyrimidin-5-yl)oxy)-3-methylphenyl)cyclobutane-1-carboxamide |
| B94 | 3,3-difluorocyclobutyl | 2-morpholinopyrimidin-5-yl | —CH₃ | —H | 3,3-difluoro-N-(3-methyl-4-((2-morpholinopyrimidin-5-yl)oxy)phenyl)cyclobutane-1-carboxamide |
| B95 | 4-methoxybicyclo[2.2.2]octanyl | 2-morpholinopyrimidin-5-yl | —CH₃ | —H | 4-methoxy-N-(3-methyl-4-((2-morpholinopyrimidin-5-yl)oxy)phenyl)bicyclo[2.2.2]octane-1-carboxamide |
| B96 | 4-methoxybicyclo[2.2.2]octanyl | 2-(4-methoxypiperidin-1-yl)pyrimidin-5-yl | —CH₃ | —H | 4-methoxy-N-(4-((2-(4-methoxypiperidin-1-yl)pyrimidin-5-yl)oxy)-3-methylphenyl)bicyclo[2.2.2]octane-1-carboxamide |

TABLE 11-continued

Compounds B1-B118

| Compound | R₁ | R₂ | R₃ | R₄ | Name |
|---|---|---|---|---|---|
| B97 | 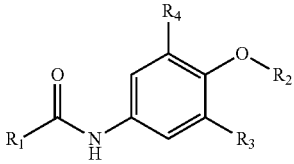 | 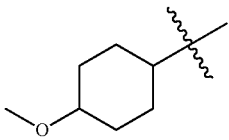 [SMILES: *C1CCC(OC)CC1] | —CH₃ | —H | 4-methoxy-N-(4-((2-(4-methoxypiperidin-1-yl)pyrimidin-5-yl)oxy)-3-methyl-phenyl)cyclohexane-1-carboxamide |
| B98 | 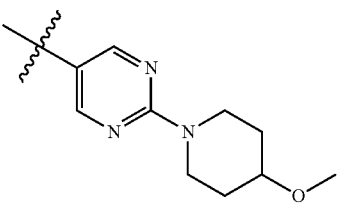 [SMILES: *c1cnc(N2CCC(OC)CC2)nc1] | 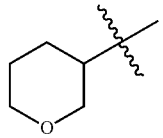 [SMILES: *C1CCCOC1] | —CH₃ | —H | N-(3-methyl-4-((2-morpholino-pyrimidin-5-yl)oxy)phenyl)tetrahydro-2H-pyran-3-carboxamide |
| B99 | 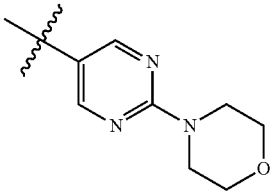 [SMILES: *c1cnc(N2CCOCC2)nc1] | 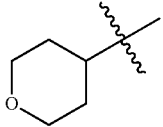 [SMILES: *C1CCOCC1] | —CH₃ | —H | N-(3-methyl-4-((2-morpholinopyrimidin-5-yl)oxy)phenyl)tetrahydro-2H-pyran-4-carboxamide |
| B100 | 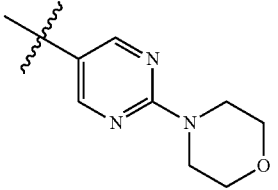 [SMILES: *c1cnc(N2CCOCC2)nc1] | 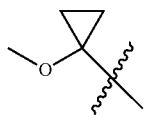 [SMILES: *C1(OC)CC1] | —CH₃ | —H | 1-methoxy-N-(3-methyl-4-((2-morpholinothiazol-5-yl)oxy)phenyl)cyclopropane-1-carboxamide |
| B101 | 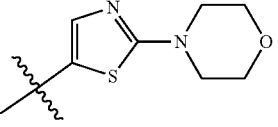 [SMILES: *c1cnc(N2CCOCC2)s1] | 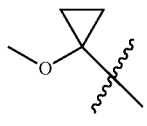 | —CH₃ | —H | 1-methoxy-N-(3-methyl-4-((2-(piperidin-1-yl)pyrimidin-5-yl)oxy)phenyl)cyclopropane-1-carboxamide |
| B102 | 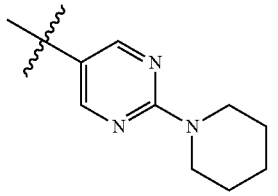 [SMILES: *c1cnc(N2CCCCC2)nc1] | 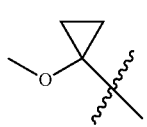 [SMILES: *C1(OC)CC1] | —CH₃ | —H | 1-methoxy-N-(3-methyl-4-((2-morpholinopyrimidin-5-yl)oxy)phenyl)cyclopropane-1-carboxamide |

TABLE 11-continued

Compounds B1-B118

| Compound | R₁ | R₂ | R₃ | R₄ | Name |
|---|---|---|---|---|---|
| B103 | (1-methoxycyclopropyl) | 5-(2-(4-methoxypiperidin-1-yl)pyrimidinyl) | —CH₃ | —H | 1-methoxy-N-(4-((2-(4-methoxypiperidin-1-yl)pyrimidin-5-yl)oxy)-3-methylphenyl)cyclopropane-1-carboxamide |
| B104 | (1-methoxycyclopropyl) | 5-(2-(3-oxa-8-azabicyclo[3.2.1]octan-8-yl)pyrimidinyl) | —CH₃ | —H | N-(4-((2-(3-oxa-8-azabicyclo[3.2.1]octan-8-yl)pyrimidin-5-yl)oxy)-3-methylphenyl)-1-methoxycyclopropane-1-carboxamide |
| B105 | (1-methoxycyclopropyl) | 2-(5-(3-oxa-8-azabicyclo[3.2.1]octan-8-yl)pyrazinyl) | —CH₃ | —H | N-(4-((5-(3-oxa-8-azabicyclo[3.2.1]octan-8-yl)pyrazin-2-yl)oxy)-3-methylphenyl)-1-methoxycyclopropane-1-carboxamide |
| B106 | (1-methoxycyclopropyl) | 4-morpholinophenyl | —CH₃ | —H | 1-methoxy-N-(3-methyl-4-(4-morpholinophenoxy)phenyl)cyclopropane-1-carboxamide |
| B107 | 1-(4-fluorophenoxy)cyclopropyl | 5-(2-morpholinopyrimidinyl) | —CH₃ | —H | 1-(4-fluorophenoxy)-N-(3-methyl-4-((2-morpholinopyrimidin-5-yl)oxy)phenyl)cyclopropane-1-carboxamide |
| B108 | 1-(4-fluorophenoxy)cyclopropyl | 5-(2-(piperidin-1-yl)pyrimidinyl) | —CH₃ | —H | 1-(4-fluorophenoxy)-N-(3-methyl-4-((2-(piperidin-1-yl)pyrimidin-5-yl)oxy)phenyl)cyclopropane-1-carboxamide |

TABLE 11-continued

Compounds B1-B118

| Compound | R₁ | R₂ | R₃ | R₄ | Name |
|---|---|---|---|---|---|
| B109 | 4-fluorophenoxy cyclopropyl | 5-chloropyridin-2-yl | —CH₃ | —H | N-(4-((5-chloropyridin-2-yl)oxy)-3-methylphenyl)-2-(4-fluorophenoxy)cyclopropane-1-carboxamide |
| B110 | 4-fluorophenoxy cyclopropyl | 5-chloropyrimidin-2-yl | —CH₃ | —H | N-(4-((5-chloropyrimidin-2-yl)oxy)-3-methylphenyl)-2-(4-fluorophenoxy)cyclopropane-1-carboxamide |
| B111 | 4-fluorophenoxy cyclopropyl | thiazol-2-yl | —CH₃ | —H | 2-(4-fluorophenoxy)-N-(3-methyl-4-(thiazol-2-yloxy)phenyl)cyclopropane-1-carboxamide |
| B112 | 4-fluorophenoxy cyclopropyl | pyrimidin-2-yl | —CH₃ | —H | 2-(4-fluorophenoxy)-N-(3-methyl-4-(pyrimidin-2-yloxy)phenyl)cyclopropane-1-carboxamide |
| B113 | 2-methoxycyclopropyl | 2-(piperidin-1-yl)thiazol-5-yl | —CH₃ | —H | 2-methoxy-N-(3-methyl-4-((2-(piperidin-1-yl)thiazol-5-yl)oxy)phenyl)cyclopropane-1-carboxamide |
| B114 | 2-methoxycyclopropyl | 2-morpholinothiazol-5-yl | —CH₃ | —H | 2-methoxy-N-(3-methyl-4-((2-morpholinothiazol-5-yl)oxy)phenyl)cyclopropane-1-carboxamide |
| B115 | 2-methoxycyclopropyl | 2-morpholinopyrimidin-5-yl | —CH₃ | —H | 2-methoxy-N-(3-methyl-4-((2-morpholinopyrimidin-5-yl)oxy)phenyl)cyclopropane-1-carboxamide |
| B116 | 2-methoxycyclopropyl | 2-(piperidin-1-yl)pyrimidin-5-yl | —CH₃ | —H | 2-methoxy-N-(3-methyl-4-((2-(piperidin-1-yl)pyrimidin-5-yl)oxy)phenyl)cyclopropane-1-carboxamide |

TABLE 11-continued

Compounds B1-B118

| Compound | R₁ | R₂ | R₃ | R₄ | Name |
|---|---|---|---|---|---|
| B117 | | | —CH₃ | —H | N-(4-((2-(2-oxa-7-azaspiro[4.4]nonan-7-yl)pyrimidin-5-yl)oxy)-3-methylphenyl)-3-methoxybicyclo[1.1.1]pentane-1-carboxamide |
| B118 | | | —CH₃ | —H | N-(4-((2-(3-oxa-8-azabicyclo[3.2.1]octan-8-yl)pyrimidin-5-yl)oxy)-3-methylphenyl)-3-methoxybicyclo[1.1.1]pentane-1-carboxamide |

In some embodiments, a compound provided herein includes a compound according to formula (II-C), (II-C)

an analog, an isomer, a pharmaceutically acceptable salt, and/or a prodrug thereof and/or formulation thereof; where $R_5$ is selected from:

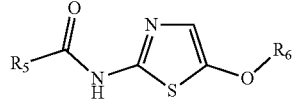
,
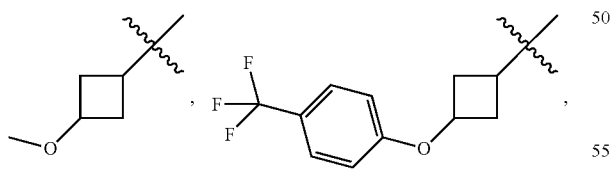
,

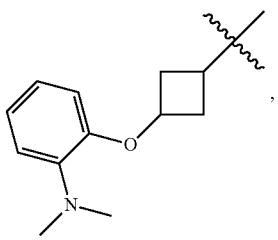
,

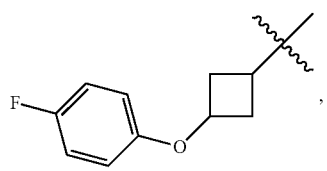
,

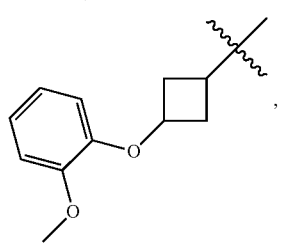
,

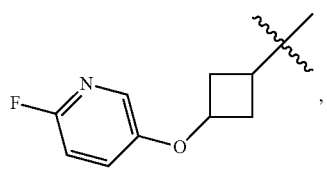
,

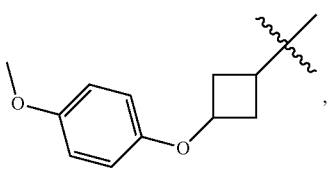
, and
R₆ is an alkyl, an aryl, and a heteroaryl, wherein the aryl and the heteroaryl are each independently unsubstituted or are optionally each independently substituted with one or more of an alkyl, alkenyl, alkynyl, alkoxyl, alkylsulfo, alkylamino, halogen, thiol, hydroxyl, nitro, cyano, cycloalkyl, heterocyclyl, heterocyclic alkyl, aryl, heteroaryl, cycloalkoxyl, heterocyclic alkoxyl, cycloalkylthio, or heterocyclic alkylthio.

In some embodiments, $R_5$ is selected from:

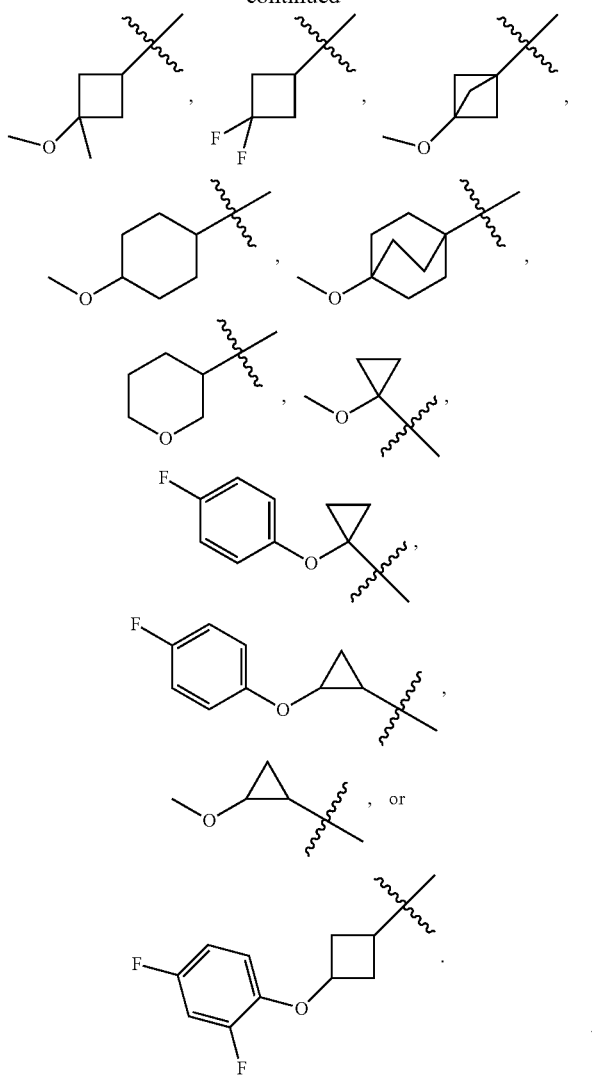
In some embodiments, $R_5$ is selected from:
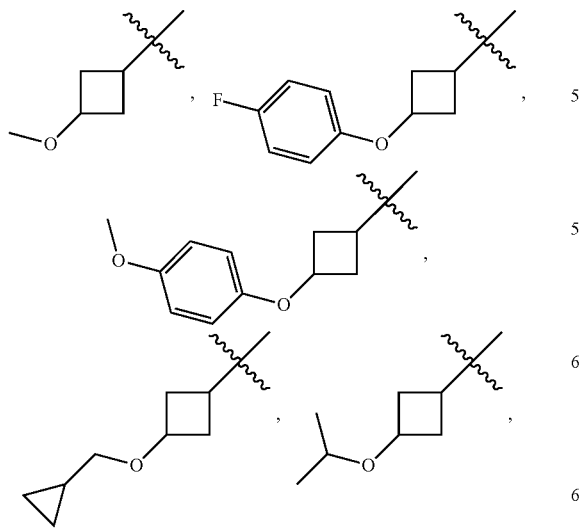
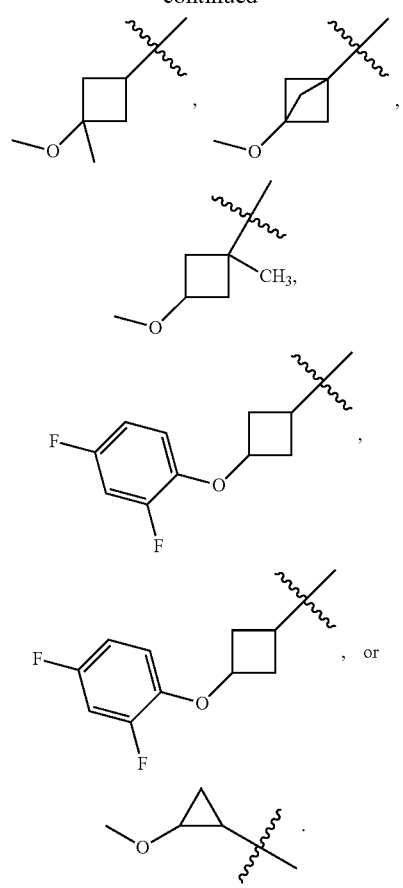
In some embodiments, $R_5$ is selected from:
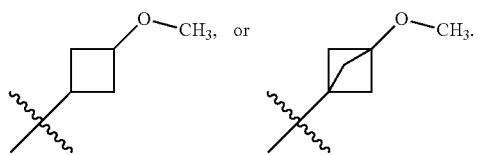 [SMILES: *C1CC(OC)C1 ; *C12CC(OC)(C1)C2]
In some embodiments, $R_6$ is selected from:
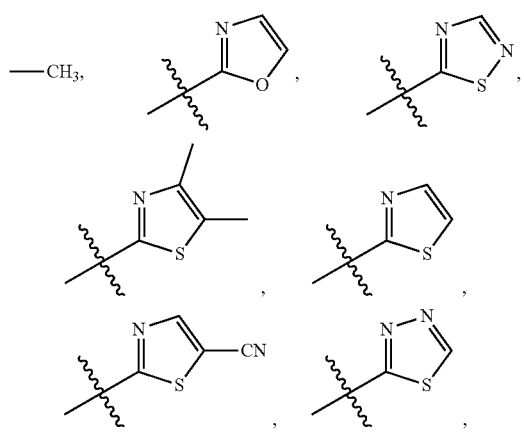

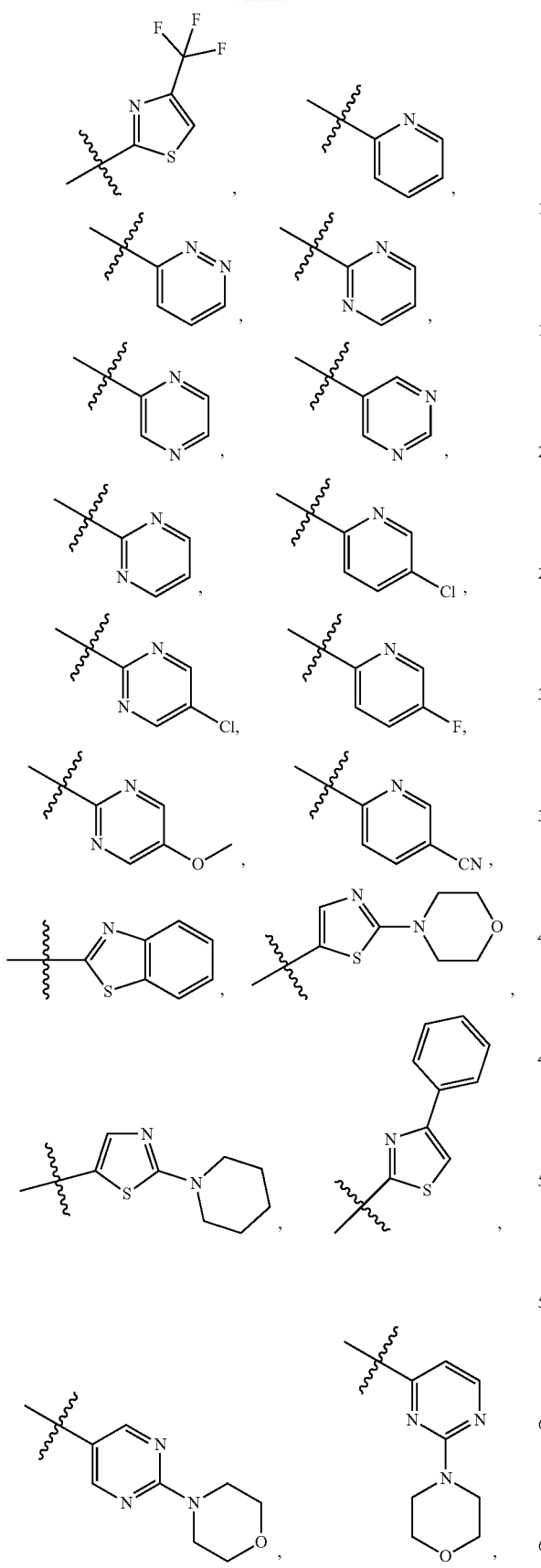
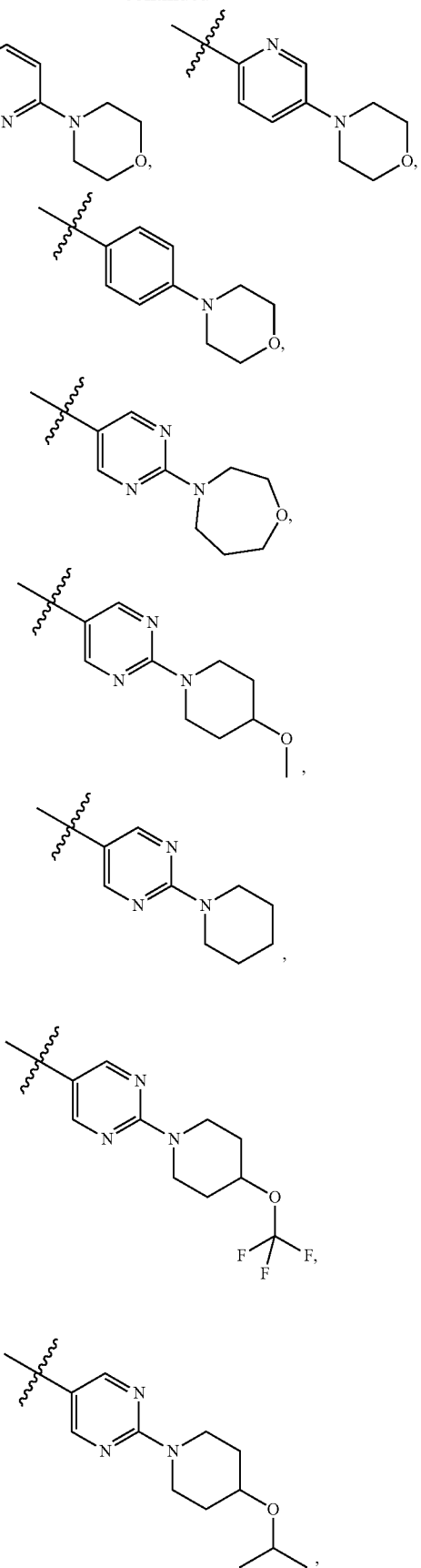

-continued
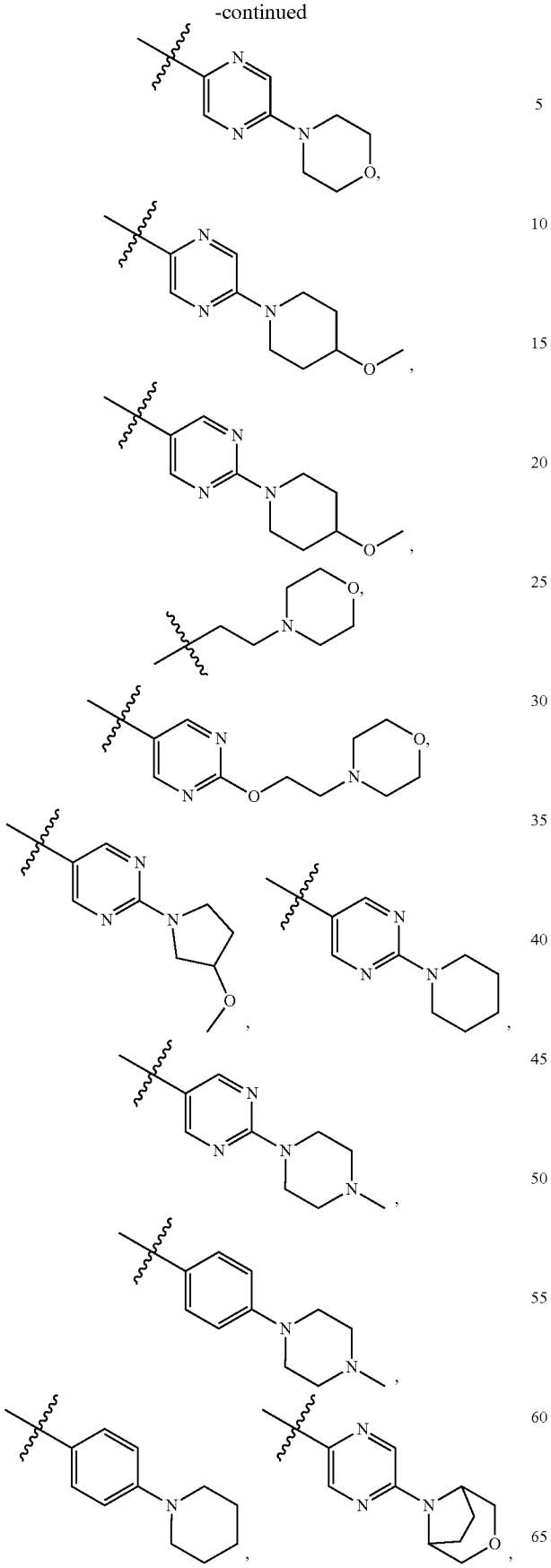
-continued
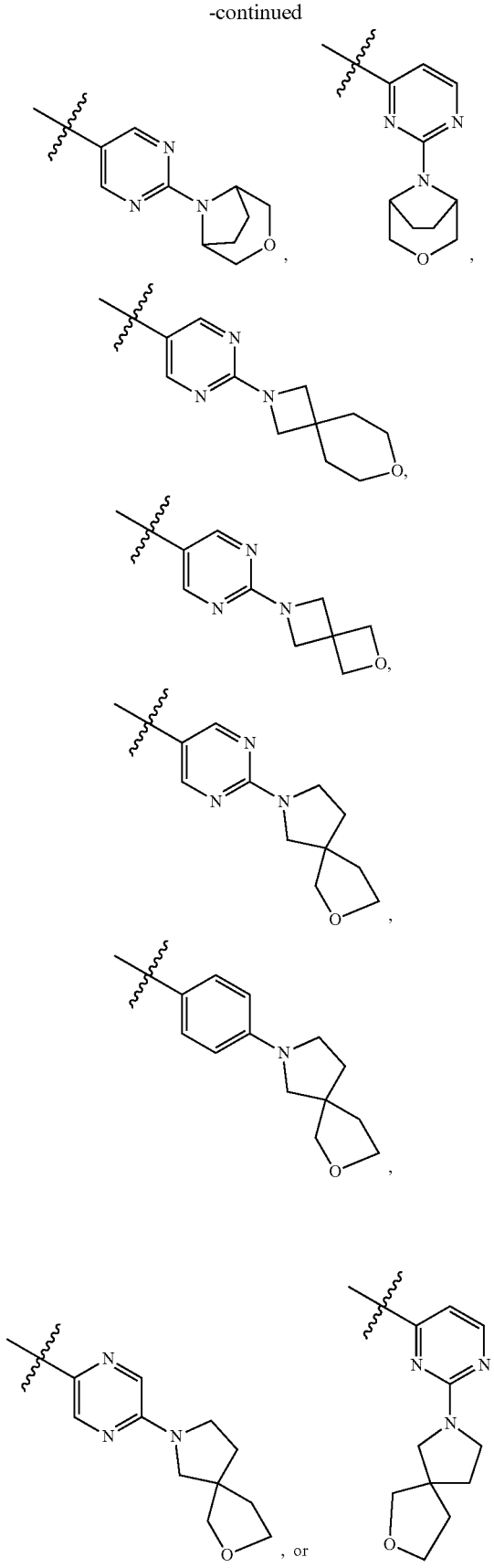

In some embodiments, $R_6$ is selected from:
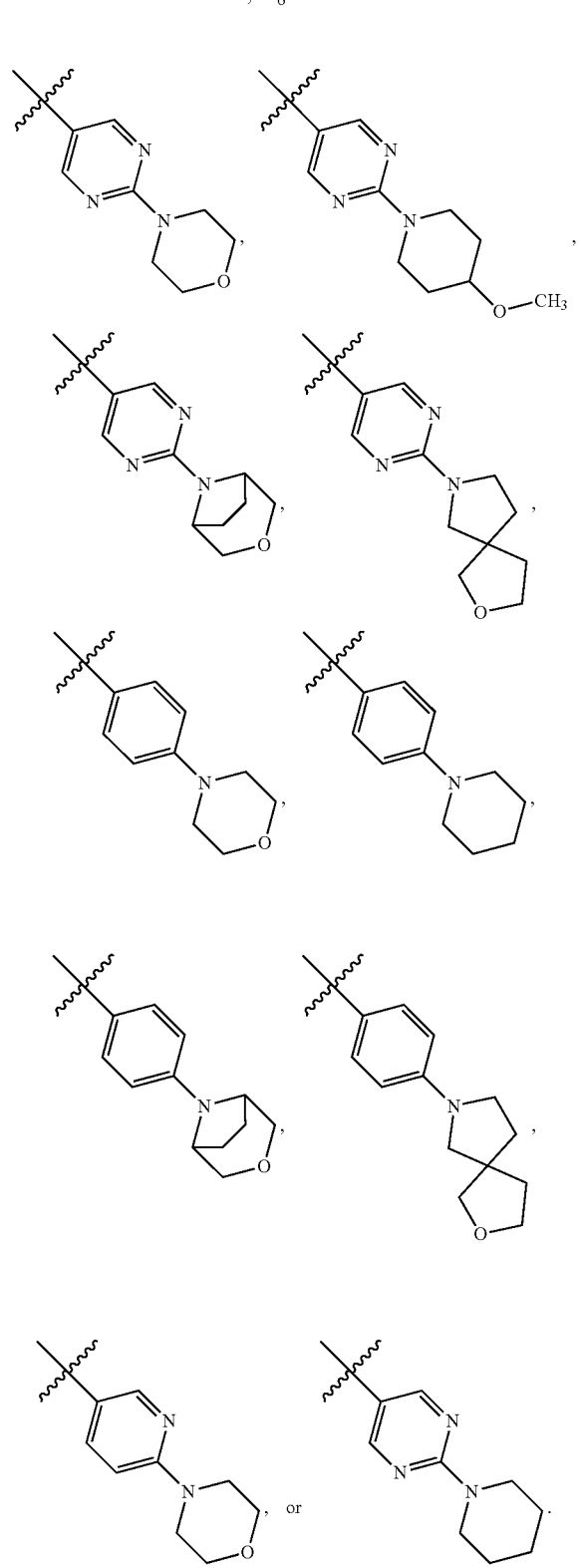
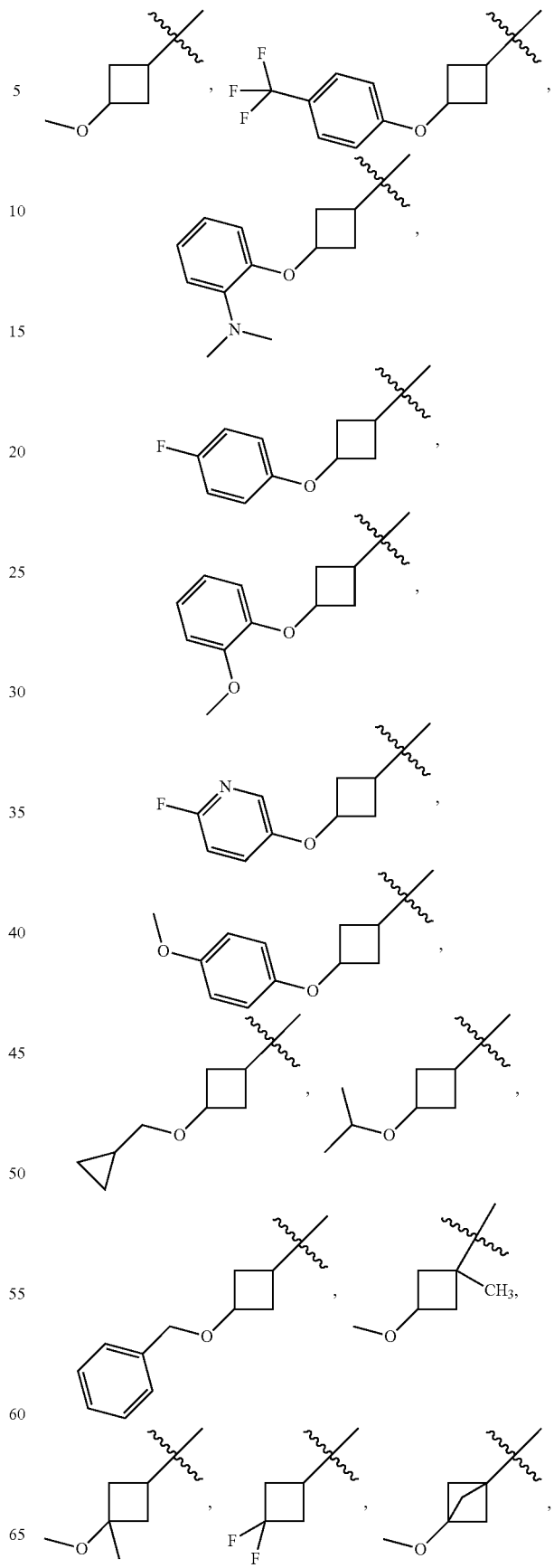
In some embodiments, a compound of the instant disclosure can be a compound of formula (II-C), an analog, an isomer, a pharmaceutically acceptable salt, and/or a prodrug thereof, and/or a formulation thereof wherein $R_5$ is selected from:

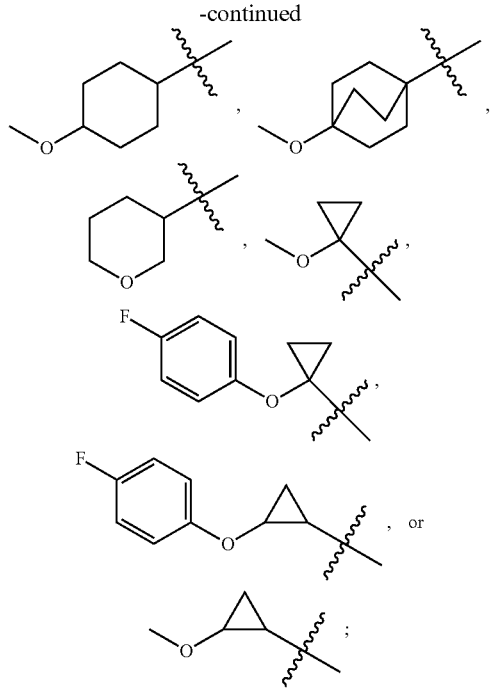
and
R_6 is selected from:
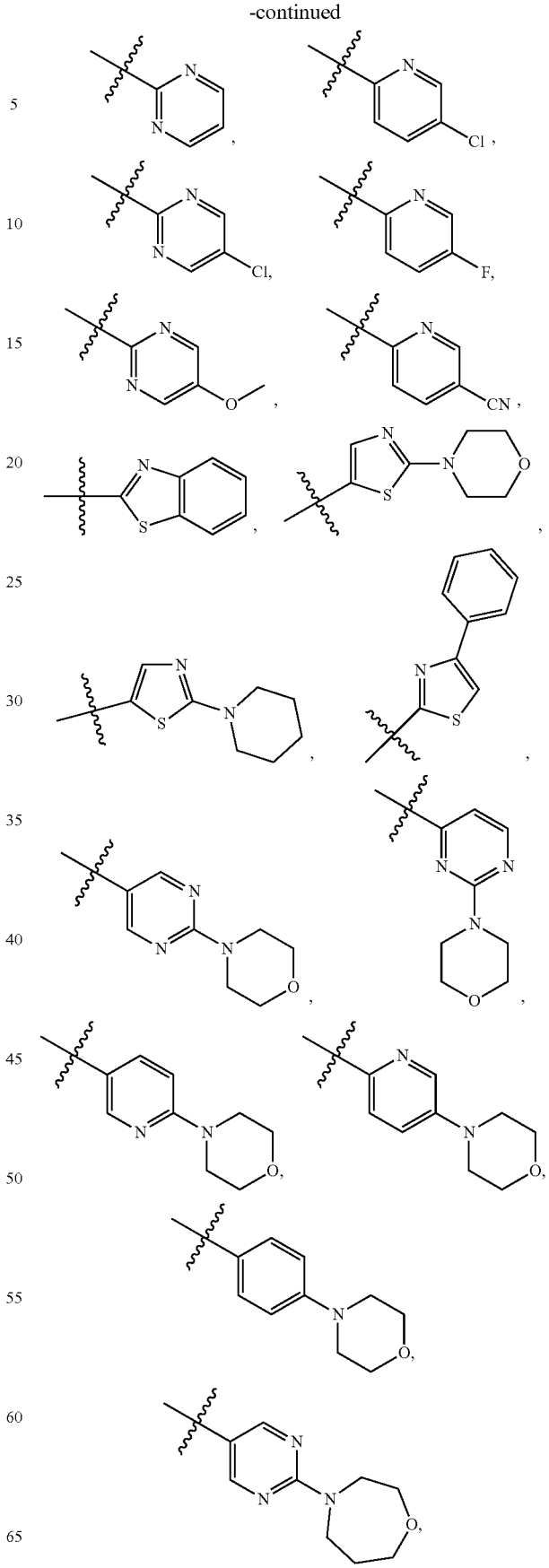

189
-continued
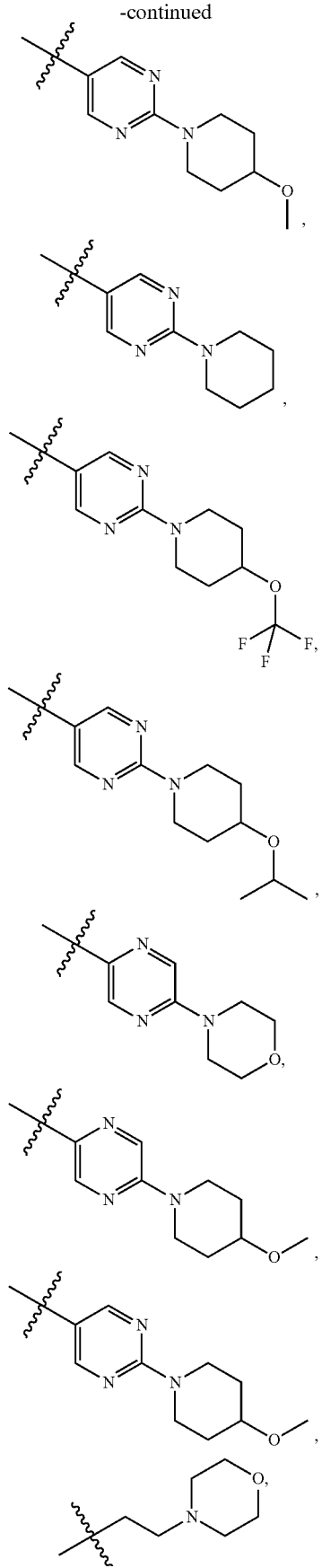
190
-continued
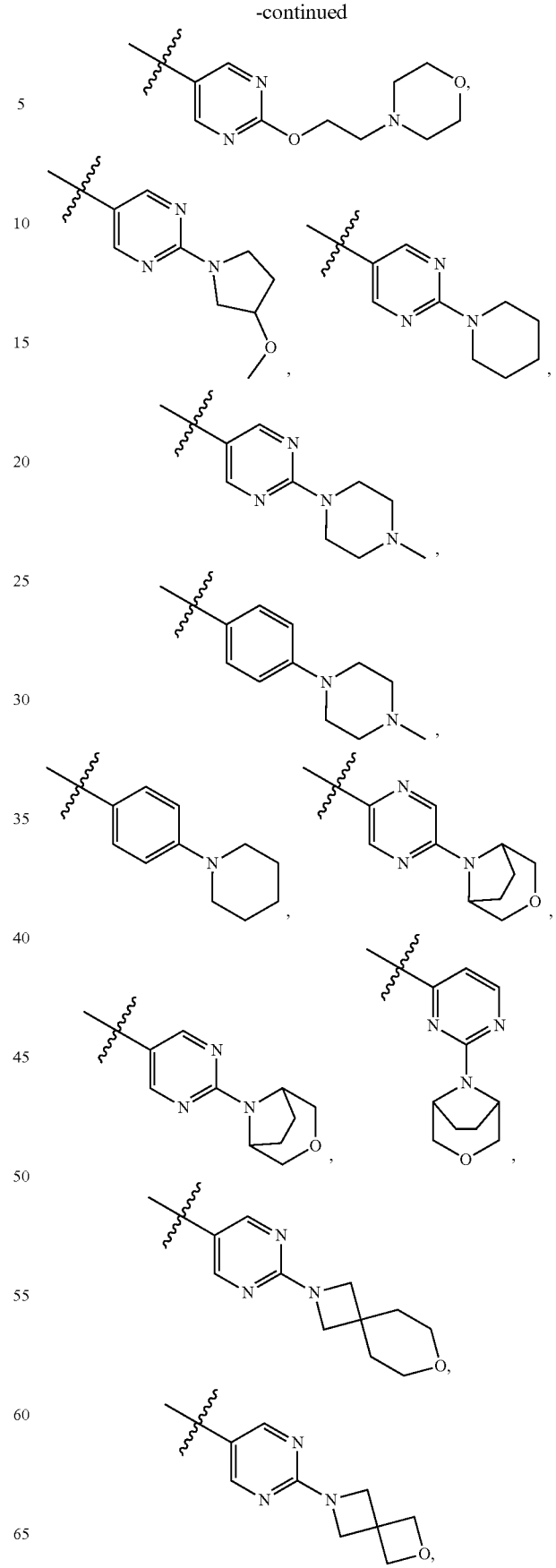

191

-continued

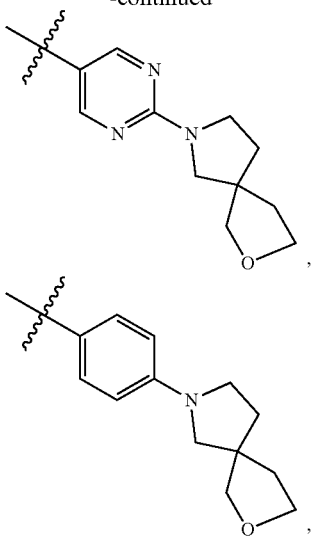

192

-continued

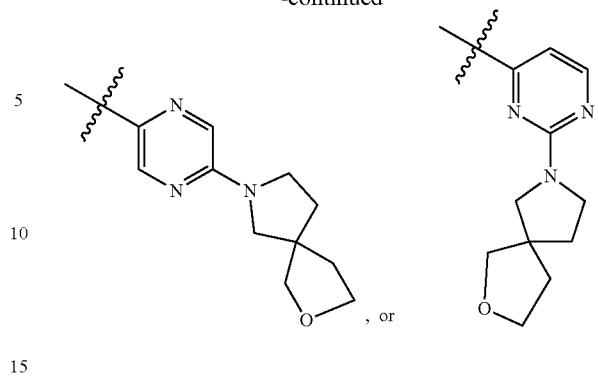

In certain embodiments, compounds of formula (II-C) can have $R_5$ and/or $R_6$ as indicated in Table 12. In other embodiments, compounds of the present disclosure can include any one of the compounds provided in Table 12.

TABLE 12

Structures of compounds B120-B157

| Compound | $R_5$ | $R_6$ | Name |
|---|---|---|---|
| B120 | | | 3-Methoxy-N-(5-((2-morpholinopyrimidin-5-yl)oxy)thiazol-2-yl)cyclobutane-1-carboxamide |
| B121 | | | 3-Methoxy-N-(5-(4-morpholinophenoxy)thiazol-2-yl)cyclobutane-1-carboxamide |
| B122 | | | 3-Methoxy-N-(5-((2-(piperidin-1-yl)pyrimidin-5-yl)oxy)thiazol-2-yl)cyclobutane-1-carboxamide |
| B123 | | | 3-methoxy-N-(5-((2-(4-methylpiperazin-1-yl)pyrimidin-5-yl)oxy)thiazol-2-yl)cyclobutane-1-carboxamide |

TABLE 12-continued

Structures of compounds B120-B157

| Compound | R₅ | R₆ | Name |
|---|---|---|---|
| B124 | 3-methoxycyclobutyl (via methoxy) | 4-(4-methylpiperazin-1-yl)phenyl | 3-methoxy-N-(5-(4-(4-methylpiperazin-1-yl)phenoxy)thiazol-2-yl)cyclobutane-1-carboxamide |
| B125 | 3-methoxycyclobutyl | 4-(piperidin-1-yl)phenyl | 3-Methoxy-N-(5-(4-(piperidin-1-yl)phenoxy)thiazol-2-yl)cyclobutane-1-carboxamide |
| B126 | 3-methoxycyclobutyl | 6-morpholinopyridin-3-yl | 3-Methoxy-N-(5-((6-morpholinopyridin-3-yl)oxy)thiazol-2-yl)cyclobutane-1-carboxamide |
| B127 | 3-methoxycyclobutyl | pyrimidin-2-yl | 3-methoxy-N-(5-(pyrimidin-2-yloxy)thiazol-2-yl)cyclobutane-1-carboxamide |
| B128 | 3-methoxycyclobutyl | pyrimidin-5-yl | 3-methoxy-N-(5-(pyrimidin-5-yloxy)thiazol-2-yl)cyclobutane-1-carboxamide |
| B129 | 3-methoxycyclobutyl | 2-(2-oxa-7-azaspiro[4.4]nonan-7-yl)pyrimidin-5-yl | N-(5-((2-(2-oxa-7-azaspiro[4.4]nonan-7-yl)pyrimidin-5-yl)oxy)thiazol-2-yl)-3-methoxycyclobutane-1-carboxamide |

TABLE 12-continued

Structures of compounds B120-B157

| Compound | R₅ | R₆ | Name |
|---|---|---|---|
| B130 | methoxycyclobutyl | 5-(3-oxa-8-azabicyclo[3.2.1]octan-8-yl)pyrimidin-2-yl | N-(5-((2-(3-oxa-8-azabicyclo[3.2.1]octan-8-yl)pyrimidin-5-yl)oxy)thiazol-2-yl)-3-methoxycyclobutane-1-carboxamide |
| B131 | methoxycyclobutyl | 5-(2-oxa-7-azaspiro[4.4]nonan-7-yl)pyrazin-2-yl | N-(5-((5-(2-oxa-7-azaspiro[4.4]nonan-7-yl)pyrazin-2-yl)oxy)thiazol-2-yl)-3-methoxycyclobutane-1-carboxamide |
| B132 | methoxycyclobutyl | 5-morpholinopyrazin-2-yl | 3-methoxy-N-(5-((5-morpholinopyrazin-2-yl)oxy)thiazol-2-yl)cyclobutane-1-carboxamide |
| B133 | 3-(4-fluorophenoxy)cyclobutyl | pyrimidin-2-yl | 3-(4-fluorophenoxy)-N-(5-(pyrimidin-2-yloxy)thiazol-2-yl)cyclobutane-1-carboxamide |
| B134 | 3-(4-fluorophenoxy)cyclobutyl | pyrazin-2-yl | 3-(4-fluorophenoxy)-N-(5-(pyrazin-2-yloxy)thiazol-2-yl)cyclobutane-1-carboxamide |
| B135 | 3-(4-fluorophenoxy)cyclobutyl | 5-chloropyridin-2-yl | N-(5-((5-chloropyridin-2-yl)oxy)thiazol-2-yl)-3-(4-fluorophenoxy)cyclobutane-1-carboxamide |
| B136 | 3-(4-fluorophenoxy)cyclobutyl | 5-chloropyrimidin-2-yl | N-(5-((5-chloropyrimidin-2-yl)oxy)thiazol-2-yl)-3-(4-fluorophenoxy)cyclobutane-1-carboxamide |

TABLE 12-continued

Structures of compounds B120-B157

| Compound | R₅ | R₆ | Name |
|---|---|---|---|
| B137 (also described as C21) | | | N-(5-((2-(2-oxa-7-azaspiro[4.4]nonan-7-yl)pyrimidin-5-yl)oxy)thiazol-2-yl)-3-methoxybicyclo[1.1.1]pentane-1-carboxamide |
| B138 (also described as C18) | | | N-(5-((2-(3-oxa-8-azabicyclo[3.2.1]octan-8-yl)pyrimidin-5-yl)oxy)thiazol-2-yl)-3-methoxybicyclo[1.1.1]pentane-1-carboxamide |
| B139 (RGN6024) | | | 3-Methoxy-N-(5-((2-morpholinopyrimidin-5-yl)oxy)thiazol-2-yl)bicyclo[1.1.1]pentane-1-carboxamide |
| B140 | | | 3-methoxy-N-(5-((2-(piperidin-1-yl)pyrimidin-5-yl)oxy)thiazol-2-yl)bicyclo[1.1.1]pentane-1-carboxamide |
| B141 (C2) | | | 3-methoxy-3-methyl-N-(5-((2-morpholinopyrimidin-5-yl)oxy)thiazol-2-yl)cyclobutane-1-carboxamide |
| B142 (C7) | | | 3-(cyclopropylmethoxy)-N-(5-((2-morpholinopyrimidin-5-yl)oxy)thiazol-2-yl)cyclobutane-1-carboxamide |

TABLE 12-continued

Structures of compounds B120-B157

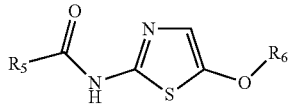

| Compound | R₅ | R₆ | Name |
|---|---|---|---|
| B143 | 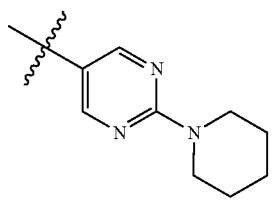 [SMILES: *c1cnc(N2CCCCC2)nc1] | 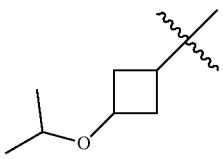 [SMILES: *C1CC(OC(C)C)C1] | 3-isopropoxy-N-(5-((2-(piperidin-1-yl)pyrimidin-5-yl)oxy)thiazol-2-yl)cyclobutane-1-carboxamide |
| B144 (C6) | 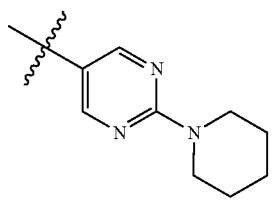 [SMILES: *c1cnc(N2CCCCC2)nc1] | 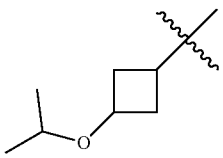 [SMILES: *C1CC(OC(C)C)C1] | 3-isopropoxy-N-(5-((2-morpholinopyrimidin-5-yl)oxy)thiazol-2-yl)cyclobutane-1-carboxamide |
| B145 | 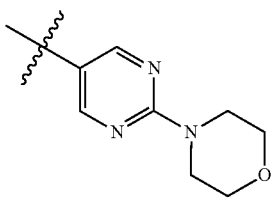 [SMILES: *c1cnc(N2CCOCC2)nc1] | 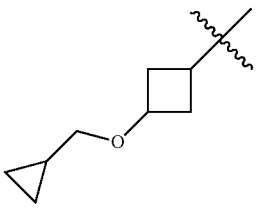 [SMILES: *C1CC(OCC2CC2)C1] | 3-(cyclopropylmethoxy)-N-(5-((2-(piperidin-1-yl)pyrimidin-5-yl)oxy)thiazol-2-yl)cyclobutane-1-carboxamide |
| B146 (C3) | 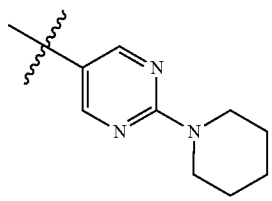 [SMILES: *c1cnc(N2CCCCC2)nc1] | 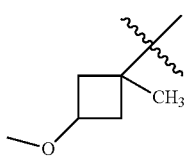 | 3-methoxy-1-methyl-N-(5-((2-morpholino-pyrimidin-5-yl)oxy)thiazol-2-yl)cyclobutane-1-carboxamide |
| B147 | 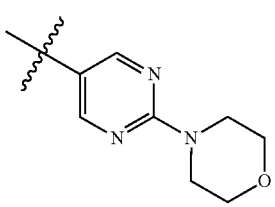 [SMILES: *c1cnc(N2CCOCC2)nc1] | 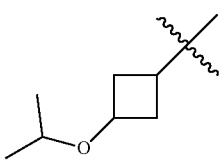 [SMILES: *C1CC(OC(C)C)C1] | N-(5-((2-(3-oxa-8-azabicyclo[3.2.1]octan-8-yl)pyrimidin-5-yl)oxy)thiazol-2-yl)-3-isopropoxycyclobutane-1-carboxamide |
| B148 | 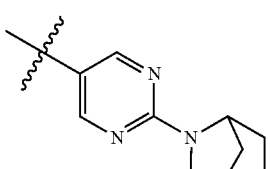 | 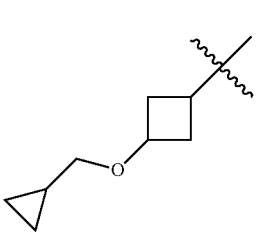 [SMILES: *C1CC(OCC2CC2)C1] | 3-(cyclopropylmethoxy)-N-(5-((6-morpholinopyridin-3-yl)oxy)thiazol-2-yl)cyclobutane-1-carboxamide |

TABLE 12-continued

Structures of compounds B120-B157

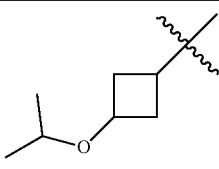

| Compound | R$_5$ | R$_6$ | Name |
|---|---|---|---|
| B149 | 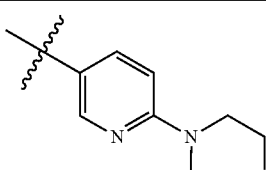 | 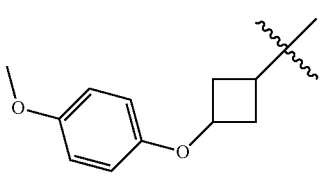 [SMILES: *C1CC(Oc2ccc(OC)cc2)C1] | 3-isopropoxy-N-(5-((6-morpholinopyridin-3-yl)oxy)thiazol-2-yl)cyclobutane-1-carboxamide |
| B150 | 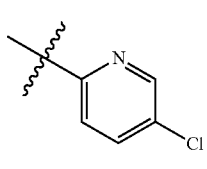 [SMILES: *c1ccc(Cl)cn1] | 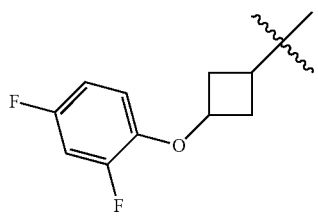 [SMILES: *C1CC(Oc2ccc(F)cc2F)C1] | N-(5-((5-chloropyridin-2-yl)oxy)thiazol-2-yl)-3-(4-methoxyphenoxy)cyclobutane-1-carboxamide |
| B151 | 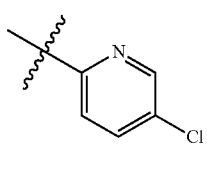 [SMILES: *c1ccc(Cl)cn1] | 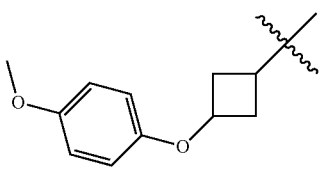 [SMILES: *C1CC(Oc2ccc(OC)cc2)C1] | N-(5-((5-chloropyridin-2-yl)oxy)thiazol-2-yl)-3-(2,4-difluorophenoxy)cyclobutane-1-carboxamide |
| B152 | 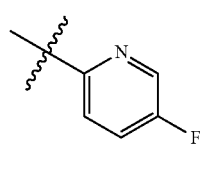 [SMILES: *c1ccc(F)cn1] | 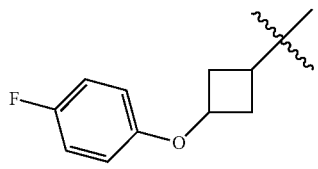 | N-(5-((5-fluoropyridin-2-yl)oxy)thiazol-2-yl)-3-(4-methoxyphenoxy)cyclobutane-1-carboxamide |
| B153 | 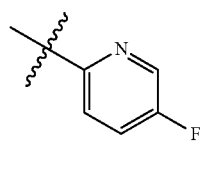 [SMILES: *c1ccc(F)cn1] | 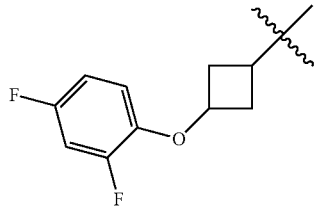 [SMILES: *C1CC(Oc2ccc(F)cc2F)C1] | 3-(4-fluorophenoxy)-N-(5-((5-fluoropyridin-2-yl)oxy)thiazol-2-yl)cyclobutane-1-carboxamide |
| B154 | 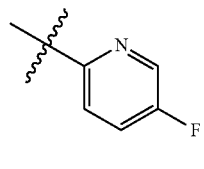 [SMILES: *c1ccc(F)cn1] | 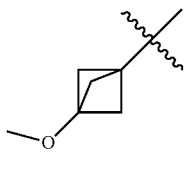 [SMILES: *C12CC(OC)(C1)C2] | 3-(2,4-difluorophenoxy)-N-(5-((5-fluoropyridin-2-yl)oxy)thiazol-2-yl)cyclobutane-1-carboxamide |
| B155 (C27 and C89) | 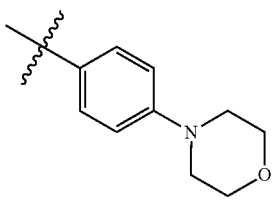 [SMILES: *c1ccc(N2CCOCC2)cc1] | | 3-Methoxy-N-(5-(4-morpholinophenoxy)thiazol-2-yl)bicyclo[1.1.1]pentane-1-carboxamide |

TABLE 12-continued

Structures of compounds B120-B157

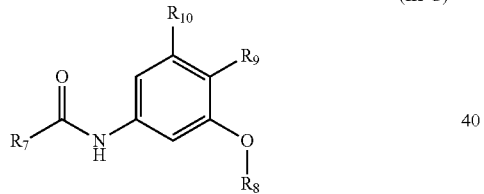

| Compound | R₅ | R₆ | Name |
|---|---|---|---|
| B156 (C14) | 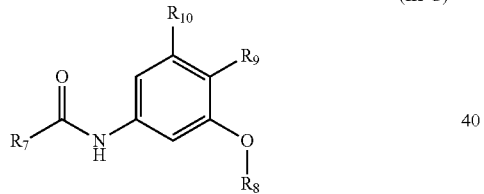 | 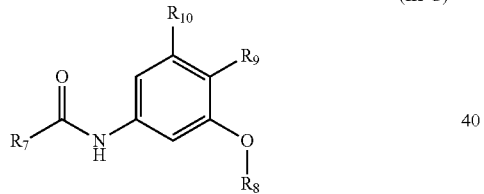 | 2-methoxy-N-(5-((2-morpholinopyrimidin-5-yl)oxy)thiazol-2-yl)cyclopropane-1-carboxamide |
| B157 | | | 3-methoxy-N-(5-((6-morpholinopyridin-3-yl)oxy)thiazol-2-yl)cyclobutane-1-carboxamide |

In some embodiments, a compound can include a compound according to formula (III-C).

$$(III-C)$$

an analog, an isomer, a pharmaceutically acceptable salt, and/or a prodrug thereof;

wherein R₇ is selected from:

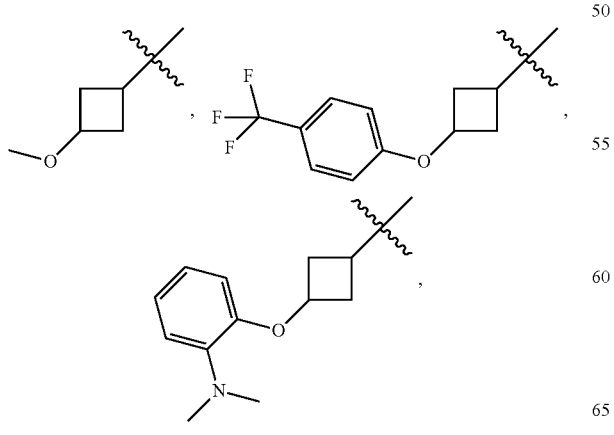

-continued

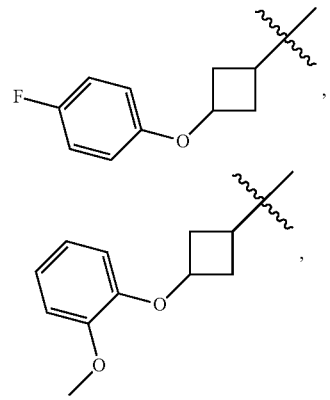

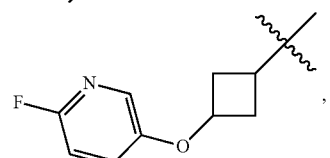

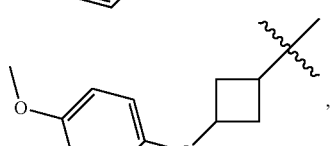

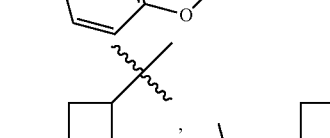

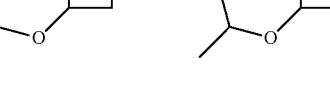

-continued

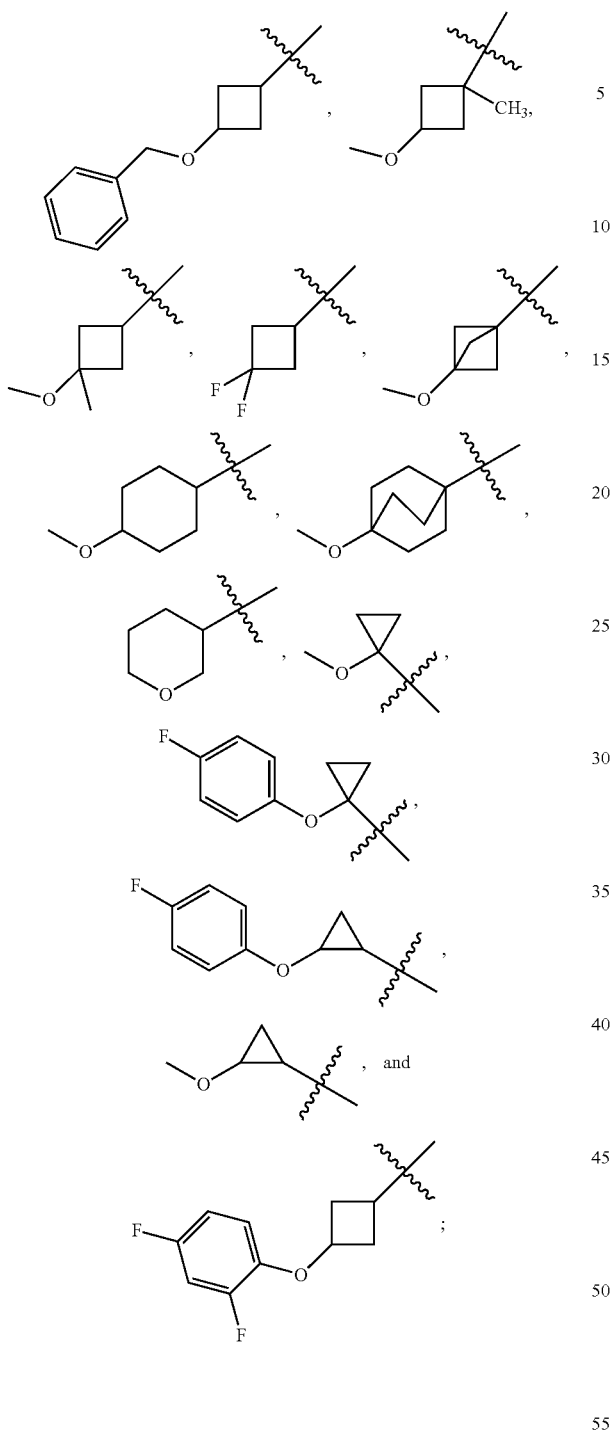

$R_8$, is an alkyl, an aryl, and a heteroaryl, wherein the aryl and the heteroaryl are each independently unsubstituted or are optionally independently substituted with one or more groups independently selected from alkyl, alkenyl, alkynyl, alkoxyl, alkylsulfo, alkylamino, halogen, thiol, hydroxyl, nitro, cyano, cycloalkyl, heterocyclyl, heterocyclic alkyl, aryl, heteroaryl, cycloalkoxyl, heterocyclic alkoxyl, cycloalkylthio, and heterocyclic alkylthio; and $R_9$ is selected from H, $CH_3$, or F; and $R_{10}$ is selected from H or F.

In some embodiments, $R_7$ of compounds of formula (III-C) disclosed herein is selected from:

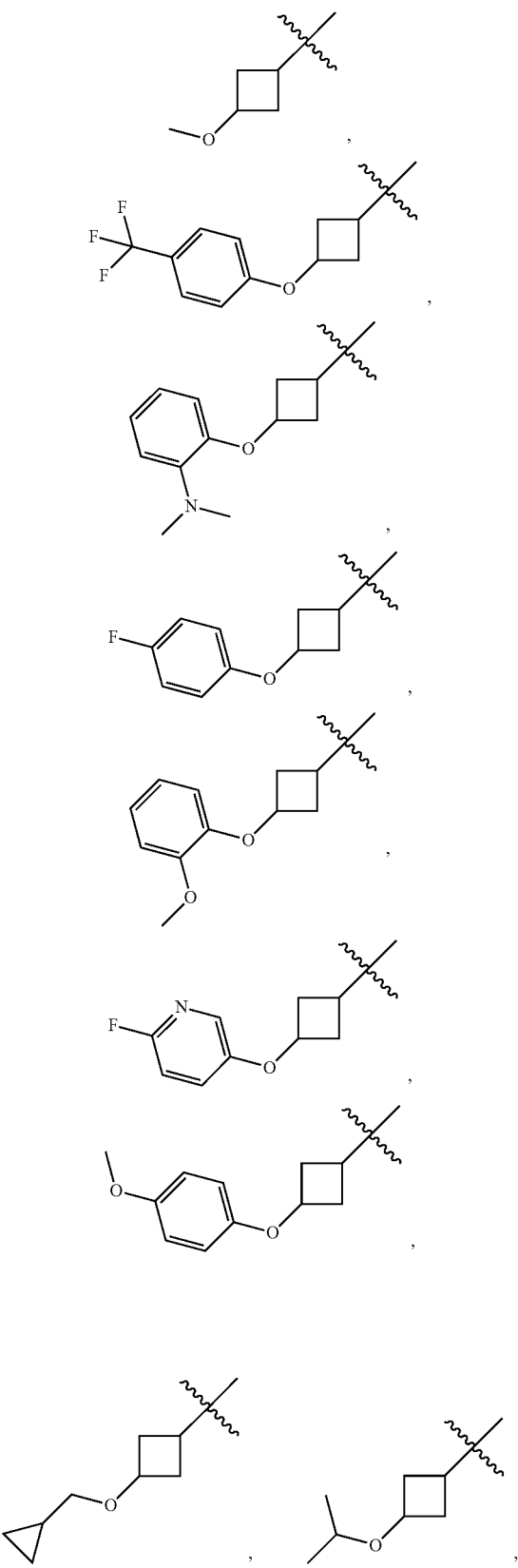

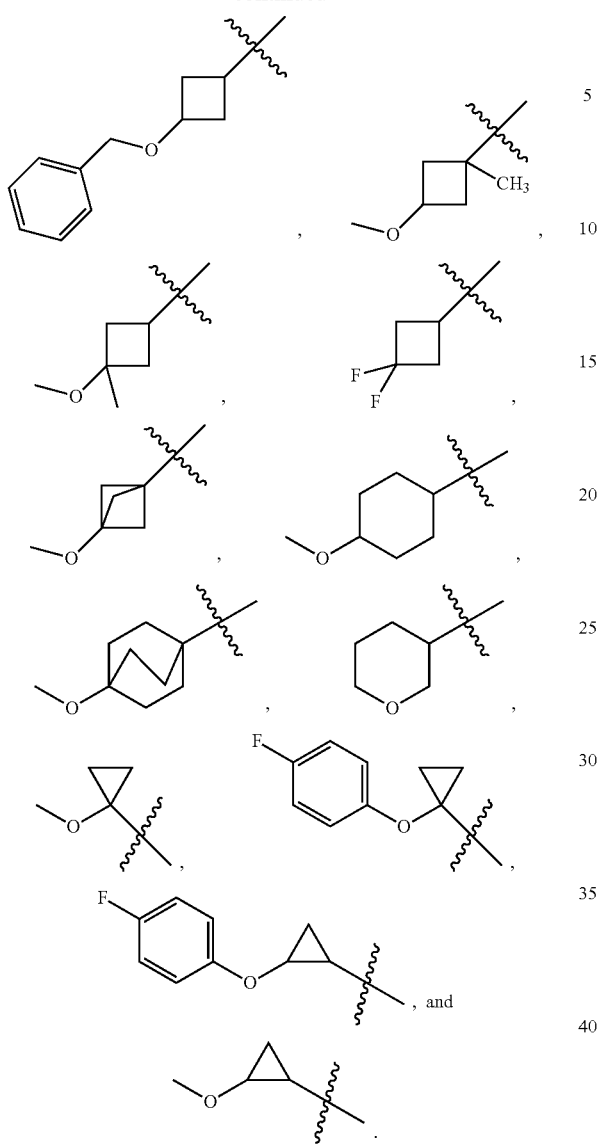
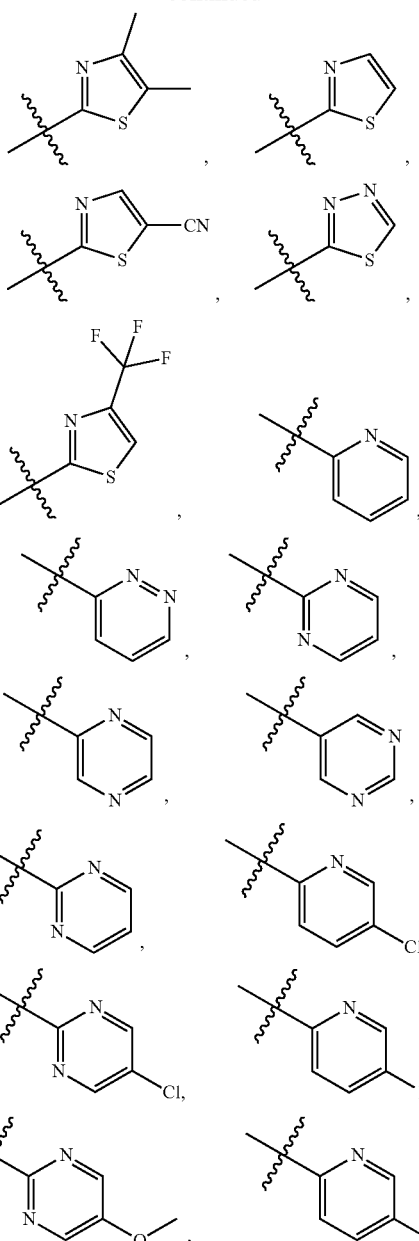
In some embodiments, R$_7$ of compounds of formula (I-C) disclosed herein is selected from:
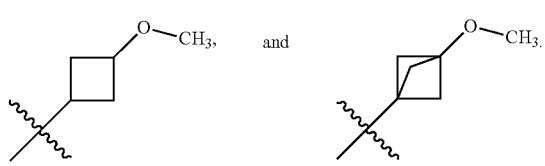 [SMILES: *C1CC(OC)C1 ; *C12CC(OC)(C1)C2]
In some embodiments, R$_8$ of compounds of formula (III-C) disclosed herein is selected from:
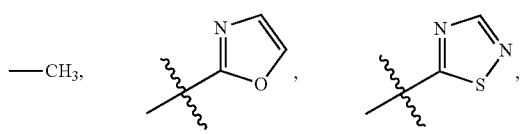
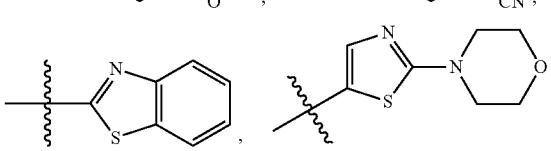
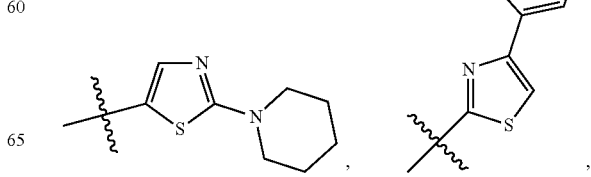

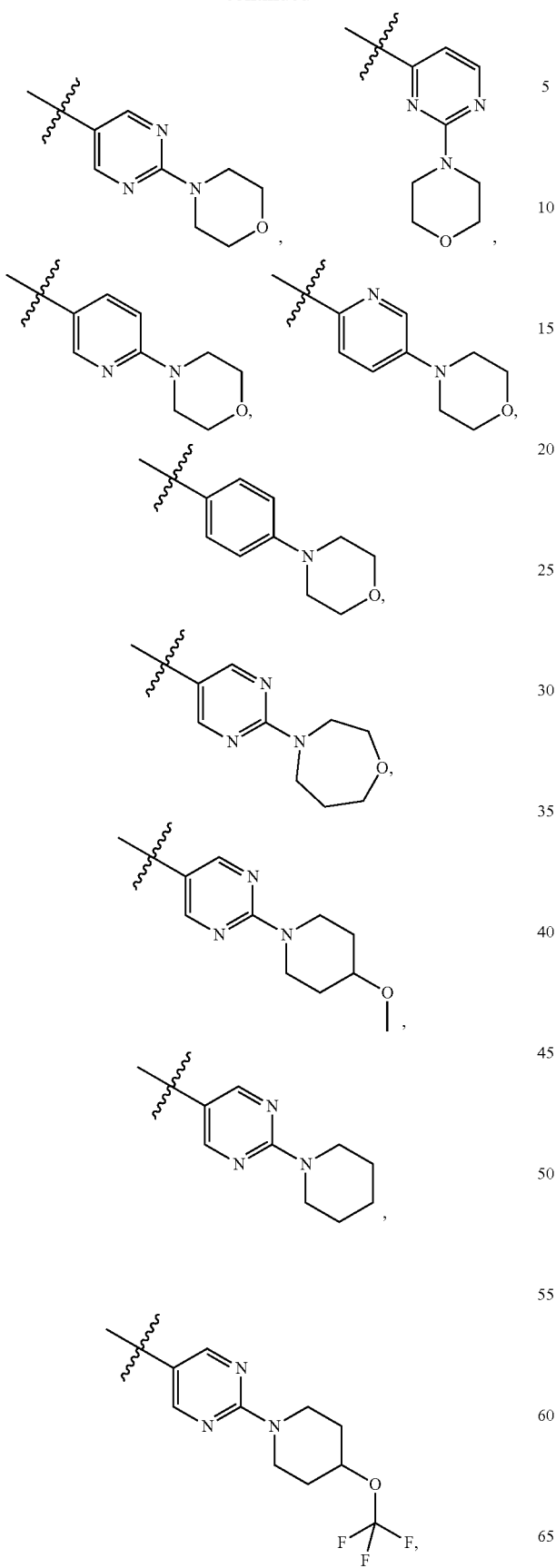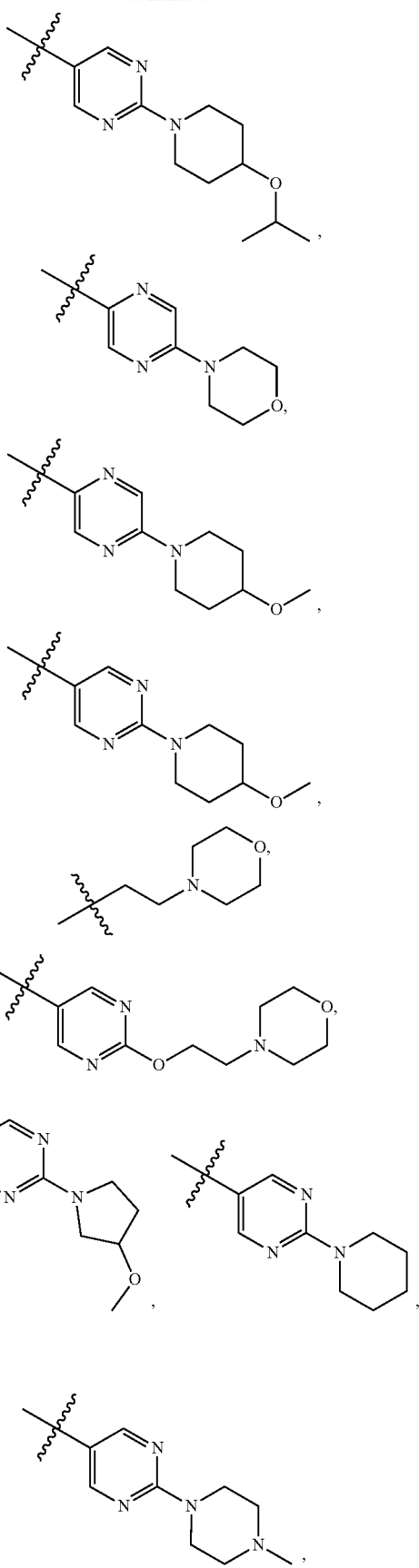

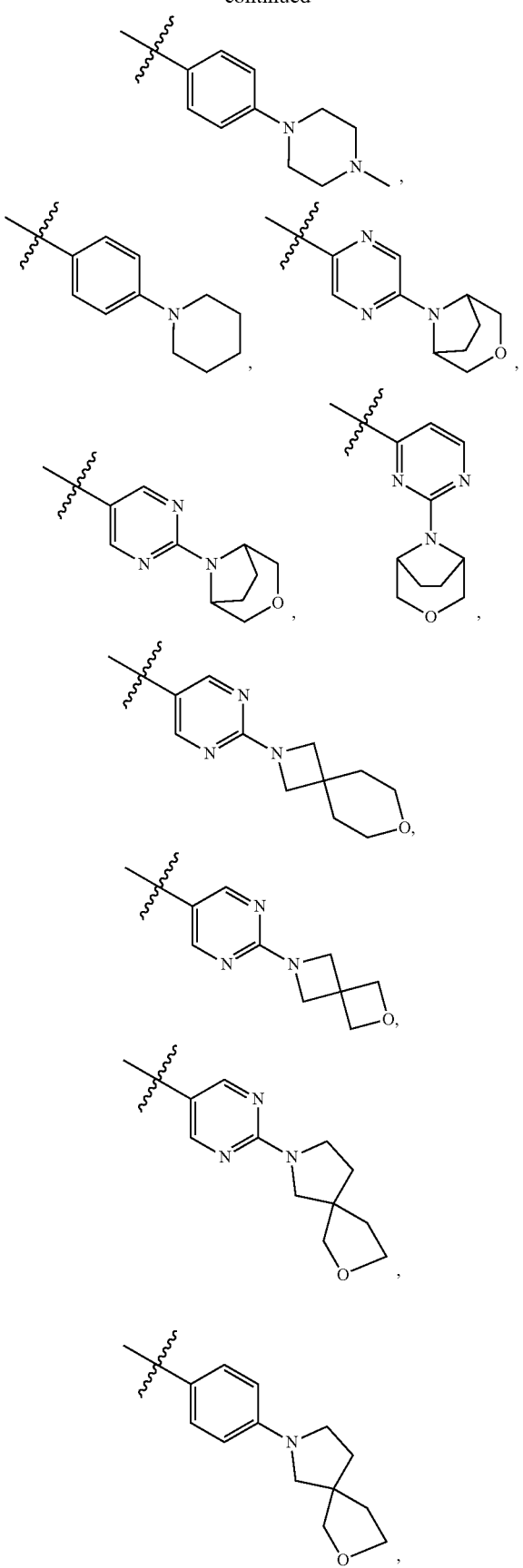
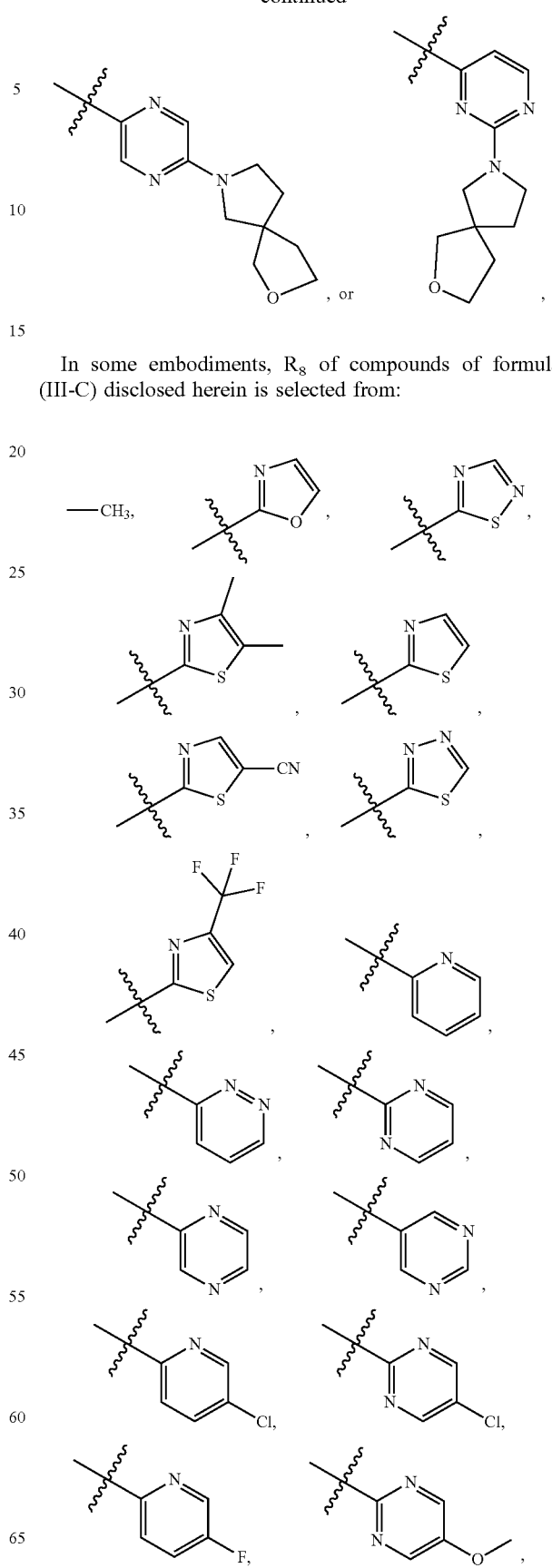
In some embodiments, $R_8$ of compounds of formula (III-C) disclosed herein is selected from:

213
-continued
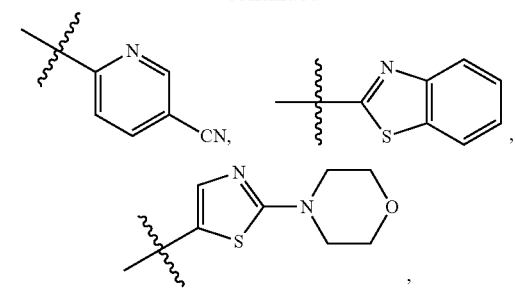
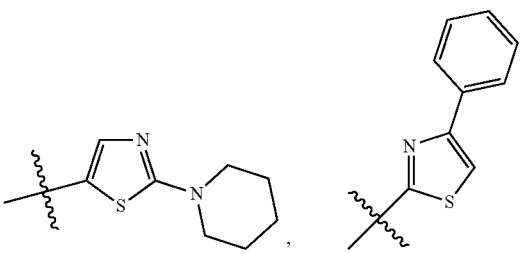
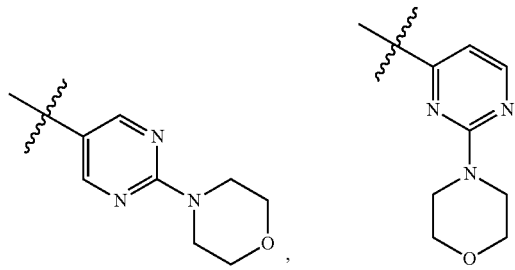
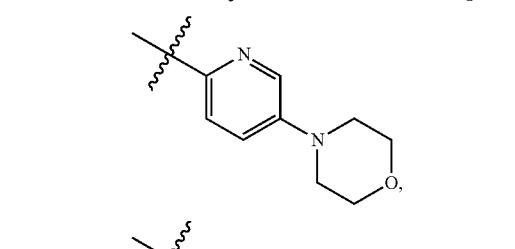
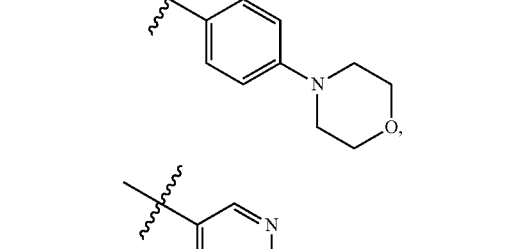
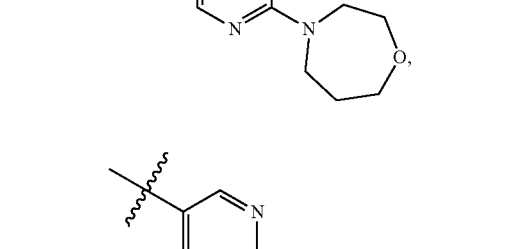
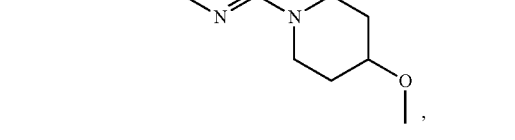
214
-continued
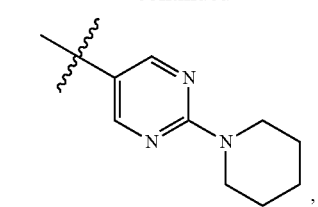
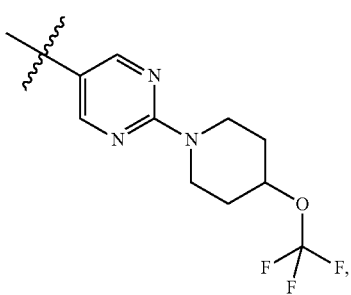
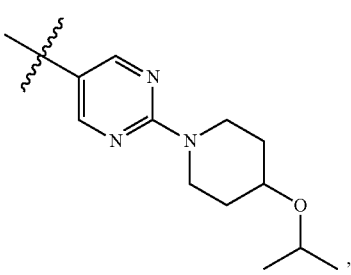
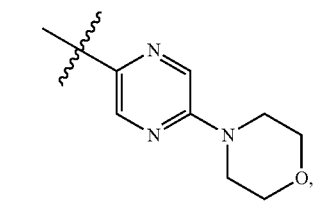
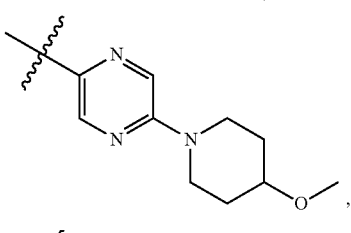
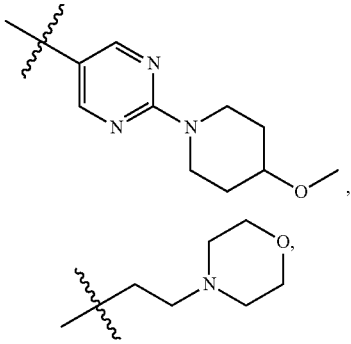
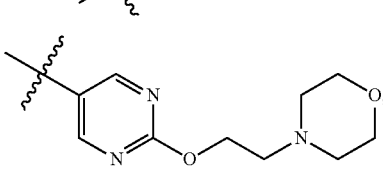

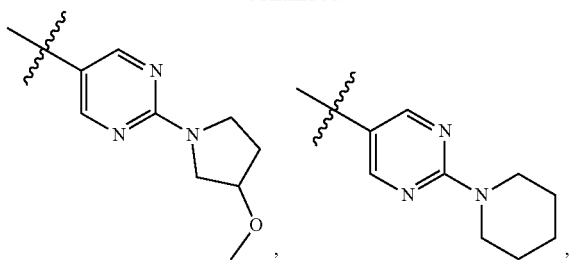
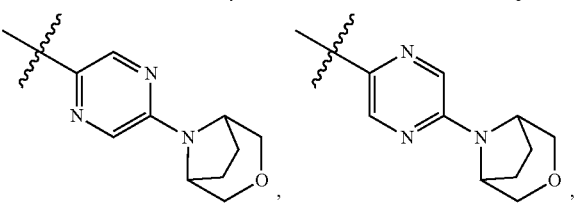
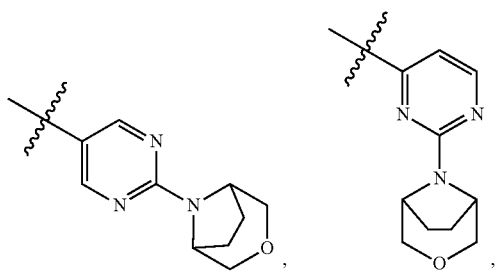
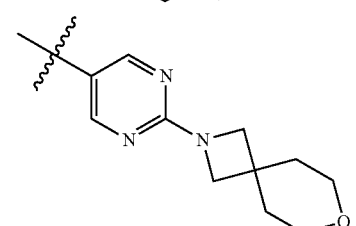
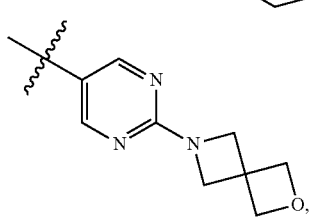
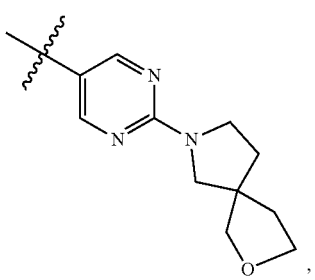
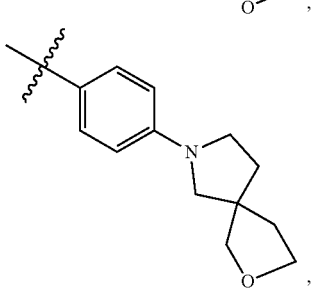
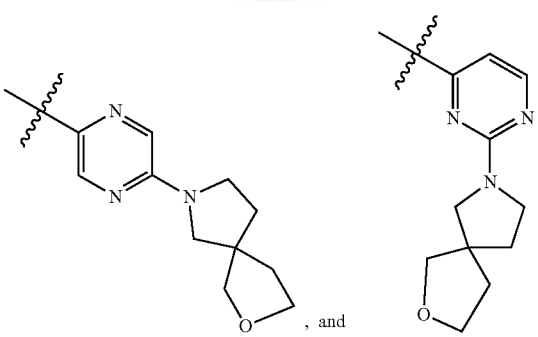
In some embodiments, R$_8$ of compounds of formula (III-C) disclosed herein is selected from:
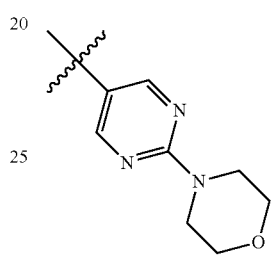
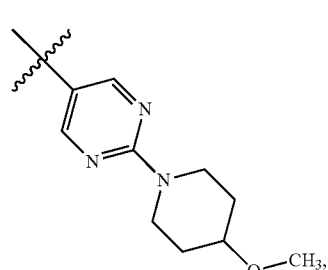
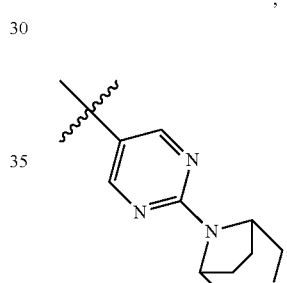
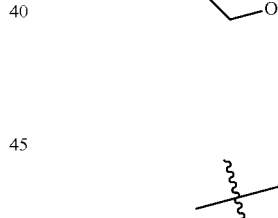
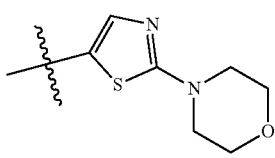
In some embodiments, R$_8$ of compounds of formula (III-C) is:
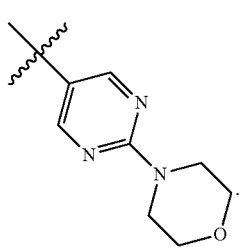 [SMILES: *c1cnc(N2CCOCC2)nc1]

In some embodiments, a compound of the instant disclosure can be a compound of formula (III-C), an analog, an isomer, a pharmaceutically acceptable salt, and/or a prodrug thereof, wherein $R_7$ is selected from:
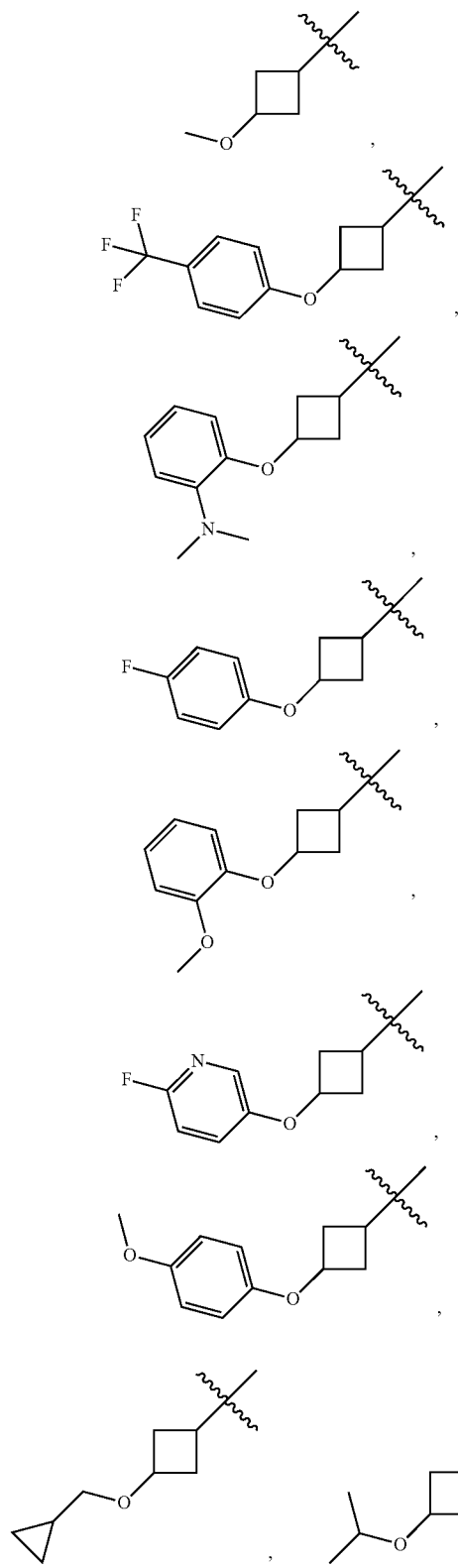
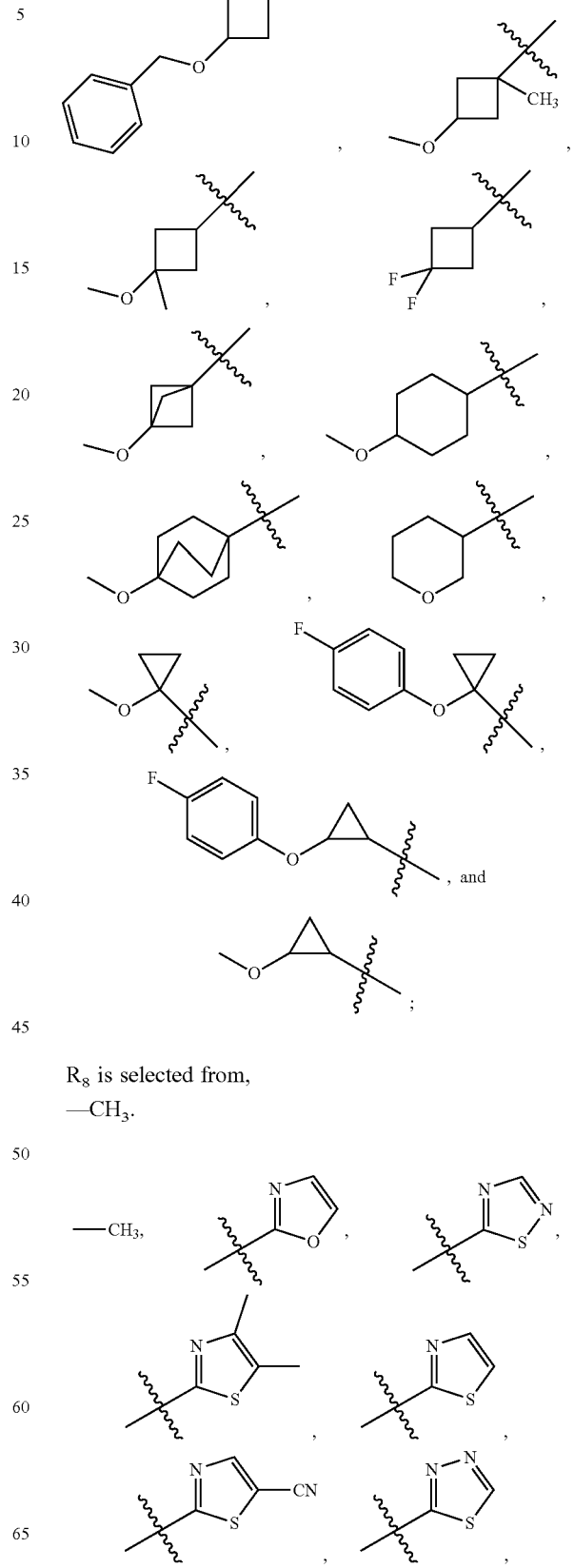
$R_8$ is selected from,
—$CH_3$.

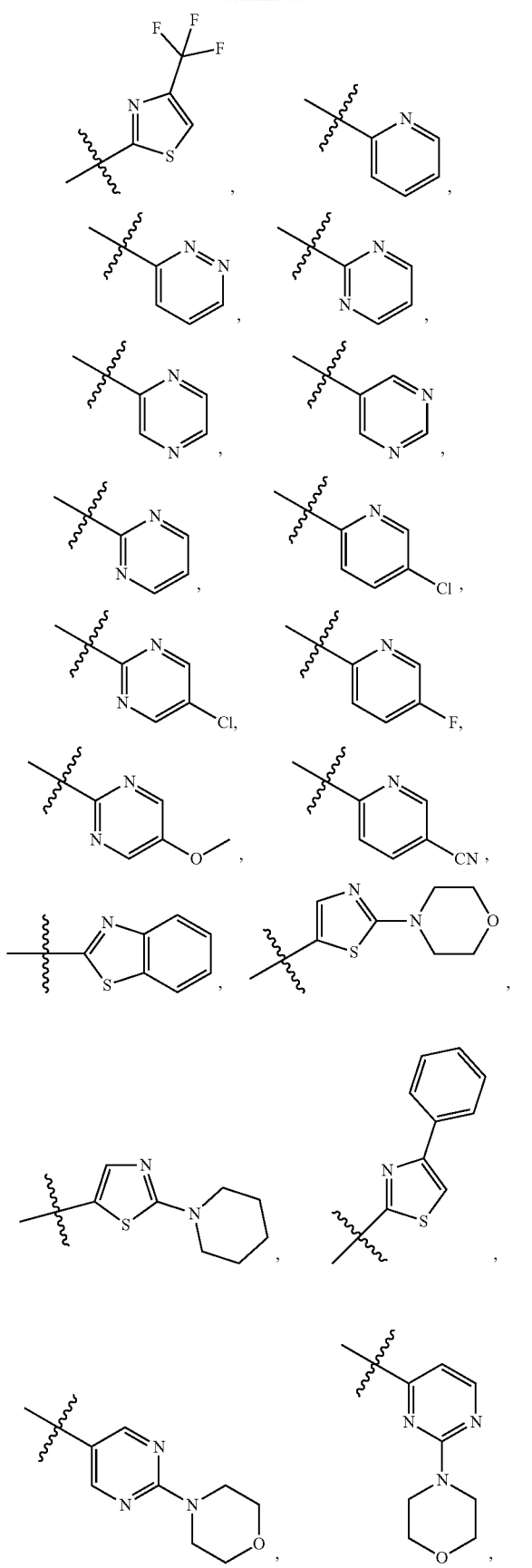
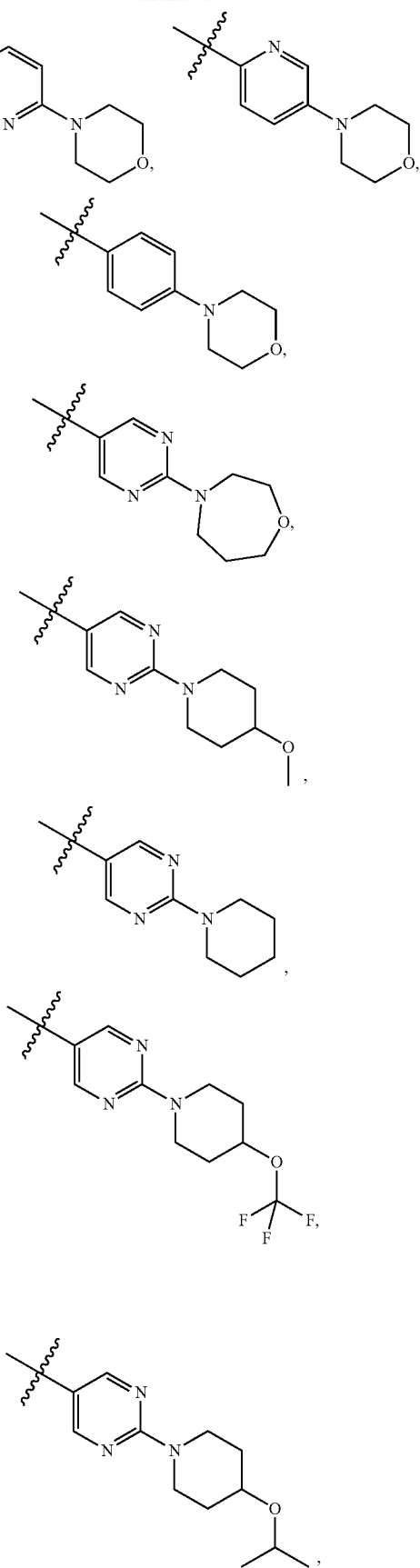

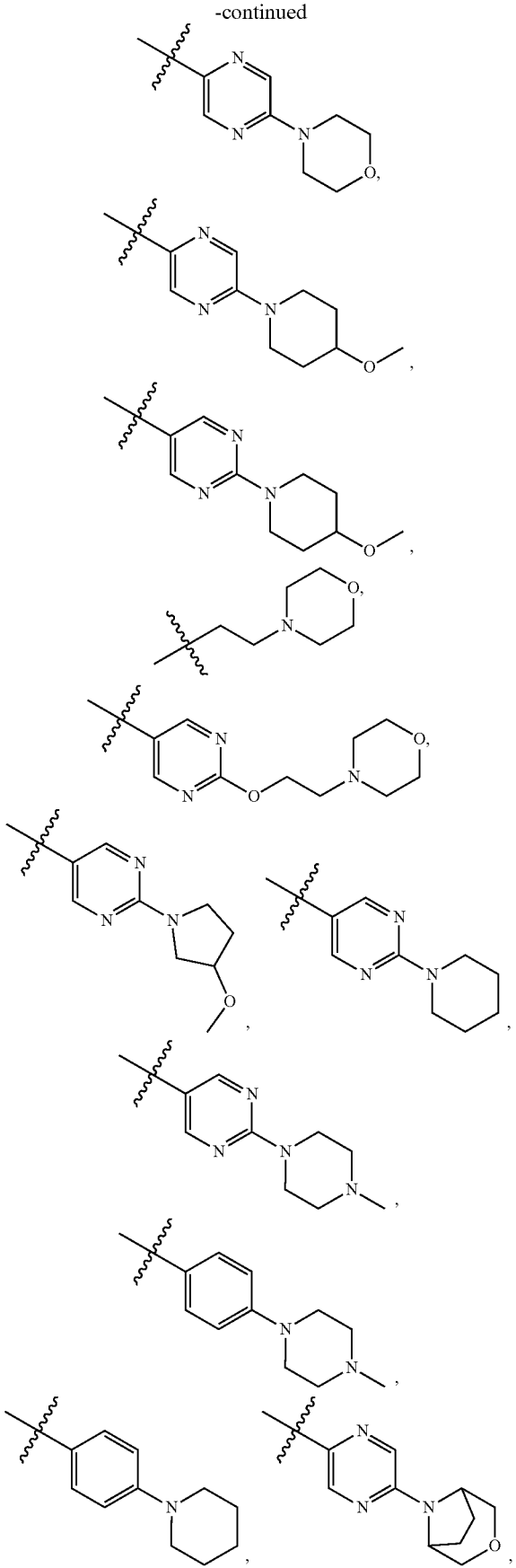
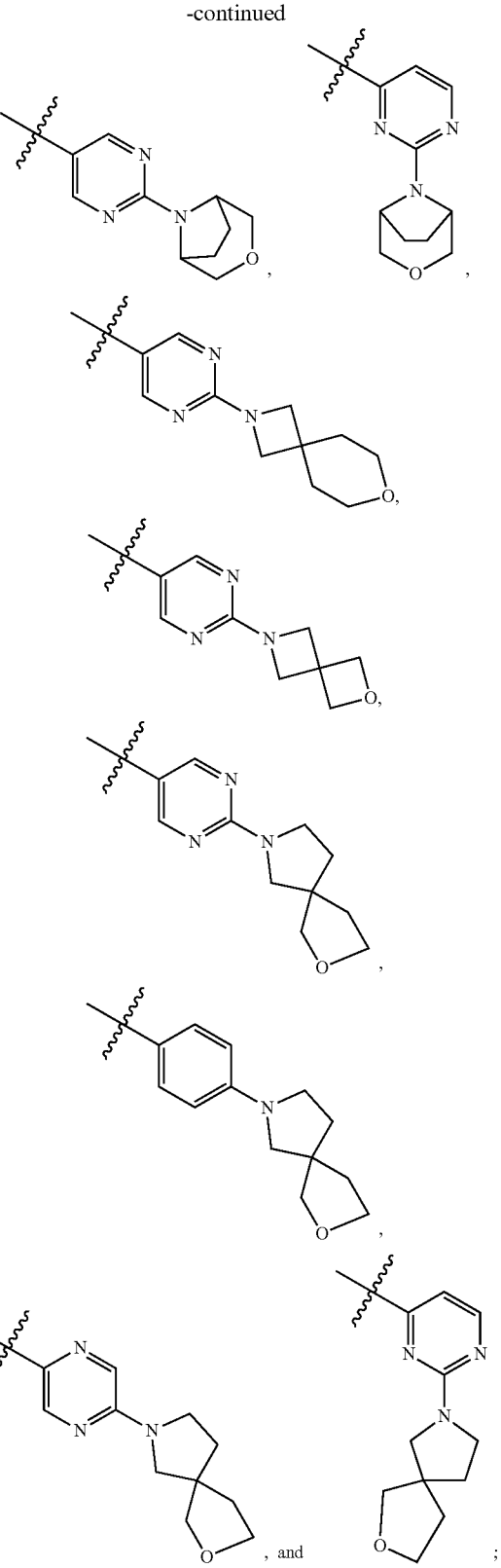
$R_9$ is selected from H and $CH_3$; and $R_{10}$ is selected from H and F.
In certain embodiments, compounds of formula (III-C) can have $R_7$, $R_8$, $R_9$, and/or $R_{10}$ as indicated in Table 13.

TABLE 13

Structure of compound B119

| Compound | R₇ | R₈ | R₉ | R₁₀ | Name |
|---|---|---|---|---|---|
| B119 | (3-methoxycyclobutyl) | (2-morpholinopyrimidin-5-yl) | —CH₃ | —H | 3-methoxy-N-(4-methyl-3-((2-morpholinopyrimidin-5-yl)oxy)phenyl)cyclobutane-1-carboxamide |

In other embodiments, compounds of the present disclosure can be any one of the compounds provided in Table 14 or a combination thereof.

TABLE 14

| Compound | Structure | Name |
|---|---|---|
| B19 | 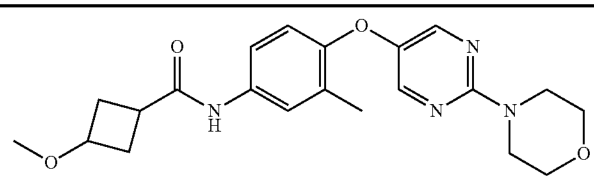 | 3-methoxy-N-(3-methyl-4-((2-morpholinopyrimidin-5-yl)oxy)phenyl)cyclobutane-1-carboxamide |
| B120 | 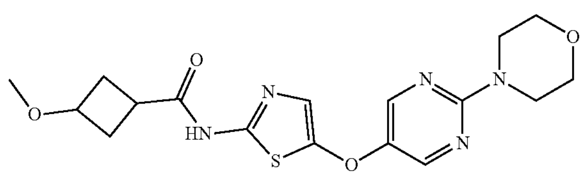 [SMILES: COC1CC(C(=O)Nc2ncc(Oc3cnc(N4CCOCC4)nc3)s2)C1] | 3-methoxy-N-(5-((2-morpholinopyrimidin-5-yl)oxy)thiazol-2-yl)cyclobutane-1-carboxamide |
| B71 | 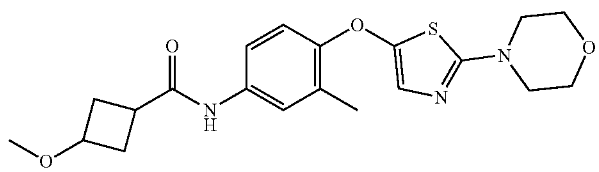 [SMILES: COC1CC(C(=O)Nc2ccc(Oc3cnc(N4CCOCC4)s3)c(C)c2)C1] | 3-methoxy-N-(3-methyl-4-((2-morpholinothiazol-5-yl)oxy)phenyl)cyclobutane-1-carboxamide |
| B122 | 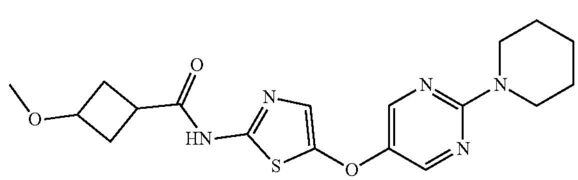 [SMILES: COC1CC(C(=O)Nc2ncc(Oc3cnc(N4CCCCC4)nc3)s2)C1] | 3-methoxy-N-(5-((2-(piperidin-1-yl)pyrimidin-5-yl)oxy)thiazol-2-yl)cyclobutane-1-carboxamide |
| B46 | 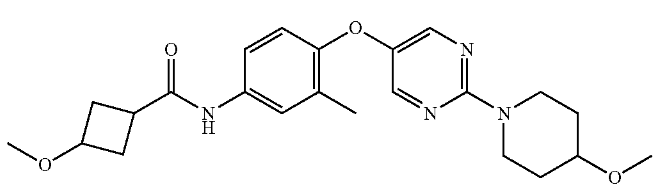 | 3-methoxy-N-(4-((2-(4-methoxypiperidin-1-yl)pyrimidin-5-yl)oxy)-3-methylphenyl)cyclobutane-1-carboxamide |

TABLE 14-continued

| Compound | Structure | Name |
|---|---|---|
| B121 | 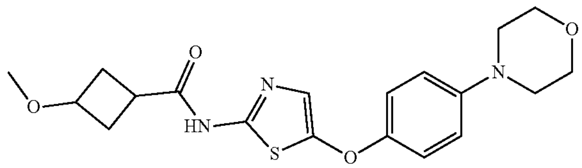 [SMILES: COC1CC(C(=O)Nc2ncc(Oc3ccc(N4CCOCC4)cc3)s2)C1] | 3-methoxy-N-(5-(4-morpholino-phenoxy)thiazol-2-yl)cyclobutane-1-carboxamide |
| B72 | 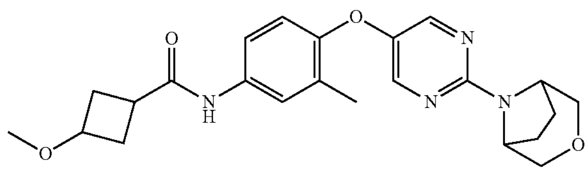 [SMILES: COC1CC(C(=O)Nc2ccc(Oc3cnc(N4C5CCC4COC5)nc3)c(C)c2)C1] | N-(4-((2-(3-oxa-8-azabicyclo[3.2.1]octan-8-yl)pyrimidin-5-yl)oxy)-3-methylphenyl)-3-methoxycyclo-butane-1-carboxamide |
| B130 | 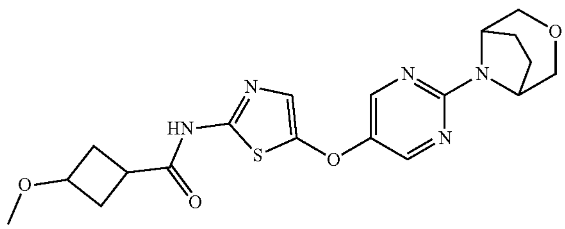 [SMILES: COC1CC(C(=O)Nc2ncc(Oc3cnc(N4C5CCC4COC5)nc3)s2)C1] | N-(5-((2-(3-oxa-8-azabicyclo[3.2.1]octan-8-yl)pyrimidin-5-yl)oxy)thiazol-2-yl)-3-methoxycyclobutane-1-carboxamide |
| B138 (C18) | 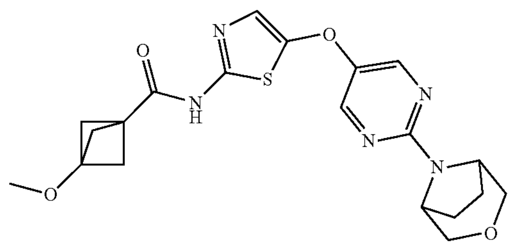 [SMILES: COC12CC(C(=O)Nc3ncc(Oc4cnc(N5C6CCC5COC6)nc4)s3)(C1)C2] | N-(5-((2-(3-oxa-8-azabicyclo[3.2.1]octan-8-yl)pyrimidin-5-yl)oxy)thiazol-2-yl)-3-methoxybicyclo[1.1.1]pentane-1-carboxamide |
| B118 | 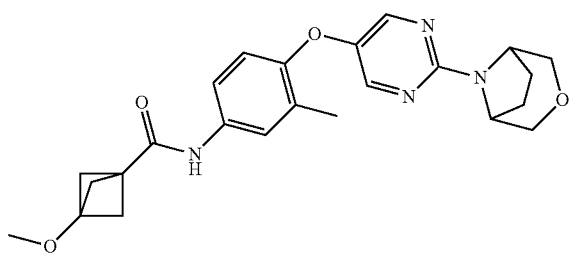 [SMILES: COC12CC(C(=O)Nc3ccc(Oc4cnc(N5C6CCC5COC6)nc4)c(C)c3)(C1)C2] | N-(4-((2-(3-oxa-8-azabicyclo[3.2.1]octan-8-yl)pyrimidin-5-yl)oxy)-3-methylphenyl)-3-methoxybicyclo[1.1.1]pentane-1-carboxamide |
| B140 | 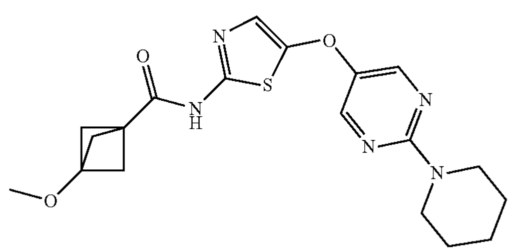 [SMILES: COC12CC(C(=O)Nc3ncc(Oc4cnc(N5CCCCC5)nc4)s3)(C1)C2] | 3-methoxy-N-(5-((2-(piperidin-1-yl)pyrimidin-5-yl)oxy)thiazol-2-yl)bicyclo[1.1.1]pentane-1-carboxamide |
| B137 (C21) | 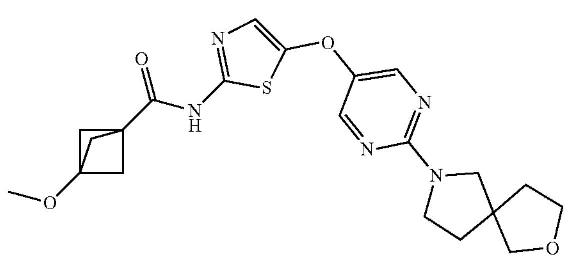 [SMILES: COC12CC(C(=O)Nc3ncc(Oc4cnc(N5CCC6(CCOC6)C5)nc4)s3)(C1)C2] | N-(5-((2-(2-oxa-7-azaspiro[4.4]nonan-7-yl)pyrimidin-5-yl)oxy)thiazol-2-yl)-3-methoxybicyclo[1.1.1]pentane-1-carboxamide |

TABLE 14-continued

| Compound | Structure | Name |
|---|---|---|
| B117 | 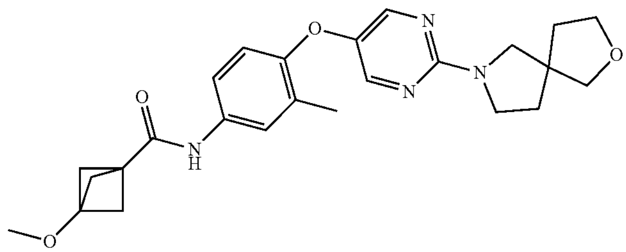 [SMILES: COC12CC(C(=O)Nc3ccc(Oc4cnc(N5CCC6(CCOC6)C5)nc4)c(C)c3)(C1)C2] | N-(4-((2-(2-oxa-7-azaspiro[4.4]nonan-7-yl)pyrimidin-5-yl)oxy)-3-methylphenyl)-3-methoxybicyclo[1.1.1]pentane-1-carboxamide |
| B139 (RGN6024) | 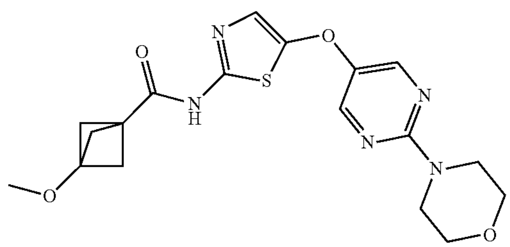 [SMILES: COC12CC(C(=O)Nc3ncc(Oc4cnc(N5CCOCC5)nc4)s3)(C1)C2] | 3-methoxy-N-(5-((2-morpholino-pyrimidin-5-yl)oxy)thiazol-2-yl)bicyclo[1.1.1]pentane-1-carboxamide |
| B89 | 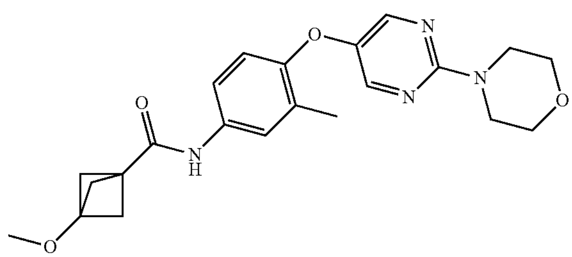 [SMILES: COC12CC(C(=O)Nc3ccc(Oc4cnc(N5CCOCC5)nc4)c(C)c3)(C1)C2] | 3-methoxy-N-(3-methyl-4-((2-morpholinopyrimidin-5-yl)oxy)phenyl)bicyclo[1.1.1]pentane-1-carboxamide |
| B155 (C27 and C89) | 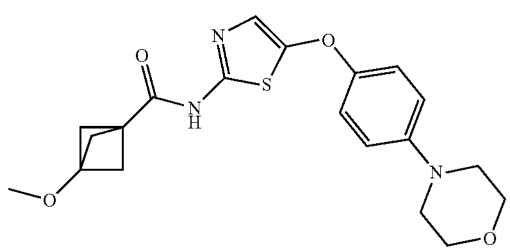 [SMILES: COC12CC(C(=O)Nc3ncc(Oc4ccc(N5CCOCC5)cc4)s3)(C1)C2] | 3-methoxy-N-(5-(4-morpholino-phenoxy)thiazol-2-yl)bicycle[1.1.1]pentane-1-carboxamide |
| B125 | 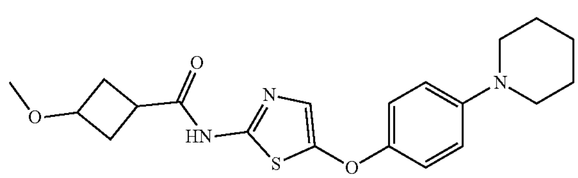 [SMILES: COC1CC(C(=O)Nc2ncc(Oc3ccc(N4CCCCC4)cc3)s2)C1] | 3-methoxy-N-(5-(4-(piperidin-1-yl)phenoxy)thiazol-2-yl)cyclobutane-1-carboxamide |
| B157 | 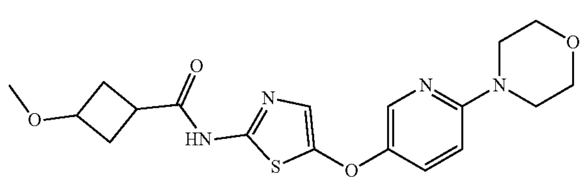 [SMILES: COC1CC(C(=O)Nc2ncc(Oc3ccc(N4CCOCC4)nc3)s2)C1] | 3-methoxy-N-(5-((6-morpholino-pyridin-3-yl)oxy)thiazol-2-yl)cyclobutane-1-carboxamide |

In some embodiments, a compound according to the instant disclosure is 3-methoxy-N-(3-methyl-4-((2-morpholinopyrimidin-5-yl)oxy)phenyl)cyclobutane-1-carboxamide,

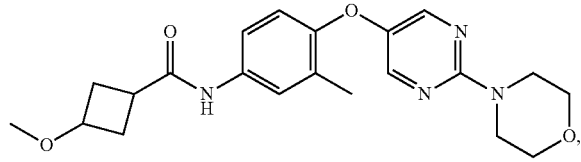 [SMILES: COC1CC(C(=O)Nc2ccc(Oc3cnc(N4CCOCC4)nc3)c(C)c2)C1]

Compound B19 an analog thereof, an isomer thereof, a pharmaceutically acceptable salt thereof, a prodrug thereof, a polymorph thereof, or any combination thereof. In some embodiments, compounds disclosed herein can have an EC$_{50}$ ranging from about 0.2 μM to about 1.0 μM in cancer cell viability (e.g., reduced viability, increased tumor cell killing) and a kinetic solubility ranging from about 0.1 μM to about 0.5 μM.

In some embodiments, a compound according to the instant disclosure is 3-methoxy-N-(5-((2-morpholinopyrimidin-5-yl)oxy)thiazol-2-yl)cyclobutane-1-carboxamide,

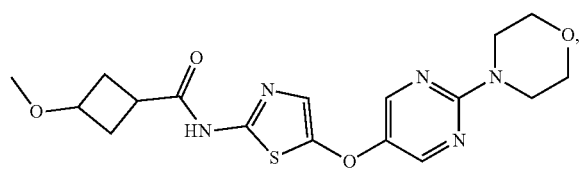 [SMILES: COC1CC(C(=O)Nc2ncc(Oc3cnc(N4CCOCC4)nc3)s2)C1]

Compound B120 an analog thereof, an isomer thereof, a pharmaceutically acceptable salt thereof, a prodrug thereof, a polymorph thereof, or any combination thereof.

In some embodiments, the compound is 3-methoxy-N-(3-methyl-4-((2-morpholinothiazol-5-yl)oxy)phenyl)cyclobutane-1-carboxamide,

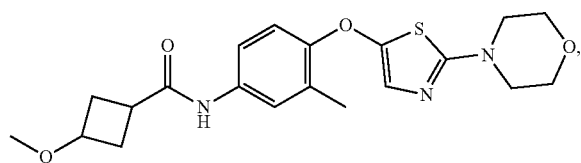 [SMILES: COC1CC(C(=O)Nc2ccc(Oc3cnc(N4CCOCC4)s3)c(C)c2)C1]

Compound B71 an analog thereof, an isomer thereof, a pharmaceutically acceptable salt thereof, a prodrug thereof, a polymorph thereof, or any combination thereof. In some embodiments, the compound has an EC$_{50}$ ranging from about 0.5 μM to 1.0 μM in cancer cell viability and a kinetic solubility ranging from about 20.0 μM to about 25.0 μM.

In some embodiments, the compound is 3-methoxy-N-(5-((2-(piperidin-1-yl)pyrimidin-5-yl)oxy)thiazol-2-yl)cyclobutane-1-carboxamide,

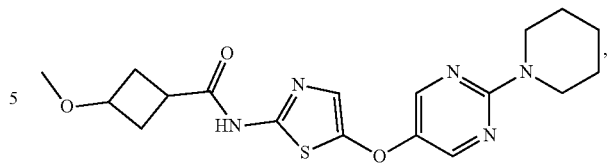

Compound B122 an analog thereof, an isomer thereof, a pharmaceutically acceptable salt thereof, a prodrug thereof, a polymorph thereof, or any combination thereof. In some embodiments, the compound has an EC$_{50}$ ranging from about 0.5 to about 2.0 μM in cancer cell viability.

In some embodiments, the compound is 3-methoxy-N-(4-((2-(4-methoxypiperidin-1-yl)pyrimidin-5-yl)oxy)-3-methylphenyl)cyclobutane-1-carboxamide,

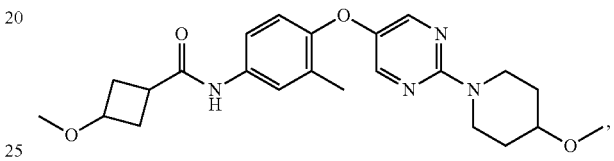

Compound B46 an analog thereof, an isomer thereof, a pharmaceutically acceptable salt thereof, a prodrug thereof, a polymorph thereof, or any combination thereof. In some embodiments, the compound has an EC$_{50}$ ranging from about 0.2 μM to about 1.0 μM in cancer cell viability and a kinetic solubility ranging from about 4.0 μM to about 7.0 μM.

In some embodiments, the compound is 3-methoxy-N-(5-(4-morpholinophenoxy)thiazol-2-yl)cyclobutane-1-carboxamide,

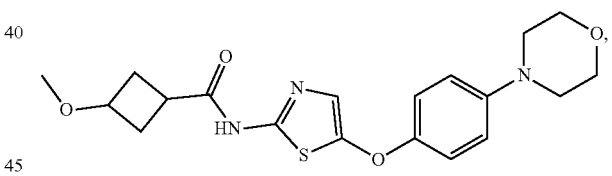

Compound B121 an analog thereof, an isomer thereof, a pharmaceutically acceptable salt thereof, a prodrug thereof, a polymorph thereof, or any combination thereof. In some embodiments, the compound has an EC$_{50}$ ranging from about 0.1 μM to about 1.0 μM in cancer cell viability and a kinetic solubility ranging from about 20.0 μM to about 30.0 μM.

In some embodiments, the compound is N-(4-((2-(3-oxa-8-azabicyclo[3.2.1]octan-8-yl)pyrimidin-5-yl)oxy)-3-methylphenyl)-3-methoxycyclobutane-1-carboxamide,

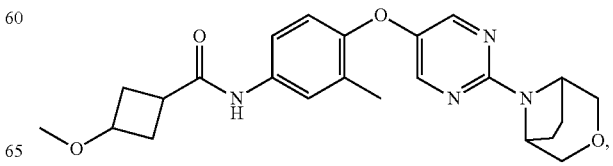

Compound B72
  an analog thereof, an isomer thereof, a pharmaceutically acceptable salt thereof, a prodrug thereof, a polymorph thereof, or any combination thereof. In some embodiments, the compound has an EC$_{50}$ ranging from about 0.5 μM to about 1.0 μM in cancer cell viability.
  In some embodiments, the compound is N-(5-((2-(3-oxa-8-azabicyclo[3.2.1]octan-8-yl)pyrimidin-5-yl)oxy)thiazol-2-yl)-3-methoxycyclobutane-1-carboxamide,

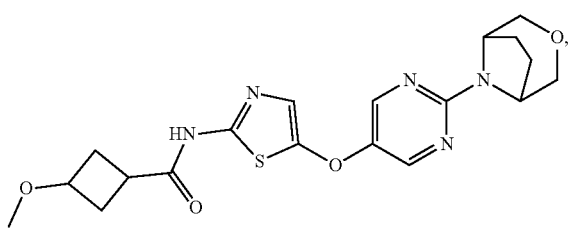 [SMILES: COC1CC(C(=O)Nc2ncc(Oc3cnc(N4C5CCC4COC5)nc3)s2)C1]

Compound B130
  an analog thereof, an isomer thereof, a pharmaceutically acceptable salt thereof, a prodrug thereof, a polymorph thereof, or any combination thereof. In some embodiments, the compound has an EC$_{50}$ ranging from about 0.5 μM to about 2.0 μM in cancer cell viability.
  In some embodiments, the compound is N-(5-((2-(3-oxa-8-azabicyclo[3.2.1]octan-8-yl)pyrimidin-5-yl)oxy)thiazol-2-yl)-3 methoxybicyclo[1.1.1]pentane-1-carboxamide,

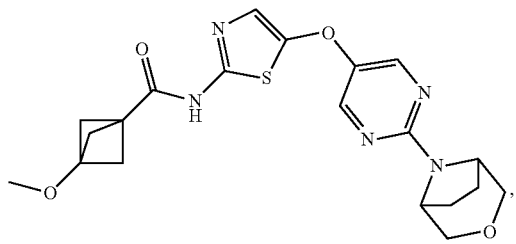 [SMILES: COC12CC(C(=O)Nc3ncc(Oc4cnc(N5C6CCC5COC6)nc4)s3)(C1)C2]

Compound B138 (also described as C18)
  an analog thereof, an isomer thereof, a pharmaceutically acceptable salt thereof, a prodrug thereof, a polymorph thereof, or any combination thereof. In some embodiments, the compound has an EC$_{50}$ ranging from about 0.001 μM to about 0.02 μM in cancer cell viability and a kinetic solubility ranging from about 85.0 μM to about 100.0 μM.
  In some embodiments, the compound is N-(4-((2-(3-oxa-8-azabicyclo[3.2.1]octan-8-yl)pyrimidin-5-yl)oxy)-3-methylphenyl)-3-methoxybicyclo[1.1.1]pentane-1-carboxamide,

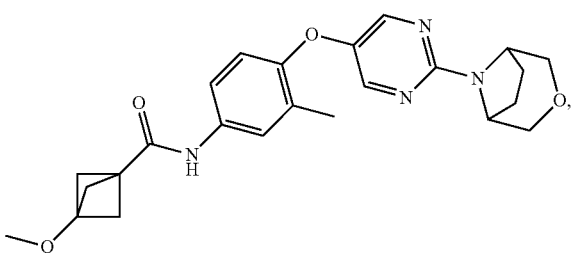 [SMILES: COC12CC(C(=O)Nc3ccc(Oc4cnc(N5C6CCC5COC6)nc4)c(C)c3)(C1)C2]

Compound B118
  an analog thereof, an isomer thereof, a pharmaceutically acceptable salt thereof, a prodrug thereof, a polymorph thereof, or any combination thereof. In some embodiments, the compound has an EC$_{50}$ ranging from about 45.0 μM to about 55.0 μM in cancer cell viability.
  In some embodiments, the compound is 3-methoxy-N-(5-((2-(piperidin-1-yl)pyrimidin-5-yl)oxy)thiazol-2-yl)bicyclo[1.1.1]pentane-1-carboxamide,

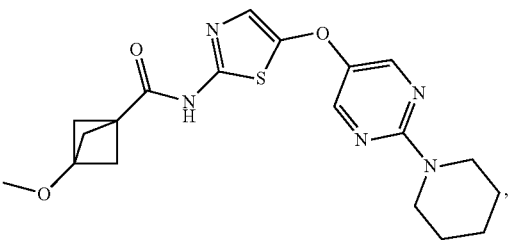 [SMILES: COC12CC(C(=O)Nc3ncc(Oc4cnc(N5CCCCC5)nc4)s3)(C1)C2]

Compound B140
  an analog thereof, an isomer thereof, a pharmaceutically acceptable salt thereof, a prodrug thereof, a polymorph thereof, or any combination thereof. In some embodiments, the compound has an EC$_{50}$ ranging from about 0.05 μM to about 1.0 μM in cancer cell viability and a kinetic solubility ranging from about 4.0 μM to about 6.0 μM.
  In some embodiments, the compound is N-(5-((2-(2-oxa-7-azaspiro[4.4]nonan-7-yl)pyrimidin-5-yl)oxy)thiazol-2-yl)-3-methoxybicyclo[1.1.1]pentane-1-carboxamide,

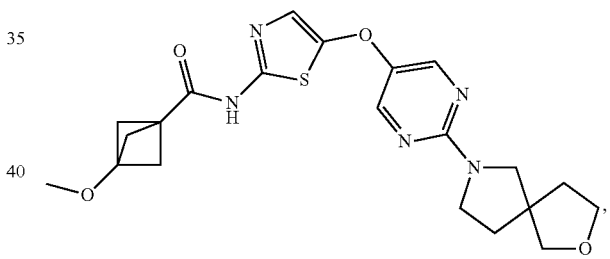

Compound B137 (also described as C21)
  an analog thereof, an isomer thereof, a pharmaceutically acceptable salt thereof, a prodrug thereof, a polymorph thereof, or any combination thereof. In some embodiments, the compound has an EC$_{50}$ ranging from about 0.01 μM to about 0.5 μM in cancer cell viability and a kinetic solubility ranging from about 80.0 μM to about 90.0 μM.
  In some embodiments, the compound is N-(4-((2-(2-oxa-7-azaspiro[4.4]nonan-7-yl)pyrimidin-5-yl)oxy)-3-methylphenyl)-3-methoxybicyclo[1.1.1]pentane-1-carboxamide,

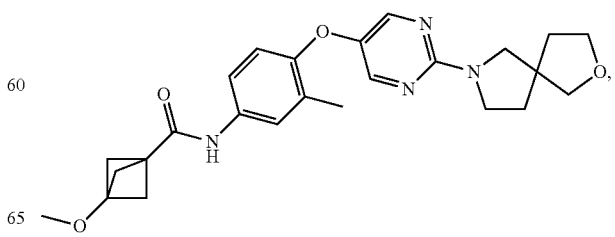

Compound B117
an analog thereof, an isomer thereof, a pharmaceutically acceptable salt thereof, a prodrug thereof, a polymorph thereof, or any combination thereof. In some embodiments, the compound has an $EC_{50}$ ranging from about 10.0 µM to about 20.0 µM in cancer cell viability.

In some embodiments, the compound is 3-methoxy-N-(5-((2-morpholinopyrimidin-5-yl)oxy)thiazol-2-yl)bicyclo[1.1.1]pentane-1-carboxamide,

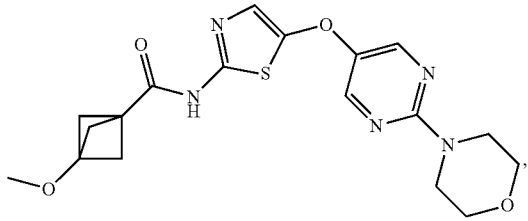 [SMILES: COC12CC(C(=O)Nc3ncc(Oc4cnc(N5CCOCC5)nc4)s3)(C1)C2]

Compound B139 (RGN6024)
an analog thereof, an isomer thereof, a pharmaceutically acceptable salt thereof, a prodrug thereof, a polymorph thereof, or any combination thereof. In some embodiments, the compound has an $EC_{50}$ ranging from about 0.01 µM to about 1.0 µM in cancer cell viability and a kinetic solubility ranging from about 4.0 µM to about 25.0 µM.

In some embodiments, the compound is 3-methoxy-N-(3-methyl-4-((2-morpholinopyrimidin-5-yl)oxy)phenyl)bicyclo[1.1.1]pentane-1-carboxamide,

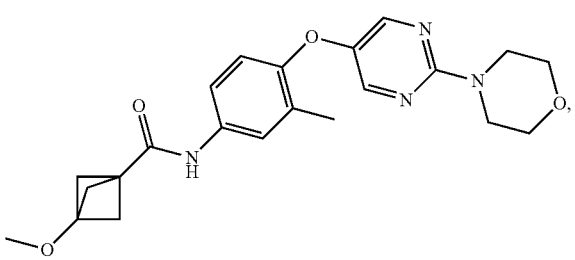 [SMILES: COC12CC(C(=O)Nc3ccc(Oc4cnc(N5CCOCC5)nc4)c(C)c3)(C1)C2]

Compound B89
an analog thereof, an isomer thereof, a pharmaceutically acceptable salt thereof, a prodrug thereof, a polymorph thereof, or any combination thereof. In some embodiments, the compound is 3-methoxy-N-(5-(4-morpholinophenoxy)thiazol-2-yl)bicyclo[1.1.1]pentane-1-carboxamide,

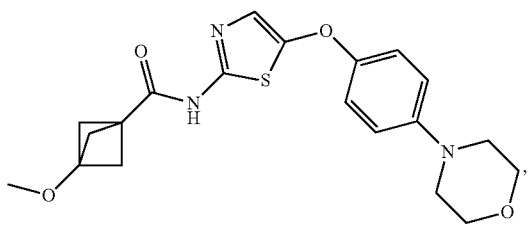 [SMILES: COC12CC(C(=O)Nc3ncc(Oc4ccc(N5CCOCC5)cc4)s3)(C1)C2]

Compound B155 (also described as C27 and C89)
an analog thereof, an isomer thereof, a pharmaceutically acceptable salt thereof, a prodrug thereof, a polymorph thereof, or any combination thereof. In some embodiments, the compound has an $EC_{50}$ ranging from about 0.001 µM to about 0.05 µM in cancer cell viability.

In some embodiments, the compound is 3-methoxy-N-(5-(4-(piperidin-1-yl)phenoxy)thiazol-2-yl)cyclobutane-1-carboxamide,

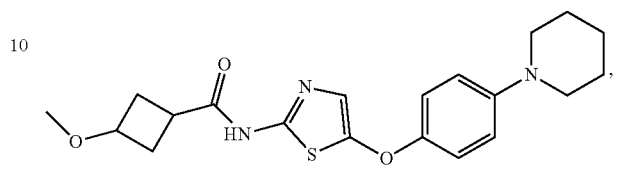

Compound B125
an analog thereof, an isomer thereof, a pharmaceutically acceptable salt thereof, a prodrug thereof, a polymorph thereof, or any combination thereof. In some embodiments, the compound has an $EC_{50}$ ranging from about 1.0 µM to about 2.0 µM in cancer cell viability.

In some embodiments, the compound is 3-methoxy-N-(5-((6-morpholinopyridin-3-yl)oxy)thiazol-2-yl)cyclobutane-1-carboxamide,

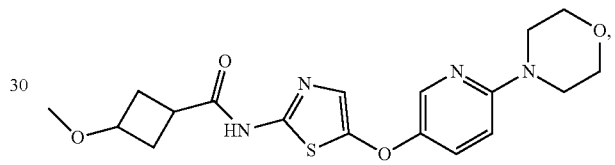

Compound B157
an analog thereof, an isomer thereof, a pharmaceutically acceptable salt thereof, a prodrug thereof, a polymorph thereof, or any combination thereof.

In some embodiments, any of the formulas described herein may exclude compounds disclosed in PCT/IB2022/062416.

In some embodiments, compounds of the present disclosure can include isomers of any one of the compounds disclosed herein, and be designated as being of a "cis" or "trans" configuration. In accordance with these embodiments, compounds of the present disclosure can be a cis or a trans isomer of any one of the compounds or formulas disclosed herein.

In some embodiments, compounds of the present disclosure can contain asymmetrically substituted carbon atoms in the R or S configuration, in which the terms "R" and "S" are as defined as known in the art. In accordance with some embodiments disclosed herein, compounds having asymmetrically substituted carbon atoms with equal amounts of R and S configurations can be racemic at those carbon atoms. In certain embodiments, the present disclosure can include racemic mixtures, relative and absolute stereoisomers, and/or mixtures of relative and absolute stereoisomers.

In other embodiments, compounds disclosed herein can be in the form of an ester such as an ester prodrug. The term "ester" herein can refer to a compound which is produced by modifying a functional group (e.g., hydroxyl, carboxyl, amino or the like group). Examples of an "ester" include "esters formed with a hydroxyl group" and "esters formed with a carboxyl group." The term "ester" can mean an ester whose ester residue is a "conventional protecting group" or a "protecting group removable in vivo by a biological method such as hydrolysis." In some embodiments, the term "conventional protecting group" can mean a protecting group removable by a chemical method such as hydrogenolysis, hydrolysis, electrolysis, or photolysis. In other embodiments, the term "protecting group removable in vivo by a biological method such as hydrolysis" can mean a protecting group removable in vivo after administration to a subject such as by hydrolysis to produce a free acid or its salt.

In certain embodiments, compounds of the present disclosure can be in the form of a pharmaceutically acceptable salt. By "salt" or "pharmaceutically acceptable salt", it is meant those salts which are, within the scope of sound medical judgment, suitable for use in contact with the tissues of humans and lower animals without undue toxicity, irritation, and allergic response, commensurate with a reasonable benefit to risk ratio, and effective for their intended use. A "pharmacologically acceptable salt" can refer to a salt, which can be formed when a compound herein has an acidic group such as carboxyl or a basic group such as amino or imino. In some embodiments, a salt of a compound disclosed herein can be formed with an acidic group, can include, but is not limited to alkali metal salts such as a sodium salt, potassium salt or lithium salt, alkaline earth metal salts such as a calcium salt or magnesium salt, metal salts such as an aluminum salt or iron salt; amine salts, e.g., inorganic salts such as an ammonium salt and organic salts such as a t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt or tris(hydroxymethyl)aminomethane salt; and amino acid salts such as a glycine salt, lysine salt, arginine salt, ornithine salt, glutamate or aspartate.

In some embodiments, a salt derivative of a compound disclosed herein formed with a basic group can include, but is not limited to, hydro-halides such as a hydrofluoride, hydrochloride, hydrobromide or hydroiodide, inorganic acid salts such as a nitrate, perchlorate, sulfate or phosphate; lower alkanesulfonates such as a methanesulfonate, trifluoromethanesulfonate or ethanesulfonate, arylsulfonates such as a benzenesulfonate or p-toluenesulfonate, organic acid salts such as an acetate, malate, fumarate, succinate, citrate, ascorbate, tartrate, oxalate or maleate; and amino acid salts such as a glycine salt, lysine salt, arginine salt, histidine salt, ornithine salt, glutamate or aspartate. In certain embodiments, when a pharmacologically acceptable salt of a compound disclosed herein remains exposed to the atmosphere or is recrystallized, it can absorb water to form a hydrate of use in formulations disclosed herein.

In certain embodiments, compounds of the present disclosure can include, but are not limited to, compounds in a solid or a liquid form or state. In some embodiments, compounds of the present disclosure can be in an amorphous form. In other embodiments, compounds of the present disclosure can be in a crystalline form or a crystalline and amorphous form combination or mixture. In accordance with some embodiments disclosed herein, compounds in a solid state can exist in a crystalline, powder, or non-crystalline form, or as a mixture thereof. In some embodiments, compounds disclosed herein in crystalline form can be used to form pharmaceutically acceptable solvates. A skilled artisan can appreciate that pharmaceutically acceptable solvates can be formed where solvent molecules are incorporated into the crystalline lattice during crystallization. In accordance with some embodiments, solvates for uses disclosed herein can include nonaqueous solvents such as ethanol, isopropanol, DMSO, acetic acid, ethanolamine, and EtOAc, or they can include water as the solvent incorporated into the crystalline lattice. Solvates where water is the solvent that is incorporated into the crystalline lattice are typically referred to as "hydrates." Hydrates can include stoichiometric hydrates as well as compositions containing variable amounts of water. The present disclosure encompasses all such solvates known in the art.

In certain embodiments, compounds of the present disclosure can exist in crystalline form, including various solvates thereof, and can exhibit polymorphism (e.g., the capacity to occur in different crystalline structures). These different crystalline forms are referred to herein as "polymorphs." Polymorphs have the same chemical composition but differ in packing, geometrical arrangement, and/or other descriptive properties of the crystalline solid state. Polymorphs, therefore, can have different physical properties such as shape, density, hardness, deformability, stability, and dissolution properties. Polymorphs typically exhibit different melting points, IR spectra, and X-ray powder diffraction patterns, NMR signatures, which can be used for identification. In certain embodiments, compounds of the present disclosure can be polymorphs. In certain embodiments, compounds of the present disclosure can be polymorphs that are identified by their melting points, IR spectra, X-ray powder diffraction patterns, NMR signatures, or any combination thereof. In some embodiments, different polymorphs of compounds herein can be produced by changing and/or adjusting the reaction conditions and/or reagents, used in making the compound. For example (but not limited to), changes in temperature, pressure, or solvent can result in polymorphs. In some embodiments, different polymorphs of compounds disclosed herein can spontaneously convert to another polymorph.

In certain embodiments and further to the previous paragraphs, compounds disclosed herein can have a sufficiently high solubility, which can be determined using kinetic or thermodynamic solubility approaches, to achieve desired bioavailability and concentrations in systemic circulation for a desired pharmacological response. In some embodiments, kinetic solubility parameters of compounds disclosed herein can be determined. In accordance with these embodiments, kinetic solubility can be determined using methods described in Example 20. In some embodiments, compounds disclosed herein can have kinetic solubility indicative of the bioavailability of formulations having the compounds, such as oral, inhalable, topical, subcutaneous and/or intravenous formulations.

In other embodiments, compounds disclosed herein can have a kinetic solubility of at least about 0.35 µM. In some embodiments, compounds disclosed herein can have a kinetic solubility ranging from about 0.35 µM to about 92 µM (e.g., about 0.35 µM, about 1 µM, about 5 µM, about 10 µM, about 20 µM, about 30 µM, about 40 µM, about 50 µM, about 60 µM, about 70 µM, about 80 µM, and about 90 µM, or about 92 µM, or any concentration in between). In yet other embodiments, compounds disclosed herein can maintain a kinetic solubility ranging from about 0.35 µM to about 92 µM (e.g., about 0.39 µM, about 1 µM, about 5 µM, about 10 µM, about 20 µM, about 30 µM, about 40 µM, about 50 µM, about 60 µM, about 70 µM, about 80 µM, and about 90 µM, or any concentration in between or greater). In additional embodiments, compounds disclosed herein can maintain a kinetic solubility for about 1 hour to about 48 hours or more (e.g., about 1 hour, about 3 hours, about 6 hours, about 12 hours, about 24 hours, about 36 hours, 48 hours, or any time in between or greater than 48 hours). In some embodiments, compounds disclosed herein can maintain a kinetic solubility ranging from about 0.35 µM to about 92 µM (e.g., about 0.39 µM, about 1 µM, about 5 µM, about 10 µM, about 20 µM, about 30 µM, about 40 µM, about 50 µM, about 60 µM, about 70 µM, about 80 µM, and about 90 µM, and about 92 µM, or any concentration in between or greater) for about 1 hour to about 48 hours (e.g., about 1 hour, about 3 hours, about 6 hours, about 12 hours, about 24 hours, about 36 hours, 48 hours or any time in between or longer).

In yet other embodiments, compounds disclosed herein can maintain a kinetic solubility at temperatures ranging from about 4° C. to about 80° C. (e.g., about 4° C., about 6° C., about 8° C., about 10° C., about 20° C., about 30° C., about 40° C., about 50° C., about 60° C., about 70° C., about 80° C. or any temperature in between). In some embodiments, compounds disclosed herein can maintain a kinetic solubility ranging from about 0.39 µM to about 92 µM (e.g., about 0.39 µM, about 1 µM, about 5 µM, about 10 µM, about 20 µM, about 30 µM, about 40 µM, about 5 µM, about 60 µM, about 70 µM, about 80 µM, and about 90 µM, or concentration in between) at temperatures ranging from about 4° C. to about 80° C. (e.g., about 4° C., about 6° C., about 8° C., about 10° C., about 20° C., about 30° C., about 40° C., about 50° C., about 60° C., about 70° C., about 80° C. or temperature in between).

In some embodiments, compounds disclosed herein can maintain a kinetic solubility ranging from about 0.35 µM to about 92 µM (e.g., about 0.39 µM, about 1 µM, about 5 µM, about 10 µM, about 20 µM, about 30 µM, about 40 µM, about 50 µM, about 6 µM, about 70 µM, about 80 µM, and about 90 µM, at room temperature (i.e., 25° C.±3° C.). In some embodiments, compounds herein can maintain a kinetic solubility ranging from about 0.39 µM to about 91.23 µM (e.g., about 0.39 µM, about 1 µM, about 5 µM, about 10 µM, about 20 µM, about 30 µM, about 40 µM, about 50 µM, about 60 µM, about 70 µM, about 80 µM, and about 90 µM, at room temperature (e.g., 25° C.±5° C.) for about 1 hour to about 48 hours (e.g., about 1 hour, about 3 hours, about 6 hours, about 12 hours, about 24 hours, about 36 hours, 48 hours or timing in between or more depending on the compound).

In some embodiments, the compound is configured to cross the blood brain barrier (BBB) of a human or non-human subject. In some embodiments, the non-human subject is a livestock, a companion animal, a lab animal, or a zoological, a wild animal, reptile, fish or bird.

In some embodiments, the compound has an $EC_{50}$ of 0.005 µM to 50 µM for inhibiting cancer cell viability or inducing cancer cell killing. In some embodiments, the compound has an $EC_{50}$ of about 0.0001 µM to 50 µM for inhibiting cancer cell viability or inducing cancer cell killing. In some embodiments, the compound has an $EC_{50}$ of about 0.0001 µM to 50 µM for inhibiting cancer cell viability or inducing cancer cell killing. In other embodiments, the compound has an $EC_{50}$ of about 0.0001 µM to 15 µM for inhibiting cancer cell viability or inducing cancer cell killing. In other embodiments, the compound has an $EC_{50}$ of about 0.0001 µM to 50 µM for inhibiting cancer cell viability or inducing cancer cell killing.

In certain embodiments, compounds disclosed herein can be analyzed and have a central nervous system multiparameter optimization (CNS MPO) score. In accordance with these embodiments, the CNS MPO score can be determined by an algorithm that uses a weighted scoring function to assess six fundamental physicochemical properties [(a) lipophilicity, calculated partition coefficient (ClogP); (b) calculated distribution coefficient at about pH 7.4 (ClogD); (c) molecular weight (MW); (d) topological polar surface area (TPSA); (e) number of hydrogen-bond donors (HBDs); and (f) most basic center (pKa)]. In these examples, the algorithm assigns a selected compound a collective score ranging from 0 to 6, wherein higher CNS MPO scores are indicative of the compound's capability to cross the blood-brain-barrier (BBB). In some embodiments, compounds disclosed herein can have a CNS MPO score indicative of BBB permeability. In other embodiments, compounds disclosed herein can have a CNS MPO score greater than or equal to 4.0 indicative of the ability to cross the BBB of use to treat health conditions where the brain of a subject is affected.

In some embodiments, the compound has a Papp score greater than 10. In other embodiments, the efflux ratio of the compound is less than 2.0.

In some embodiments, the compound is a drug conjugate or a prodrug.

In certain embodiments and further to the previous paragraphs, compounds disclosed herein can decrease viability or induce cell killing of at least one cancer cell. In some embodiments, compounds disclosed herein can decrease viability or induce cell killing of at least one cancer cell in a subject by about 10.0% to about 99% or up to 100% (e.g., about 1.0% or up to 100%, about 25.0% or up to 100%, about 50.0% or up to 100%, about 75.0% or up to about 100%, about 99% to about 100%) when compared to cancer cells not exposed to a compound or mixture of compounds or formulation thereof disclosed herein. In other embodiments, compounds disclosed here can reduce tumor volume by about 10% up to 100% compared to cancer cells not exposed to a compound or mixture of compounds or formulation thereof disclosed herein. In yet other embodiments, compounds disclosed herein can reduce metastasis of a tumor by about 10% up to about 100% in a subject compared to cancer cells not exposed to a compound or mixture of compounds or formulation thereof disclosed herein. In some embodiments, compounds disclosed herein can have a half maximal effective concentration (i.e., $EC_{50}$) for decreasing cancer cell viability, reducing tumor volume and/or reducing metastasis of a tumor of at least about 0.001 µM. In some embodiments, compounds disclosed herein can have an $EC_{50}$ for decreasing or inhibiting cancer cell viability or killing cancer cells, reducing tumor volume and/or reducing metastasis of a tumor ranging from about 0.001 µM to about 50 µM (e.g., about 0.001 µM, about 0.1 µM, about 0.1 µM, about 0.25 µM, about 0.5 µM, about 0.75 µM, about 1.0 µM, about 2.0 µM, about 5.0 µM, about 10.0 µM, about 15.0 µM, about 20.0 µM, about 25.0 µM, about 30.0 µM, about 35.0 µM, about 40.0 µM, about 45.0 µM, up to about 50.0 µM) or about 0.0001 µM to about 15 µM.

In certain embodiments and further to the previous paragraphs, compounds disclosed herein can include a cell cycle inhibitor or other anti-tumor agent or anti-neoplasia agent or compound able to reduce aberrant cell growth or cell expansion. Cell cycle inhibitors reduce or stop cell cycle progression through various mechanisms. Cell cycle arrest can be induced at different stages, decreasing the rate of cell division and reduce or inhibit the number of actively cycling cells. In some embodiments, compounds disclosed herein can arrest a cell cycle at G2M. In other embodiments, compounds disclosed herein can arrest cell proliferation of at least one cancer cell or non-cancerous aberrant cell proliferation at the G2M cell cycle stage.

In other embodiments, the compounds disclosed herein are effective for treating a health condition. In some embodiments, the compounds are effective for preventing cancer cells from dividing. In other embodiments, the compounds are effective for inhibiting tubulin polymerization. In other embodiments, the compounds are effective for destabilizing microtubules. In other embodiments, the compounds are effective for arresting cell division in the G2/M phase. In some embodiments, the compounds are effective for cytoxicity against multiple cancer cell lines. In some embodiments, the compounds are effective for treating a cancer or metastasis.

In some embodiments, the compounds disclosed herein are effective for treating a health condition. In some embodiments, the compounds are effective for treating non-neoplastic conditions.

In some embodiments, the compounds disclosed herein are effective for treating gout, familial Mediterranean fever, or nail fungus. In other embodiments, the compound is effective as a vascular targeting agent.

In some embodiments, compounds disclosed herein are effective for reducing tumor growth in a subject up to 70% as compared to a subject not treated with the compound.

II. Tagged Compounds/Prodrugs/Conjugate Drugs

In some embodiments, the present invention features a tagged compound comprising one or more compounds. In other embodiments, the tagged compound further comprises a tag linked to the compound. In further embodiments, the tag is a fluorescent tag, radioactive tag, biotin, or combination thereof.

In some embodiments, the present invention features a prodrug comprising one or more compounds. In other embodiments, the prodrug further comprises an inactive moiety linked to the compound. In further embodiments, the inactive moiety is an ester, carbamate, aminoacyl ester, or combination thereof.

In some embodiments, the present invention features a drug conjugate comprising one or more compounds. In other embodiments, the drug conjugate further comprises a targeting moiety linked to the compound. In some embodiments, targeting moiety is an antibody, polyethylene glycol (PEG) conjugate, long chain polymer, peptide sequence, or combination thereof.

III. Pharmaceutical Compositions

In other embodiments, the present disclosure provides pharmaceutical compositions. The pharmaceutical compositions include at least one compound, tagged compound, prodrug, or drug conjugate according to the instant disclosure for use to treat health conditions in a subject in need thereof. The compound can be as described, for example, herein.

In some embodiments, pharmaceutical compositions can include at least one compound disclosed herein and at least one pharmaceutically acceptable carrier. In certain embodiments, pharmaceutical compositions can include pharmaceutically acceptable carriers, excipients, and/or stabilizers that are nontoxic to recipients at dosages and/or concentrations used to practice the methods disclosed herein.

In certain embodiments, weight fraction of the excipient or combination of excipients in the composition can be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In some embodiments, the pharmaceutically acceptable excipient can include, but is not limited to a diluent, a binder, a filler, a buffering agent, a pH modifying agent, a disintegrant, a dispersant, a preservative, a lubricant, taste-masking agent, a flavoring agent, or a coloring agent and can be as described herein below. The concentrations and types of excipients utilized to form pharmaceutical compositions disclosed herein and contemplated herein can be selected according to known principles of pharmaceutical science and knowledge in the art.

Excipients and Other Supplementary Agents

In some embodiments, the excipient can be a diluent. The diluent can be compressible (i.e., plastically deformable) or abrasively brittle. Non-limiting examples of suitable compressible diluents can include, but are not limited to, microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, maltitol, sorbitol, xylitol, maltodextrin, dextran, and trehalose or the like. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient can be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient can be a filler. Suitable fillers include, but are not limited to, carbohydrates, inorganic compounds, and polyvinylpyrrolidone. By way of non-limiting example, the filler can be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient can be a buffering agent. Representative examples of suitable buffering agents include, but are not limited to, phosphates, carbonates, citrates, tris buffers, polysaccharide buffers, and buffered saline salts (e.g., Tris buffered saline, or phosphate buffered saline). In various embodiments, the excipient can be a pH modifier. By way of non-limiting example, the pH modifying agent can be sodium carbonate, sodium bicarbonate, sodium citrate, citric acid, or phosphoric acid. In a further embodiment, the excipient can be a disintegrant. The disintegrant can be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. Non-limiting examples of suitable effervescent disintegrants include sodium bicarbonate in combination with citric acid and sodium bicarbonate in combination with tartaric acid.

In yet another embodiment, the excipient can be a dispersant or dispersing enhancing agent. Suitable dispersants can include, but are not limited to, starch, alginic acid, polyvinylpyrrolidones, guar gum, kaolin, bentonite, purified wood cellulose, sodium starch glycolate, isomorphous silicate, and microcrystalline cellulose.

In another embodiment, the excipient can be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient can be a lubricant. Non-limiting examples of suitable lubricants include minerals such as talc or silica; and fats such as vegetable stearin, magnesium stearate, or stearic acid.

In yet another embodiment, the excipient can be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient can be a flavoring agent. Flavoring agents can be chosen from synthetic flavor oils and flavoring aromatics and/or natural oils, extracts from plants, leaves, flowers, fruits, and combinations thereof.

In still a further embodiment, the excipient can be a coloring agent. Suitable color additives include, but are not limited to, food, drug and cosmetic colors (FD&C), drug and cosmetic colors (D&C), or external drug and cosmetic colors (Ext. D&C).

Other pharmaceutically acceptable carriers, excipients, and/or stabilizers can include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Dosage Forms

In certain embodiments, the present disclosure provides dosages and dosage forms including at least one compound disclosed herein. In some embodiments, the dosage or dosage form includes a pharmaceutical composition or formulation including at least one compound according to the instant disclosure. The compound and pharmaceutical compositions or formulations can be as described herein and above.

In certain embodiments, pharmaceutical compositions or formulations disclosed herein can be in unit dosage forms such as tablets, pills, capsules, powders, granules, solutions, pastes, salves, or suspensions, patches (e.g., dissolvable or un-dissolvable), particles, micro- or nanoparticles or suppositories, for oral, intravenous, subcutaneous, ophthalmic drops or other drops, or rectal administration, or administration by inhalation or insufflation. In some embodiments, for preparing solid compositions such as tablets or capsules, the principal active agent (e.g., a compound disclosed herein) can be mixed with a pharmaceutically-acceptable carrier, e.g., conventional tableting agents such as corn starch, lactose, sucrose, sorbitol, talc, stearic acid, magnesium stearate, dicalcium phosphate or gums, and other pharmaceutically acceptable diluents, e.g., water, to form a solid pre-formulation composition containing a homogeneous mixture of a compound according to the present invention, or a pharmaceutically acceptable salt thereof. When referring to these pre-formulation compositions as homogeneous, it is meant that the active agent or compound is dispersed evenly throughout the composition so that the composition can be readily subdivided into equally effective unit dosage forms such as tablets, pills, and capsules. In some embodiments, solid pre-formulation compositions disclosed herein can then subdivided into unit dosage forms of the type described above containing from about 0.1 mg/kg to about 500 mg/kg (e.g., about 0.1 mg/kg, about 0.5 mg/kg, about 1.0 mg/kg, about 5.0 mg/kg, about 10 mg/kg, about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, about 250 mg/kg, about 275 mg/kg, about 300 mg/kg, about 325 mg/kg, about 350 mg/kg, about 375 mg/kg, about 400 mg/kg, about 425 mg/kg, about 450 mg/kg, about 475 mg/kg, about 500 mg/kg or higher, or any concentration in between) of a compound disclosed herein.

In some embodiments, tablets and/or pills disclosed herein can be coated or otherwise compounded to provide a dosage form affording the advantage of prolonged action. In some embodiments, a tablet and/or pill herein can have an inner dosage and an outer dosage component, the latter being in the form of an envelope over the former. In accordance with embodiments herein, the two components can be separated by an enteric layer that serves to resist disintegration in the stomach and permits the inner component to pass intact into the duodenum or to be delayed in release. In certain embodiments, two or more compounds disclosed herein can be mixed together in a single dosage form. In some embodiments, tablets and/or pills disclosed herein can include one or more agents that can be used for such enteric layers or coatings, such agents can include, but are not limited to, a number of polymeric acids and mixtures of polymeric acids with such materials as shellac, cetyl alcohol and cellulose acetate. Non-limiting surface-active agents (surfactants) suitable for use herein can include non-ionic agents or other similar agents, such as polyoxyethylenesorbitans (e.g., Tween™ 20, 40, 60, 80 or 85) and other sorbitans (e.g., Span™ 20, 40, 60, 80 or 85). In some embodiments, compositions disclosed herein with a surface-active agent can have about 0.05% and about 5.0% surface-active agent. In some embodiments, other ingredients can be added to pharmaceutical compositions disclosed herein, for example mannitol or other pharmaceutically acceptable vehicles, as deemed appropriate.

In some embodiments, pharmaceutical compositions disclosed herein can be tablets. In accordance with some embodiments herein, tablets contemplated herein can contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. In accordance with some embodiments disclosed herein, tablets contemplated herein can further contain lubricating agents such as magnesium stearate, stearic acid, glyceryl behenate and talc. In some embodiments, pharmaceutical compositions can be solid compositions employed as fillers in gelatin capsules. In accordance with some embodiments disclosed herein, excipients included in gelatin capsules contemplated herein can include lactose, starch, cellulose, milk sugar or high molecular weight polyethylene glycols or the like.

In certain embodiments, pharmaceutical compositions disclosed herein can include emulsions. In some embodiments, emulsions disclosed herein can be prepared using commercially available fat emulsions, such as Intralipid™, Liposyn™, Infonutrol™, Lipofundin™ and Lipiphysan™. The active ingredient (e.g., the one or more aminopeptidase inhibitors and/or one or more chemotherapeutics) can either be dissolved in a pre-mixed emulsion composition or dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. In some embodiments, other ingredients can be added to the compositions disclosed herein, for example glycerol or glucose, to adjust the tonicity of the emulsion. In other embodiments, emulsions can contain up to 20% (w/v) oil, for example, between about 5.0% and about 20.0% (w/v). In some embodiments, emulsions can have fat droplets between about 0.1 μm and about 1.0 μm and/or have a pH in the range of about 5.5 to about 8.0.

In certain embodiments, pharmaceutical compositions disclosed herein can be formulated for parenteral administration or any other acceptable mode of administration, such as intravenous, intracerebroventricular injection, intra-cisterna magna injection, intra-parenchymal injection, or a combination thereof. In some embodiments, pharmaceutical compositions herein formulated for parenteral administration can include one or more sterile liquids as pharmaceutically acceptable carriers. Non-limiting examples of sterile liquids suitable for use as pharmaceutically acceptable carriers disclosed herein can be water and oil, including, but not limited to, those of petroleum, animal, vegetable, or synthetic origin, such as peanut oil, soybean oil, mineral oil, and the like. Saline solutions and aqueous dextrose, polyethylene glycol (PEG) and glycerol solutions can also be employed as liquid carriers, for example as injectable solutions. Pharmaceutical compositions disclosed herein can further include additional agents, for example preservatives, buffers, tonicity agents, antioxidants and stabilizers, nonionic wetting or clarifying agents, viscosity-increasing agents, and the like. In some embodiments, pharmaceutical compositions disclosed herein can be packaged in single unit dosages or in multi-dosage forms.

In some embodiments, pharmaceutical compositions disclosed herein suitable for administration to a subject can include aqueous and non-aqueous sterile injection solutions. In accordance with these embodiments, these solutions can further contain antioxidants, buffers, bacteriostats and solutes which render the formulation isotonic in blood of the intended recipient; and aqueous and non-aqueous sterile suspensions which can include, but are not limited to, suspending agents and thickening agents. Aqueous solutions can be suitably buffered (e.g., a pH of about 3.0 to about 9.0 or about 5.0 to about 8.5 or about 6.5 to about 8.0). The preparation of suitable parenteral formulations under sterile conditions is readily accomplished by standard pharmaceutical techniques well known to those skilled in the art.

In some embodiments, pharmaceutical compositions described herein can further include one or more of an anti-microbial agent, a chemotherapeutic agent, other anti-cancer therapeutic, or antibody or fragment thereof. In accordance with these embodiments, the anti-microbial agent can, in one example, be an anti-viral, bactericidal agent, anti-fungal, or anti-bacterial agent or other anti-microbial agent. For example, the anti-microbial agent can be an anti-bacterial agent (antibiotic) such as doxycycline, tetracycline, or other antibiotics such as a generally applicable antibiotic.

In other embodiments, the present disclosure provides pharmaceutical compositions. The pharmaceutical composition includes at least one compound according to the instant disclosure for use to treat health conditions in a subject in need thereof. The compound can be as described, for example as described herein.

In some embodiments, pharmaceutical compositions can include at least one compound disclosed herein and at least one pharmaceutically acceptable carrier. In certain embodiments, pharmaceutical compositions can include pharmaceutically acceptable carriers, excipients, and/or stabilizers are nontoxic to recipients at dosages and/or concentrations used to practice the methods disclosed herein.

In certain embodiments, weight fraction of the excipient or combination of excipients in the composition can be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In some embodiments, the pharmaceutically acceptable excipient can include, but is not limited to a diluent, a binder, a filler, a buffering agent, a pH modifying agent, a disintegrant, a dispersant, a preservative, a lubricant, taste-masking agent, a flavoring agent, or a coloring agent and can be as described herein below. The concentrations and types of excipients utilized to form pharmaceutical compositions disclosed herein and contemplated herein can be selected according to known principles of pharmaceutical science and knowledge in the art.

IV. Methods of Treatment

In certain embodiments, the present disclosure provides methods for treating, preventing, reducing onset of, or ameliorating a health condition in a subject having, is suspected of developing, or is at risk of developing the health condition. In accordance with these embodiments, the methods can include administering to the subject a therapeutically effective amount of a compound according to the instant disclosure alone or as combination therapies in treating, reducing onset or ameliorating a health condition in a subject in need thereof. In accordance with these embodiments, the compound can be in the form of a therapeutic composition including at least one compound according to the instant disclosure or can be a dosage form including at least one compound according to the instant disclosure. In certain embodiments, the health condition can be cancer or a non-cancerous growth. In other embodiments, the health condition can be any health condition treatable by compounds disclosed herein. Certain embodiments of the method and health conditions are described below. Disclosed compounds, therapeutic compositions and formulations, and dosage forms are described above and herein, respectively.

Cancer

In some embodiments, the health condition can include, but is not limited to, cancer. Accordingly, in certain embodiments, methods of the instant disclosure include treating, ameliorating, or reducing the risk of onset of cancer in a subject. In accordance with these embodiments, the cancer can include any type of cancer or tumor. In some embodiments, the cancer can be a solid tumor or non-solid, or other tumor. In other embodiments, the cancer can be malignant or non-malignant, or metastatic or non-metastatic. In some embodiments, the cancer health condition can include a vascularized cancer.

Certain embodiments disclosed herein concern treating, ameliorating, or reducing the risk of onset of cancer using at least one compound disclosed herein. Non-limiting examples of cancer can include, but are not limited to, carcinoma, sarcoma, myeloma, leukemia, lymphoma, and mixed types. Other non-limiting examples of cancers include, but are not limited to, connective tissue, bladder cancer, breast cancer, kidney (renal) cancer, lung cancer, lymphoma, pancreatic cancer, prostate cancer, skin cancer, uterine cancer, other organ- or tissue-related cancer and the like. In accordance with these embodiments, a method of the instant disclosure can include the use of a compound according to the instant disclosure to treat, ameliorate, prevent, or reduce the risk of onset of any type of cancer. Non-limiting examples of types of cancers to be treated, ameliorated, reduce onset of, or prevent can include, but is not limited to, adrenocortical carcinoma, AIDS-related cancers, pathogen-related cancer (e.g., HPV), anal cancer, appendix cancer, glioblastomas, medulloblastoma, basal cell carcinoma, bladder cancer, bone cancer, brain tumors, breast cancer, bronchial adenomas/carcinoids, carcinoid tumors (childhood, gastrointestinal), carcinoma of unknown primary, cerebellar astrocytoma, cervical cancer, childhood cancers, chronic myeloproliferative disorders, colon cancer, desmoplastic small round cell tumor, endometrial cancer, ependymoma, esophageal cancer, extrahepatic bile duct cancer, bile duct cancer, eye cancers (intraocular melanoma, retinoblastoma), gallbladder cancer, gastric (stomach) cancer, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic, cerebral glioma, malignant glioma), head and neck cancer, hepatocellular (liver) cancer, hypopharyngeal cancer, laryngeal cancer, leukemias (acute lymphoblastic, acute myeloid, chronic lymphocytic, chronic myelogenous, hairy cell), lip and oral cavity cancer, lung cancers (non-small cell, small cell), lymphomas (AIDS-related, Burkitt, cutaneous T-cell, Hodgkin, non-Hodgkin, primary central nervous system), macroglobulinemia (Waldenström), medulloblastoma (childhood), mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, nasal cavity and paranasal sinus cancer, nasopharyngeal carcinoma, neuroblastoma, oropharyngeal cancer, osteosarcoma/malignant fibrous histiocytoma of bone, ovarian cancer, ovarian epithelial cancer (surface epithelial-stromal tumor), ovarian low malignant potential tumor, pancreatic cancer, pancreatic cancer (islet cell), parathyroid cancer, penile cancer, pharyngeal cancer, pheochromocytoma, pineal astrocytoma, pineal germinoma, pineoblastoma, and supratentorial primitive neuroectodermal tumors (childhood), pituitary adenoma, pleuropulmonary blastoma, primary prostate cancer, rectal cancer, renal cell carcinoma (kidney cancer), rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), squamous cell carcinoma, testicular cancer, throat cancer, thymoma (childhood), thymoma and thymic carcinoma, thyroid cancer, thyroid cancer (childhood), transitional cell cancer of the renal pelvis and ureter, unknown primary site (adult, childhood), urethral cancer, vaginal cancer, vulvar cancer, and Wilms tumor (childhood).

In some embodiments, non-cancerous growths can also be treated by at least one compound disclosed herein to reduce progression to a cancerous lesion or contain expansion of for example, a neoplasia or benign tumor. In accordance with these embodiments, a method of the instant disclosure can also include use of a compound according to the instant disclosure to treat, ameliorate, prevent, or reduce the risk of onset of non-cancerous growths in a subject suspected of developing, or is at risk of developing any type of non-cancerous growths.

In certain embodiments, methods of the instant disclosure can include use of at least one compound disclosed herein to treat, ameliorate, prevent, or reduce the risk of onset of a cancer at any stage of development. For instance, the cancer can be a stage 0 cancer, a stage I, II, or III which can be used to describe the number of tumors in the body of a subject, the size of the tumor, and the degree of spread into nearby tissues, or a stage IV cancer or metastatic cancer that has spread to other organs, lymph nodes or distant parts of the body.

In some embodiments, cancers to be treated or prevented by compounds and/or compositions disclosed herein can include, but are not limited to, prostate cancer, brain cancer, metastatic cancers, pancreatic cancer, lung cancer, breast cancer, kidney cancer, skin cancer, liver cancer, bladder cancer, bone sarcoma, ovarian cancer, rectal cancer, blood cancer, gastrointestinal cancer, medulloblastoma, or any combination thereof. In some embodiments, the cancer is prostate cancer. In certain embodiments, the cancer is breast cancer. In some embodiments, the cancer is bone cancer. In other embodiments, the cancer is Ewing's sarcoma. In additional embodiments, the cancer is lung cancer. In yet other embodiments, the cancer is non-small cell lung cancer (NSCLC). In some embodiments, the cancer is skin cancer. In other embodiments, the cancer is melanoma.

In certain embodiments and further to all paragraphs above, the cancer can be brain cancer. Non-limiting examples of brain cancer can include, but are not limited to, brainstem glioma, cerebellar astrocytoma, cerebral astrocytoma/malignant glioma, ependymoma, medulloblastoma, supratentorial primitive neuroectodermal tumors, visual pathway and hypothalamic gliomas. In some embodiments, the brain cancer can be glioblastoma, high-grade glioma, other brain cancer, or any combination thereof. In certain embodiments, methods disclosed herein include treating, ameliorating, or reducing onset of glioblastoma. In other embodiments, methods disclosed herein include treating, ameliorating, or preventing onset of high-grade gliomas.

In some embodiments, the compounds disclosed herein, such as compound B19, compound B120, compound B71, compound B122, compound B46, compound B121, compound B72, compound B130, compound B138, compound B118, compound B140, compound B137, or RGN6024, compound B89, compound B155, compound B125, compound B157, or compound B117, or any combination thereof or composition or formulation thereof, can be administered to treat brain cancer. In accordance with these embodiments, the brain cancer can include, but is not limited to, brainstem glioma, cerebellar astrocytoma, cerebral astrocytoma/malignant glioma, ependymoma, medulloblastoma, supratentorial primitive neuroectodermal tumors, visual pathway and hypothalamic gliomas. In some embodiments, the compounds disclosed herein, such as compound B19, compound B120, compound B71, compound B122, compound B46, compound B121, compound B72, compound B130, compound B138, compound B118, compound B140, compound B137, or RGN6024, compound B89, compound B155, compound B125, compound B157, or compound B117, or any combination thereof or composition or formulation thereof, can be administered to treat glioblastoma, high grade glioma, other brain cancer, or any combination thereof. In certain embodiments, the compounds disclosed herein, such as compound B19, compound B120, compound B71, compound B122, compound B46, compound B121, compound B72, compound B130, compound B138, compound B118, compound B140, compound B137, or RGN6024, compound B89, compound B155, compound B125, compound B157, or compound B117, or any combination thereof or composition or formulation thereof, can be administered to treat, ameliorate, or reduce onset of glioblastoma. In other embodiments, methods disclosed herein include administering the compounds disclosed herein, such as compound B19, compound B120, compound B71, compound B122, compound B46, compound B121, compound B72, compound B130, compound B138, compound B118, compound B140, compound B137, or RGN6024, compound B89, compound B155, compound B125, compound B157, or compound B117, or any combination thereof or composition or formulation thereof, to treat, ameliorate, or prevent onset of high-grade gliomas.

In other embodiments, RGN6024 or a formulation thereof can be administered to treat brainstem glioma, cerebellar astrocytoma, cerebral astrocytoma/malignant glioma, ependymoma, medulloblastoma, supratentorial primitive neuroectodermal tumors, visual pathway and hypothalamic gliomas. In some embodiments, RGN6024 or a formulation thereof can be administered to treat glioblastoma, high grade glioma, other brain cancer, or any combination thereof. In certain embodiments, RGN6024 or formulation thereof can be administered to treat, ameliorate, or reduce onset of glioblastoma. In other embodiments, methods disclosed herein include administering compound RGN6024 or formulation thereof to treat, ameliorate, or prevent onset of high-grade gliomas.

In some embodiments and further to paragraphs the previous paragraphs and further to paragraphs above, the cancer is cancer that metastasizes to the brain. Non-limiting examples of cancers that are most likely to cause brain metastases include, but are not limited to, lung, breast, colon, kidney, and melanoma. In some embodiments, the cancer is lung cancer, lung cancer that has metastasized to the brain, breast cancer, breast cancer that has metastasized to the brain, colon cancer, colon cancer that has metastasized to the brain, kidney cancer, kidney cancer that has metastasized to the brain, melanoma, or melanoma that has metastasized to the brain, or any combination thereof. In other embodiments, the cancer is non-small cell lung cancer (NSCLC) that has metastasized to the brain. In some embodiments, the cancer is breast cancer that has metastasized to the brain.

In some embodiments, methods of treating, ameliorating, or preventing cancer, metastasis, tumor formation or progression, or a combination thereof in a subject can include, but are not limited to, administration of an effective amount of any or the compounds and/or pharmaceutical compositions disclosed herein. "An effective amount" as used herein refers to a dose of any the compounds, formulations and/or pharmaceutical compositions disclosed herein that is sufficient to confer a therapeutic effect on a subject having or suspected of developing cancer. In certain embodiments, a therapeutic effect for a subject having or suspected of having cancer can include reducing the symptoms or consequences of the cancer, such as reducing expansion of, shrinking of a tumor, killing tumor cells, preventing or reducing the occurrence of metastases from a primary tumor, reducing the number of tumor cells of a tumor or tumor volume, reducing or preventing metastasis of a tumor, inhibiting the growth or expansion of tumor cells of a primary tumor, secondary tumor and/or a metastatic tumor, eliminating or killing tumor cells and the like.

Non-Neoplastic Conditions

In some embodiments, the health condition can include, but is not limited to, non-neoplastic conditions. Non-neoplastic conditions refer to a non-cancerous, non-malignant, or benign disease or lesion that is not abnormal tissue growth resulting from uncontrolled cell proliferation. Accordingly, in certain embodiments, methods of the instant disclosure include treating, ameliorating, or reducing the risk of onset of gout, familial Mediterranean fever, or nail fungus. In other embodiments, the health condition can include, but is not limited to, vascular disease.

Subjects

In some embodiments, the subject to be treated by any compound or any composition disclosed herein for any health condition can be human. In other embodiments, the subject can be a non-human animal or other mammal. In some embodiments, a subject can be livestock, a companion animal, a lab animal, or a zoological, a wild animal, reptile, fish or bird. Non-limiting examples of livestock can include, but is not limited to, pigs, cows, buffalo goats, sheep, chickens, ducks, geese, turkeys, llamas, and alpacas. Non-limiting examples of companion animals can include pets such as dogs, cats, rabbits, horses, and birds. As used herein, a zoological animal can include any animal found in a zoo. Zoo and wild animals can include, but are not limited to, non-human primates, wild cats, wolves, and bears. Non-limiting examples of a laboratory animal can include rodents, canines, felines, and non-human primates. In some embodiments, the subject is a human subject such as a fetus, infant, child, adolescent, young adult, adult, or elderly adult.

In some embodiments, a subject can be any subject for whom treatment or therapy is needed. In other embodiments, a subject to be treated by the methods described herein can be a human subject having, having had, suspected of having, or at risk of developing a health condition. In certain embodiments, the health condition is cancer. In some embodiments, a subject can have, have had, is suspected of having, or is at risk of developing cancer. In some embodiment, a subject can have, have had, is suspected of having, or is at risk of developing a solid tumor. In certain embodiments, a subject can be a mammal. In some embodiments, a subject can be human. In other embodiments, a subject in need of methods disclosed herein can be identified by routine medical examination, e.g., laboratory tests, biopsy, magnetic resonance imaging (MRI) scans, ultrasound exams, and the like. In some embodiments, the subject to be treated by methods described herein can have undergone or is undergoing an anti-cancer therapy, for example, chemotherapy, radiotherapy, immunotherapy, and/or surgery.

In some embodiments, a subject to be treated by the methods described herein can be a human subject having, having had, suspected of having, or at risk of developing cancer. In some embodiments, a subject to be treated by the methods described herein can be a human subject having, suspected of having, or at risk of developing, without limitation, prostate cancer, brain cancer, metastatic cancers, pancreatic cancer, lung cancer, breast cancer, kidney cancer, skin cancer, liver cancer, bladder cancer, bone sarcoma, prostate cancer, ovarian cancer, rectal cancer, blood cancer, skin cancer, gastrointestinal cancer, medulloblastoma, or any combination thereof, or any combination thereof. In some embodiments, a subject to be treated by the methods described herein can be a human subject having, having had, suspected of having, or at risk of developing adenocarcinoma of the prostate (e.g., acinar adenocarcinoma and/or prostatic ductal adenocarcinoma). In certain embodiments, a subject to be treated by the methods described herein can be a human subject having, having had, suspected of having, or at risk of developing astrocytoma, glioblastoma, and/or meningioma. In some embodiments, a subject to be treated by the methods described herein can be a human subject having, having had, suspected of having, or at risk of developing exocrine pancreatic cancer (e.g., adenocarcinoma, squamous cell carcinoma, adenosquamous carcinoma, colloid carcinoma) and/or neuroendocrine pancreatic cancer. In some embodiments, a subject to be treated by the methods described herein can be a human subject having, suspected of having, or a risk for developing ductal carcinoma in situ, invasive ductal carcinoma, breast cancer including, but not limited to, inflammatory breast cancer, and/or metastatic breast cancer. In other embodiments, a subject to be treated by the methods disclosed herein can be a human subject having, suspected of having, having had, or at risk of developing osteosarcoma, chondrosarcoma, poorly differentiated round/spindle cell tumors, Ewing sarcoma, hemangioendothelioma, angiosarcoma, fibrosarcoma/myofibrosarcoma, chordoma, adamantinoma, liposarcoma, leiomyosarcoma, malignant peripheral nerve sheath tumor, rhabdomyosarcoma, synovial sarcoma, and/or malignant solitary fibrous tumor. In additional embodiments, a subject to be treated by the methods disclosed herein can be a human subject having, having had, suspected of having, or at risk of developing hepatocellular carcinoma (HCC), fibrolamellar HCC, cholangiocarcinoma, hemangiosarcoma, secondary liver cancer, and/or hepatoblastoma. In other embodiments, a subject to be treated by the methods described herein can be a human subject having, suspected of having, having had, or at risk of developing urothelial carcinoma, squamous cell carcinomas, adenocarcinomas, and/or small-cell carcinomas of the bladder.

In certain embodiments, a subject to be treated by the methods disclosed herein can be a human subject having, having had, suspected of having, or at risk of developing prostate cancer. In some embodiments, a subject to be treated by the methods disclosed herein can be a human subject having, having had, suspected of having, or at risk of developing breast cancer. In other embodiments, a subject to be treated by the methods disclosed herein can be a human subject having, having had, suspected of having, or at risk of developing bone cancer. In yet other embodiments, a subject to be treated by the methods disclosed herein can be a human subject having, having had, suspected of having, or at risk of developing Ewing's sarcoma. In some embodiments, a subject to be treated by the methods disclosed herein can be a human subject having, having had, suspected of having, or at risk of developing lung cancer. In additional embodiments, a subject to be treated by the methods disclosed herein can be a human subject having, having had, suspected of having, or at risk of developing non-small cell lung cancer (NSCLC). In some embodiments, a subject to be treated by the methods disclosed herein can be a human subject having, having had, suspected of having, or at risk of developing non-small cell lung cancer (NSCLC) metastasizing to brain. In other embodiments, a subject to be treated by the methods disclosed herein can be a human subject having, having had, suspected of having, or at risk of developing skin cancer. In some embodiments, a subject to be treated by the methods disclosed herein can be a human subject having, having had, suspected of having, or at risk of developing melanoma.

Administration

A composition of the instant disclosure can be administered to a subject by any method known in the art. In some embodiments, the compounds disclosed herein, such as compound B19, compound B120, compound B71, compound B122, compound B46, compound B121, compound B72, compound B130, compound B138, compound B118, compound B140, compound B137, or RGN6024, compound B89, compound B155, compound B125, compound B157, or compound B117, or any combination thereof or composition or formulation thereof, can be administered parenterally, buccally, intranasally, by inhalation, intraperitoneally, intrauterine, intratumorally, intravascularly, transdermally, subcutaneously, rectally, or intrapulmonary. Non-limiting examples of administering the compounds disclosed herein, such as compound B19, compound B120, compound B71, compound B122, compound B46, compound B121, compound B72, compound B130, compound B138, compound B118, compound B140, compound B137, or RGN6024, compound B89, compound B155, compound B125, compound B157, or compound B117, or any combination thereof or composition or formulation thereof, include intravenous, intramuscular, intrathecal, or intrasternal administration, oral administration, subcutaneous administration, intratumoral, intravascular, intracerebral injection, intracisternal, intracerebroventricular, intranasal or inhalation, parenteral, buccal, enteral, intraperitoneal, inhalable, infused, ophthalmic, intravitreal, otic, rectal, sublingual, topical, transdermal, intrapulmonary, intrauterine, vaginal, via ultrasound-mediated blood brain barrier disruption, implantable devices, infusion techniques, or nanoparticle-based delivery.

In certain embodiments, compositions disclosed herein can be administered topically. Topical administration can include the use of transdermal administration such as transdermal patches or iontophoresis devices. In some embodiments, compositions disclosed herein can be formulated in dosage unit formulations for administration that further include, but are not limited to, conventional nontoxic pharmaceutically acceptable adjuvants, carriers, excipients, and vehicles as described in herein and above, respectively.

In certain embodiments, dosage levels of compounds disclosed herein in a therapeutic composition of the disclosure can be varied to administer a concentration of compounds or mixtures of compounds that is effective to achieve the desired therapeutic response for a particular subject. A selected dosage level can depend upon a variety of factors, including the particular compound or mixture of compounds in a composition, the activity of the therapeutic composition, formulation, the combination with other drugs or treatments, disease and disease duration, and the physical condition and prior medical history of the subject being treated. Determination of the proper dosage for a particular situation is within the skill of a health professional.

In some embodiments, a composition disclosed herein is administered as needed, upon development or shortly before development of symptoms. In some embodiments, the composition is administered regularly by following a prescribed treatment schedule. For instance, a composition of the instant disclosure can be administered routinely, at various intervals. In another example, compositions can be administered daily, weekly, monthly, or over several months. In some embodiments, compositions are administered daily. In other embodiments, compositions are administered weekly. In yet other embodiments, compositions are administered monthly. Compositions can also be administered every three to six months or by longer intervals as determined is appropriate for prolonged administration or treatment. As it will be recognized in the art, the duration of treatment can and will vary and can be determined by a health professional.

Administration of compositions described herein can also be carried out as part of a treatment regimen that can include multiple instances of administration of one or more compositions or mixture of compositions. Such a regimen can be designed as a method of immediately treating a condition and/or as a method of long-term maintenance of the health of a subject after having been treated for a condition (e.g., prevention). For instance, a treatment regimen can be designed to delay the onset of the condition of interest in a subject. It will be appreciated that determination of appropriate treatment regimens is within the skill of a health professional.

It will also be appreciated by those skilled in the art that a composition of the present disclosure can be co-administered with other therapeutic agents before, after, and/or during treatment with a composition of the disclosure. The term "co-administer" refers to administration of more than one active ingredient at the same time, just prior to, or just after the administration of one or more additional therapies. The compounds of the disclosure can be administered alone or can be co-administered to the subject along with another compound or a standard agent known in the art. Co-administration is meant to include simultaneous or sequential administration of the compounds individually or in combination. Dosage amounts and intervals can be adjusted individually to provide levels of the administered compound effective for the particular clinical indication being treated. This will provide a therapeutic regimen that is commensurate with the severity of the individual's disease state.

In certain embodiments, a subject treated with one or more compounds or compositions disclosed herein can have completed at least one additional cancer therapeutic regimen, be receiving an additional cancer therapeutic regimen, or can receive an additional cancer therapeutic regimen following treatment disclosed herein or surgery before or after administering a compound or composition disclosed herein. In some embodiments, an additional therapeutic regimen of use to treat cancer disclosed herein can include administering one or more anti-cancer therapeutic or treatment, e.g., one or more of chemotherapeutic agents, radiation therapies, small molecules, and an immunomodulatory agent. In some embodiments, anti-cancer therapeutics or treatments can be administered separately from a compound disclosed herein or a derivative thereof. In certain embodiments, anti-cancer therapeutics or treatments can be administered to a subject before, during, or after at least one compound is administered to a subject disclosed herein at least once daily, every other day, every third day, twice weekly, weekly, every other week, twice monthly or monthly, every other month, every six months, or other suitable dosing regimen.

In certain embodiments, the present invention further comprises administration of one or more of an anti-microbial agent, a chemotherapeutic agent, other anti-cancer therapy, or antibody or fragment thereof. In some embodiments, the anti-microbial agent comprises one or more of an anti-viral, bactericidal agent, anti-fungal, or anti-bacterial agent or other anti-microbial agent. In other embodiments, the anti-bacterial agent comprises one or more of doxycycline or tetracycline.

In some embodiments, pharmaceutical compositions disclosed herein can be administered before, during, or after at least one or more chemotherapeutic agents. Non-limiting examples of a chemotherapeutic agent can include, but is not limited to, temozolomide, lomustine, belzutifan, cisplatin, carboplatin, nedaplatin, triplatin tetranitrate, phenanthriplatin, picoplatin, satraplatin, Doxorubicin, Melphalan, Roscovitine, Mitomycin C, Hydroxyurea, 5-Fluorouracil, AraC (cytarabine), 6-mercaptopurine, 6-thioguanine, Cisplatin, Ara-C, Etoposide, Gemcitabine, Bortezomib, Sunitinib, Sorafenib, Sodium Valproate, a HDAC Inhibitor, a DNA synthesis inhibitor, or Dacarbazine or a combination thereof. Non-limiting examples of HDAC inhibitors include FR01228, Trichostatin A, SAHA and/or PDX101. Non-limiting examples of DNA synthesis inhibitors include, but are not limited to, capecitabine, floxuridine, decitabine, vidaza, fludarabine, nelarabine, cladribine, clofarabine, pentostatin, thiarabine, troxacitabine, sapacitabine or forestine. More examples of additional chemotherapeutic agents include, but are not limited to, FLT3 inhibitors such as Semexanib (SCT5416). Sunitinib (SU 11248), Midostaurin (PKC412), Lestautinib (CEP-701), Tandutinib (MLN518), CHIR-258, Sorafenib (BAY-43-9006) and/or KW-2449. Other non-limiting examples of additional chemotherapeutic agents include farnesyltransferase inhibitors such as tipifarnib (R1 15777, Zarnestra), lonafarnib (SCH66336, Sarasar™) and/or BMS-214662. Other chemotherapeutic agents include, but are not limited to, topoisomerase II inhibitors such as the epipodophyllotoxins etoposide, teniposide, anthracyclines doxorubicin and/or 4-epi-doxorubicin. More non-limiting examples of additional chemotherapeutic agents include P-glycoprotein modulators such as zosuquidar trihydrochloride (Z.3HCL), vanadate, or verapamil. More non-limiting examples of chemotherapeutic agents include hypomethylating agents such as 5-aza-cytidine or 2' deoxyazacitidine.

In certain embodiments, pharmaceutical compositions disclosed herein can be administered before, during, or after at least one or more other agents. Non-limiting examples of such other agents or molecules can include, but are not limited to, imatinib, dasatinib, nilotinib, bosutinib, regorafenib, ponatinib, sunitinib, sorafenib, erdafitinib, lenvatinib, pazopanib, afatinib, gefitinib, osimertinib, vandetanib, erlotinib, lapatinib, dacomitinib, neratinib, ribociclib, abemaciclib, palbociclib, cabozantinib, crizotinib, axitinib, alectinib, vemurafenib, encorafenib, dabrafenib, olaparib, rucaparib, talazoparib, niraparib, larotrectinib, entrectinib, lorlatinib, ibrutinib, cobimetinib, binimetinib, trametinib, brigatinib, cgilteritinib, ceritinib, ivosidenib, carfilzomib, marizomib, alpelisib, duvelisib, copanlisib, and the like.

In other embodiments, pharmaceutical compositions disclosed herein can be administered alone or in combination with at least one immunomodulatory agent. Non-limiting examples of such immunomodulatory agents include, but are not limited to, anti-PD1, anti-PD-L1, anti-CTLA-4, anti-OX40, anti-CD137, etc. Non-limiting examples of PD-1 inhibitors include, but are not limited to, anti-PD-1 antibodies, such as pembrolizumab, nivolumab, and cemiplimab. Non-limiting examples of PD-L1 inhibitors can include atezolizumab, durvalumab, and avelumab. A non-limiting example of a CTLA-4 inhibitor is the anti-CTLA-4 antibody ipilimumab. In some embodiments, an immunomodulatory agent can be one or more inhibitors that target a checkpoint molecule selected from CD40, GITR, LAG-3, OX40, TIGIT and TIM-3.

In certain embodiments and further to the preceding paragraphs, at least one additional therapeutic regimen in combination therapies disclosed herein can include administering radiation. In some embodiments, a subject can be treated by radiation therapy by at least one of before, during or after administration of a compound and/or pharmaceutical composition disclosed herein. In other embodiments, a subject can be treated by radiation therapy at least 12 hours, about 24 hours, about 2 days, about 3 days, about 4 days, about 5 days, about 6 days, about 1 week, or about 2 weeks or about 3 weeks or more before and/or after administration of a compound and/or pharmaceutical composition disclosed herein. In yet other embodiments, a subject can be treated by radiation therapy using ionizing radiation. In some embodiments, a subject can be treated by radiation therapy delivered by a linear accelerator. In additional embodiments, a subject can be treated by radiation therapy delivered directly to a tumor. In certain embodiments, radiation therapy can be delivered directly to a tumor at a dose of radiation ranging from about 2 Gy to about 150 Gy (e.g., about 2, about 5, about 10, about 20, about 30, about 40, about 50, about 75, about 100, about 125, about 150 Gy or other suitable radiation range or dose).

In some embodiments, at least one compound disclosed herein can be administered with radiation to treat a subject having or suspected of developing brain cancer (e.g., glioblastoma, high grade glioma, or cancer that metastasizes to the brain). In certain embodiments, the compounds disclosed herein, such as compound B19, compound B120, compound B71, compound B122, compound B46, compound B121, compound B72, compound B130, compound B138, compound B118, compound B140, compound B137, or RGN6024, compound B89, compound B155, compound B125, compound B157, or compound B117, or any combination thereof or composition or formulation thereof, can be administered before, during and/or after radiation to treat a subject having or suspected of developing brain cancer.

In certain embodiments, RGN6024 or a formulation thereof can be administered with, before or after radiation to treat a subject having or suspected of developing brain cancer (e.g., glioblastoma, high grade glioma, or cancer that metastasizes to the brain). In certain embodiments, RGN6024 or a formulation thereof can be administered at the same time or consecutively following radiation to treat a subject having or suspected of developing brain cancer or other cancer.

In some embodiments, at least one compound disclosed herein can be administered before, during and/or after at least one chemotherapy agent to treat a subject having or suspected of developing brain cancer (e.g., glioblastoma, high grade glioma, or cancer that metastasizes to the brain). In certain embodiments, the compounds disclosed herein, such as compound B19, compound B120, compound B71, compound B122, compound B46, compound B121, compound B72, compound B130, compound B138, compound B118, compound B140, compound B137, or RGN6024, compound B89, compound B155, compound B125, compound B157, or compound B117, or any combination thereof or composition or formulation thereof, can be administered before, during and/or after at least one chemotherapy agent to treat a subject having or suspected of developing brain cancer. In some embodiments, at least one compound herein can be administered before, during and/or after temozolomide to treat a subject having or suspected of having brain cancer (e.g., glioblastoma, high grade glioma, or cancer that metastasizes to the brain).

In some embodiments, at least one compound herein can be administered before, during and/or after lomustine to treat a subject having or suspected of having brain cancer. In some embodiments, at least one compound herein can be administered before, during and/or after belzutifan to treat a subject having or suspected of having brain cancer. In other embodiments, at least one compound herein can be administered before, during and/or after crizotinib to treat a subject having or suspected of having non-small cell lung cancer (NSCLC) that has metastasized to the brain. In yet other embodiments, at least one compound herein can be administered before, during and/or after osimertinib to treat a subject having or suspected of having non-small cell lung cancer (NSCLC) that has metastasized to the brain.

In certain embodiments, RGN6024 or a formulation thereof can be administered with at least one chemotherapy agent to treat a subject having or suspected of developing brain cancer (e.g., glioblastoma, high grade glioma, or cancer that metastasizes to the brain). In some embodiments, RGN6024 or a formulation thereof can be administered before, during and/or after temozolomide to treat a subject having or suspected of having brain cancer (e.g., glioblastoma, high grade glioma, or cancer that metastasizes to the brain). In some embodiments, RGN6024 or formulation thereof can be administered before, during and/or after lomustine to treat a subject having or suspected of having brain cancer. In some embodiments, RGN6024 or a formulation thereof can be administered before, during and/or after belzutifan to treat a subject having or suspected of having brain cancer. In other embodiments, RGN6024 or a formulation thereof can be administered before, during and/or after crizotinib to treat a subject having or suspected of having non-small cell lung cancer (NSCLC) that has metastasized to the brain. In yet other embodiments, RGN6024 can be administered before, during and/or after osimertinib to treat a subject having or suspected of having non-small cell lung cancer (NSCLC) that has metastasized to the brain.

In some embodiments, at least one compound or formulation thereof disclosed herein can be administered with radiation to treat a subject having or suspected of developing prostate cancer and/or Ewing sarcoma. In certain embodiments, the compounds disclosed herein, such as compound B19, compound B120, compound B71, compound B122, compound B46, compound B121, compound B72, compound B130, compound B138, compound B118, compound B140, compound B137, or RGN6024, compound B89, compound B155, compound B125, compound B157, or compound B117, or any combination thereof or composition or formulation thereof, can be administered before, during and/or after radiation to treat a subject having or suspected of developing prostate cancer and/or Ewing sarcoma.

In certain embodiments, at least one compound disclosed herein can be administered with at least one inhibitor of an ataxia telangiectasia and Rad3-related (ATR) protein to treat a subject having, having had, suspected of having, or at risk of developing prostate cancer and/or Ewing sarcoma. Non-limiting examples of inhibitors of ATR proteins (i.e., ATR inhibitors) suitable for use herein can include Schisandrin B, NU6027, BAY 1895344, Dactolisib (NVP-BEZ235), EPT-46464, Torin 2, VE-821, AZ20, M4344 (VX-803), Ceralasertib (AZD6738), Berzosertib (M6620, VX-970), and the like. In certain embodiments, at least one compound herein can be administered with Berzosertib to treat a subject having or suspected of having Ewing sarcoma and/or prostate cancer.

In other embodiments, at least one compound disclosed herein can be administered with at least one inhibitor of serine/threonine kinase Checkpoint a 1 (CHK1) to treat a subject having or suspected of having prostate cancer and/or Ewing sarcoma. Non-limiting examples of CHK1 inhibitors can include MK-8776 (SCH 900776), PF-477736, Prexasertib (LY2606368), Rabusertib (LY2603618), and the like. In certain embodiments, at least one compound herein can be administered with Rabusertib to treat a subject having or suspected of developing Ewing sarcoma and/or prostate cancer.

In some embodiments, at least one compound disclosed herein can be administered with at least one inhibitor of PARP1 (poly(ADP)-ribose polymerase-1) to treat a subject having or suspected of developing pancreatic cancer. Non-limiting examples of PARP1 inhibitors suitable for use herein can include, but are not limited to, Veliparib, Pamiparib (BGB-290), CEP 9722, E7016, Rucaparib, Niraparib, Talazoparib, Olaparib, and the like. In some embodiments, at least one compound disclosed herein can be administered before, during and/or after Olaparib to treat a subject having or suspected of developing pancreatic cancer.

Dose

In some embodiments, the effective dose in a human is about 0.5-5 mg/kg. In some embodiments, the effective dose in a human is about 0.5-1 mg/kg. In some embodiments the effective dose in a human is about 1-2 mg/kg. In some embodiments, the effective dose in a human is about 2-3 mg/kg. In some embodiments, the effective dose in a human is about 3-4 mg/kg. In some embodiments, the effective dose in a human is about 4-5 mg/kg. In some embodiments, the effective dose in a human is about 0.5-1.5 mg/kg. In some embodiments, the effective dose in a human is about 1-1.5 mg/kg. In some embodiments, the effective dose in a human is about 2.5-3 mg/kg. In some embodiments, the effective dose in a human is about 1.5-2.5 mg/kg. In some embodiments, the effective dose in a human is about 2-2.5 mg/kg. In some embodiments, the effective dose in a human is about 2.5-3.5 mg/kg. In some embodiments, the effective dose in a human is about 3-3.5 mg/kg. In some embodiments, the effective dose in a human is about 3.5-4.5 mg/kg. In some embodiments, the effective dose in a human is about 3.5-5 mg/kg. In some embodiments, the effective dose in a human is about 3.5-4 mg/kg. In some embodiments, the effective dose in a human is about 4-4.5 mg/kg. In some embodiments, the effective dose in a human is about 4.5-5 mg/kg. In some embodiments, the effective dose in a human is about 1-3 mg/kg. In some embodiments, the effective dose in a human is about 3-5 mg/kg. In some embodiments, the effective dose in a human is about 3-4.5 mg/kg.

In some embodiments, the effective dose in a human is 0.5 mg/kg. In some embodiments, the effective dose in a human is 1.0 mg/kg. In some embodiments, the effective dose in a human is 1.25 mg/kg. In some embodiments, the effective dose in a human is 1.5 mg/kg. In some embodiments, the effective dose in a human is 1.75 mg/kg. In some embodiments, the effective dose in a human is 2.0 mg/kg. In some embodiments, the effective dose in a human is 2.25 mg/kg. In some embodiments, the effective dose in a human is 2.5 mg/kg. In some embodiments, the effective dose in a human is 2.75 mg/kg. In some embodiments, the effective dose in a human is 3.0 mg/kg. In some embodiments, the effective dose in a human is 3.25 mg/kg. In some embodiments, the effective dose in a human is 3.5 mg/kg. In some embodiments, the effective dose in a human is 3.75 mg/kg. In some embodiments, the effective dose in a human is 4 mg/kg. In some embodiments, the effective dose in a human is 4.25 mg/kg. In some embodiments, the effective dose in a human is 4.5 mg/kg. In some embodiments, the effective dose in a human is 4.75 mg/kg. In some embodiments, the effective dose in a human is 5 mg/kg.

In some embodiments, the effective dose in a mouse is 1-25 mg/kg. In some embodiments, the effective dose in a mouse is 1-5 mg/kg. In some embodiments, the effective dose in a mouse is 5-10 mg/kg. In some embodiments, the effective dose in a mouse is 10-15 mg/kg. In some embodiments, the effective dose in a mouse is 15-20 mg/kg. In some embodiments, the effective dose in a mouse is 20-25 mg/kg. In some embodiments, the effective dose in a mouse is 1-3 mg/kg. In some embodiments, the effective dose in a mouse is 3-5 mg/kg. In some embodiments, the effective dose in a mouse is 5-8 mg/kg. In some embodiments, the effective dose in a mouse is 8-10 mg/kg. In some embodiments, the effective dose in a mouse is 10-12 mg/kg. In some embodiments, the effective dose in a mouse is 12-15 mg/kg. In some embodiments, the effective dose in a mouse is 15-17 mg/kg. In some embodiments, the effective dose in a mouse is 17-19 mg/kg. In some embodiments, the effective dose in a mouse is 17-19 mg/kg. In some embodiments, the effective dose in a mouse is 1-21 mg/kg. In some embodiments, the effective dose in a mouse is 21-23 mg/kg. In some embodiments, the effective dose in a mouse is 23-25 mg/kg. In some embodiments, the effective dose in a mouse is 1-10 mg/kg. In some embodiments, the effective dose in a mouse is 10-20 mg/kg. In some embodiments, the effective dose in a mouse is 10-25 mg/kg.

In some embodiments, the effective dose in a mouse is 1 mg/kg. In some embodiments, the effective dose in a mouse is 1.5 mg/kg. In some embodiments, the effective dose in a mouse is 2 mg/kg. In some embodiments, the effective dose in a mouse is 2.5 mg/kg. In some embodiments, the effective dose in a mouse is 3.0 mg/kg. In some embodiments, the effective dose in a mouse is 3.5 mg/kg. In some embodiments, the effective dose in a mouse is 4.0 mg/kg. In some embodiments, the effective dose in a mouse is 4.5 mg/kg. In some embodiments, the effective dose in a mouse is 5 mg/kg. In some embodiments, the effective dose in a mouse is 5.5 mg/kg. In some embodiments, the effective dose in a mouse is 6 mg/kg. In some embodiments, the effective dose in a mouse is 6.5 mg/kg. In some embodiments, the effective dose in a mouse is 6.5 mg/kg. In some embodiments, the effective dose in a mouse is 7 mg/kg. In some embodiments, the effective dose in a mouse is 7.5 mg/kg. In some embodiments, the effective dose in a mouse is 10 mg/kg. In some embodiments, the effective dose in a mouse is 12 mg/kg. In some embodiments, the effective dose in a mouse is 15 mg/kg. In some embodiments, the effective dose in a mouse is 20 mg/kg. In some embodiments, the effective dose in a mouse is 23 mg/kg. In some embodiments, the effective dose in a mouse is 25 mg/kg.

In some embodiments, the effective dose is administered after at least one compound is administered. In some embodiments, the effective dose is administered to a subject before at least one compound is administered. In some embodiments, the effective dose is administered to a subject during (e.g. at the same time) at least one compound is administered. In some embodiments, the effective dose is administered alone.

In some embodiments, the effective dose is administered at least once daily. In some embodiments, the effective dose is administered every other day. In some embodiments, the effective dose is administered every third day. In some embodiments, the effective dose is administered twice weekly. In some embodiments, the effective dose is administered weekly. In some embodiments, the effective dose is administered every other week. In some embodiments, the effective dose is administered twice monthly. In some embodiments, the effective dose is administered monthly. In some embodiments, the effective dose is administered every other month. In some embodiments, the effective dose is administered every six months. In some embodiments, the effective dose is administered by some other suitable dosing regimen.

In certain embodiments, the present disclosure provides methods for treating, preventing, reducing onset of, or ameliorating a health condition in a subject having, is suspected of developing, or is at risk of developing the health condition. In accordance with these embodiments, the methods can include administering to the subject a therapeutically effective amount of a compound according to the instant disclosure alone or as combination therapies in treating, reducing onset or ameliorating a health condition in a subject in need thereof. In accordance with these embodiments, the compound can be in the form of a therapeutic composition including at least one compound according to the instant disclosure or can be a dosage form including at least one compound according to the instant disclosure. In certain embodiments, the health condition can be cancer or a non-cancerous growth. In other embodiments, the health condition can be any health condition treatable by compounds disclosed herein. Certain embodiments of the method and health conditions are described below. Disclosed compounds, therapeutic compositions and formulations, and dosage forms are described herein and above, respectively.

Methods of Use

In some embodiments, the present invention is a method of modulating abnormal cell division, the method comprising the steps of: (a) identifying a cell with abnormal cell division; and (b) administering the compounds or compositions as disclosed herein or a derivative thereof.

In some embodiments, the present invention is a method of drug screening to identify a therapeutically effective drug candidate to treat a health condition in a subject in need thereof, the method comprising the steps of: (a) identifying an in vitro or in vivo model for a health condition; (b) administering the drug candidate and RGN6024 to the in vitro or in vivo model; (c) determining efficacy, toxicity, or side effects of the drug candidate and RGN6024; and (d) comparing the efficacy, toxicity, or side effects of the drug candidate and RGN6024 to identify the therapeutically effective drug candidate.

In some embodiments, the present invention is a method of detecting a target cell with abnormal cell division, the method comprising the steps of: (a) identifying a sample comprising the target cell with abnormal cell division; (b) performing an affinity-based assay using a small molecule conjugated with a tag to contact the target cell with abnormal cell division with the small molecule conjugated with the tag; and (c) determining whether the small molecule conjugated with a tag binds to the target cell with abnormal cell division. In some embodiments, the small molecule is RGN6024, or the compounds or compositions as disclosed herein or a derivative thereof. In further embodiments, the affinity-based assay is an immuno-based assay, receptor-based assay, antibody-based assay, nanoparticle-based assay, chemical assay, optical assay, or kinetic binding assay. In other embodiments, the affinity-based assay is a gel electrophoresis, enzyme-linked immunosorbent assay, immunoblot assay, fluorescence intensity assay, fluorescence anisotropy assay, fluorescence energy transfer assay, surface plasmon resonance (SPR) assay, light scattering assay, forward binding assay, dissociation assay, or reverse binding assay. In some embodiments, the affinity-based assay is a colchicine competitive binding assay.

A method of detecting a protein expressed by a target cell with abnormal cell division, wherein the method comprises the steps of: (a) identifying a sample comprising the protein expressed by the target cell with abnormal cell division; (b) performing an affinity-based assay using a small molecule conjugated with a tag to contact the protein expressed by the target cell with abnormal cell division with the small molecule conjugated with the tag; and (c) determining whether the small molecule conjugated with a tag binds to protein expressed by the target cell with abnormal cell division. In some embodiments, the small molecule is RGN6024, or the compounds or compositions as disclosed herein or a derivative thereof. In further embodiments, the affinity-based assay is an immuno-based assay, receptor-based assay, antibody-based assay, nanoparticle-based assay, chemical assay, optical assay, or kinetic binding assay. In other embodiments, the affinity-based assay is a gel electrophoresis, enzyme-linked immunosorbent assay, immunoblot assay, fluorescence intensity assay, fluorescence anisotropy assay, fluorescence energy transfer assay, surface plasmon resonance (SPR) assay, light scattering assay, forward binding assay, dissociation assay, or reverse binding assay. In some embodiments, the affinity-based assay is a colchicine competitive binding assay.

In some embodiments, the present invention is a method of detecting or isolating a target cell with abnormal cell division, wherein the method comprises the steps of: (a) identifying a sample comprising the target cell with abnormal cell division; (b) performing an affinity-based pull-down assay using a small molecule conjugated with a tag to contact the target cell with abnormal cell division with the small molecule conjugated with the tag; and (c) selectively isolating the target cell with abnormal cell division. In some embodiments, the small molecule is RGN6024, or the compounds or compositions as disclosed herein or a derivative thereof.

In other embodiments, the method of detecting or isolating a protein expressed by a target cell with abnormal cell division, wherein the method comprises the steps of: (a) identifying a sample comprising the protein expressed by the target cell with abnormal cell division; (b) performing an affinity-based pull-down assay using a small molecule conjugated with a tag to contact the protein expressed by the target cell with abnormal cell division with the small molecule conjugated with the tag; and (c) selectively isolating the protein expressed by the target cell with abnormal cell division. In other embodiments, the small molecule is RGN6024, or the compounds or compositions as disclosed herein or a derivative thereof.

Kits

In certain embodiments, kits are provided herein for use in treating or alleviating or preventing a targeted disease or condition treatable by at least one compound disclosed herein. In certain embodiments, the kit can include at least one compound or composition containing at least one compound disclosed herein, and at least one container. In some embodiments, the kit can include instructions for use in accordance with any of the methods described herein. In other embodiments, instructions can include a description for administering at least one compound and/or pharmaceutical composition disclosed herein to a subject. In accordance with embodiments herein, kits can include instructions that provide information as to dosage, dosing schedule, and route of administration for the intended treatment.

In some embodiments, kits disclosed herein can include at least one container. In accordance with embodiments herein, containers can be any container capable of storing at least one compound or at least one composition containing at least one compound disclosed herein such as tubes, vials, bottles, syringe, such as unit doses, bulk packages (e.g., multi-dose packages) or sub-unit doses. Instructions supplied in the kits of the invention can be written instructions on a label or package insert (e.g., a paper sheet included in the kit), but machine-readable instructions (e.g., instructions carried on a magnetic or optical storage disk) are also acceptable. The label or package insert indicates that the composition is used for treating, delaying the onset and/or alleviating onset of a health condition or disease contemplated herein. Instructions can be provided for practicing any of the methods described herein.

Kits disclosed herein can include suitable packaging. Suitable packaging includes, but is not limited to, vials, bottles, jars, flexible packaging (e.g., sealed Mylar or plastic bags), and the like. Also contemplated herein are packages for use in combination with a specific device, such as an inhaler, nasal administration device (e.g., an atomizer), patch or an infusion device such as a minipump. A kit can have a sterile access port (for example the container can be an intravenous solution bag or a vial having a stopper pierceable by a hypodermic injection needle). The container can also have a sterile access port (for example the container can be an intravenous solution bag or a vial having a stopper pierceable by a hypodermic injection needle). At least one active agent in the composition can be a compound disclosed herein.

Kits can optionally provide additional components such as buffers and interpretive information. Normally, the kit includes a container and a label or package insert(s) on or associated with the container. In some embodiments, the invention provides articles of manufacture including contents of the kits described above.

EXAMPLES

The following examples are included to illustrate certain embodiments. It should be appreciated by those of skill in the art that the techniques disclosed in the examples which follow represent techniques discovered to function well in the practice of the claimed methods, compositions and apparatus. However, those of skill in the art should, in light of the present disclosure, appreciate that changes can be made in some embodiments which are disclosed and still obtain a like or similar result without departing from the spirit and scope of embodiments of the inventions.

Example 1

In one exemplary method, 3-Methoxy-N-(3-methyl-4-((2-morpholinopyrimidin-5-yl)oxy)phenyl)cyclobutane-1-carboxamide (Compound B19) was synthesized. FIG. 1 illustrates the chemical reaction equation for synthesis of Compound B19.

3-Methoxycyclobutane-1-carboxylic acid (45.5 mg, 0.35 mmol), 2-(1H-benzotriazol-1-yl)-1,1,3,3-tetramethyluronium hexafluorophosphate (132.7 mg, 0.35 mmol) and diisopropylethylamine (200 µL, 1 mmol) were dissolved in dry tetrahydrofuran (6 mL). The resulting mixture was stirred at room temperature for 10 min, then cooled to 0° C. A solution of 3-methyl-4-((2-morpholinopyrimidin-5-yl)oxy)aniline (100 mg, 0.35 mmol) in tetrahydrofuran (1 mL) was added, and the resulting mixture was stirred at room temperature for 3 hr. The mixture was then concentrated under vacuum. The resulting residue was taken up in dichloromethane (25 mL), and the organic phase was washed with water (10 mL), and then with aqueous saturated hydrogen carbonate (3×10 mL). The organic layer was collected, dried over magnesium sulfate, filtered, and concentrated under vacuum. The residue was purified HPLC to give 3-methoxy-N-(3-methyl-4-((2-morpholinopyrimidin-5-yl)oxy)phenyl) cyclobutane-1-carboxamide (56.4 mg, 0.14 mmol, yield: 40.5%) as an off-white solid. LC-MS and HPLC analysis were performed as described in exemplary methods disclosed herein. LC-MS (ESI$^+$): m/z 399.3 (M+H)$^+$. $^1$H NMR (400 MHz, DMSO-d$_6$) δ 9.79 (s, 1H), 8.22 (s, 2H), 7.53-7.52 (m, 1H), 7.36-7.33 (m, 1H), 6.74-6.71 (m, 1H), 3.79-3.76 (m, 1H), 3.65-3.64 (m, 8H), 3.12 (s, 3H), 2.69-2.65 (m, 1H), 2.40-2.37 (m, 2H), 2.22 (s, 3H), 2.04-1.97 (m, 2H).

Example 2

Figure 2:
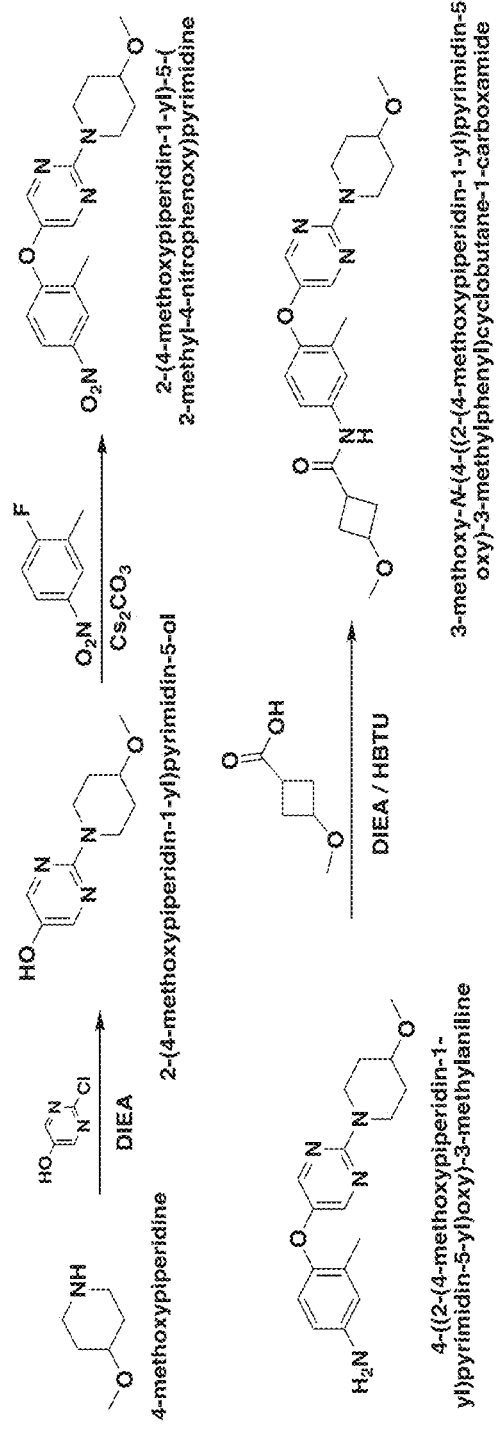
FIG. 2 shows an exemplary experiment illustrating a chemical reaction equation for synthesis of 3-methoxy-N-(4-((2-(4-methoxypiperidin-1-yl)pyrimidin-5-yl)oxy)-3-methylphenyl) cyclobutane-1-carboxamide (Compound B46) in accordance with certain embodiments of the present disclosure.

In another exemplary method, 3-Methoxy-N-(4-((2-(4-methoxypiperidin-1-yl)pyrimidin-5-yl)oxy)-3-methylphenyl)cyclobutane-1-carboxamide 2-(4-methoxypiperidin-1-yl)pyrimidin-5-ol (Compound B46) was synthesized. FIG. 2 illustrates the chemical reaction equation for synthesis of Compound B46.

A solution of 4-methoxypiperidine (1.50 g, 13.02 mmol), 2-chloropyrimidin-5-ol (1.70 g, 13.02 mmol) and N,N-diisopropylethylamine (5.04 g, 39.06 mmol) in 1,4-dioxane (20 mL) was stirred at 100° C. for 16 hours under nitrogen. After quenching the reaction, the reaction mixture was extracted with ethyl acetate (100 mL×3). The organic layer was washed with brine (300 mL), dried over Na$_2$SO$_4$, filtered and concentrated. The crude product was purified by flash column chromatography (petroleum ether:ethyl acetate=3:1) to get 2-(4-methoxypiperidin-1-yl)pyrimidin-5-ol (600.0 mg, 2.87 mmol) (yield=22.0%) as a white solid. LC-MS analysis was performed as described in exemplary methods disclosed herein. LC-MS (ESI$^+$): m/z 210.1 (M+H)$^+$.

2-(4-methoxypiperidin-1-yl)-5-(2-methyl-4-nitrophenoxy)pyrimidine. A solution of 2-(4-methoxypiperidin-1-yl) pyrimidin-5-ol (500.0 mg, 2.39 mmol), 1-fluoro-2-methyl-4-nitrobenzene (307.7 mg, 2.39 mmol) and cesium carbonate (2.34 g, 7.17 mmol) in 1,4-dioxane (10 mL) was stirred at 100° C. for 6 hours under nitrogen. The reaction mixture was concentrated and purified by flash column chromatography (petroleum ether:ethyl acetate=10:1) to get 2-(4-methoxypiperidin-1-yl)-5-(2-methyl-4-nitrophenoxy) pyrimidine (460.0 mg, 1.34 mmol) (Yield 56.1%) as a yellow solid. LC-MS analysis was performed as described in exemplary methods disclosed herein. LC-MS (ESI$^+$): m/z 345.2 (M+H)$^+$.

4-((2-(4-methoxypiperidin-1-yl)pyrimidin-5-yl)oxy)-3-methylaniline. A suspension of 2-(4-methoxypiperidin-1-yl)-5-(2-methyl-4-nitrophenoxy)pyrimidine (460.0 mg, 1.34 mmol) and 10% palladium-carbon (50.0 mg) in methanol (5 mL) was stirred at room temperature under hydrogen atmosphere for 16 hours. The insoluble material was filtered off, and the filtrate was concentrated to afford 4-((2-(4-methoxypiperidin-1-yl)pyrimidin-5-yl)oxy)-3-methylaniline (220.0 mg, 0.70 mmol) (Yield 52.2%) as a brown oil. LC-MS analysis was performed as described in exemplary methods disclosed herein. LC-MS (ESI$^+$): m/z 315.2 (M+H)$^+$.

3-Methoxy-N-(4-((2-(4-methoxypiperidin-1-yl)pyrimidin-5-yl)oxy)-3-methylphenyl)cyclobutane-1-carboxamide. The solution of 3-methoxycyclobutane-1-carboxylic acid (50.0 mg, 0.38 mmol), N,N-diisopropylethylamine (147.0 mg, 1.14 mmol) and O-benzotriazole-N,N,N',N'-tetramethyl-uronium-hexafluorophosphate (217.0 mg, 0.57 mmol) was stirred at 0° C. for 30 minutes. Then 4-((2-(4-methoxypiperidin-1-yl)pyrimidin-5-yl)oxy)-3-methylaniline (120.0 mg, 0.38 mmol) was added at 0° C. and the reaction solution was stirred at room temperature for 16 hours. The reaction mixture was washed with water, brine, dried over Na$_2$SO$_4$, concentrated and purified by HPLC to give 3-methoxy-N-(4-((2-(4-methoxypiperidin-1-yl)pyrimidin-5-yl)oxy)-3-methylphenyl)cyclobutane-1-carboxamide (54.1 mg, yield 34.2%) as a light yellow solid. NMR and LC-MS analysis were performed as described in exemplary methods disclosed herein. LC-MS (ESI$^+$): m/z 427.3 (M+H)$^+$. $^1$H NMR (400 MHz, DMSO-d$_6$): δ 9.82 (s, 1H), 8.18 (s, 2H), 7.54-7.53 (m, 1H), 7.36-7.33 (m, 1H), 6.73-6.70 (m, 1H), 4.16-4.12 (m, 2H), 3.81-3.74 (m, 1H), 3.45-3.40 (m, 1H), 3.35-3.32 (m, 2H), 3.28 (s, 3H), 3.13 (s, 3H), 2.72-2.64 (m, 1H), 2.39-2.35 (m, 2H), 2.23 (s, 3H), 2.04-1.99 (m, 2H), 1.89-1.85 (m, 2H), 1.43-1.35 (m, 2H).

Example 3

In one exemplary method, 3-Methoxy-N-(5-((2-morpholinopyrimidin-5-yl)oxy)thiazol-2-yl)cyclobutane-1-carboxamide (Compound B120) was synthesized. FIG. 3 illustrates the chemical reaction equation for synthesis of Compound B120.

5-((2-chloropyrimidin-5-yl)oxy)thiazol-2-amine. A mixture of 5-bromothiazol-2-amine (1.14 g, 6.4 mmol), 2-chloropyrimidin-5-ol (1.1 g, 6.4 mmol), Cs$_2$CO$_3$ (6.2 g, 19.1 mmol) in acetone (50 ml) was stirred at 60° C. for 4 h. The mixture was cooled to room temperature, diluted with water (500 mL) and extracted with EtOAc (3×200 mL). The combined organic layers washed with water and brine, dried over anhydrous sodium sulfate, filtered, and concentrated in vacuo. The residue was purified by column chromatography (petroleum ether:ethyl acetate=1:2) to give the desired compound (600 mg, 2.2 mmol) (Yield 35.1%) as a yellow solid. NMR and HPLC analysis were performed as described in exemplary methods herein. LC-MS analysis was performed as described in exemplary methods disclosed herein. LC-MS (ESI$^+$): m/z 271.3 (M+H)$^+$.

5-((2-morpholinopyrimidin-5-yl)oxy)thiazol-2-amine. A mixture of 5-((2-chloropyrimidin-5-yl)oxy)thiazol-2-amine (200 mg, 0.87 mmol), morpholine (229 mg, 2.62 mmol) and Cs$_2$CO$_3$ (850 mg, 2.62 mmol) in acetone (10 mL) was degassed with nitrogen. The mixture was heated to 85° C. and stirred for 16 hours under nitrogen atmosphere. After completion, the reaction was cooled to room temperature, diluted with water, and extracted with EA. The combined organic layers were washed with brine, dried over anhydrous sodium sulfate, filtered, and concentrated in vacuo. The residue was purified by HPLC to give 5-((2-morpholinopyrimidin-5-yl)oxy)thiazol-2-amine (100 mg, 0.36 mmol) (Yield 40.9%) as a yellow oil. NMR and HPLC analysis were performed as described in exemplary methods disclosed herein. LC-MS analysis was performed as described in exemplary methods disclosed herein. LC-MS (ESI$^+$): m/z 280.2 (M+H)$^+$.

3-Methoxy-N-(5-((2-morpholinopyrimidin-5-yl)oxy)thiazol-2-yl)cyclobutane-1-carboxamide. 3-Methoxycyclobutane-1-carboxylic acid (46.6 mg, 0.36 mmol), 2-(1H-benzotriazole-1-yl)-1,1,3,3-tetramethyluronium hexafluorophosphate (205 mg, 0.54 mmol), and N,N-diisopropylethylamine (148 μL, 2.31 mmol) were dissolved in dry tetrahydrofuran (6 mL). The resulting mixture was stirred at room temperature for 10 min, and then cooled to 0° C. A solution of 5-((2-morpholinopyrimidin-5-yl)oxy) thiazol-2-amine (100 mg, 0.36 mmol) in tetrahydrofuran (1 mL) was added, and the resulting mixture was stirred at room temperature for 3 hours. The mixture was then concentrated under vacuum. The resulting residue was taken up in dichloromethane (25 mL), and the organic phase was washed with water (10 mL), and then with aqueous saturated hydrogen carbonate (3×10 mL). The organic layer was collected, dried over magnesium sulfate, filtered, and concentrated under vacuum. The residue was purified by HPLC to give 3-methoxy-N-(5-((2-morpholinopyrimidin-5-yl)oxy) thiazol-2-yl)cyclobutane-1-carboxamide (25.8 mg, 0.066 mmol, yield: 8.6%) as an off-white solid. LC-MS (ESI$^+$): m/z 392.2 (M+H)$^+$. NMR and HPLC analysis were performed as described in exemplary methods herein. $^1$H NMR (400 MHz, DMSO-d$_6$) δ 8.45-8.43 (m, 2H), 7.14 (s, 1H), 3.80-3.76 (m, 1H), 3.65 (s, 8H), 3.11-3.09 (m, 3H), 2.83-2.78 (m, 1H), 2.41-2.35 (m, 2H), 2.02-1.95 (m, 2H).

Example 4

In one exemplary method, 3-Methoxy-N-(5-(4-morpholinophenoxy)thiazol-2-yl)cyclobutane-1-carboxamide (Compound B121) was synthesized. FIG. 4 illustrates the chemical reaction equation for synthesis of Compound B121.

5-((2-chloropyrimidin-5-yl)oxy)thiazol-2-amine. A mixture of 5-bromothiazol-2-amine (1.14 g, 6.4 mmol), 4-bromophenol (1.1 g, 6.4 mmol), Cs$_2$CO$_3$ (6.2 g, 19.1 mmol) in acetone (50 ml) was stirred at 60° C. for 4 hours. The mixture was cooled to room temperature, diluted with water (500 ml) and extracted with EA (3×200 ml). The combined organic layers washed with water and brine, dried over anhydrous sodium sulfate, filtered, and concentrated in vacuo. The residue was purified by column chromatography (petroleum ether:ethyl acetate=1:2) to give the desired compound (600 mg, 2.2 mmol) (Yield 35.1%) as a yellow solid. NMR and HPLC analysis were performed as described in exemplary methods herein. LC-MS analysis was performed as described in exemplary methods disclosed herein. LC-MS (ESI$^+$): m/z 271.3 (M+H)$^+$.

N-(5-(4-bromophenoxy)thiazol-2-yl)-3-methoxycyclobutane-1-carboxamide. 3-Methoxycyclobutane-1-carboxylic acid (286.0 mg, 2.2 mmol), 2-(1H-benzotriazol-1-yl)-1,1,3,3-tetramethyluronium hexafluorophosphate (834.4 mg, 2.2 mmol), and diisopropylethylamine (385 μL, 6 mmol) were dissolved in dry tetrahydrofuran (6 mL). The resulting mixture was stirred at room temperature for 10 min, and then cooled to 0° C. A solution of 5-(4-bromophenoxy)thiazol-2-amine (600 mg, 2.2 mmol) in tetrahydrofuran (1 mL) was added, and the resulting mixture was stirred at room temperature for 3 hrs. The mixture was then concentrated under vacuum. The resulting residue was taken up in dichloromethane (25 mL), and the organic phase was washed with water (10 mL), and then with aqueous saturated hydrogen carbonate (3×10 mL). The organic layer was collected, dried over magnesium sulfate, filtered, and concentrated under vacuum. The residue was purified by column chromatography (petroleum ether:ethyl acetate=1:1) to give N-(5-(4-bromophenoxy)thiazol-2-yl)-3-methoxycyclobutane-1-carboxamide (420 mg, 1.1 mmol, yield: 49.8%) as a yellow oil. LC-MS analysis was performed as described in exemplary methods disclosed herein. LC-MS (ESI$^+$): m/z 383.3 (M+H)$^+$.

3-methoxy-N-(5-(4-morpholinophenoxy)thiazol-2-yl)cyclobutane-1-carboxamide. A mixture of N-(5-(4-bromophenoxy)thiazol-2-yl)-3-methoxycyclobutane-1-carboxamide (420 mg, 1.1 mmol), morpholine (144 mg, 1.7 mmol), Pd$_2$(dba)$_3$ (201 mg. 0.22 mmol) and CyJohnPhos (116 mg, 0.33 mmol) in THF (15 mL) was degassed with nitrogen. The mixture was heated to 85° C. and stirred for 16 hours under nitrogen atmosphere. After completion, the reaction was cooled to r.t, diluted with water and extracted with EA. The combined organic layers were washed with brine, dried over anhydrous sodium sulfate, filtered, and concentrated in vacuo. The residue was purified by HPLC to give 3-methoxy-N-(5-(4-morpholinophenoxy)thiazol-2-yl)cyclobutane-1-carboxamide (30 mg, 7% yield) as a white solid. LC-MS (ESI$^+$): m/z 390.2 (M+H)$^+$. NMR and HPLC analysis were performed as described in exemplary methods herein. $^1$H NMR (400 MHz, DMSO-d$_6$) δ 8.38 (s, 1H), 7.13 (s, 1H), 7.06-7.03 (m, 2H), 6.97-6.95 (m, 2H). 3.81-3.77 (m, 1H), 3.74-3.72 (m, 4H), 3.13-3.12 (m, 3H), 3.07-3.04 (m, 4H), 2.85-2.80 (m, 1H), 2.50-2.41 (m, 2H), 2.04-1.97 (m, 2H).

Example 5

Figure 5:
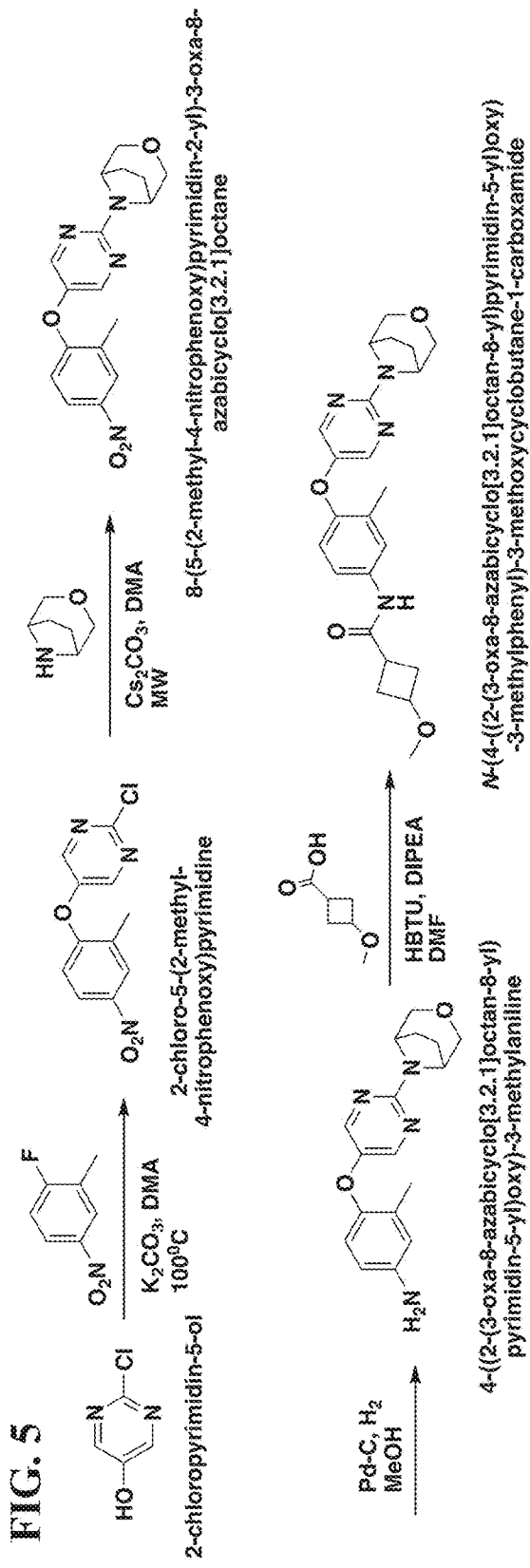
FIG. 5 shows an exemplary experiment illustrating a chemical reaction equation for synthesis of N-(4-((2-(3-oxa-8-azabicyclo[3.2.1]octan-8-yl)pyrimidin-5-yl)oxy)-3-methylphenyl)-3-methoxycyclobutane-1-carboxamide (Compound B72) in accordance with certain embodiments of the present disclosure.

In one exemplary method, N-(4-((2-(3-oxa-8-azabicyclo[3.2.1]octan-8-yl)pyrimidin-5-yl)oxy)-3-methylphenyl)-3-methoxycyclobutane-1-carboxamide (Compound B72) was synthesized. FIG. 5 illustrates the chemical reaction equation for synthesis of Compound B72.

2-chloro-5-(2-methyl-4-nitrophenoxy)pyrimidine. To a solution of 2-chloropyrimidin-5-ol (839.1 mg, 6.41 mmol) in DMA (20.0 mL) was added 1-fluoro-2-methyl-4-nitrobenzene (1.01 g, 6.41 mmol) and potassium carbonate (6.22 g, 19.21 mmol), the mixture was stirred at 100° C. for overnight. After quenched the reaction, the reaction mixture was extracted with ethyl acetate (100.0 mL×3). The organic layer was washed with brine (150.0 mL), dried over Na$_2$SO$_4$, filtered and concentrated. The crude product was purified by flash column chromatography (petroleum ether:ethyl acetate=5:1) to afford 2-chloro-5-(2-methyl-4-nitrophenoxy)pyrimidine (110.5 mg, 0.31 mmol) (Yield 6.41%) as a yellow solid. NMR and HPLC analysis were performed as described in exemplary methods disclosed herein. LC-MS analysis was performed as described in exemplary methods disclosed herein. LC-MS (ESI$^+$): m/z 266.7 (M+H)$^+$.

8-(5-(2-methyl-4-nitrophenoxy)pyrimidin-2-yl)-3-oxa-8-azabicyclo[3.2.1]octane. To a solution of 2-chloro-5-(2-methyl-4-nitrophenoxy)pyrimidine (110.5 mg, 0.31 mmol) in DMA (2.0 mL) was added 3-oxa-8-azabicyclo[3.2.1]octane (34.1 mg, 0.31 mmol) and cesium carbonate (293.4 mg, 0.91 mmol). The mixture was stirred at 150° C. for 4 hours. After quenching the reaction, the reaction mixture was extracted with ethyl acetate (40.0 mL×3). The organic layer was washed with brine (50.0 mL), dried over Na$_2$SO$_4$, filtered and concentrated. The crude product was purified by flash column chromatography (petroleum ether:ethyl acetate=3:1) to afford 8-(5-(2-methyl-4-nitrophenoxy)pyrimidin-2-yl)-3-oxa-8-azabicyclo[3.2.1]octane (98.1 mg, 0.28 mmol) (Yield 68.29%) as a yellow solid. LC-MS analysis was performed as described in exemplary methods disclosed herein. LC-MS (ESI$^+$): m/z 343.1 (M+H)$^+$.

4-((2-(3-oxa-8-azabicyclo[3.2.1]octan-8-yl)pyrimidin-5-yl)oxy)-3-methylaniline. A suspension of 8-(5-(2-methyl-4-nitrophenoxy)pyrimidin-2-yl)-3-oxa-8-azabicyclo[3.2.1]octane (98.1 mg, 0.28 mmol) and 10% palladium-carbon (10.5 mg) in methanol (2.0 mL) was stirred at room temperature under hydrogen atmosphere for 4 hours. The insoluble material was filtered off, and the filtrate was concentrated to afford 4-((2-(3-oxa-8-azabicyclo[3.2.1]octan-8-yl)pyrimidin-5-yl)oxy)-3-methylaniline (81.2 mg, 0.26 mmol) (Yield 92.85%) as a yellow solid. LC-MS analysis was performed as described in exemplary methods disclosed herein. LC-MS (ESI$^+$): m/z 313.1 (M+H)$^+$.

N-(4-((2-(3-oxa-8-azabicyclo[3.2.1]octan-8-yl)pyrimidin-5-yl)oxy)-3-methylphenyl)-3-methoxycyclobutane-1-carboxamide. To a solution of 3-methoxycyclobutane carboxylic acid (34.1 mg, 0.26 mmol) in DMF (2.0 mL) at room temperature was added HBTU (118.2 mg, 0.31 mmol) and DIPEA (100.6 mg, 0.78 mmol). The reaction mixture was stirred at 25° C. for 10 mins. And then was added 4-((2-(3-oxa-8-azabicyclo[3.2.1]octan-8-yl)pyrimidin-5-yl)oxy)-3-methylaniline (81.2 mg, 0.26 mmol) and stirred at room temperature for overnight. After quenching the reaction, the reaction mixture was extracted with ethyl acetate (20 mL×3). The organic layer was washed with brine (30.0 mL), dried over Na$_2$SO$_4$, filtered and concentrated. The residue was purified by HPLC to afford N-(4-((2-(3-oxa-8-azabicyclo[3.2.1]octan-8-yl)pyrimidin-5-yl)oxy)-3-methylphenyl)-3-methoxycyclobutanecarboxamide (25.9 mg, 0.06 mmol) (Yield 23.0%) as a white solid. NMR and LC-MS analysis were performed as described in exemplary methods disclosed herein. LC-MS (ESI$^+$): m/z 425.3 (M+H)$^+$. JH NMR (400 MHz, DMSO-d$_6$) δ 9.90 (s, 1H), 8.23 (s, 2H), 7.55 (s, 1H), 7.39-7.36 (m, 1H), 6.77 (d, J=8.8 Hz, 1H), 4.55 (s, 2H), 3.82-3.75 (m, 1H), 3.64-3.57 (m, 2H), 3.56-3.54 (m, 2H), 3.13 (s, 3H), 2.71-2.70 (m, 1H), 2.37-2.35 (m, 2H), 2.22 (s, 3H), 2.01-1.95 (m, 4H), 1.94-1.87 (m, 2H).

Example 6

Figure 6:
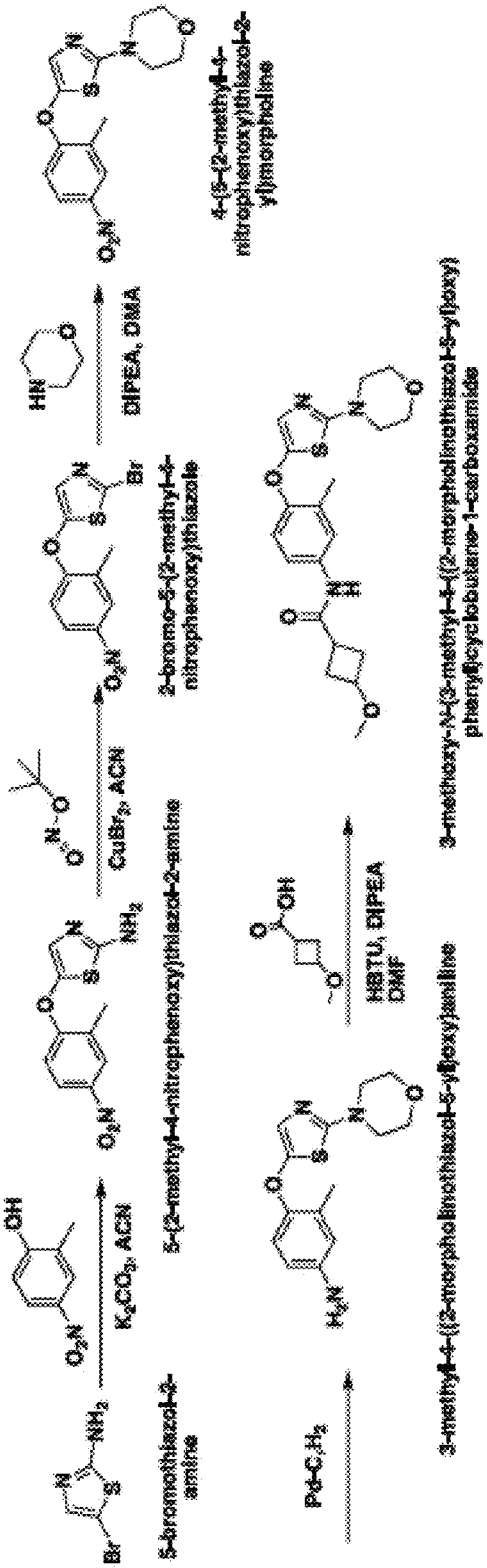
FIG. 6 shows an exemplary experiment illustrating a chemical reaction equation for synthesis of 3-methoxy-N-(3-methyl-4-((2-morpholinothiazol-5-yl)oxy)phenyl)cyclobutane-carboxamide (Compound B71) in accordance with certain embodiments of the present disclosure.

In one exemplary method, 3-Methoxy-N-(3-methyl-4-((2-morpholinothiazol-5-yl)oxy)phenyl)cyclobutanecarboxamide 5 (Compound B71) was synthesized. FIG. 6 illustrates the chemical reaction equation for synthesis of Compound B71.

5-(2-methyl-4-nitrophenoxy)thiazol-2-amine. To a solution of 2-methyl-4-nitrophenol (2.05 g, 11.17 mmol) in ACN (20.0 mL) was added 5-bromothiazol-2-amine (2.01 g, 13.07 mmol) and potassium carbonate (4.91 g, 35.51 mmol), the mixture was stirred at 80° C. for 1 h. After quenching the reaction, the reaction mixture was extracted with ethyl acetate (100.0 mL×3). The organic layer was washed with brine (150.0 mL), dried over Na$_2$SO$_4$, filtered and concentrated. The crude product was purified by flash column chromatography (petroleum ether:ethyl acetate=3:1) to afford 5-(2-methyl-4-nitrophenoxy)thiazol-2-amine (1.51 g, 6.01 mmol) (Yield 53.8%) as a yellow solid. NMR and HPLC analysis were performed as described in exemplary methods disclosed herein. LC-MS analysis was performed as described in exemplary methods disclosed herein. LC-MS (ESI$^+$): m/z 252.3 (M+H)$^+$.

2-bromo-5-(2-methyl-4-nitrophenoxy)thiazole. To a solution of 5-(2-methyl-4-nitrophenoxy)thiazol-2-amine (700.1 mg, 2.81 mmol) in ACN (10.0 mL) was added cupric bromide (630.2 mg, 2.81 mmol) and tert-butyl nitrite (432.5 mg, 4.21 mmol), the mixture was stirred at 25° C. for overnight. After quenching the reaction, the reaction mixture was extracted with ethyl acetate (50.0 mL×3). The organic layer was washed with brine (100 mL), dried over Na$_2$SO$_4$, filtered and concentrated. The crude product was purified by flash column chromatography (petroleum ether: ethyl acetate=6:1) to afford 2-bromo-5-(2-methyl-4-nitrophenoxy)thiazole (450.5 mg, 1.43 mmol) (Yield 50.8%) as a yellow solid. LC-MS analysis was performed as described in exemplary methods disclosed herein. LC-MS (ESI$^+$): m/z 316.2 (M+H)$^+$.

4-(5-(2-methyl-4-nitrophenoxy)thiazol-2-yl)morpholine. To a solution of 2-bromo-5-(2-methyl-4-nitrophenoxy)thiazole (400.5 mg, 1.28 mmol) in DMF (10.0 mL) was added morpholine (1.12 g, 12.82 mmol) and DIPEA (489.5 mg, 3.86 mmol), the solution was stirred at 100° C. for 16 hours. After quenching the reaction, the reaction mixture was extracted with ethyl acetate (40.0 mL×3). The organic layer was washed with brine (50.0 mL), dried over Na$_2$SO$_4$, filtered and concentrated. The crude product was purified by flash column chromatography (petroleum ether: ethyl acetate=3:1) to afford 4-(5-(2-methyl-4-nitrophenoxy)thiazol-2-yl)morpholine (360.5 mg, 1.12 mmol) (Yield 87.46%) as a yellow solid. LC-MS analysis was performed as described in exemplary methods disclosed herein. LC-MS (ESI$^+$): m/z 322.3 (M+H)$^+$.

3-methyl-4-((2-morpholinothiazol-5-yl)oxy)aniline. A suspension of 4-(5-(2-methyl-4-nitrophenoxy)thiazol-2-yl) morpholine (360.5 mg. 1.12 mmol) and 10% palladium-carbon (36.1 mg) in methanol (5.0 mL) was stirred at room temperature under hydrogen atmosphere for 4 hours. The insoluble material was filtered off, and the filtrate was concentrated to afford 3-methyl-4-((2-morpholinothiazol-5-yl)oxy)aniline (240.5 mg. 0.82 mmol) (Yield 73.6%) as a yellow solid. LC-MS analysis was performed as described in exemplary methods disclosed herein. LC-MS (ESI$^+$): m/z 292.2 (M+H)$^+$.

3-Methoxy-N-(3-methyl-4-((2-morpholinothiazol-5-yl) oxy)phenyl)cyclobutane-1-carboxamide. To a solution of 3-methoxycyclobutane carboxylic acid (54.4 mg, 0.41 mmol) in DMF (2.0 mL) at room temperature was added HBTU (183.5 mg, 0.43 mmol) and DIPEA (444.3 mg, 1.23 mmol). The reaction mixture was stirred at 25° C. for 10 mins. And then was added 3-methyl-4-((2-morpholinothiazol-5-yl)oxy)aniline (120.2 mg, 0.41 mmol) and stirred at room temperature for overnight. After quenching the reaction, the reaction mixture was extracted with ethyl acetate (20 mL×3). The organic layer was washed with brine (30.0 mL), dried over Na$_2$SO$_4$, filtered and concentrated. The residue was purified by HPLC to afford 3-methoxy-N-(3-methyl-4-((2-morpholinothiazol-5-yl)oxy)phenyl)cyclobutanecarboxamide (31.0 mg, 0.07 mmol) (Yield 17.0%) as a white solid. NMR and HP-LC analysis were performed as described in exemplary methods disclosed herein. LC-MS (ESI$^+$): m/z 404.2 (M+H)$^+$. $^1$H NMR (400 MHz, DMSO-d$_6$) δ 10.04 (s, 1H), 7.56 (s, 1H), 7.45 (d, J=9.2 Hz, 1H), 7.15 (s, 1H), 7.02 (d, J=8.8 Hz, 1H), 3.77-3.75 (m, 1H), 3.72-3.70 (m, 4H), 3.46 (s, 4H), 3.13 (s, 3H), 3.12-3.11 (m, 0.2H), 2.75-2.77 (m, 0.8H), 2.37-2.35 (m, 2H), 2.24 (s, 3H), 2.01-1.98 (m, 2H).

Example 7

Figure 7:
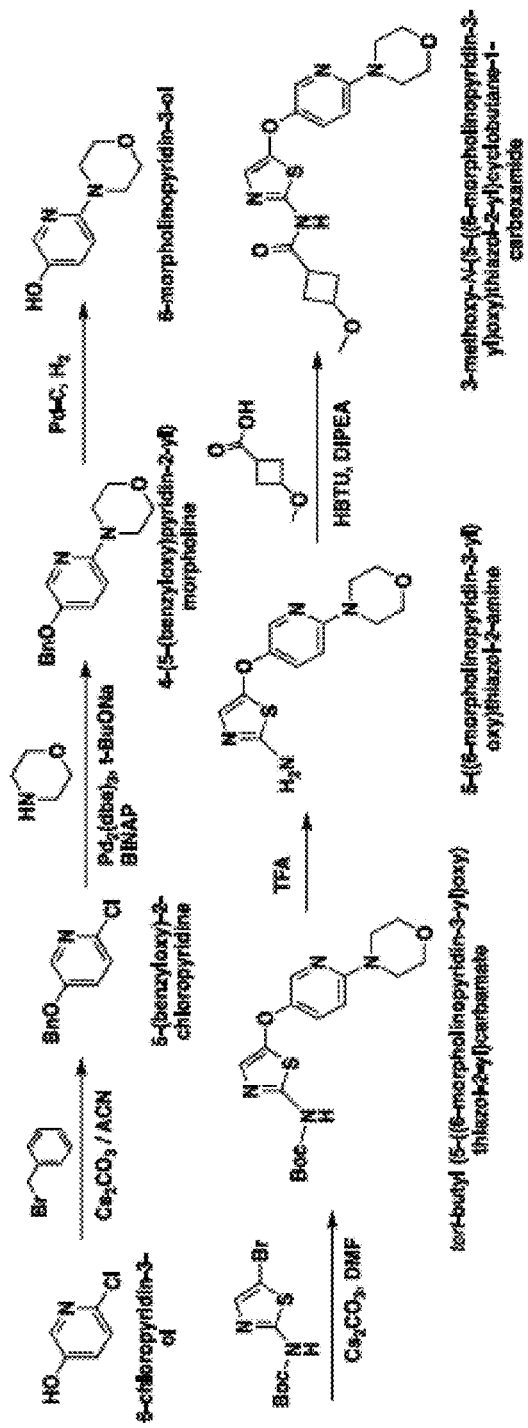
FIG. 7 shows an exemplary experiment illustrating a chemical reaction equation for synthesis of Compound 126: 3-Methoxy-N-(5-((6-morpholinopyridin-3-yl)oxy)thiazol-2-yl)cyclobutane-1-carboxamide (Compound B126) in accordance with certain embodiments of the present disclosure.

In one exemplary method, 3-Methoxy-N-(5-((6-morpholinopyridin-3-yl)oxy)thiazol-2-yl)cyclobutane-1-carboxamide (Compound B126) was synthesized. FIG. 7 illustrates the chemical reaction equation for synthesis of Compound B126.

5-(benzyloxy)-2-chloropyridine. A solution of 6-chloropyridin-3-ol (1 g, 7.7 mmol) and Cs$_2$CO$_3$ (7.5 g, 23.1 mmol) in ACN (30 mL), then (bromomethyl)benzene (1.59 g, 9.3 mmol) was added to the mixture and stirred at 80° C. for 4 h. The reaction mixture was extracted with ethyl acetate (300 mL×3). The organic layer was washed with brine (300 mL), dried over Na$_2$SO$_4$, filtered and concentrated. The crude product was purified by flash column chromatography (petroleum ether:ethyl acetate=10:1) to get 5-(benzyloxy)-2-chloropyridine (1.66 g, 7.7 mmol) (Yield 99%) as a brown solid. LC-MS analysis was performed as described in exemplary methods disclosed herein. LC-MS (ESI$^+$): m/z 220.67 (M+H)$^+$.

4-(5-(benzyloxy)pyridin-2-yl)morpholine. To a solution of 5-(benzyloxy)-2-chloropyridine (1.66 g, 7.7 mmol), morpholine (1.4 g, 16.2 mmol), Pd$_2$(dba)$_3$ (743 mg, 0.82 mmol), t-BuONa (2.3 g, 24.3 mmol), BINAP (1.0 g, 1.62 mmol) in toluene (30 mL) was stirred at 100° C. for 16 h under N$_2$. After quenching the reaction, the mixture was purified by flash column chromatography (petroleum ether:ethyl acetate=8:1) to get 4-(5-(benzyloxy)pyridin-2-yl)morpholine (2.0 g, 7.5 mmol) (Yield 97%) as a yellow oil. LC-MS analysis was performed as described in exemplary methods disclosed herein. LC-MS (ESI$^+$): m/z 271.32 (M+H)$^+$.

6-morpholinopyridin-3-ol. To a solution of 4-(5-(benzyloxy)pyridin-2-yl)morpholine (2.0 g, 7.4 mmol) in MeOH (20 mL) at room temperature was added Pd/C (200 mg) was stirred at room temperature for 4 h under H2. After quenching the reaction, the reaction mixture was filtered and washed with DCM/MeOH (300 mL). The organic layer was concentrated to get 6-morpholinopyridin-3-ol (1.3 g, 7.2 mmol) (Yield 97%). LC-MS analysis was performed as described in exemplary methods disclosed herein. LC-MS (ESI$^+$): m/z 181.2 (M+H)$^+$.

tert-butyl (5-((6-morpholinopyridin-3-yl)oxy)thiazol-2-yl)carbamate. A solution of 6-morpholinopyridin-3-ol (629 mg, 3.49 mmol), tert-butyl (5-bromothiazol-2-yl)carbamate (650 mg, 2.3 mmol) and Cs$_2$CO$_3$ (2.2 g, 6.9 mmol) in DMF (20 mL), the mixture was stirred at 100° C. for 1 h. The reaction mixture was extracted with ethyl acetate (300 mL×3). The organic layer was washed with brine (300 mL), dried over Na$_2$SO$_4$, filtered and concentrated. The crude product was purified by flash column chromatography (petroleum ether:ethyl acetate=3:1) to get tert-butyl (5-((6-morpholinopyridin-3-yl)oxy)thiazol-2-yl)carbamate (80 mg, 0.21 mmol) (Yield 9%). LC-MS analysis was performed as described in exemplary methods disclosed herein. LC-MS (ESI$^+$): m/z 379.45 (M+H)$^+$.

5-((6-morpholinopyridin-3-yl)oxy)thiazol-2-amine. To a solution of tert-butyl-(5-((6-morpholinopyridin-3-yl)oxy) thiazol-2-yl)carbamate (80 mg, 0.21 mmol) in DCM (10 mL) at room temperature was added TFA (2 mL) was stirred at room temperature for 4 hrs. The mixture was concentrated to get 5-((6-morpholinopyridin-3-yl)oxy)thiazol-2-amine (58 mg, 0.2 mmol) (Yield 99%) as a yellow oil. LC-MS analysis was performed as described in exemplary methods disclosed herein. LC-MS (ESI$^+$): m/z 279.48 (M+H)$^+$.

3-methoxy-N-(5-((6-morpholinopyridin-3-yl)oxy)thiazol-2-yl)cyclobutane-1-carboxamide. A solution of 5-((6-morpholinopyridin-3-yl)oxy)thiazol-2-amine (58 mg, 0.2 mmol), 3-methoxycyclobutane-1-carboxylic acid (55 mg, 0.43 mmol), DIPEA (81.2 mg, 0.63 mmol), HBTU (95 mg, 0.25 mmol) in DMF (2 mL), the mixture was stirred at room temperature for 2 hrs. The reaction mixture was extracted with ethyl acetate (20 mL×3). The organic layer was washed with brine (50 mL), dried over Na$_2$SO$_4$, filtered and concentrated. The crude product was purified by HPLC to get 3-methoxy-N-(5-((6-morpholinopyridin-3-yl)oxy)thiazol-2-yl)cyclobutane-1-carboxamide (36.5 mg, 0.09 mmol) (Yield 46%). NMR and HP-LC analysis were performed as described in exemplary methods disclosed herein. LC-MS (ESI$^+$): m/z 391.2 (M+H)$^+$. $^1$H NMR (400 MHz, DMSO-d$_6$) δ 12.13 (s, 1H), 7.98-7.97 (m, 1H), 7.83-7.79 (m, 1H), 7.22-7.18 (m, 2H), 3.81-3.79 (m, 1H), 3.74-3.71 (m, 4H), 3.57-3.55 (m, 4H), 3.12-3.10 (m, 3H), 2.85-2.84 (m, 1H), 2.40-2.37 (m, 2H), 2.02-1.98 (m, 2H).

Example 8

Figure 8:
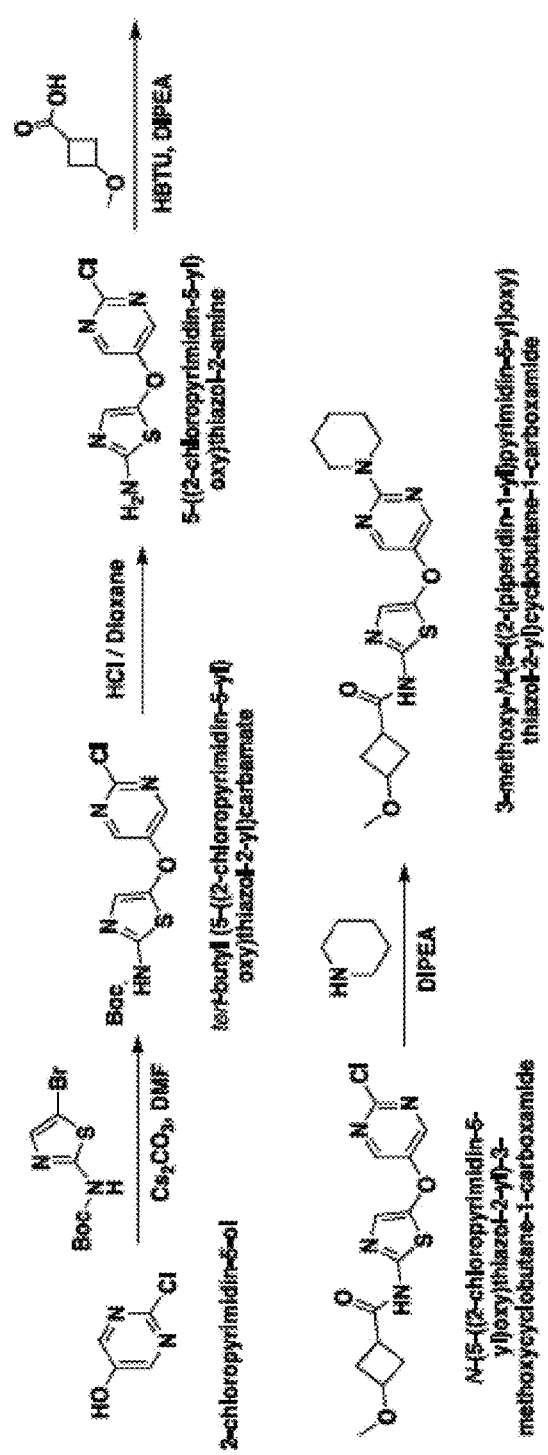
FIG. 8 shows an exemplary experiment illustrating a chemical reaction equation for synthesis of 3-methoxy-N-(5-((2-(piperidin-1-yl)pyrimidin-5-yl)oxy)thiazol-2-yl)cyclobutane-1-carboxamide (Compound B122) in accordance with certain embodiments of the present disclosure.

In one exemplary method, 3-Methoxy-N-(5-((2-(piperidin-1-yl)pyrimidin-5-yl)oxy)thiazol-2-yl)cyclobutane-1-carboxamide (Compound B122) was synthesized. FIG. 8 illustrates the chemical reaction equation for synthesis of Compound B122.

tert-butyl (5-((2-chloropyrimidin-5-yl)oxy)thiazol-2-yl)carbamate. To a solution of tert-butyl (5-bromothiazol-2-yl)carbamate (1.02 g, 3.61 mmol) in ACN (10.0 mL) was added 2-chloropyrimidin-5-ol (470.5 mg, 3.61 mmol) and cesium carbonate (2.91 g, 8.93 mmol), the mixture was stirred at 60° C. for 16 hrs. After quenching the reaction, the reaction mixture was extracted with ethyl acetate (100 mL×3). The organic layer was washed with brine (150.0 mL), dried over Na$_2$SO$_4$, filtered and concentrated. The crude product was purified by flash column chromatography (petroleum ether:ethyl acetate=3:1) to afford tert-butyl (5-((2-chloropyrimidin-5-yl)oxy)thiazol-2-yl)carbamate (420.2 mg, 1.28 mmol) (Yield 35.48%) as a yellow solid. LC-MS analysis was performed as described in exemplary methods disclosed herein. LC-MS (ESI$^+$): m/z 329.7 (M+H)$^+$.

5-((2-chloropyrimidin-5-yl)oxy)thiazol-2-amine. To a solution of tert-butyl (5-((2-chloropyrimidin-5-yl)oxy)thiazol-2-yl)carbamate (420.1 mg, 1.27 mmol) in MeOH (4.0 mL) was added HCl/dioxane (2.0 mL), the solution was stirred at 25° C. for 4 hrs. The solution was concentrated to afford 5-((2-chloropyrimidin-5-yl)oxy)thiazol-2-amine (365.2 mg, 1.59 mmol) (Yield 100%) as a yellow solid. NMR and HPLC analysis were performed as described in exemplary methods disclosed herein. LC-MS analysis was performed as described in exemplary methods disclosed herein. LC-MS (ESI$^+$): m/=229.7 (M+H)$^+$.

N-(5-((2-chloropyrimidin-5-yl)oxy)thiazol-2-yl)-3-methoxycyclobutane-1-carboxamide. To a solution of 3-methoxycyclobutanecarboxylic acid (205.3 mg, 1.57 mmol) in DMF (2.0 mL) at room temperature was added HBTU (714.5 mg, 1.88 mmol) and DIPEA (607.2 mg, 4.71 mmol). The reaction mixture was stirred at 25° C. for 10 mins. And then was added 5-((2-chloropyrimidin-5-yl)oxy)thiazol-2-amine (365.2 mg, 1.59 mmol) and stirred at room temperature for overnight. After quenching the reaction, the reaction mixture was extracted with ethyl acetate (20.0 mL×3). The organic layer was washed with brine (30.0 mL), dried over Na$_2$SO$_4$, filtered and concentrated. The residue was purified by HPLC to afford N-(5-((2-chloropyrimidin-5-yl)oxy)thiazol-2-yl)-3-methoxycyclobutanecarboxamide (220.3 mg, 0.64 mmol) (Yield 41.2%) as a yellow solid. LC-MS analysis was performed as described in exemplary methods disclosed herein. LC-MS (ESI$^+$): m/z 341.7 (M+H)$^+$.

3-Methoxy-N-(5-((2-(piperidin-1-yl)pyrimidin-5-yl)oxy)thiazol-2-yl)cyclobutane-1-carboxamide. To a solution of N-(5-((2-chloropyrimidin-5-yl)oxy)thiazol-2-yl)-3-methoxycyclobutanecarboxamide (100.2 mg, 0.31 mmol) in dioxane (4.0 mL) was added piperidine (75.2 mg, 0.93 mmol) and DIPEA (116.5 mg, 0.93 mmol), the solution was stirred at 100° C. for 2 hrs. After quenching the reaction, the reaction mixture was extracted with ethyl acetate (50.0 mL×3). The organic layer was washed with brine (100.0 mL), dried over Na$_2$SO$_4$, filtered and concentrated. The crude product was purified by HPLC to afford 3-methoxy-N-(5-((2-(piperidin-1-yl)pyrimidin-5-yl)oxy)thiazol-2-yl) cyclobutanecarboxamide (45.7 mg, 0.12 mmol) (Yield 37.85%) as a yellow solid. NMR and LC-MS analysis were performed as described in exemplary methods disclosed herein. LC-MS (ESI$^+$): m/z 390.2 (M+H)$^+$. $^1$H NMR (400 MHz, DMSO-d$_6$) δ 12.02 (s, 1H), 8.37 (s, 2H), 7.13 (s, 1H), 3.97-3.95 (m, 0.2H), 3.80-3.78 (m, 0.8H), 3.77-3.69 (m, 4H), 3.21-3.20 (m, 0.2H), 3.19 (s, 3H), 2.82-2.80 (m, 0.8H), 2.372.36 (m, 2H), 2.13-2.12 (m, 0.4H), 2.02-1.94 (m, 1.6H), 1.62-1.61 (m, 2H), 1.54-1.51 (m, 4H).

Example 9

Figure 9:
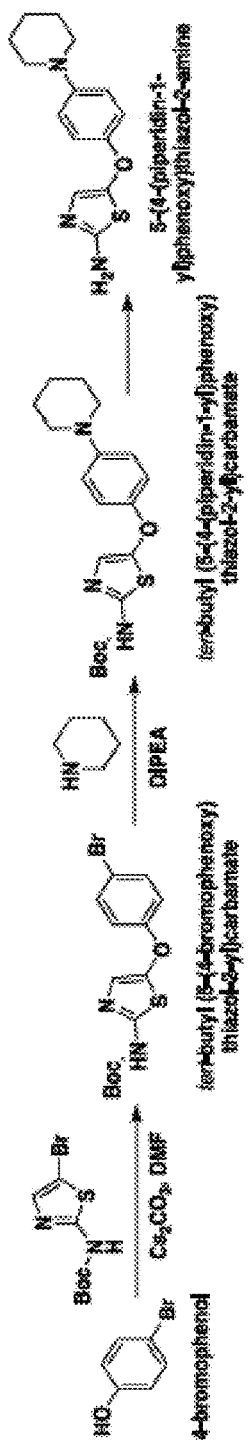
FIG. 9 shows an exemplary experiment illustrating a chemical reaction equation for synthesis of 3-methoxy-N-(5-(4-(piperidin-1-yl)phenoxy)thiazol-2-yl)cyclobutane-1-carboxamide (Compound B125) in accordance with certain embodiments of the present disclosure.

In one exemplary method, 3-Methoxy-N-(5-(4-(piperidin-1-yl)phenoxy)thiazol-2-yl)cyclobutane-1-carboxamide (Compound B125) was synthesized. FIG. 9 illustrates the chemical reaction equation for synthesis of Compound B125.

tert-butyl (5-(4-bromophenoxy)thiazol-2-yl)carbamate. To a solution of 4-bromophenol (1.01 g, 5.83 mmol) in DMA (10.0 mL) was added tert-butyl (5-bromothiazol-2-yl)carbamate (1.63 g, 5.83 mmol) and potassium carbonate (2.41 g, 17.49 mmol), the mixture was stirred at 100° C. for overnight. After quenching the reaction, the reaction mixture was extracted with ethyl acetate (50.0 mL×3). The organic layer was washed with brine (100.0 mL), dried over Na$_2$SO$_4$, filtered and concentrated. The crude product was purified by flash column chromatography (petroleum ether:ethyl acetate=6:1) to afford tert-butyl (5-(4-bromophenoxy)thiazol-2-yl)carbamate (260.5 mg, 0.70 mmol) (Yield 12.0%) as a yellow solid. LC-MS analysis was performed as described in exemplary methods disclosed herein. LC-MS (ESI$^+$): m/z 372.2 (M+H)$^+$.

tert-butyl (5-(4-(piperidin-1-yl)phenoxy)thiazol-2-yl)carbamate. To a solution of tert-butyl (5-(4-bromophenoxy)thiazol-2-yl)carbamate (260.5 mg, 0.70 mmol) in dioxane (5.0 mL) was added piperidine (119.5 mg, 1.41 mmol), tri-tert-butylphosphine (28.5 mg, 0.14 mmol), Pd$_2$(dba)$_3$ (81.2 mg, 0.07 mmol) and sodium tert-butoxide (202.3 mg, 2.12 mmol), the mixture was stirred at 100° C. for 16 hours. After quenching the reaction, the reaction mixture was extracted with ethyl acetate (40.0 mL×3). The organic layer was washed with brine (100.0 mL), dried over Na$_2$SO$_4$, filtered and concentrated. The crude product was purified by flash column chromatography (petroleum ether:ethyl acetate=2:1) to afford tert-butyl (5-(4-(piperidin-1-yl)phenoxy)thiazol-2-yl)carbamate (121.3 mg, 0.32 mmol) (Yield 46.15%) as a yellow solid. LC-MS analysis was performed as described in exemplary methods disclosed herein. LC-MS (ESI$^+$): m/z 376.5 (M+H)$^+$.

5-(4-(piperidin-1-yl)phenoxy)thiazol-2-amine. To a solution of tert-butyl (5-((2-chloropyrimidin-5-yl)oxy)thiazol-2-yl)carbamate (121.5 mg, 0.32 mmol) in DCM (3.0 mL) was added TFA (1.0 ml), the solution was stirred at 25° C. for 4 h. The solution was concentrated to afford 5-(4-(piperidin-1-yl)phenoxy)thiazol-2-amine (165.2 mg, 0.59 mmol) (Yield 100%) as a brown oil. LC-MS analysis was performed as described in exemplary methods disclosed herein. LC-MS (ESI$^+$): m/z 276.5 (M+H)$^+$.

3-methoxy-N-(5-(4-(piperidin-1-yl)phenoxy)thiazol-2-yl)cyclobutane-1-carboxamide. To a solution of 3-methoxycyclobutane carboxylic acid (76.5 mg, 0.59 mmol) in DMF (2.0 mL) at room temperature was added HBTU (272.8 mg, 0.72 mmol) and DIPEA (234.2 mg, 1.82 mmol). The reaction mixture was stirred at 25° C. for 10 mins. And then 5-(4-(piperidin-1-yl)phenoxy)thiazol-2-amine (165.2 mg, 0.59 mmol) was added and stirred at room temperature for overnight. After quenching the reaction, the reaction mixture was extracted with ethyl acetate (20.0 mL×3). The organic layer was washed with brine (30.0 mL), dried over $Na_2SO_4$, filtered and concentrated. The residue was purified by HPLC to afford 3-methoxy-N-(5-(4-(piperidin-1-yl)phenoxy)thiazol-2-yl)cyclobutanecarboxamide (28.1 mg, 0.33 mmol) (Yield 56.0%) as a white solid. NMR and LC-MS analysis were performed as described in exemplary methods disclosed herein. LC-MS (ESI$^+$): m/z 425.3 (M+H)$^+$. $^1$H NMR (400 MHz, DMSO-$d_6$) δ 12.08 (s, 0.5H), 7.90 (d, J=9.2 Hz, 2H), 7.31-7.29 (m, 3H), 3.81-3.80 (m, 1H), 3.51-3.49 (m, 4H), 3.12 (s, 3H), 2.85-2.83 (m, 1H), 2.44-2.39 (m, 2H), 2.03-1.97 (m, 6H), 1.66 (s, 2H).

Example 10

Figure 10:
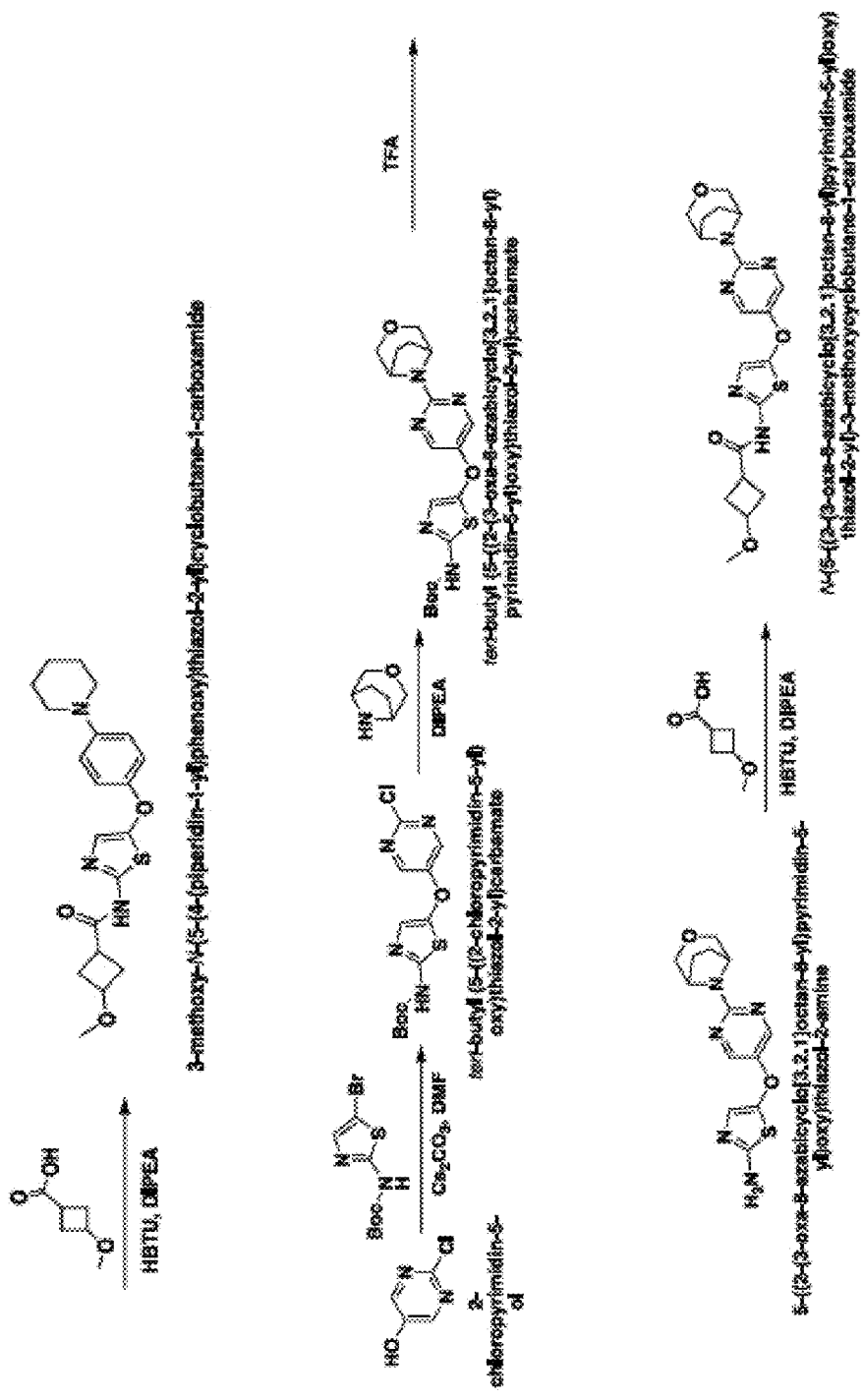
FIG. 10 shows an exemplary experiment illustrating a chemical reaction equation for synthesis of N-(5-((2-(3-oxa-8-azabicyclo[3.2.1]octan-8-yl)pyrimidin-5-yl)oxy)thiazol-2-yl)-3-methoxycyclobutane-1-carboxamide (Compound B130) in accordance with certain embodiments of the present disclosure.

In one exemplary method, N-(5-((2-(3-oxa-8-azabicyclo[3.2.1]octan-8-yl)pyrimidin-5-yl)oxy)thiazol-2-yl)-3-methoxycyclobutane-1-carboxamide (Compound B130) was synthesized. FIG. 10 illustrates the chemical reaction equation for synthesis of Compound B130.

tert-butyl(5-((2-chloropyrimidin-5-yl)oxy)thiazol-2-yl)carbamate. A solution of tert-butyl (5-bromothiazol-2-yl)carbamate (1 g, 3.5 mmol) and $Cs_2CO_3$ (3.4 g, 10.5 mmol) in ACN (20 mL), then 2-chloropyrimidin-5-ol (600 mg, 4.6 mmol) was added to the mixture and stirred at 70° C. for 4 hrs. The reaction mixture was extracted with ethyl acetate (100 mL×3). The organic layer was washed with brine (300 mL), dried over $Na_2SO_4$, filtered and concentrated. The crude product was purified by flash column chromatography (petroleum ether:ethyl acetate=5:1) to get tert-butyl(5-((2-chloropyrimidin-5-yl)oxy)thiazol-2-yl)carbamate (600 mg, 1.8 mmol) (Yield 50%) as a yellow solid. LC-MS analysis was performed as described in exemplary methods disclosed herein. LC-MS (ESI$^+$): m/z 329.72 (M+H)$^+$.

tert-butyl(5-((2-(3-oxa-8-azabicyclo[3.2.1]octan-8-yl)pyrimidin-5-yl)oxy)thiazol-2-yl)carbamate. To a solution of tert-butyl (5-((2-chloropyrimidin-5-yl)oxy)thiazol-2-yl)carbamate (200 mg, 0.6 mmol), 3-oxa-8-azabicyclo[3.2.1]octane (68 mg, 0.6 mmol), DIPEA (235 mg, 1.8 mmol) in 1,4-dioxane (20 mL) was stirred at 100° C. for 16 hrs. The reaction mixture was extracted with ethyl acetate (50 mL×3). The organic layer was washed with brine (50 mL), dried over $Na_2SO_4$, filtered and concentrated. The crude product was purified by flash column chromatography (petroleum ether:ethyl acetate=3:1) to get tert-butyl(5-((2-(3-oxa-8-azabicyclo[3.2.1]octan-8-yl)pyrimidin-5-yl)oxy)thiazol-2-yl)carbamate (140 mg, 0.34 mmol) (Yield 57%). LC-MS analysis was performed as described in exemplary methods disclosed herein. LC-MS (ESI$^+$): m/z 406.51 (M+H)$^+$.

5-((2-(3-oxa-8-azabicyclo[3.2.1]octan-8-yl)pyrimidin-5-yl)oxy)thiazol-2-amine. To a solution of tert-butyl(5-((2-(3-oxa-8-azabicyclo[3.2.1]octan-8-yl)pyrimidin-5-yl)oxy)thiazol-2-yl) carbamate (140 mg, 0.34 mmol) in DCM (10 mL) at room temperature was added TFA (2 mL) was stirred at room temperature for 4 hrs. The mixture was concentrated to get 5-((2-(3-oxa-8-azabicyclo[3.2.1]octan-8-yl)pyrimidin-5-yl)oxy) thiazol-2-amine (107 mg, 0.32 mmol) (Yield 99%). LC-MS analysis was performed as described in exemplary methods disclosed herein. LC-MS analysis was performed as described in exemplary methods disclosed herein. LC-MS (ESI$^+$): m/z 406.51 (M+H)$^+$.

N-(5-((2-(3-oxa-8-azabicyclo[3.2.1]octan-8-yl)pyrimidin-5-yl)oxy)thiazol-2-yl)-3-methoxycyclobutane-1-carboxamide. A solution of 5-((2-(3-oxa-8-azabicyclo[3.2.1]octan-8-yl)pyrimidin-5-yl)oxy)thiazol-2-amine (107 mg, 0.32 mmol), 3-methoxycyclobutane-1-carboxylic acid (63 mg, 0.49 mmol), DIPEA (123 mg, 0.96 mmol), HBTU (145 mg, 0.38 mmol) in DMF (2 mL), the mixture was stirred at room temperature for 2 hrs. The reaction mixture was extracted with ethyl acetate (20 mL×3). The organic layer was washed with brine (50 mL), dried over $Na_2SO_4$, filtered and concentrated. The crude product was purified by Prep-HPLC to get N-(5-((2-(3-oxa-8-azabicyclo[3.2.1]octan-8-yl)pyrimidin-5-yl)oxy)thiazol-2-yl)-3-methoxycyclobutane-1-carboxamide (19.3 mg, 0.04 mmol) (Yield 14%). NMR and HPLC analysis were performed as described in exemplary methods disclosed herein. LC-MS (ESI$^+$): m/z 418.2 (M+H)$^+$. $^1$H NMR (400 MHz, DMSO-$d_6$) δ 12.1 (s, 1H), 8.42 (s, 2H), 7.16 (s, 1H), 4.53 (s, 2H), 3.99-3.76 (m, 1H), 3.62-3.54 (m, 4H), 3.12-3.11 (m, 3H), 2.84-2.80 (m, 1H), 2.40-2.37 (m, 2H), 1.97-1.93 (m, 4H), 1.88-1.86 (m, 2H).

Example 11

Figure 11:
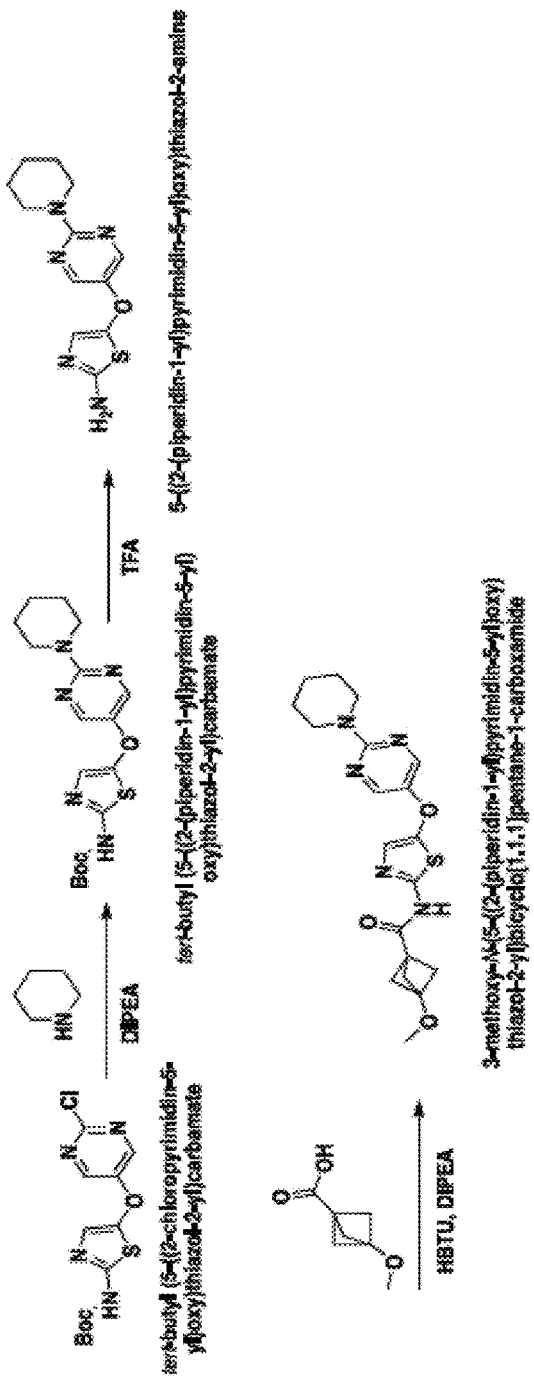
FIG. 11 shows an exemplary experiment illustrating a chemical reaction equation for synthesis of 3-methoxy-N-(5-((2-(piperidin-1-yl)pyrimidin-5-yl)oxy)thiazol-2-yl)bicyclo[1.1.1]pentane-1-carboxamide (Compound B140) in accordance with certain embodiments of the present disclosure.

In one exemplary method, 3-methoxy-N-(5-((2-(piperidin-1-yl)pyrimidin-5-yl)oxy)thiazol-2-yl)bicyclo[1.1.1]pentane-1-carboxamide (Compound B140) was synthesized. FIG. 11 illustrates the chemical reaction equation for synthesis of Compound B140.

tert-butyl (5-((2-chloropyrimidin-5-yl)oxy)thiazol-2-yl)carbamate. To a solution of tert-butyl (5-bromothiazol-2-yl)carbamate (400 mg, 1.44 mmol) in DMF (10 mL) was added 2-chloropyrimidin-5-ol (222.9 mg, 1.73 mmol) and $Cs_2CO_3$ (1.4 g, 4.32 mmol). The mixture was stirred for 12 hours at 100° C. After quenching the reaction, the reaction mixture was extracted with ethyl acetate (100 mL×3). The organic layer was washed with brine (300 mL), dried over $Na_2SO_4$, filtered and concentrated. The residue was purified by flash column chromatography (petroleum ether:ethyl acetate=3:1) to get tert-butyl (5-((2-chloropyrimidin-5-yl)oxy)thiazol-2-yl)carbamate (250.0 mg, 0.76 mmol) (Yield 53.0%) as a yellow solid. LC-MS analysis was performed as described in exemplary methods disclosed herein. LC-MS (ESI$^+$): m/z 328.04 (M+H)$^+$.

tert-butyl (5-((2-(piperidin-1-yl)pyrimidin-5-yl)oxy)thiazol-2-yl)carbamate. To a solution of tert-butyl (5-((2-chloropyrimidin-5-yl)oxy)thiazol-2-yl)carbamate (250 mg, 0.76 mmol) in DMF (5 mL) was added piperidine (331.2 mg, 3.8 mmol) and DIPEA (294.1 mg, 2.28 mmol). The mixture was stirred for 12 hours at 100° C. After quenching the reaction, the reaction mixture was extracted with ethyl acetate (100 mL×3). The organic layer was washed with brine (300 mL), dried over $Na_2SO_4$, filtered and concentrated. The residue was purified by flash column chromatography (petroleum ether:ethyl acetate=3:2) to get tert-butyl (5-((2-(piperidin-1-yl)pyrimidin-5-yl)oxy)thiazol-2-yl)carbamate (180.0 mg, 0.48 mmol) (Yield 62.9%) as a yellow solid. LC-MS analysis was performed as described in exemplary methods disclosed herein. LC-MS (ESI$^+$): m/z 377.15 (M+H)$^+$.

5-((2-(piperidin-1-yl)pyrimidin-5-yl)oxy)thiazol-2-amine. A solution of tert-butyl (5-((2-(piperidin-1-yl)pyrimidin-5-yl)oxy)thiazol-2-yl)carbamate (180 mg, 0.47 mmol), TFA (3 mL) in DCM (5 mL) was stirred at 0° C. for 3 hours. After quenching the reaction, the solution was concentrated to afford 5-((2-(piperidin-1-yl)pyrimidin-5-yl)oxy)thiazol-2-amine with TFA salt (120.0 mg, 0.43 mmol) (Yield 99.01%) as a yellow solid. LC-MS analysis was performed as described in exemplary methods disclosed herein. LC-MS (ESI$^+$): m/z 277.1 (M+H)$^+$.

3-methoxy-N-(5-((2-(piperidin-1-yl)pyrimidin-5-yl)oxy) thiazol-2yl)bicyclo[1.1.1]pentane-1-carboxamide. To a solution of 5-((2-(piperidin-1-yl)pyrimidin-5-yl)oxy)thiazol-2-amine (120 mg, 0.43 mmol) in DMF (3 mL) was added 3-methoxybicyclo[1.1.1]pentane-1-carboxylic acid (50 mg, 0.35 mmol), HBTU (159.9 mg, 0.42 mmol) and DIPEA (136.2 mg, 1.06 mmol). The mixture was stirred for 3 hours at room temperature. After quenching the reaction, the reaction mixture was extracted with ethyl acetate (100 mL×3). The organic layer was washed with brine (300 mL), dried over $Na_2SO_4$, filtered and concentrated. The residue was purified by HPLC to afford 3-methoxy-N-(5-((2-(piperidin-1-yl)pyrimidin-5-yl)oxy)thiazol-2-yl)bicyclo[1.1.1] pentane-1-carboxamide (63.9 mg, 0.16 mmol) (Yield 45.3%) as a yellow solid. NMR and LC-MS analysis were performed as described in exemplary methods disclosed herein. LC-MS (ESI$^+$): m/z 401.2 (M+H)$^+$. $^1$H NMR (400 MHz, DMSO-$d_6$) δ 12.12 (s, 1H), 8.38 (s, 2H), 7.16 (s, 1H), 3.72-3.69 (m, 4H), 3.21 (s, 3H), 2.17 (s, 6H), 1.63-1.59 (m, 2H), 1.54-1.48 (m, 4H).

Example 12

Figure 12A:
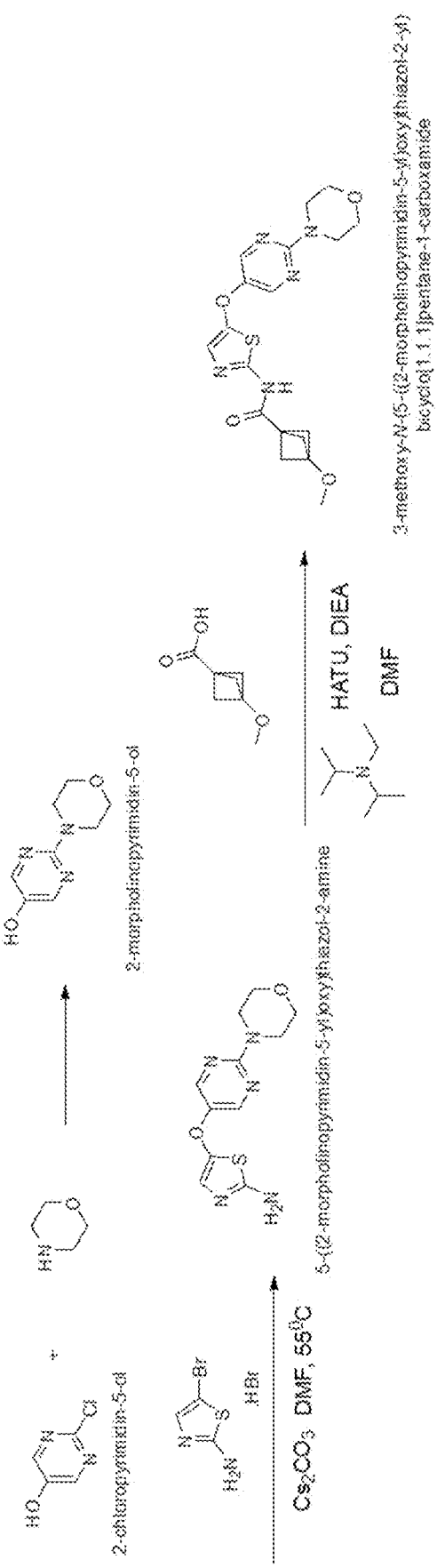
FIG. 12A shows an exemplary experiment illustrating a chemical reaction equation for synthesis of 3-Methoxy-N-(5-((2-morpholinopyrimidin-5-yl)oxy)thiazol-2-yl)bicyclo[1.1.1]pentane-1-carboxamide (RGN6024) in accordance with certain embodiments of the present disclosure.
Figure 12B:
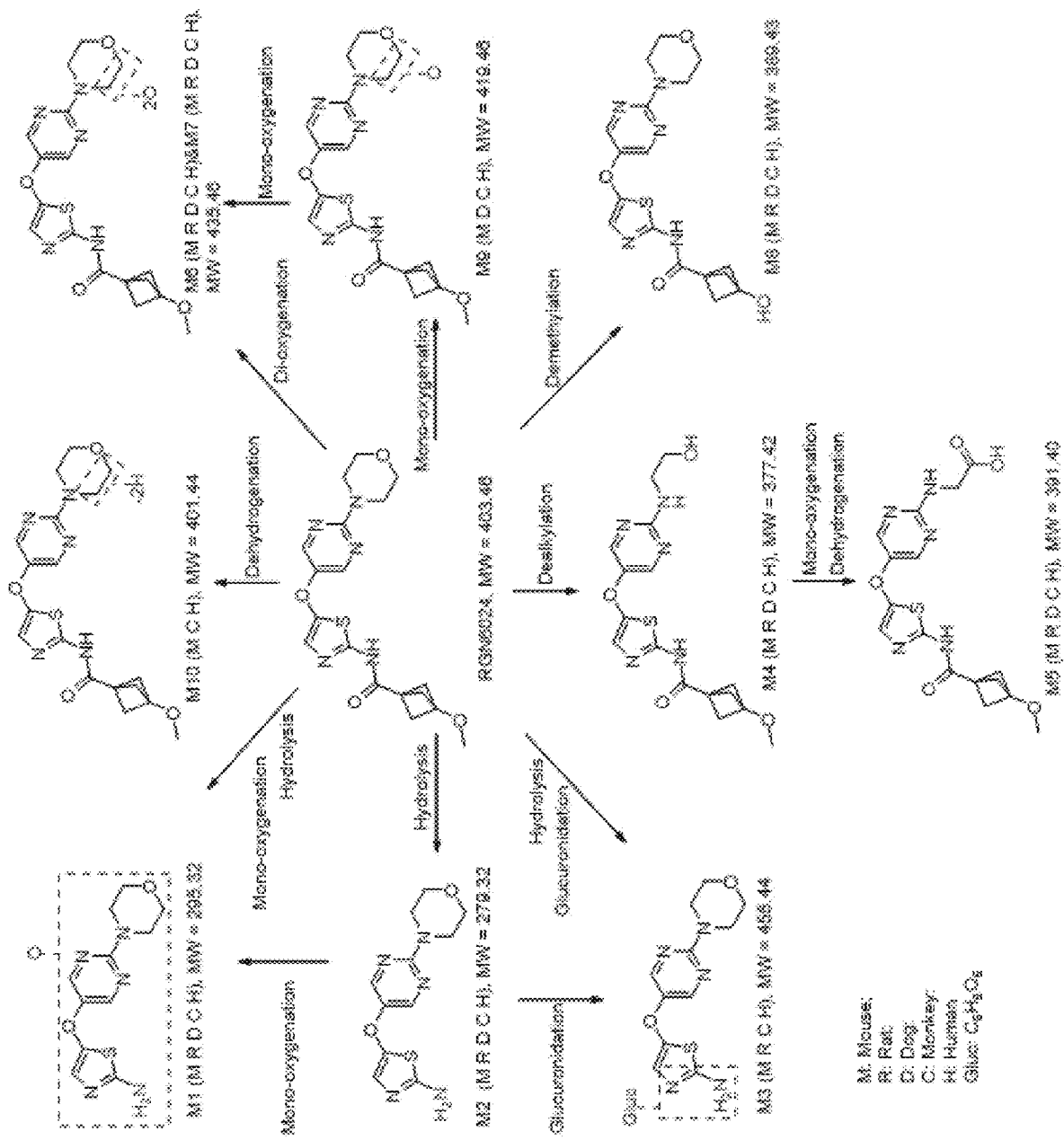
FIG. 12B shows proposed metabolic pathways of RGN6024 in Mouse, Rat, Dog, Monkey and Human Hepatocytes.

In one exemplary method, 3-Methoxy-N-(5-((2-morpholinopyrimidin-5-yl)oxy)thiazol-2-yl)bicyclo[1.1.1]pentane-1-carboxamide (RGN6024) was synthesized. FIG. 12A illustrates the chemical reaction equation for synthesis of RGN6024.

2-morpholinopyrimidin-5-ol. The solution of 2-chloropyrimidin-5-ol (150 g, 1.15 mol) in morpholine (400 mL) was stirred at 80° for 16 hours under nitrogen atmosphere. After which period, the reaction mixture was concentrated under vacuum. The residue was purified by column chromatography (petroleum ether:ethyl Acetate=1:2) to get 2-morpholinopyrimidin-5-ol (150 g). LC-MS (ESI$^+$): m/z 182.1 [M+H]$^+$.

5-((2-morpholinopyrimidin-5-yl)oxy)thiazol-2-amine. To the solution of 2-morpholinopyrimidin-5-ol (80.0 g, 442 mmol) and 5-bromothiazol-2-amine hydrobromide (229 g, 883 mmol) in N,N-dimethylformamide (500 mL) was added $Cs_2CO_3$ (431 g, 1.33 mol). The resulting solution was stirred at 55° C. overnight under nitrogen atmosphere. After cooling down to room temperature the mixture was poured into water (2 L) and then extracted with ethyl acetate (300 mL×3). The combined organic layers were washed with brine and dried over anhydrous sodium sulfate, filtered and concentrated to dryness. The residue was purified by column chromatography (petroleum Ether:ethyl Acetate=1:1) to obtain 5-((2-morpholinopyrimidin-5-yl)oxy)thiazol-2-amine (50.0 g) as a yellow solid. LC-MS (ESI$^+$): m/z 280.1 [M+H]$^+$.

3-methoxy-N-(5-((2-morpholinopyrimidin-5-yl)oxy)thiazol-2-yl)bicyclo[1.1.1]pentane-1-carboxamide. To the solution of 5-((2-morpholinopyrimidin-5-yl)oxy)thiazol-2-amine (50.0 g, 0.18 mol), 3-methoxybicyclo[1.1.1]pentane-1-carboxylic acid (25.0 g, 0.18 mol) and N,N-diisopropylethylamine (69.0 g, 0.54 mol) in DMF (300 mL) was added HATU (136.1 g, 0.36 mol). The resulting mixture was stirred at room temperature for 16 hours under nitrogen atmosphere. After which period, the mixture was poured into water (1.5 L) and then extracted with ethyl acetate (250 mL×3). The combined organic layers were washed with brine and dried over anhydrous sodium sulfate, filtered and concentrated to dryness. The residue was purified by column chromatography (petroleum Ether:ethyl Acetate=1:2) to get 3-methoxy-N-(5-((2-morpholinopyrimidin-5-yl)oxy)thiazol-2-yl)bicyclo[1.1.1]pentane-1-carboxamide (24.1 g) as a yellowish white solid. LC-MS (ESI$^+$): m/z 404.0 [M+H]$^+$. $^1$H NMR (400 MHz, DMSO-$d_6$) δ 12.14 (s, 1H), 8.44 (s, 2H), 7.18 (m, 1H), 3.66 (s, 8H), 3.20 (s, 3H), 2.17 (s, 6H).

Example 13

Figure 13:
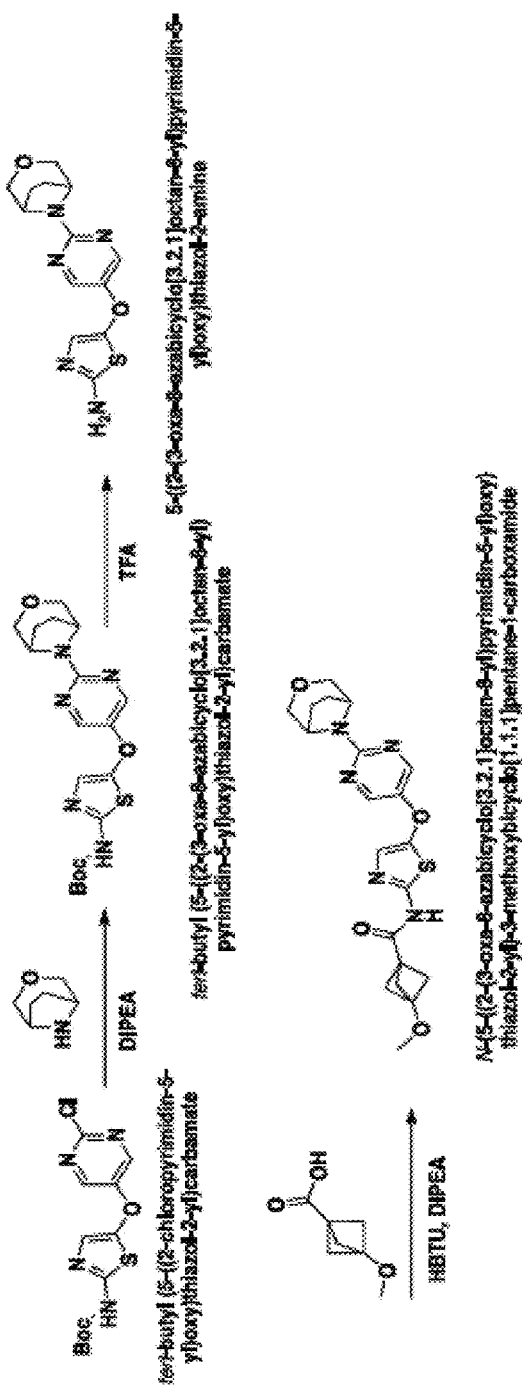
FIG. 13 shows an exemplary experiment illustrating a chemical reaction equation for synthesis of N-(5-((2-(3-oxa-8-azabicyclo[3.2.1]octan-8-yl)pyrimidin-5-yl)oxy)thiazol-2-yl)-3-methoxybicyclo[1.1.1]pentane-1-carboxamide (Compound B138) in accordance with certain embodiments of the present disclosure.

In one exemplary method, N-(5-((2-(3-oxa-8-azabicyclo [3.2.1]octan-8-yl)pyrimidin-5-yl)oxy)thiazol-2-yl)-3-methoxybicyclo[1.1.1]pentane-1-carboxamide (Compound B138) was synthesized. FIG. 13 illustrates the chemical reaction equation for synthesis of Compound B138.

tert-butyl(5-((2-(3-oxa-8-azabicyclo[3.2.1]octan-8-yl)pyrimidin-5-yl)oxy)thiazol-2-yl)carbamate. To a solution of tert-butyl (5-((2-chloropyrimidin-5-yl)oxy)thiazol-2-yl)carbamate (101.7 mg, 0.31 mmol) in DMF (5 mL) was added piperidine (36.9 mg, 0.31 mmol) and DIPEA (119.9 mg, 0.93 mmol). The mixture was stirred for 12 hours at 100° C. After quenching the reaction, the reaction mixture was extracted with ethyl acetate (100 mL×3). The organic layer was washed with brine (300 mL), dried over $Na_2SO_4$, filtered and concentrated. The residue was purified by flash column chromatography (petroleum ether:ethyl acetate=3:2) to get tert-butyl (5-((2-morpholinopyrimidin-5-yl)oxy)thiazol-2-yl)carbamate (90.0 mg, 0.22 mmol) (Yield 75.4%) as a yellow solid. LC-MS analysis was performed as described in exemplary methods disclosed herein. LC-MS (ESI$^+$): m/z 405.15 (M+H)$^+$.

5-((2-(3-oxa-8-azabicyclo[3.2.1]octan-8-yl)pyrimidin-5-yl)oxy)thiazol-2-amine. A solution of tert-butyl (5-((2-(3-oxa-8-azabicyclo[3.2.1]octan-8-yl)pyrimidin-5-yl)oxy)thiazol-2-yl)carbamate (90 mg, 0.22 mmol), TFA (3 mL) in DCM (5 mL) was stirred at 0° C. for 3 hours. After quenching the reaction, the solution was concentrated to afford 5-((2-(3-oxa-8-azabicyclo[3.2.1]octan-8-yl)pyrimidin-5-yl)oxy)thiazol-2-amine (65.1 mg, 0.21 mmol) (Yield 97.0%) as a yellow solid. LC-MS analysis was performed as described in exemplary methods disclosed herein. LC-MS (ESI$^+$): m/z 305.1 (M+H)$^+$.

N-(5-((2-(3-oxa-8-azabicyclo[3.2.1]octan-8-yl)pyrimidin-5-yl)oxy)thiazol-2-yl)-3-methoxybicyclo[1.1.1]pentane-1-carboxamide. To a solution of 5-((2-(3-oxa-8-azabicyclo[3.2.1]octan-8-yl)pyrimidin-5-yl)oxy)thiazol-2-amine (65.1 mg, 0.21 mmol) in DMF (3 mL) was added 3-methoxybicyclo[1.1.1]pentane-1-carboxylic acid (40 mg, 0.28 mmol), HBTU (128.3 mg, 0.34 mmol) and DIPEA (109.1 mg, 0.85 mmol). The mixture was stirred for 3 hours at room temperature. After quenching the reaction, the reaction mixture was extracted with ethyl acetate (100 mL×3). The organic layer was washed with brine (300 mL), dried over $Na_2SO_4$, filtered and concentrated. The residue was purified by HPLC to afford N-(5-((2-(3-oxa-8-azabicyclo[3.2.1]octan-8-yl)pyrimidin-5-yl)oxy)thiazol-2-yl)-3-methoxybicyclo[1.1.1]pentane-1-carboxamide (33.8 mg, 0.08 mmol) (Yield 28.0%) as a yellow solid. NMR and LC-MS analysis were performed as described in exemplary methods disclosed herein. LC-MS (ESI$^+$): m/z 428.2 (M+H)$^+$. $^1$H NMR (400 MHz, DMSO-$d_6$) δ 12.14 (s, 1H), 8.43 (s, 2H), 7.20 (s, 1H), 4.54 (s. 2H), 3.62-3.55 (m, 4H), 3.21 (s, 3H), 2.18 (s, 6H), 1.97-1.94 (m, 2H), 1.89-1.87 (m, 2H).

Example 14

Figure 14:
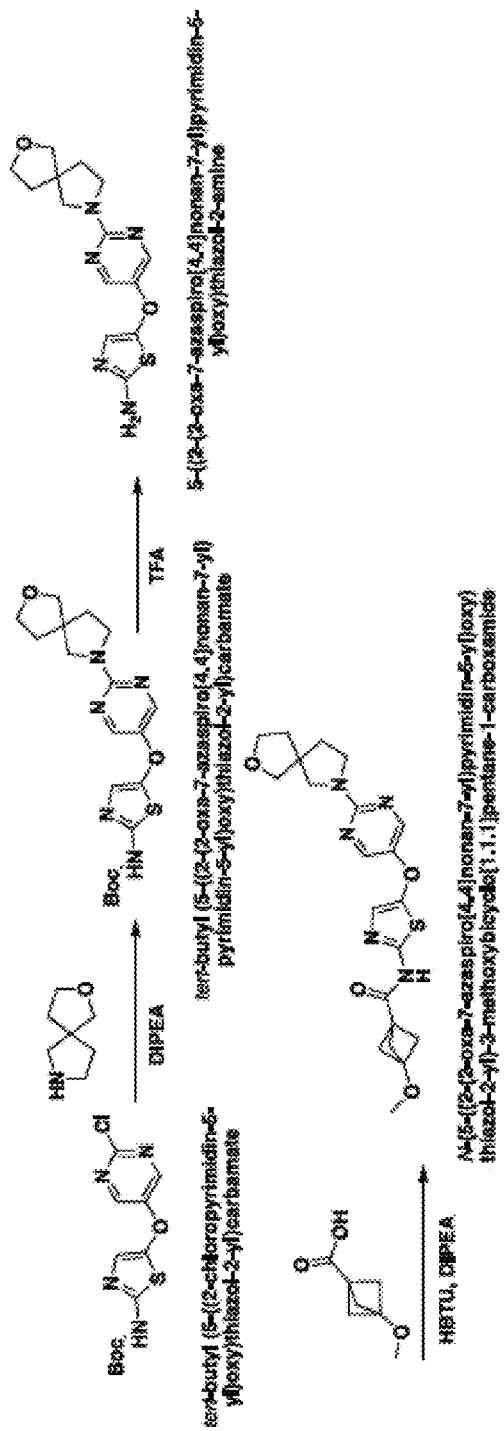
FIG. 14 shows an exemplary experiment illustrating a chemical reaction equation for synthesis of N-(5-((2-(2-oxa-7-azaspiro[4.4]nonan-7-yl)pyrimidin-5-yl)oxy)thiazol-2- yl)-3-methoxybicyclo[1.1.1]pentane-1-carboxamide (Compound B137) in accordance with certain embodiments of the present disclosure.

In one exemplary method, N-(5-((2-(2-oxa-7-azaspiro [4.4]nonan-7-yl)pyrimidin-5-yl)oxy)thiazol-2-yl)-3- methoxybicyclo[1.1.1]pentane-1-carboxamide (Compound B137) was synthesized. FIG. 14 illustrates the chemical reaction equation for synthesis of Compound B137.

tert-butyl(5-((2-(2-oxa-7-azaspiro[4.4]nonan-7-yl)pyrimidin-5-yl)oxy)thiazol-2-y)carbamate. A solution of tert-butyl (5-((2-chloropyrimidin-5-yl)oxy)thiazol-2-yl)carbamate (222.3 mg, 0.68 mmol), 2-oxa-7-azaspiro[4.4]nonane (129 mg, 1.0 mmol) and $K_2CO_3$ (279.8 mg, 2.03 mmol) in dioxane (5 mL) was heated to 100° C. for 3 hours under nitrogen. After quenching the reaction, the reaction mixture was extracted with ethyl acetate (100 mL×3). The organic layer was washed with brine (300 mL), dried over $Na_2SO_4$ to get tert-butyl (5-((2-(2-oxa-7-azaspiro[4.4]nonan-7-yl)pyrimidin-5-yl)oxy)thiazol-2-yl)carbamate (180.0 mg, 0.43 mmol) (Yield 63.3%) as a yellow solid. LC-MS analysis was performed as described in exemplary methods disclosed herein. LC-MS (ESI$^+$): m/z 419.2 (M+H)$^+$.

5-((2-(2-oxa-7-azaspiro[4.4]nonan-7-yl)pyrimidin-5-yl)oxy)thiazol-2-amine. A solution of tert-butyl (5-((2-(2-oxa-7-azaspiro[4.4]nonan-7-yl)pyrimidin-5-yl)oxy)thiazol-2-yl)carbamate (180.0 mg, 0.43 mmol), TFA (3 mL) in DCM (5 mL) was stirred at 0° C. for 3 hours. After quenching the reaction, the solution was concentrated to afford 5-((2-(2-oxa-7-azaspiro[4.4]nonan-7-yl)pyrimidin-5-yl)oxy)thiazol-2-amine (132.2 mg, 0.41 mmol) (Yield 96.4%) as a yellow solid. LC-MS analysis was performed as described in exemplary methods disclosed herein. LC-MS (ESI$^+$): m/z 319.1 (M+H)$^+$.

N-(5-((2-(2-oxa-7-azaspiro[4.4]nonan-7-yl)pyrimidin-5-yl)oxy)thiazol-2-yl)-3-methoxybicyclo[1.1.1]pentane-1-carboxamide. To a solution of 5-((2-(2-oxa-7-azaspiro[4.4]nonan-7-yl)pyrimidin-5-yl)oxy)thiazol-2-amine (132.2 mg, 0.41 mmol) in DMF (3 mL) was added 3-methoxybicyclo[1.1.1]pentane-1-carboxylic acid (58.2 mg, 0.41 mmol), HBTU (233.1 mg, 0.62 mmol) and DIPEA (158.7 mg, 1.23 mmol). The mixture was stirred for 3 hours at room temperature. After quenching the reaction, the reaction mixture was extracted with ethyl acetate (100 mL×3). The organic layer was washed with brine (300 mL), dried over $Na_2SO_4$, filtered and concentrated. The residue was purified by HPLC to afford N-(5-((2-(2-oxa-7-azaspiro[4.4]nonan-7-yl)pyrimidin-5-yl)oxy)thiazol-2-yl)-3-methoxybicyclo[1.1.1]pentane-1-carboxamide (33.0 mg, 0.08 mmol) (Yield 18.6%) as a yellow solid. NMR and LC-MS analysis were performed as described in exemplary methods disclosed herein. LC-MS (ESI$^+$): m/z 433.2 (M+H)$^+$. $^1$H NMR (400 MHz, DMSO-d$_6$) δ 12.10 (s, 1H), 8.39 (s, 2H), 7.14 (s, 1H), 3.82-3.78 (m, 2H), 3.60-3.58 (m, 2H), 3.56-3.52 (m, 2H), 3.49-3.46 (m, 2H), 3.20 (s, 3H), 2.17 (s. 6H), 1.98-1.94 (m, 2H), 1.93-1.86 (m, 2H).

Example 15

In one exemplary method, 3-Methoxy-N-(3-methyl-4-((2-morpholinopyrimidin-5-yl)oxy)phenyl)bicyclo[1.1.1]pentane-1-carboxamide (Compound B89) was synthesized. FIG. 15 illustrates the chemical reaction equation for synthesis of Compound B89.

2-morpholinopyrimidin-5-ol. A solution of 2-chloropyrimidin-5-ol (800.0 mg, 6.13 mmol), morpholine (5.3 g, 61.29 mmol) and DIPEA (2.4 g, 18.39 mmol) in 1,4-dioxane (10 mL) was stirred at 100° C. for 3 hours. After quenching the reaction, the reaction mixture was extracted with ethyl acetate (100 mL×3). The organic layer was washed with brine (300 mL), dried over $Na_2SO_4$, filtered and concentrated. The crude product was purified by flash column chromatography (petroleum ether:ethyl acetate=3:1) to get 2-morpholinopyrimidin-5-ol (650.0 mg, 3.59 mmol) (yield 58.6%) as a yellow solid. LC-MS analysis was performed as described in exemplary methods disclosed herein. LC-MS (ESI$^+$): m/z 182.1 (M+H)$^+$.

4-(5-(2-methyl-4-nitrophenoxy)pyrimidin-2-yl)morpholine. To a solution of 2-morpholinopyrimidin-5-ol (300.0 mg, 1.66 mmol) in DMF (4 mL) at room temperature was added 1-fluoro-2-methyl-4-nitrobenzene (257.5 mg, 1.66 mmol) and $Cs_2CO_3$ (1.6 g, 4.98 mmol). The reaction mixture was stirred at room temperature for 3 hours. After quenching the reaction, the reaction mixture was extracted with ethyl acetate (100 mL×3). The organic layer was washed with brine (300 mL), dried over $Na_2SO_4$, filtered and concentrated. The crude product was purified by flash column chromatography (petroleum ether:ethyl acetate=3:1) to get 4-(5-(2-methyl-4-nitrophenoxy)pyrimidin-2-yl)morpholine (200.0 mg, 0.63 mmol) (yield 51.46%) as a yellow solid. LC-MS analysis was performed as described in exemplary methods disclosed herein. LC-MS (ESI$^+$): m/z 317.3 (M+H)$^+$.

3-methyl-4-((2-morpholinopyrimidin-5-yl)oxy)aniline. To a solution of 4-(5-(2-methyl-4-nitrophenoxy)pyrimidin-2-yl)morpholine (200.0 mg, 0.63 mmol) in MeOH (4 mL) at room temperature was added Pd/C (20 mg). The reaction mixture was stirred at room temperature for 3 hours at hydrogen atmosphere. After filtered and concentrated, the crude product was purified by flash column chromatography (petroleum ether:ethyl acetate=2:1) to get 3-methyl-4-((2-morpholinopyrimidin-5-yl)oxy)aniline (120.0 mg, 0.42 mmol) (Yield 66.7%) as a yellow solid. LC-MS analysis was performed as described in exemplary methods disclosed herein. LC-MS (ESI$^+$): m/z 287.1 (M+H)$^+$.

3-methoxy-N-(3-methyl-4-((2-morpholinopyrimidin-5-yl)oxy)phenyl)bicyclo[1.1.1]pentane-1-carboxamide. To a solution of 3-methyl-4-((2-morpholinopyrimidin-5-yl)oxy)aniline (120.0 mg, 0.42 mmol) in DMF (3 mL) at room temperature was added 3-methoxybicyclo[1.1.1]pentane-1-carboxylic acid (59.64 mg, 0.42 mmol), HBTU (238.77 mg, 0.63 mmol) and DIPEA (162.54 mg, 1.26 mmol). The reaction mixture was stirred at room temperature for 4 hours. After quenching the reaction, the reaction mixture was extracted with ethyl acetate (100 mL×3). The organic layer was washed with brine (300 mL), dried over $Na_2SO_4$, filtered and concentrated. The crude product was purified by HPLC to get 3-methoxy-N-(3-methyl-4-((2-morpholinopyrimidin-5-yl)oxy)phenyl)bicyclo[1.1.1]pentane-1-carboxamide (78.5 mg, 0.19 mmol) (Yield 45.53%) as a yellow oil. NMR and LC-MS analysis were performed as described in exemplary methods disclosed herein. LC-MS (ESI$^+$): m/z 411.4 (M+H)$^+$. $^1$H NMR (400 MHz, DMSO-d$_6$) δ 9.53 (s, 1H), 8.23 (s, 2H), 7.55 (d, J=2.4 Hz, 1H), 7.41-7.38 (m, 1H), 6.74-6.72 (m, 1H), 3.68-3.63 (m, 8H), 3.22 (s, 3H), 2.23 (s, 3H), 2.13 (s, 6H).

Example 16

In one exemplary method, 3-Methoxy-N-(5-(4-morpholinophenoxy)thiazol-2-yl)bicyclo[1.1.1]pentane-1-carboxamide (Compound B155) was synthesized. FIG. 16 illustrates the chemical reaction equation for synthesis of Compound B155.

4-morpholinophenol. A solution of 4-bromophenol (1.0 g, 5.78 mmol), morpholine (2.5 g, 28.90 mmol), Cy-JohnPhos (405.0 mg, 1.156 mmol), Pd$_2$(dba)$_3$ (264.5 mg, 0.29 mmol), NaHMDS (8.8 ml, 17.34 mmol) at 0° C. in DMF (10 mL) was stirred at 100° C. for 6 hours with $N_2$ protection. After quenching the reaction, the reaction mixture was extracted with ethyl acetate (100 mL×3). The organic layer was washed with brine (300 mL), dried over $Na_2SO_4$, filtered and concentrated. The crude product was purified by flash column chromatography (petroleum ether:ethyl acetate=3:1) to get 4-morpholinophenol (535.1 mg, 2.99 mmol) (Yield 51.66%) as a pink solid. LC-MS analysis was performed as described in exemplary methods disclosed herein. LC-MS (ESI$^+$): m/z 180.1 (M+H)$^+$.

tert-butyl(5-(4-morpholinophenoxy)thiazol-2-yl)carbamate. To a solution of 4-morpholinophenol (260.0 mg, 1.45 mmol) in DMF (5 mL) at room temperature was added tert-butyl (5-bromothiazol-2-yl)carbamate (443.3 mg, 1.59 mmol) and $Cs_2CO_3$ (1.4 g, 4.35 mmol) The reaction mixture was heated at 80° C. for 4 hours. After quenching the reaction, the reaction mixture was extracted with ethyl acetate (100 mL×3). The organic layer was washed with brine (300 mL), dried over $Na_2SO_4$, filtered and concentrated. The crude product was purified by flash column chromatography (petroleum ether:ethyl acetate=3:1) to get tert-butyl(5-(4-morpholinophenoxy)thiazol-2-yl)carbamate (80.0 mg, 0.22 mmol) (Yield 14.63%) as a yellow oil. LC-MS analysis was performed as described in exemplary methods disclosed herein. LC-MS (ESI$^+$): m/=378.14 (M+H)$^+$.

5-(4-morpholinophenoxy)thiazol-2-amine. To a solution of tert-butyl(5-(4-morpholinophenoxy)thiazol-2-yl)carbamate (80.0 mg, 0.22 mmol) in DCM (3 mL) at 0° C. was added TFA (1 mL). The reaction mixture was stirred at room temperature for 4 hours. The reaction mixture was concentrated to get 5-(4-morpholinophenoxy)thiazol-2-amine (50.0 mg, 0.18 mmol) (Yield 81.9%) as a yellow solid. LC-MS analysis was performed as described in exemplary methods disclosed herein. LC-MS (ESI$^+$): m/z 278.1 (M+H)$^+$.

3-methoxy-N-(5-(4-morpholinophenoxy)thiazol-2-yl)bicyclo[1.1.1]pentane-1-carboxamide. To a solution of 5-(4-morpholinophenoxy)thiazol-2-amine (50.0 mg, 0.18 mmol) in DMF (3 mL) at room temperature was added 3-methoxybicyclo[1.1.1]pentane-1-carboxylic acid (25.6 mg, 0.18 mmol), HATU (102.6 mg, 0.27 mmol) and DIPEA (69.7 mg, 0.54 mmol). The reaction mixture was stirred at room temperature for 4 hours. After quenching the reaction, the reaction mixture was extracted with ethyl acetate (100 mL×3). The organic layer was washed with brine (300 mL), dried over $Na_2SO_4$, filtered and concentrated. The crude product was purified by HPLC to get 3-methoxy-N-(5-(4-morpholinophenoxy)thiazol-2-yl)bicyclo[1.1.1]pentane-1-carboxamide (7.8 mg, 0.02 mmol) (Yield 10.8%) as a yellow oil. NMR and LC-MS analysis were performed as described in exemplary methods disclosed herein. LC-MS (ESI$^+$): m/z 401.8 (M+H)$^+$. $^1$H NMR (400 MHz, DMSO-$d_6$) δ10.81 (s, 1H), 7.15 (s, 1H), 7.03 (d, J=9.2 Hz, 2H), 6.95 (d, J=9.2 Hz, 2H), 3.74-3.71 (m, 4H), 3.20 (s, 3H), 3.06-3.04 (m, 4H), 2.17 (s, 6H).

Example 17

In one exemplary method, N-(4-((2-(3-oxa-8-azabicyclo[3.2.1]octan-8-yl)pyrimidin-5-yl)oxy)-3-methylphenyl)-3-methoxybicyclo[1.1.1]pentane-1-carboxamide (Compound B118) was synthesized. FIG. 17 illustrates the chemical reaction equation for synthesis of Compound B118.

2-chloro-5-(2-methyl-4-nitrophenoxy)pyrimidine. A solution of 1-fluoro-2-methyl-4-nitrobenzene (5.00 g, 33.26 mmol), 2-chloropyrimidin-5-ol (5.05 g, 38.71 mmol), potassium carbonate (13.36 g, 96.78 mmol) in DMA (70 mL) was stirred at 100° C. for 8 hours under nitrogen. The reaction mixture was extracted with ethyl acetate (100 mL×3). The organic layer was washed with brine (100 mL), dried over $Na_2SO_4$, filtered and concentrated. The crude product was purified by flash column chromatography (petroleum ether: ethyl acetate=1:1) to get 2-chloro-5-(2-methyl-4-nitrophenoxy)pyrimidine (220.0 mg, 0.83 mmol) (Yield 2.5%) as a yellow solid. LC-MS analysis was performed as described in exemplary methods disclosed herein. LC-MS (ESI$^+$): m/z 266.0 (M+H)$^+$ 8-(5-(2-methyl-4-nitrophenoxy)pyrimidin-2-yl)-3-oxa-8-azabicyclo[3.2.1]octane. A mixture of 2-chloro-5-(2-methyl-4-nitrophenoxy)pyrimidine (200.0 mg, 0.75 mmol), 3-oxa-8-azabicyclo[3.2.1]octane hydrochloride (338.0 mg, 2.26 mmol) and cesium carbonate (1.22 g, 3.75 mmol) in DMA (2 mL) was under microwave conditions (150° C., 3 hours) and then cooled to room temperature. The reaction mixture was purified by flash column chromatography to give 8-(5-(2-methyl-4-nitrophenoxy)pyrimidin-2-yl)-3-oxa-8-azabicyclo[3.2.1]octane (210.0 mg, 0.61 mmol) (Yield 81.3%) as a yellow solid. NMR and HPLC analysis were performed as described in exemplary methods disclosed herein. LC-MS analysis was performed as described in exemplary methods disclosed herein. LC-MS (ESI$^+$): m/z 343.1 (M+H)$^+$ 4-((2-(3-oxa-8-azabicyclo[3.2.1]octan-8-yl)pyrimidin-5-yl)oxy)-3-methylaniline. A suspension of 8-(5-(2-methyl-4-nitrophenoxy)pyrimidin-2-yl)-3-oxa-8-azabicyclo[3.2.1]octane (210.0 mg, 0.61 mmol) and 10% palladium-carbon (21.0 mg) in methanol (5 mL) was stirred at room temperature under hydrogen atmosphere for 16 h. The insoluble material was filtered off, and the filtrate was concentrated to afford 4-((2-(3-oxa-8-azabicyclo[3.2.1]octan-8-yl)pyrimidin-5-yl)oxy)-3-methylaniline (150.0 mg, 0.48 mmol) (Yield 78.%) as a light yellow solid. LC-MS analysis was performed as described in exemplary methods disclosed herein. LC-MS (ESI$^+$): m/z 313.2 (M+H)$^+$.

N-(4-((2-(3-oxa-8-azabicyclo[3.2.1]octan-8-yl)pyrimidin-5-yl)oxy)-3-methylphenyl)-3-methoxybicyclo[1.1.1]pentane-1-carboxamide. The solution of 3-methoxybicyclo[1.1.1]pentane-1-carboxylic acid (50.0 mg, 0.38 mmol), N,N-diisopropylethylamine (68.0 mg, 0.48 mmol) and O-benzotriazole-N,N,N',N'-tetramethyl-uronium-hexafluorophosphate (235.0 mg, 0.62 mmol) was stirred at room temperature for 30 minutes. Then 4-((2-(3-oxa-8-azabicyclo[3.2.1]octan-8-yl)pyrimidin-5-yl)oxy)-3-methylaniline (150.0 mg, 0.48 mmol) was added at room temperature and the reaction solution was stirred at room temperature for 16 hours. The reaction mixture was washed with water and brine, dried over $Na_2SO_4$, concentrated and purified by HPLC to give N-(4-((2-(3-oxa-8-azabicyclo[3.2.1]octan-8-yl)pyrimidin-5-yl)oxy)-3-methylphenyl)-3-methoxybicyclo[1.1.1]pentane-1-carboxamide (152.9 mg, 0.35 mmol) (Yield 73%) as a yellow solid. NMR and LC-MS analysis were performed as described in exemplary methods disclosed herein. LC-MS (ESI$^+$): m/z 437.6 (M+H)$^+$. $^1$H NMR (400 MHz, DMSO-$d_6$) δ 9.57 (s, 1H), 8.24 (s, 2H), 7.56 (d, J=2.4 Hz, 1H), 7.44-7.38 (m, 1H), 6.77 (d, J=8.4 Hz, 1H), 4.57-4.52 (m, 2H), 3.64-3.62 (m, 2H), 3.57-3.54 (m, 2H), 3.22 (s, 3H), 2.23 (s, 3H), 2.13 (s, 6H), 1.98-1.93 (m, 2H), 1.92-1.82 (m, 2H).

Example 18

In one exemplary method, N-(4-((2-(2-oxa-7-azaspiro[4.4]nonan-7-yl)pyrimidin-5-yl)oxy)-3-methylphenyl)-3-methoxybicyclo[1.1.1]pentane-1-carboxamide (Compound B117) was synthesized. FIG. 18 illustrates the chemical reaction equation for synthesis of Compound B117.

2-(2-oxa-7-azaspiro[4.4]nonan-7-yl)pyrimidin-5-ol. A solution of 2-chloropyrimidin-5-ol (300.0 mg, 2.31 mmol), 2-oxa-7-azaspiro[4.4]nonane (881.0 mg, 6.93 mmol), DIPEA (894.0 mg. 6.93 mmol) in 1,4-Dioxane (8 mL) was stirred at 80° C. for 16 hours under nitrogen. After quenching the reaction, the reaction mixture was extracted with ethyl acetate (50 mL×3). The organic layer was washed with brine (100 mL), dried over $Na_2SO_4$, filtered and concentrated. The crude product was purified by flash column chromatography (DCM:MeOH=93:7) to give 2-(2-oxa-7-azaspiro[4.4]nonan-7-yl)pyrimidin-5-ol (150 mg, 0.68 mmol) (Yield 29.3%) as a brown oil. LC-MS analysis was performed as described in exemplary methods disclosed herein. LC-MS (ESI$^+$): m/z 222.1 (M+H)$^+$ 7-(5-(2-methyl-4-nitrophenoxy)pyrimidin-2-yl)-2-oxa-7-azaspiro[4.4]nonane. A solution of 2-(2-oxa-7-azaspiro[4.4]nonan-7-yl)pyrimidin-5-ol (150 mg, 0.68 mmol), 1-fluoro-2-methyl-4-nitrobenzene (105.0 mg. 0.68 mmol). $Cs_2CO_3$ (665.0 mg, 3.04 mmol) in DMF (3 mL) was stirred at room temperature for 3 hours. After quenching the reaction, the reaction mixture was extracted with ethyl acetate (50 mL×3). The organic layer was washed with brine (100 mL), dried over $Na_2SO_4$, filtered and concentrated. The crude product was purified by flash column chromatography (petroleum ether:ethyl acetate=1:2) to get 7-(5-(2-methyl-4-nitrophenoxy)pyrimidin-2-yl)-2-oxa-7-azaspiro[4.4]nonane (150 mg, 0.42 mmol) (Yield 61.9%) as a yellow oil. LC-MS analysis was performed as described in exemplary methods disclosed herein. LC-MS (ESI$^+$): m/z 357.3 (M+H)$^+$ 4-((2-(2-oxa-7-azaspiro[4.4]nonan-7-yl)pyrimidin-5-yl)oxy)-3-methylaniline. A suspension of 7-(5-(2-methyl-4-nitrophenoxy)pyrimidin-2-yl)-2-oxa-7-azaspiro[4.4]nonane (150 mg, 0.42 mmol) in methanol (10 mL) was stirred at room temperature under hydrogen atmosphere for 16 hours. The insoluble material was filtered off, and the filtrate was concentrated to afford 4-((2-(2-oxa-7-azaspiro[4.4]nonan-7-yl)pyrimidin-5-yl)oxy)-3-methylaniline (120.0 mg, 0.37 mmol) (Yield 81.8%) as a black oil. LC-MS analysis was performed as described in exemplary methods disclosed herein. LC-MS (ESI$^+$): m/z 327.6 (M+H)$^+$.

N-(4-((2-(2-oxa-7-azaspiro[4.4]nonan-7-yl)pyrimidin-5-yl)oxy)-3-methylphenyl)-3-methoxybicyclo[1.1.1]pentane-1-carboxamide. The solution of 3-methoxybicyclo[1.1.1]pentane-1-carboxylic acid (53.0 mg, 0.37 mmol), N,N-diisopropylethylamine (143.0 mg, 1.11 mmol) and O-benzotriazole-N,N,N',N'-tetramethyl-uronium-hexafluorophosphate (182.0 mg, 0.48 mmol) was stirred at room temperature for 30 minutes. Then 4-((2-(2-oxa-7-azaspiro[4.4]nonan-7-yl)pyrimidin-5-yl)oxy)-3-methylaniline (120.0 mg, 0.37 mmol) was added at room temperature and the reaction solution was stirred at room temperature for 16 hours. The reaction mixture was washed with water and brine, dried over $Na_2SO_4$, concentrated and purified by HPLC to give N-(4-((2-(2-oxa-7-azaspiro[4.4]nonan-7-yl)pyrimidin-5-yl)oxy)-3-methylphenyl)-3-methoxybicyclo[1.1.1]pentane-1-carboxamide (145.5 mg, 0.32 mmol) (Yield 87.3%) as a yellow solid. NMR and LC-MS analysis were performed as described in exemplary methods disclosed herein. LC-MS (ESI$^+$): m/z 451.5 (M+H)$^+$. $^1$H NMR (400 MHz, DMSO-$d_6$) δ 9.55 (s, 1H), 8.23 (s, 2H), 7.55 (d, J=2 Hz, 1H), 7.39 (d, J=8.8 Hz, 1H), 6.69 (d, J=8.8 Hz, 1H), 3.83-3.76 (m, 2H), 3.62-3.58 (m, 2H), 3.57-3.49 (m, 2H), 3.48-3.46 (m, 2H), 3.21 (s, 3H), 2.24 (s, 3H), 2.12 (s, 6H), 2.00-1.96 (m, 2H), 1.93-1.88 (m, 2H).

Example 19

In another exemplary method, half maximal effective concentration ($EC_{50}$) was determined for some compounds and their isomers as disclosed herein in a variety of cancer cell lines (e.g., human cancer cell lines). In brief, cells from one prostate cancer cell lines (22RV1) and four glioblastoma cell lines (U87, LN-18, LN-229 and T98G) were plated in a multi-well plate. After 24 hours, one of the compounds disclosed herein was added to the well at increasing concentrations. After 72 hours of treatment, cell viability was assessed using alamarBlue® (Invitrogen) and fluorescence was read using the CLARIOstar Plus Multilabel Plate Reader (BMG Labtech). Samples were normalized to no treatment controls. $EC_{50}$ values were determined using GraphPad Prism. The $EC_{50}$ of the compounds tested in each of the cell lines is provided in Tables 15 and 16 where "inactive" means less than 50% inhibition at the highest concentration tested at 50 μM and "NT" means not tested.

TABLE 15

| Compound | 22RV1- $EC_{50}$ (uM) | U87- $EC_{50}$ (uM) |
|---|---|---|
| B1 | Inactive | — |
| B2 | Inactive | Inactive |
| B3 | 27.5 | Inactive |
| B4 | 17.4 | 32 |
| B5 | 36 | Inactive |
| B6 | Inactive | Inactive |
| B7 | Inactive | Inactive |
| B8 | 12.9 | Inactive |
| B9 | 10.3 | Inactive |
| B10 | 5 | Inactive |
| B11 | 13.1 | Inactive |
| B12 | 13.6 | Inactive |
| B13 | 16.3 | 44 |
| B14 | 3.7 | Inactive |
| B15 | 8.4 | 22 |
| B16 | 14.1 | Inactive |
| B17 | 23.5 | Inactive |
| B18 | Inactive | Inactive |
| B19 | 0.295 | 0.48 |
| B20 | 7.15 | 7 |
| B21 | 17.3 | 18.2 |
| B22 | Inactive | Inactive |
| B31 | Inactive | Inactive |
| B32 | Inactive | Inactive |
| B33 | Inactive | Inactive |
| B34 | Inactive | Inactive |
| B35 | Inactive | Inactive |
| B36 | Inactive | Inactive |
| B37 | Inactive | Inactive |
| B38 | Inactive | Inactive |
| B39 | Inactive | 32 |
| B41 | 32 | — |
| B42 | Inactive | Inactive |
| B43 | Inactive | Inactive |
| B44 | Inactive | Inactive |
| B45 | Inactive | Inactive |
| B46 | 0.36 | 0.495 |
| B47 | Inactive | Inactive |
| B48 | Inactive | Inactive |
| B49 | Inactive | Inactive |
| B50 | Inactive | Inactive |
| B51 | Inactive | Inactive |
| B52 | 4.8 | 3.6 |
| B53 | Inactive | Inactive |
| B54 | Inactive | Inactive |
| B55 | 15 | 24 |
| B56 | 26 | 33 |
| B57 | Inactive | Inactive |
| B58 | Inactive | Inactive |
| B59 | 0.62 | — |
| B60 | Inactive | — |
| B61 | 3.6 | — |
| B62 | 27 | — |
| B63 | 21 | — |
| B64 | 1.115 | — |
| B65 | 5.25 | 4.0 |
| B66 | 1.8 | 3.0 |
| B67 | Inactive | — |

TABLE 15-continued

| Compound | 22RV1- EC$_{50}$ (uM) | U87- EC$_{50}$ (uM) |
|---|---|---|
| B68 | Inactive | — |
| B69 | Inactive | — |
| B70 | 2.15 | 2.6 |
| B71 | 0.83 | — |
| B72 | 0.645 | — |
| B73 | Inactive | — |
| B74 | 1.185 | — |
| B75 | 4.15 | — |
| B76 | 0.605 | — |
| B77 | 7.5 | — |
| B78 | Inactive | — |
| B83 | 2 | 3.2 |
| B84 | 0.925 | — |
| B85 | 4.15 | — |
| B86 | 0.245 | 2.6 |
| B87 | 12 | — |
| B89 | 3.1 | 3.9 |
| B88 | Inactive | — |
| B91 | 7.25 | — |
| B117 | 16 | — |
| B118 | 49 | — |
| B90 | 1.9 | — |
| B120 | 1.42 | 1.3 |
| B121 | 0.235 | 0.37 |
| B122 | 1 | 1.15 |
| B123 | 17 | Inactive |
| B124 | 7.7 | 13.65 |
| B125 | 1.175 | 1.65 |
| B126 | 0.9 | 1.3 |
| B127 | Inactive | Inactive |
| B128 | Inactive | Inactive |
| B129 | 3.6 | 6.9 |
| B130 | 0.79 | 1.4 |
| B131 | 5.55 | 6.6 |
| B132 | 5.2 | 7.7 |
| B133 | Inactive | Inactive |
| B134 | 25 | Inactive |
| B135 | 5 | Inactive |
| B136 | Inactive | Inactive |
| B137 | 0.014 | 0.42 |
| B138 | 0.015 | 0.004 |
| B139 (RGN6024) | 0.038 | 0.68 |
| B140 | 0.09 | 0.77 |
| B141 | 2 | 10.55 |
| B142 | Inactive | Inactive |
| B143 | Inactive | Inactive |
| B144 | Inactive | Inactive |
| B145 | Inactive | Inactive |
| B146 | Inactive | Inactive |
| B147 | 8.9 | Inactive |
| B148 | 21 | Inactive |
| B149 | 3.65 | 1.75 |
| B150 | Inactive | Inactive |
| B151 | 5.9 | Inactive |
| B152 | Inactive | Inactive |
| B153 | 16.5 | Inactive |
| B154 | Inactive | Inactive |
| B155 | 0.002 | 0.03 |
| B156 | Inactive | Inactive |
| B157 | 0.9 | 1.3 |

TABLE 16

| Compound | LN-18 EC$_{50}$ (uM) | T98G EC$_{50}$ (uM) | LN-229 EC$_{50}$ (uM) |
|---|---|---|---|
| B139 (RGN6024) | 0.069 | 0.152 | 0.123 |
| B155 | 0.017 | 0.036 | 0.030 |

Example 20

In another exemplary method, central nervous system multiparameter optimization (CNS MPO) score, the kinetic solubility, and cellular permeability of selected compounds were determined. CNS MPO score for compounds and their isomers disclosed herein were calculated using an algorithm that uses a weighted scoring function assessing 6 key physicochemical properties (clogP, clogD, MW, TPSA, HBD, and pKa) for blood-brain-barrier (BBB) penetration). CNS MPO score ranged from 0 and 6.0 with scores≥4.0 used as a cut-off to select compounds that can have a high probability of accumulating in the CNS. Kinetic solubility of a compound is the maximum solubility of the fastest precipitating species of the compound. Kinetic solubility was determined by preparing a concentrated stock solution for compounds and their isomers disclosed herein in an organic solvent (DMSO), after which the solution was mixed with an aqueous PBS buffer and then filtered. Filtrate was tested to quantify the kinetic solubility using HPLC-MS calibration curve. Cellular permeability was determined by calculating the apparent permeability coefficient ($P_{app}$), and the efflux ratio ($P_{app\ BA}/P_{app\ AB}$). Apparent permeability coefficients (Papp) were calculated from the equation:

$$P_{app} = \frac{\Delta Q}{\Delta t} \times \frac{1}{AC_0}$$

where $\Delta Q/\Delta t$ is the steady-state flux (mol/s), $C_0$ is the initial concentration in the donor chamber at each time interval (mol/mL), and A is the surface area of the filter (cm$^2$). The data are presented as means±SD of six independent monolayers.

The CNS MPO Score, kinetic solubility, $P_{app}$ and efflux ratio of the compounds tested are provided in Table 17 where "ND" means not determined.

TABLE 17

| Compound | CNS MPO score | Kinetic Solubility (uM) | Papp (A-B) (10$^{-6}$, cm/s) (cm/s) | Efflux ratio |
|---|---|---|---|---|
| B4 | 3.62 | 0.39 | — | — |
| B19 | 5.38 | 21.36 | 24.2 | 0.881 |
| B46 | 5.09 | 5.6 | — | — |
| B52 | 4.97 | 87.89 | — | — |
| B121 | 5.38 | 24.49 | — | — |
| B64 | 4.65 | 3.25 | — | — |
| B70 | 4.94 | 49.42 | — | — |
| B71 | 4.92 | 22.76 | — | — |
| B137 | 4.95 | 83.6 | 26.2 | 1.08 |
| B138 | 5.05 | 91.23 | 26 | 0.93 |
| B139 (RGN6024) | 5.23 | 5.24 | 21.1 | 1 |
| B140 | 5.38 | 4.55 | 11.9 | 0.85 |
| B91 | 4.83 | 2.64 | — | — |
| B89 | 5.29 | 1 | — | — |
| B117 | 4.88 | 79.2 | — | — |

Example 21

In another exemplary method, the effect of the compounds of the instant disclosure on tubulin polymerization was determined. It is noted that tubulin polymerization is a key system or target for controlling aberrant cell growth or expansion (e.g., in tumor growth or expansion) FIG. 19A and FIG. 19B illustrate effects of compounds B130, B144, and B147 (FIG. 19A) and compounds B137, B138, RGN6024 (FIG. 19B) at 5 uM concentrations on tubulin polymerization. Colchicine and Nocodazole are positive controls and DMSO is a negative control used in these studies. The results demonstrate that many compounds, including compounds B137, B138, and RGN6024 significantly inhibit tubulin polymerization.

These results were further confirmed using the colchicine competitive binding assay (FIG. 21) and the N,N'-ethylene-bis(iodoacetamide) (EBI) competition assay (FIG. 22). Microtubule-targeting agents that bind at the colchicine-site of tubulin are of interest in antitumoral therapy due to their action as anti-mitotics. The results demonstrate that RGN6024 significantly inhibits microtubule assembly (FIG. 21). Nocodazole was used as a positive control. Compound B138 was demonstrated to be an inhibitor of EBI binding using the MCF7 cell lines demonstrating binding of compounds in a colchicine binding site (FIG. 22). Colchicine (COL) is a positive control while vinblastine was used as a negative control.

Example 22

In another exemplary method, levels of compound 138 and RGN6024 were determined in plasma following oral administration. For these studies, ICR1 male mouse strain was used as an acceptable mouse model. Compound B138 or RGN6024 were then administered to the mice orally as a solution in 30% hydroxypropyl-β-cyclodextrin in saline. A single dose of 30 mg/kg of compound B138 or RGN6024 was administered in this manner. Concentrations of compound B138 or RGN6024 in plasma were measured using HPLC-MS quantitation (FIGS. 23 and 24). The levels of compound B138 and RGN6024 in plasma were higher than concentration required to kill cancer cells in vitro.

Example 23

In another exemplary method, levels of RGN6024 were determined in brain tissue following oral administration. For these studies, a ICR1 male mouse strain was used as an acceptable mouse model. RGN6024 was then administered to the mice orally as a solution in 30% hydroxypropyl-β-cyclodextrin in saline. A single dose of 30 mg/kg of RGN6024 was administered in this manner. Concentrations of RGN6024 in brain tissue were measured using HPLC-MS quantitation (FIG. 25). The levels of RGN6024 in plasma and brain were higher than concentration required to kill cancer cells in vitro.

Example 24

In another exemplary method, RGN6024 was tested in LN-18 xenograft models in CB17 SCID female mice. For this study, CB17 SCID mice were engrafted with LN-18 cancer cells. Tumor volumes were measured on days 2, 4, 6, 8, 10, 13 and 15. RGN6024 was administered orally at dose of 15 mg/kg (from day 1-day 5) and at 7.5 mg/kg (day 9, 10 and from day 12-day 15). Concentrations of RGN6024 in plasma, brain and tumor tissue at 30 and 90 minutes were measured using HPLC-MS quantitation (FIG. 26A). Amounts of compounds RGN6024 in plasma, brain and tumor were greater than levels required to kill LN-18 cancer cells.

Example 25

In another exemplary method, RGN6024 was further characterized as illustrated and as described herein below.

As disclosed herein, it was discovered that compounds of the instant application can be used to treat health conditions such as cancer. In addition, it was observed that many of the compounds target cell cycle elements and can induce cancer cell death. For example, it was observed that RGN6024 targets and binds to tubulin. In brief, in one experiment, U-87 cells were plated at a density of 4000 cells/well in black 96-well plates (PhenoPlate, Perkin Elmer) and grown overnight. These cells were treated with compounds for 24 h, then fixed with 4% paraformaldehyde for 20 min. The cells were washed with PBS, followed by permeabilization with FoxP3 perm buffer (BD Biosciences) for 10 min at room temperature. Cells were incubated with anti-TUBB3 (1:1000; Tuj1, STEMCELL Technologies) antibodies overnight, followed by incubation with secondary antibody for 1 h. The nuclear DNA was labeled with Hoechst. Representative images (40×) were obtained using an automated high content imaging microscope (Operetta, Perkin Elmer).

In another experiment, it was found that RGN6024 had improved ability to cross the blood brain barrier compared to other known products in the market where many fail to cross into the brain and others cross the BBB at much lower success rates than observed herein for RGN6024 and related compounds thereof.

In one example, RGN6024 was tested against placebo and a standard of care therapy for the treatment of glioblastoma, temozolomide. A gold standard cell line representing drug therapy resistant glioblastoma, LN-18, was grown in mice and the mice divided into three cohorts. For these studies, CB17 SCID mice were engrafted with LN-18 cancer cells. Tumor volumes were measured every second day. RGN6024 was administered orally at dose of 15 mg/kg (from day 1-day 5) and at 7.5 mg/kg (day 9, 10 and from day 12-day 15). Temozolomide was administered orally at a dose of 25 mg/kg daily with 7 days schedule (5 days ON and 2 days OFF) schedule. The mice receiving RGN6024 had about an average of 54% reduction in tumor growth rate relative to placebo and a better outcome than with the standard of care drug glioblastoma. Further, fifty percent of the mice in the RGN6024 group experienced marked tumor shrinkage in a brain cancer model. This is a remarkable result compared to a standard of care molecule such as temozolomide which demonstrated only about a 40% reduction in tumor volume.

It is observed that current FDA approved therapies related to tubulin interactions bind to tubulin in large clefts on the surface of the protein. Consequently, these drugs are large themselves. For brain penetration, the larger the molecule, the less likely it will penetrate the brain. Therefore, large molecules struggle to cross the blood brain barrier. If these large molecules do cross the blood brain barrier or are directly administered into the brain, these molecules are often actively removed from the brain by molecular pumps designed to remove toxins. Therefore, these molecules not only have issues penetrating the brain barrier but are often pumped back out. This can result in higher doses being needed to overcome these issues with reduced efficacy and efficiency and more likelihood of toxicity issues.

Using a different approach, as disclosed herein, some molecules of the instant application were designed to bind to a small cleft on the surface of the tubulin protein. This change permits molecules of smaller size and these properties affect and improve brain penetration and avoid the efflux pumps that would otherwise remove these molecules from the brain. For example, RGN6024 is half the size the FDA approved therapies as are many of the related molecules disclosed herein.

In another exemplary method, to further study RGN6024 and its treatment of brain cancer, LN-18 xenograft tumors and brains were excised from the mouse brain cancer model after the last dose. This was done at two time points. 30 minutes for half the mice and 90 minutes for the other half of the mice. The concentration of the target agent in the brain mirrored the concentration of the target agent in the tumor at both time points. As demonstrated herein, brain concentration of RGN6024 exceeded the amount needed to shrink tumors in animals and therefore is more effective as treating these tumors using lower doses.

In other exemplary methods, RGN6024 was tested in a variety of high-grade glioma lines and breast, lung, and melanoma tumors with a propensity for brain metastasis. A 91 nM median potency was observed. Comparatively, RGN6024's brain penetration level is 100 times the concentration required to see an efficacious response in these cancer models.

Example 26

In another exemplary method, a patient with therapy-resistant glioblastoma can be or will be treated with a once daily oral administration of RGN6024 either as a single agent or in combination with other treatments. Brain and tumor biopsies or other less invasive analysis such as blood analysis or other fluid analysis will confirm that RGN6024 achieves high concentration directly in the tumor(s) and brain. Remarkably, the patient will also experience marked tumor shrinkage. Surprisingly, the patient will continue to survive significantly beyond five years, the period at which only 5% of patients survive when currently available treatment is used.

Example 27

In another exemplary method, the use of one or more of the compounds disclosed herein as a lead for drug screening using artificial intelligence (AI) was further characterized as illustrated and as described herein below.

In some embodiments, the present invention features a system for using artificial intelligence (AI) to generate one or more candidate compounds. The one or more candidate compounds may be derived from RGN6024, incorporate RGN6024, or a combination thereof. In some embodiments, the system may comprise a processor configured to execute computer-readable instructions, and a memory component communicatively coupled to the processor. The memory component may comprise an AI model comprising one or more neural networks, trained with a training data set comprising chemical training data. Training the AI model may comprise feeding the training data set as input into the AI model. The AI model may be trained to generate the one or more candidate compounds as output. The memory component may further comprise computer-readable instructions. The computer-readable instructions may comprise inputting chemical data into the AI model. The chemical data may comprise data unique to RGN6024. The computer-readable instructions may further comprise generating, by the AI model, the one or more candidate compounds.

In some embodiments, the present invention features a method for using artificial intelligence (AI) to generate one or more candidate compounds. The one or more candidate compounds may be derived from RGN6024, incorporate RGN6024, or a combination thereof. The method may comprise providing an AI model comprising one or more neural networks, trained with a training data set comprising chemical training data. Training the AI model may comprise feeding the training data set as input into the AI model. The AI model may be trained to generate the one or more candidate compounds as output. The method may further comprise inputting chemical data into the AI model, wherein the chemical data comprises data unique to RGN6024, and generating, by the AI model, the one or more candidate compounds.

In some embodiments, the one or more candidate compounds may comprise one or more candidate drug compounds. In some embodiments, the data unique to RGN6024 may comprise one or more structural properties, one or more physical properties, one or more interactions between RGN6024 and one or more other chemical compounds, one or more molecular pathways, one or more molecular cell profiles, or a combination thereof.

In some embodiments, the present invention features a method for training an artificial intelligence (AI) model to generate one or more candidate compounds. The one or more candidate compounds may be derived from RGN6024, incorporate RGN6024, or a combination thereof. The AI model may comprise one or more neural networks. The training method may comprise feeding a training data set comprising chemical training data unique to RGN6024 as input into the AI model. The method may further comprise inputting chemical data into the AI model, wherein the chemical data comprises data unique to RGN6024. The AI model may be trained to generate the one or more candidate compounds as output.

In some embodiments, the chemical training data may comprise data pertaining to one or more chemical compounds. The data pertaining to the one or more chemical compounds may comprise one or more structural properties of the one or more chemical compounds, one or more physical properties of the one or more chemical compounds, one or more interactions between the one or more chemical compounds, one or more molecular pathways of the one or more chemical compounds, one or more molecular cell profiles of the one or more chemical compounds, or a combination thereof.

In some embodiments, the chemical training data may comprise one or more vector representations of the one or more chemical compounds. In some embodiments, the chemical training data may comprise one or more knowledge graphs representing the one or more chemical compounds. In some embodiments, the chemical training data may comprise any single or multi-dimensional representation of the one or more chemical compounds.

In some embodiments, the chemical training data may comprise one or more training labels associated with the one or more chemical compounds. In some embodiments, the one or more training labels may comprise one or more label elements having predetermined values. In some embodiments, the one or more training labels may comprise bioassay results, toxicity, cross-reactivity, pharmacokinetics, pharmacodynamics, bioavailability, solubility data, or a combination thereof.

In some embodiments, the chemical data may comprise data pertaining to one or more chemical compounds. The data pertaining to the one or more chemical compounds may comprise one or more structural properties of the one or more chemical compounds, one or more physical properties of the one or more chemical compounds, one or more interactions between the one or more chemical compounds, one or more molecular pathways of the one or more chemical compounds, one or more molecular cell profiles of the one or more chemical compounds, or a combination thereof.

In some embodiments, the chemical data may comprise one or more vector representations of the one or more chemical compounds. In some embodiments, the chemical data may comprise one or more knowledge graphs representing the one or more chemical compounds. In some embodiments, the chemical data may comprise any single or multi-dimensional representation of the one or more chemical compounds.

In some embodiments, the chemical data may comprise one or more labels associated with the one or more chemical compounds. In some embodiments, the one or more labels may comprise one or more label elements having predetermined values. In some embodiments, the one or more labels may comprise bioassay results, toxicity, cross-reactivity, pharmacokinetics, pharmacodynamics, bioavailability, solubility data, or a combination thereof.

The AI model may be stored, trained, and/or executed entirely on the user's computer, partly on the user's computer, as a stand-alone software package, partly on the user's computer and partly on a remote computer, or entirely on the remote computer or server. The AI model may be stored in the form of program code, as described above. The one or more neural networks of the AI model, in some embodiments, may comprise a perceptron neural network, a feed-forward neural network, a multilayer perceptron neural network, a radial basis functional neural network, a recurrent neural network, a long short-term memory neural network, a sequence-to-sequence neural network model, a modular neural network, a graph-based convolutional neural network, an instance-based model, a feature attribution model, or the like.

In a non-limiting example, the AI model of the presently claimed invention may comprise a perceptron neural network, configured to accept the chemical data as input, execute one or more functions on the input, multiply the output of the one or more functions by a plurality of weights, and generating a final output comprising the one or more candidate compounds. In another non-limiting example, the AI model of the presently claimed invention may comprise a multilayer perceptron neural network comprising a plurality of layers, each layer configured to execute the process of a single perceptron network, each layer linked to an input and output feed such that the output of one layer is the input of a subsequent layer. The input to the first layer may be the chemical data and the output of the last layer may be the one or more candidate compounds.

In another non-limiting example, the AI model may comprise a graph-based convolutional neural network comprising a plurality of layers. Each layer of the plurality of layers may be linked to an input and output feed such that the output of one layer is the input of a subsequent layer. The input to the first layer may be the chemical data and the output of the last layer may be the one or more candidate compounds. The chemical data may be converted into one or more graph structures before being transmitted to the plurality of layers. In some embodiments, the plurality of layers and the functions therein may be configured to extract one or more subgraphs from the input graph comprising one or more relevant node features and apply one or more attention-based functions to the subgraphs and relevant node features to assign importance to certain molecules, connections, atoms, etc. such that the model is able to generate and/or predict new candidate compounds based on the input comprising RGN6024, utilizing the most relevant patterns determined by the one or more attention-based functions. Determining which patterns are relevant and important for discovery may be a component of the training data set.

The one or more candidate compounds may comprise one or more chemical compounds linked to RGN6024, one or more chemical compounds reassembled from the components of RGN6024, one or more chemical compounds deriving from RGN6024 by way of a chemical reaction, one or more chemical compounds related to RGN6024, or a combination thereof.

With regards to the methods for implementing AI for discovering chemical compounds related to RGN6024 and the AI-based systems thereof, the specifications of U.S. Pat. No. 10,776,712, issued Sep. 15, 2020, and U.S. Pat. No. 11,462,304, issued Oct. 4, 2022, are incorporated herein in their entirety by reference.

Example 28

In another exemplary method, the use of one or more of the compounds disclosed herein as a drug screening tool using in vitro, ex vivo and in vivo assays was further characterized as illustrated and as described herein below.

The present invention features a method for screening one or more potential drug candidate compounds to determine whether it is therapeutically effective using any one of the compounds disclosed herein as a reference compound. The method comprises: (a) identifying one or more of an in vitro, ex vivo or in vivo model for experimentation; (b) contacting at least one of a cell, fluid, tissue, organ or animal with at least of one of the reference compound, the potential drug candidate compound, or a negative control compound; (c) determining in parallel one or more drug parameter or characteristic from contacting the cell, fluid, tissue, organ, or animal with at least one of the reference compound, the potential drug candidate compound or the negative control compound; and (d) comparing the drug parameter or characteristic of one or more of the negative control, the reference compound, or the drug candidate compound to determine whether the drug candidate compound is therapeutically effective.

In a non-limiting example, the in vitro model may comprise a cell viability assay, cell cycle analysis, immunofluorescent staining assay, immunofluorescent staining of cellular beta tubulin, tubulin polymerization assay, competitive binding assay, colchicine competitive binding assay, binding site cellular assay, colchicine-binding site cellular assay, reversibility assay, kinetic solubility assay, microsomal stability assay, plasma protein binding study, cellular permeability study, or cell cycle analysis by flow cytometry. In another non-limiting example, the ex vivo model comprises an excised tumor in a chicken egg model. In another non-limiting example, the in vivo model comprises a pharmacokinetic (PK) study, brain pharmacokinetic (PK) study, maximum tolerated dose study, efficacy study, metabolite profiling in hepatocytes, survivability study, or tumor size study.

In some non-limiting examples, the drug parameter or characteristic analyzed comprises pharmacokinetics (PK), pharmacodynamics (PD), brain pharmacokinetics (brain PK), target-site binding, cell viability, cellular permeability, blood brain barrier permeability, efficacy, toxicity and safety, stability, microsomal stability, kinetic solubility, plasma protein binding, microsomal stability, or effects on cell cycle.

In some non-limiting examples, cells may be contacted with the reference compound, the potential drug candidate compound, or a negative control compound. The cell may comprise a primary tumor cells, cancer cell, U87 glioblastoma cells, LN-18 glioblastoma cells, HMC3 microglial cells, patient-derived GBM cells, MDR1-MDCK (multi-drug-resistant-1-Mandin-Darby canine kidney) cells, human cryopreserved hepatocytes, or cells used in a patient-derived xenograft model. In other non-limiting examples, fluids may be contacted with the reference compound, the potential drug candidate compound, or a negative control compound. The fluids may comprise plasma, cerebrospinal fluid, brain homogenate, urine, whole blood, serum, or tumor homogenate. In some non-limiting examples, tissue may be contacted with the reference compound, the potential drug candidate compound, or a negative control compound. The tissues may comprise a brain tumor tissue, normal brain tissue, tumor tissue, or solid tumor tissue. In other non-limiting examples, organs may be contacted with the reference compound, the potential drug candidate compound, or a negative control compound. The organs may comprise a brain, breast, skin, lungs, liver, bones, or connective tissue. In other non-limiting examples, animals may be contacted with the reference compound, the potential drug candidate compound, or a negative control compound. The animals may comprise a mouse, rat, dog, monkey, rabbit, or pig.

Example 29

The following is a non-limiting example of the present invention. It is to be understood that said example is not intended to limit the present invention is any way. Equivalents or substitutes are within the scope of the present invention.

Example 29.1 Oral Administration to Treat a Brain Cancer (Glioblastoma). (Related Examples: Combining Oral Administration with any of Standard of Care Options for Treating Cancer (i.e. Chemotherapy and/or Temazolamide)

A 60-year-old man visits his physician, troubled by weakness and paralysis in the right side of his body, loss of balance, drowsiness, and persistent nausea and vomiting. Sensing the urgency of his condition, the physician takes an in-depth history, performs a neurological exam and orders a brain MRI with contrast to ascertain the underlying cause of his symptoms. The man's test results reveal that he has a brain cancer that is suspected to be a glioblastoma. Brain biopsy confirms Glioblastoma. The physician prescribes an oral composition comprising a 1 mg/kg dosage of the RGN6024 compound, as described herein, in the form tablets taken once daily, to treat the brain cancer. The man adheres to the prescribed regimen and experiences a gradual alleviation of his symptoms with each dose over the course of the next month. Patient experiences mild nausea which is well controlled with anti-nausea medications. Follow up MRI after 4 weeks of treatment demonstrates reduction in overall size of Glioblastoma.

Example 29.2 Subcutaneous Administration to Treat a Brain Cancer (Glioblastoma)

A 60-year-old man visits his physician, troubled by weakness and paralysis in the right side of his body, loss of balance, drowsiness, and persistent nausea and vomiting. Sensing the urgency of his condition, the physician takes an in-depth history, performs a neurological exam and orders a brain MRI with contrast to ascertain the underlying cause of his symptoms. The man's test results reveal that he has a brain cancer that is suspected to be a glioblastoma. Brain biopsy confirms Glioblastoma. The physician prescribes a composition comprising a compound, as described herein, at a dose of 2 mg/kg in a 5 mL syringe, to be injected subcutaneously once weekly, to treat the brain cancer. The man adheres to the prescribed regimen and experiences a gradual alleviation of his symptoms with each dose over the course of the next month. Patient experiences mild nausea which is well controlled with anti-nausea medications. Follow up MRI after 4 weeks of treatment demonstrates reduction in overall size of Glioblastoma.

Example 29.3 Intravenous Administration to Treat a Brain Cancer (Glioblastoma)

A 60-year-old man visits his physician, troubled by weakness and paralysis in the right side of his body, loss of balance, drowsiness, and persistent nausea and vomiting. Sensing the urgency of his condition, the physician takes an in-depth history, performs a neurological exam and orders a brain MRI with contrast to ascertain the underlying cause of his symptoms. The man's test results reveal that he has a brain cancer that is suspected to be a glioblastoma. Brain biopsy confirms Glioblastoma. The physician prescribes a composition comprising a compound, as described herein, at a dose of 5 mg/kg infused over 30 minutes, once weekly, to treat the brain cancer. The man adheres to the prescribed regimen and experiences a gradual alleviation of his symptoms with each dose over the course of the next month. Patient experiences mild nausea which is well controlled with anti-nausea medications. Follow up MRI after 4 weeks of treatment demonstrates reduction in overall size of Glioblastoma.

Example 29.4 Oral Administration to Treat a Non-Small Cell Lung Cancer (NSCLC) that is Metastasizing to the Brain. [Related Examples: EGFR Mutated, ROS-1 Mutated, K-RAS Mutated Lung Cancers; Combining Oral Administration with any of Standard of Care Options for Treating Cancer (i.e. Immunotherapy, Targeted Treatment)]

A 75-year-old man visits his physician after being diagnosed one year prior with non-small cell lung cancer (NSCLC) and is currently taking crizotinib to treat the NSCLC. The man complains of headaches, mild seizures, memory loss and morning nausea and vomiting. Sensing the urgency of his condition, the physician takes an in-depth history, performs a neurological exam and orders a brain MRI with contrast to ascertain the underlying cause of his symptoms. The man's test results reveal that the NSCLC is metastasizing to his brain. The physician prescribes an oral pill comprising 0.5 mg/kg dosage of the RGN6024 compound, as described herein, to treat the brain metastases to be administered during the same time he is taking crizotinib. The man adheres to the prescribed regimen and experiences a gradual alleviation of his symptoms with each dose. Patient experiences mild nausea which is well controlled with anti-nausea medications.

Example 29.5 Oral Administration to Treat a Triple Negative, Her2 Positive Breast Cancer Metastasizing to the Brain. [Related Example: Hormone Receptor Positive Breast Cancers that is Metastasizing to the Brain]

A 53-year-old woman visits her physician after being diagnosed six months prior with breast cancer. The woman complains of dull and constant tension-type headaches, mild slurred speech and sudden mood changes. Sensing the urgency of her condition, the physician takes an in-depth history, performs a neurological exam and orders a head CT scan with contrast to ascertain the underlying cause of her symptoms. The woman's test results reveal brain metastasizing. The physician prescribes an oral composition comprising a compound, as described herein, to treat the brain metastases. The woman adheres to the prescribed regimen and experiences a gradual alleviation of her symptoms with each dose. Patient experiences mild nausea which is well controlled with anti-nausea medications.

Example 29.6 Oral Administration to Treat a Skin Cancer (Melanoma) that is Metastasizing to the Brain A 23-year-old woman visits her physician after being diagnosed two years prior with skin cancer believed to be a melanoma. The woman complains of dizziness, balance problems and memory problems. Sensing the urgency of her condition, the physician takes an in-depth history, performs a neurological exam and orders a head CT scan with contrast to ascertain the underlying cause of her symptoms. The woman's test results reveal brain metastasizing. The physician prescribes an oral composition comprising a compound, as described herein, to treat the brain metastases. The woman adheres to the prescribed regimen and experiences a gradual alleviation of her symptoms with each dose. Patient experiences mild nausea which is well controlled with anti-nausea medications.

Example 29.7 Oral Administration to Treat Prostate Cancer that is Metastasizing to the Brain. [Related Example: Prostate Cancer with Extensive Bone Metastasis that is Progressing on Androgen Deprivation Therapy]

A 90-year-old man visits his physician after being diagnosed one year prior with pancreatic cancer. The man complains of weakness, dizziness, diplopia, and decreased appetite. Sensing the urgency of his condition, the physician performs takes an in-depth history, a neurological exam and orders a brain MRI with contrast to ascertain the underlying cause of his symptoms. The man's test results reveal that the prostate cancer is metastasizing to his brain. The physician prescribes an oral composition comprising a compound, as described herein, to treat the brain metastases. The man adheres to the prescribed regimen and experiences a gradual alleviation of his symptoms with each dose. Patient experiences mild nausea which is well controlled with anti-nausea medications.

Example 29.8 Oral Administration to Treat Kidney Cancer that is Metastasizing to the Brain A 63-year-old man visits his physician after being diagnosed 6 months prior with kidney cancer. The man complains of numbness, mild seizures, memory problems and dizzy spells. Sensing the urgency of his condition, the physician takes an in-depth history, performs a neurological exam and orders a brain MRI with contrast to ascertain the underlying cause of his symptoms. The man's test results reveal that the kidney cancer is metastasizing to his brain. The physician prescribes an oral composition comprising a compound, as described herein, to treat the brain metastases. The man adheres to the prescribed regimen and experiences a gradual alleviation of his symptoms with each dose. Patient experiences mild nausea which is well controlled with anti-nausea medications.

Example 29.9 Oral Administration to Treat a Medulloblastoma

A 51-year-old man visits his physician, troubled by morning headaches, ataxia, diplopia, and extreme lethargy and confusion. Sensing the urgency of his condition, the physician takes an in-depth history, performs a neurological exam and orders a head CT scan with contrast to ascertain the underlying cause of his symptoms. The man's test results reveal that he has a medulloblastoma. The physician prescribes an oral composition comprising a compound, as described herein, to treat the medulloblastoma. The man adheres to the prescribed regimen and experiences a gradual alleviation of his symptoms with each dose. Patient experiences mild nausea which is well controlled with anti-nausea medications.

Example 29.10 Oral Administration to Treat a High-Grade Glioma

A 36-year-old man visits his physician, troubled by morning headaches, fatigue, and problems with his vision and speech. Sensing the urgency of his condition, the physician takes an in-depth history, performs a neurological exam and orders a head CT scan with contrast to ascertain the underlying cause of his symptoms. The man's test results reveal that he has a high-grade glioma. The physician prescribes an oral composition comprising a compound, as described herein, to treat the high-grade glioma. The man adheres to the prescribed regimen and experiences a gradual alleviation of his symptoms with each dose. Patient experiences mild nausea which is well controlled with anti-nausea medications.

Example 29.11 Oral Administration to Treat a Vascularized Cancer (Stage II Cancer)

A 66-year-old woman visits her physician, troubled by fatigue, unexplained weight loss, persistent indigestion, persistent muscle pain and unexplained bruising. Sensing the urgency of her condition, the physician orders multiple imaging tests and a comprehensive blood analysis to ascertain the underlying cause of her symptoms. The woman's test results reveal that she has Stage II cancer. Biopsy reveals the cancer is highly vascularized. The physician prescribes an oral composition comprising a compound, as described herein, to treat the Stage II cancer. The woman adheres to the prescribed regimen and experiences a gradual alleviation of her symptoms with each dose. Patient experiences mild nausea which is well controlled with anti-nausea medications.

Example 29.12 Oral Administration to Treat Ewing Sarcoma

An 18-year-old woman visits her physician, troubled by bone pain, fever and unexplained weight loss. Sensing the urgency of her condition, the physician orders multiple imaging tests, including an X-ray and an MRI, and a comprehensive blood analysis to ascertain the underlying cause of her symptoms. The woman's test results reveal that she has Ewing sarcoma. The physician prescribes an oral composition comprising a compound, as described herein, to treat the Ewing sarcoma. The woman adheres to the prescribed regimen and experiences a gradual alleviation of her symptoms with each dose. Patient experiences mild nausea which is well controlled with anti-nausea medications.

Example 29.13 Oral Administration to Treat Acute Gout. [Related Examples: Prophylaxis Against Gout, Refractory Gout, Pseudo Gout, Recurrent Pericarditis]

A 72-year-old woman visits her physician, troubled by sudden and severe pain in her feet, swelling and swelling, redness and tenderness in her joints. Sensing the urgency of her condition, the physician performs a physical examination and orders an X-ray and a comprehensive blood analysis to ascertain the underlying cause of her symptoms. The woman's test results reveal that she has acute gout. The physician prescribes an oral composition comprising a compound, as described herein, to treat the gout. The woman adheres to the prescribed regimen and experiences a gradual alleviation of her symptoms with each dose. Patient experiences mild nausea which is well controlled with anti-nausea medications.

Example 29.14 Oral Administration to Treat Mediterranean Fever

A 17-year-old man visits his physician, troubled by recurrent episodes of fever, muscle pain, a red rash below the knees and pain in the abdomen and chest. Sensing the urgency of his condition, the physician performs a physical examination and orders a comprehensive blood and urine analysis and genetic testing to ascertain the underlying cause of his symptoms. The man's test results reveal that he has Mediterranean fever. The physician prescribes an oral composition comprising a compound, as described herein, to treat the Mediterranean fever. The man adheres to the prescribed regimen and experiences a gradual alleviation of his symptoms with each dose. Patient experiences mild nausea which is well controlled with anti-nausea medications.

Example 29.15 Oral Administration to Treat Nail Fungus

A 23-year-old man visits his physician, troubled by discoloration of his pointer fingernail in his right hand and pain and discomfort when using his finger. Sensing the urgency of his condition, the physician performs a physical examination and collects nail clippings for laboratory testing. The man's test results reveal that he has nail fungus. The physician prescribes an oral composition comprising a compound, as described herein, to treat the nail fungus. The man adheres to the prescribed regimen and experiences a gradual alleviation of his symptoms with each dose. Patient experiences mild nausea which is well controlled with anti-nausea medications.

Example 30

The following is a non-limiting example of the present invention. It is to be understood that said example is not intended to limit the present invention is any way. Equivalents or substitutes are within the scope of the present invention.

Example 30.1 Method of Drug Screening Using an In Vitro Experimental Model to Identify a BBB Penetrant Drug Candidate for Treating a Brain Cancer A researcher is seeking to identify a therapeutically effective drug candidate to treat brain cancer. The researcher identifies an in vitro experimental model to perform the drug screening in a model of the blood brain barrier. The researcher then administers the potential drug candidate and RGN6024 to use as a standard and compares the ability of the two drugs to penetrate the model blood brain barrier. Using the data from the experiment, the researcher identifies the potential drug candidate more likely to be therapeutically effective for treating a brain cancer.

Example 30.2 Method of Drug Screening Using an In Vivo Experimental Model to Identify a BBB Penetrant Drug Candidate for Treating a Brain Cancer by Determining Effect on Tumor Size A researcher is seeking to identify a therapeutically effective drug candidate to treat brain cancer. The researcher identifies an in vivo experimental model to perform the drug screening in an animal model where a tumor is induced in the brain. The researcher then administers the potential drug candidate and RGN6024 to use as a standard and compares the efficacy of the drug on the tumor in the brain by approximating the tumor size with a reporter (e.g. luciferase). Using the data from the experiment, the researcher identifies the potential drug candidate more likely to be therapeutically effective for treating a brain cancer.

Example 30.3 Method of Drug Screening Using an In Vivo Experimental Model to Identify a BBB Penetrant Drug Candidate for Treating Cancer by Determining Effect on Survivability A researcher is seeking to identify a therapeutically effective drug candidate to treat brain cancer. The researcher identifies an in vivo experimental model to perform the drug screening in an animal model where a tumor is induced. The researcher then administers the potential drug candidate and RGN6024 to use as a standard and compares the efficacy of the drug on the tumor by measuring the length of time the animals survive the tumor. Using the data from the experiment, the researcher identifies the potential drug candidate as more likely to be therapeutically effective for treating cancer.

Example 30.4 Method of Drug Screening Using an In Vivo Experimental Model to Identify a Therapeutically Effective Drug Candidate for Treating a Brain Cancer by Determining Effect on Tumor Growth A researcher is seeking to identify a therapeutically effective drug candidate to treat brain cancer. The researcher identifies an experimental animal model to perform the drug screening. The researcher then administers the potential drug candidate and RGN6024 to determine the effect on tumor growth and compares the size of the tumor following administration of each of the two drugs. Using the data from the experiment, the researcher identifies the drug candidate as potentially therapeutically effective for treating a brain cancer.

Example 30.5 Method of Drug Screening Using an In Vivo Experimental Model to Identify a Therapeutically Effective Drug Candidate for Treating a Brain Cancer by Determining Effect on Tumor Growth A researcher is seeking to identify a therapeutically effective drug candidate to treat brain cancer. The researcher identifies an experimental animal model using cancer cells with a quantitive biomarker (e.g., luciferase) to perform the drug screening. The researcher then administers the potential drug candidate and RGN6024 to determine the effect on tumor growth and compares the level of biomarker in the tumor following administration of each of the two drugs. Using the data from the experiment, the researcher identifies the drug candidate as potentially therapeutically effective for treating a brain cancer.

Example 30.6 Method of Drug Screening Using an In Vitro Experimental Model to Identify a Therapeutically Effective Drug Candidate for Treating Cancer by Determining Effect on Cell Viability A researcher is seeking to identify a therapeutically effective drug candidate to treat brain cancer. The researcher identifies an in vitro model using cancer cells with a quantitive biomarker of cell viability to perform the drug screening. The researcher then administers the potential drug candidate and RGN6024 to determine the effect on cell viability and compares the relative number of cells remaining alive following administration of each of the two drugs. Using the data from the experiment, the researcher identifies the drug candidate as potentially therapeutically effective for treating a brain cancer.

EMBODIMENTS

The following embodiments are for illustrative purposes only, and are not intended to limit the present invention in any way.

Embodiment 1: A compound according to formula (I-D),

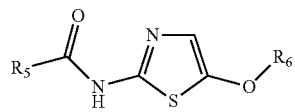

(I-D)

wherein $R_5$ is selected from:

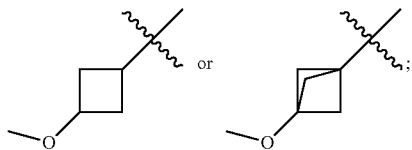

and $R_6$ is an aryl or a heteroaryl, wherein the aryl and the heteroaryl are each independently unsubstituted or are optionally each independently substituted with one or more of an alkyl, alkenyl, alkynyl, alkoxyl, alkylsulfo, alkylamino, halogen, thiol, hydroxyl, nitro, cyano, cycloalkyl, heterocyclyl, heterocyclic alkyl, aryl, heteroaryl, cycloalkoxyl, heterocyclic alkoxyl, cycloalkylthio, or heterocyclic alkylthio.

Embodiment 2: The compound of embodiment 1, wherein $R_6$ is one of the following:

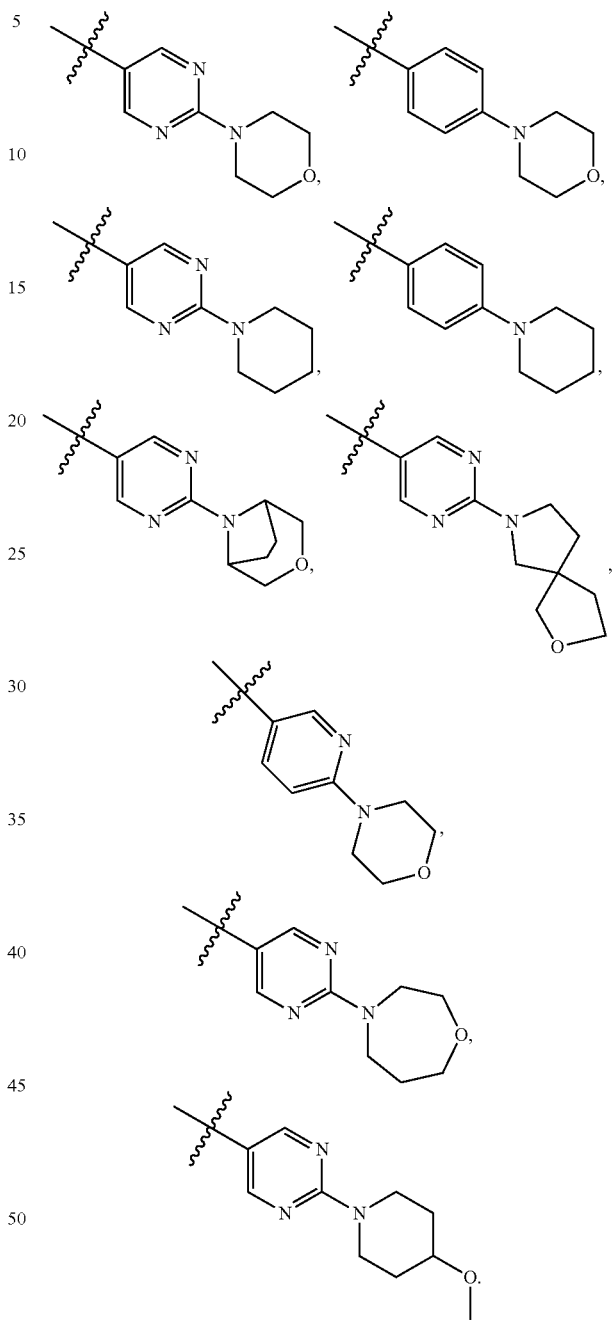

Embodiment 3: The compound of embodiment 1 or embodiment 2, wherein the compound is configured to cross the blood brain barrier (BBB) of a human or non-human subject. Embodiment 4: The compound of any one of embodiments 1-3, wherein the compound has a central nervous system multiparameter optimization (CNS MPO) score greater than or equal to 4.0, a Papp score greater than 10, or an efflux ratio of the compound is less than 2.0.

Embodiment 5: The compound of any one of embodiments 1-4, wherein the compound is effective for treating a health condition, treating a cancer or metastasis, preventing cancer cells from dividing, inhibiting tubulin polymerization, destabilizing microtubules, arresting cell division in the G2/M phase, cytotoxicity against multiple cancer cell lines, targeting blood vessels and vasculature of a cancer or tumor, treating non-neoplastic conditions, treating gout, treating familial Mediterranean fever, treating nail fungus, targeting blood vessels or vasculature, or any combination thereof.

Embodiment 6: The compound of embodiment 1, having the formula:

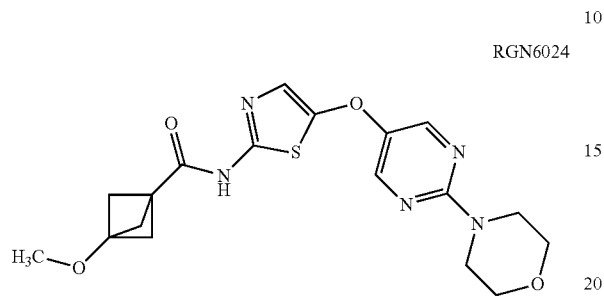

RGN6024

Embodiment 7: A composition comprising at least one compound according to any one of embodiments 1-6 and one or more of the following: a tag, an inactive moiety or a targeting moiety linked to the compound. Embodiment 7: The composition of embodiment 7, wherein the tag is a fluorescent tag, radioactive tag, biotin, or any combination thereof. Embodiment 8: The composition of embodiment 7, wherein the inactive moiety is an ester, carbamate, aminoacyl ester, or any combination thereof. Embodiment 9: The composition of embodiment 7, wherein the targeting moiety is an antibody, polyethylene glycol (PEG) conjugate, or long chain polymer, peptide sequence, or any combination thereof.

Embodiment 10: A composition comprising the compound according to any one of embodiments 1-6.

Embodiment 12: A compound according to formula II-D,

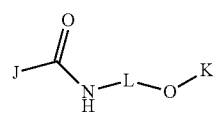

(formula II-D)

wherein J is:

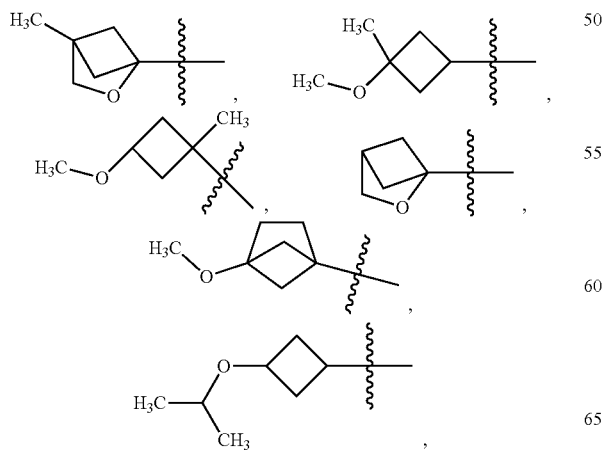

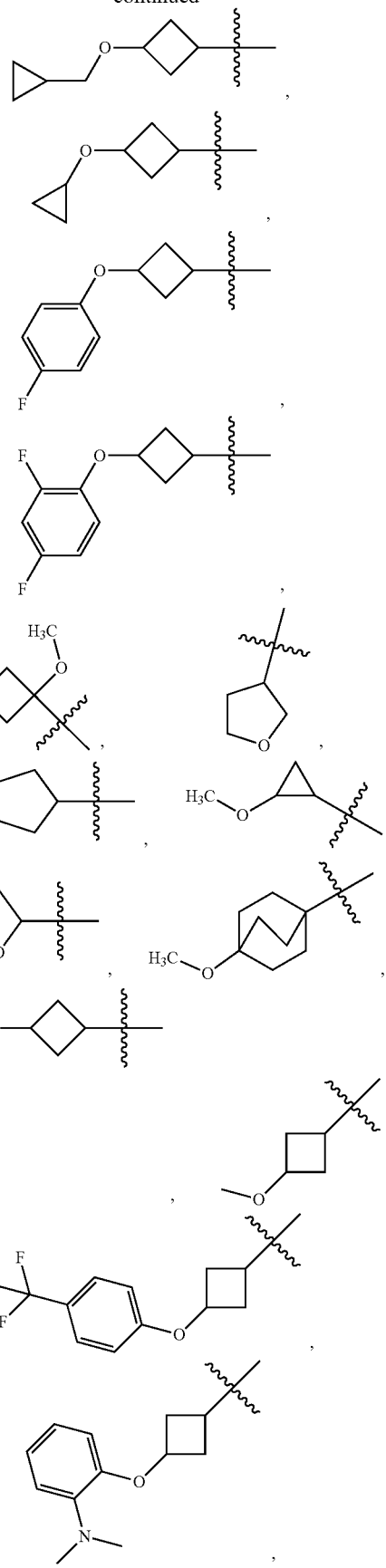

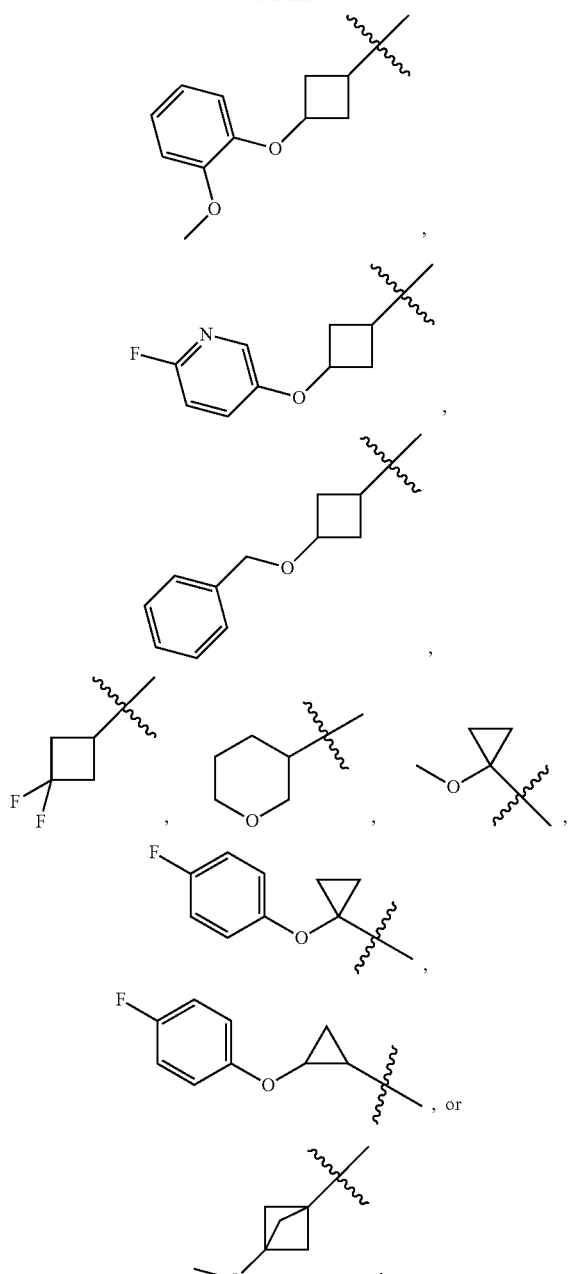
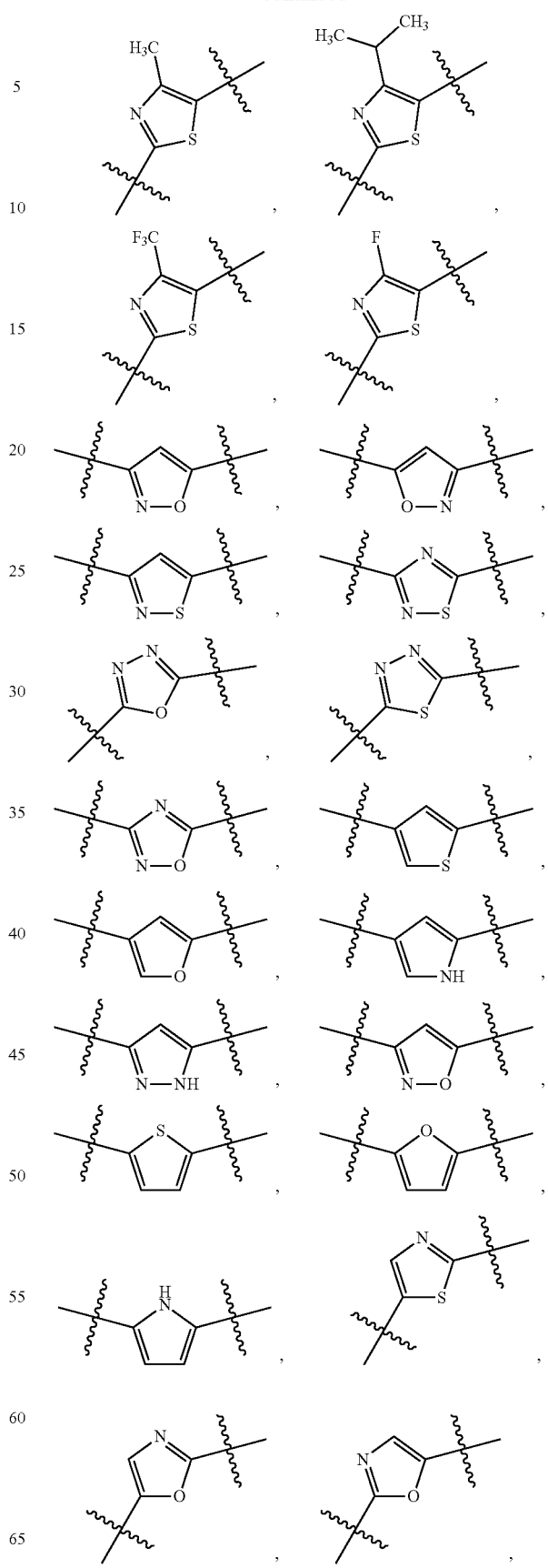
wherein L is:
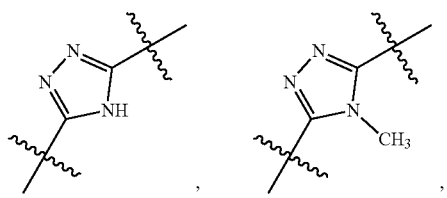

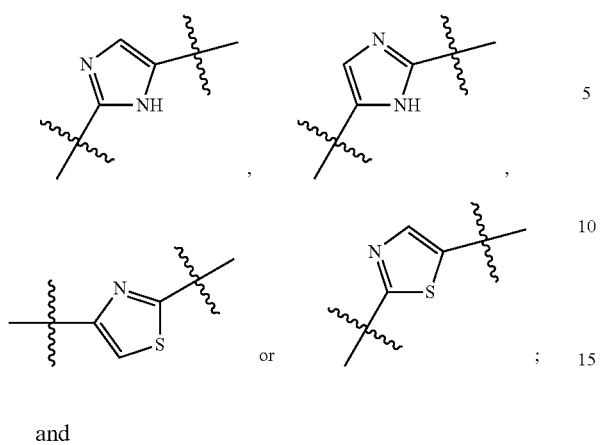

and wherein K is an aryl or a heteroaryl, wherein the aryl and the heteroaryl are each independently unsubstituted or are optionally independently substituted with one or more groups selected from alkyl, alkenyl, alkynyl, alkoxyl, alkylsulfo, alkylamino, halogen, thiol, hydroxyl, nitro, cyano, cycloalkyl, heterocyclic alkyl, aryl, heterocyclyl, heteroaryl, cycloalkoxyl, heterocyclic alkoxyl, cycloalkylthio, and heterocyclic alkylthio.

Embodiment 13: The compound of embodiment 12, wherein K is selected from the following:

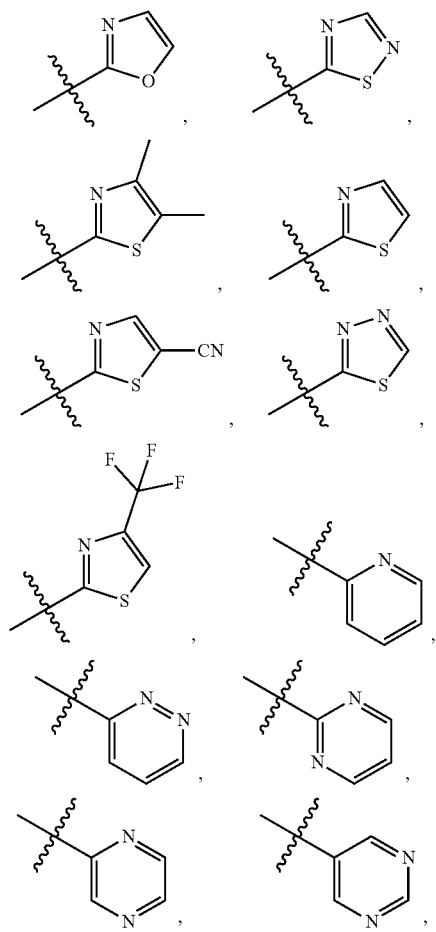

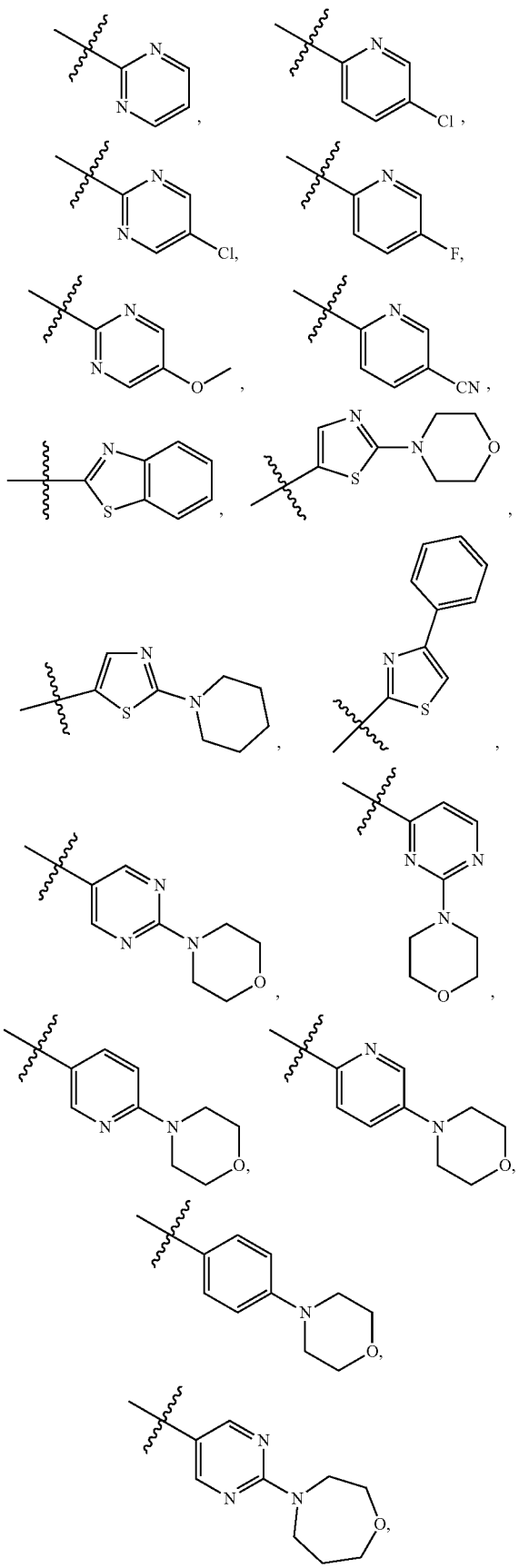

301
-continued
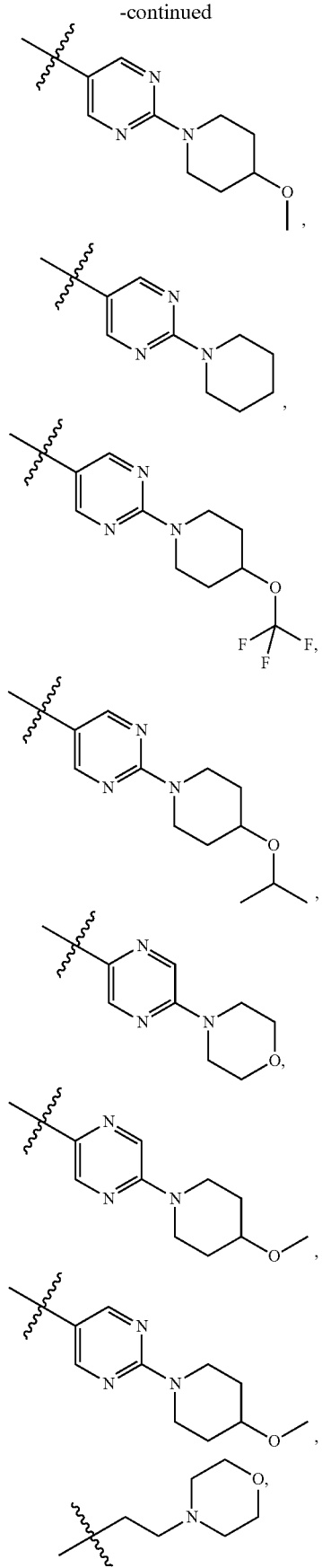
302
-continued
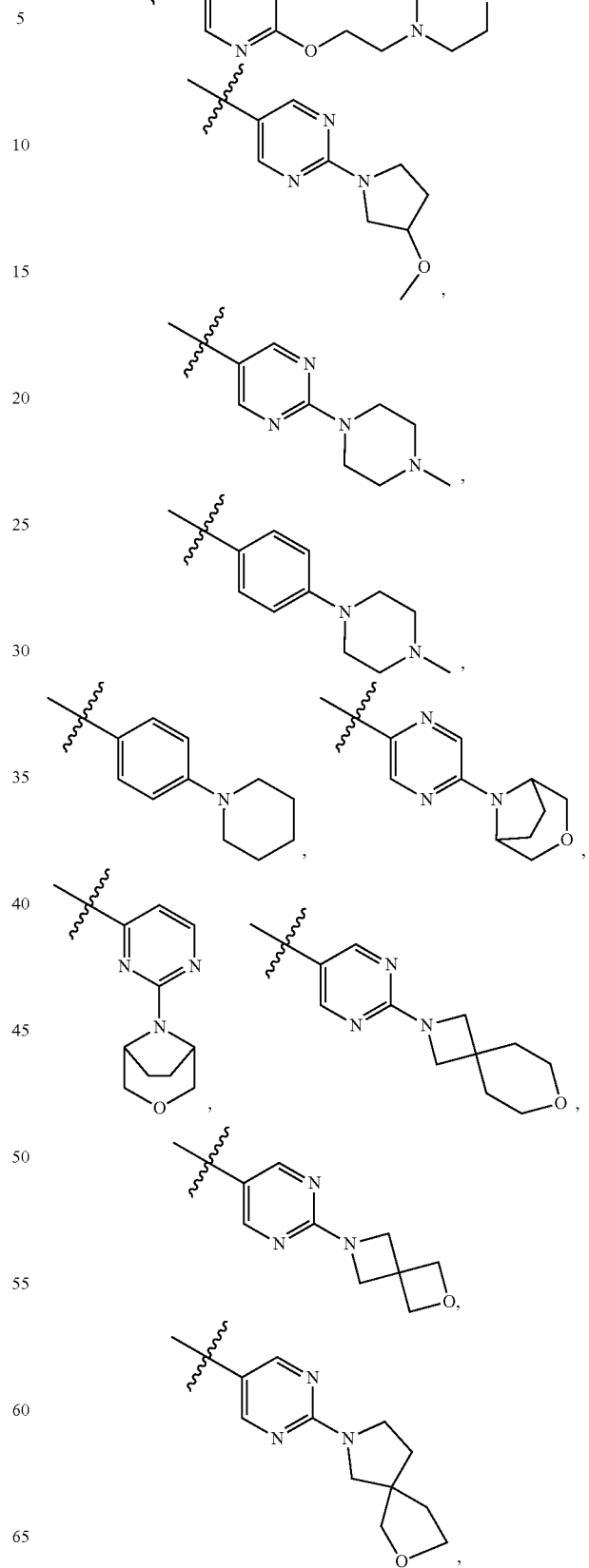

303
-continued

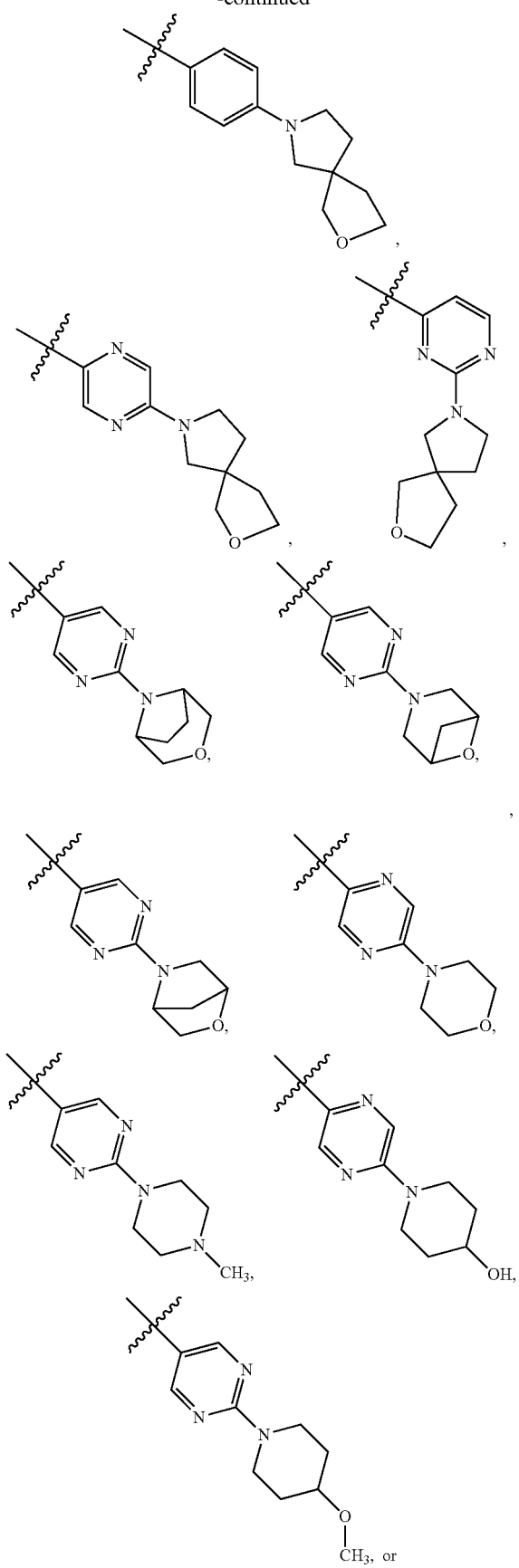

304
-continued

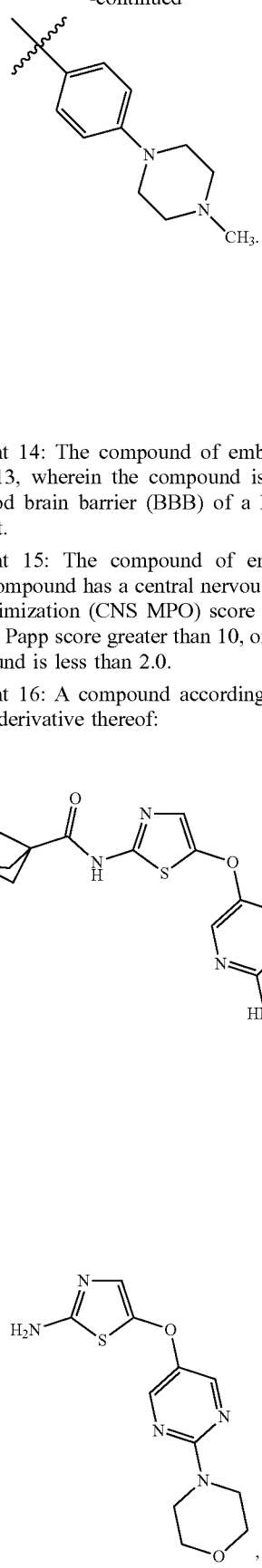

Embodiment 14: The compound of embodiment 12 or embodiment 13, wherein the compound is configured to cross the blood brain barrier (BBB) of a human or non-human subject.

Embodiment 15: The compound of embodiment 14, wherein the compound has a central nervous system multi-parameter optimization (CNS MPO) score greater than or equal to 4.0, a Papp score greater than 10, or an efflux ratio of the compound is less than 2.0.

Embodiment 16: A compound according to one of the following, or derivative thereof:

305
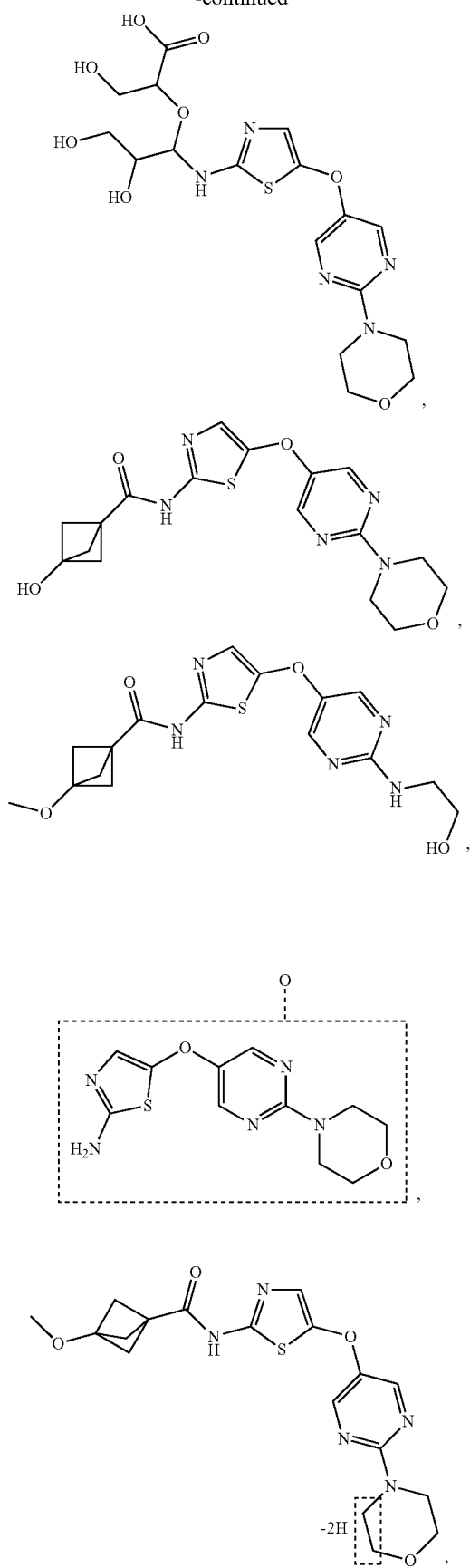
306
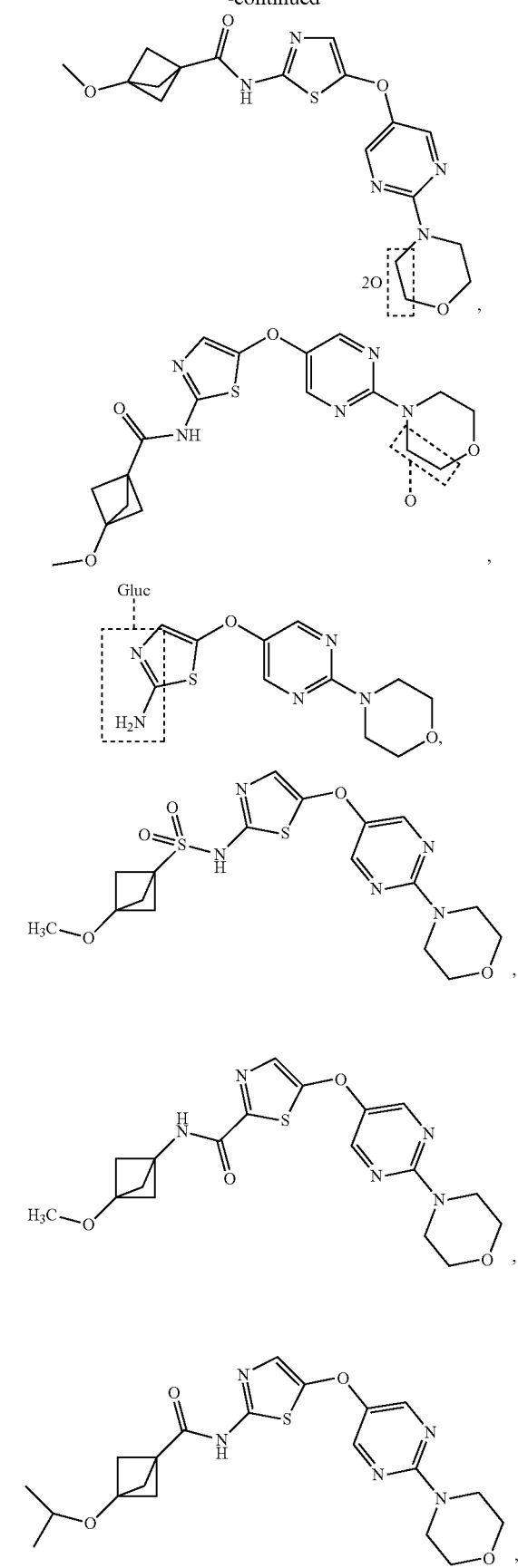

307
-continued
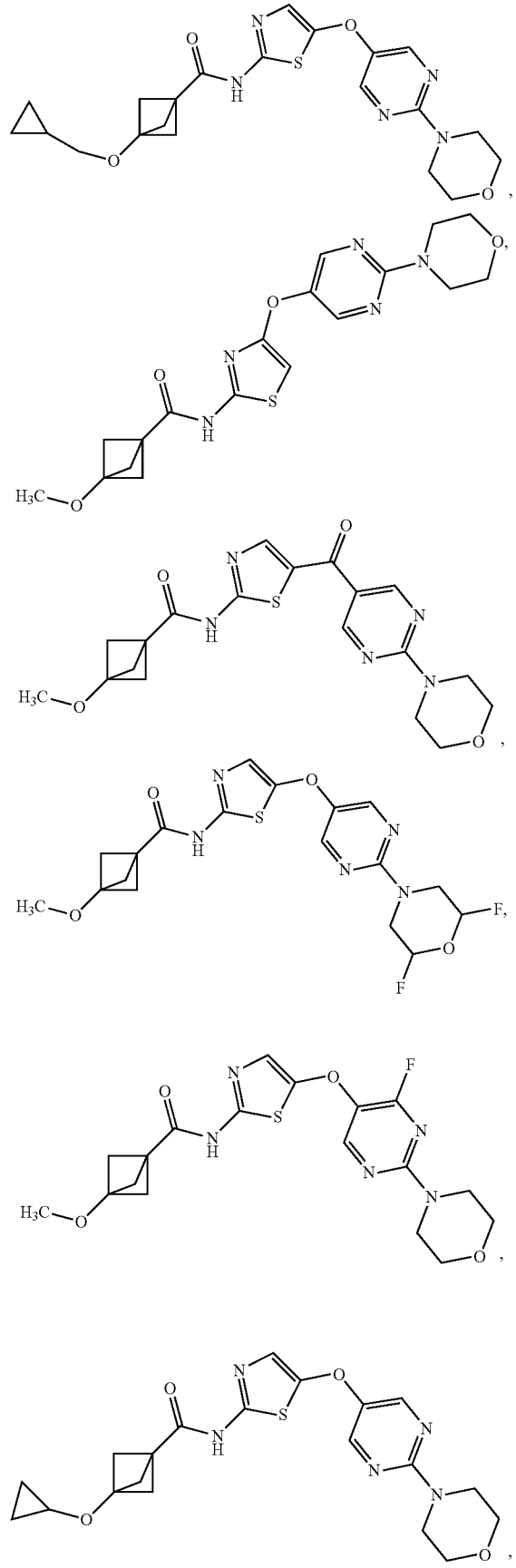
308
-continued
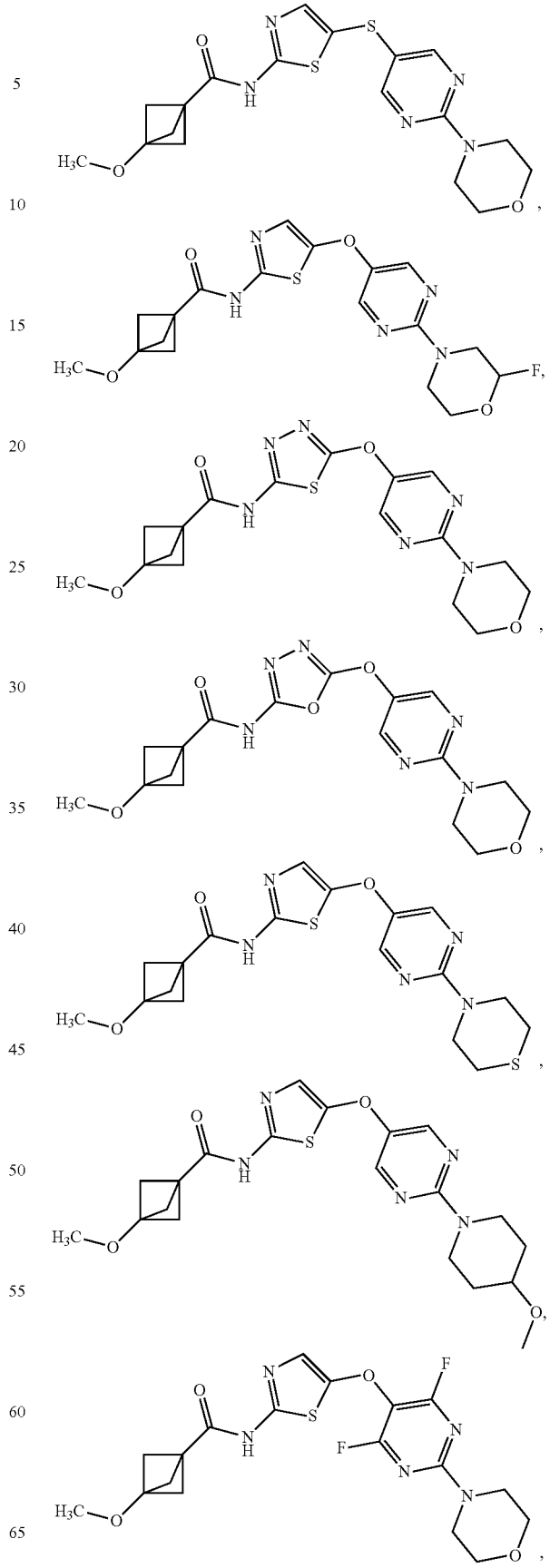

309
-continued
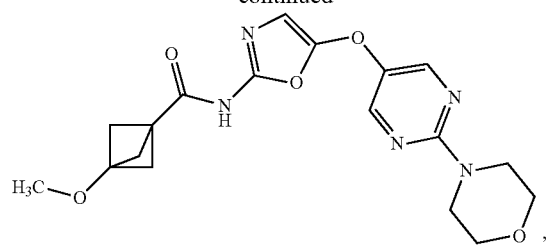
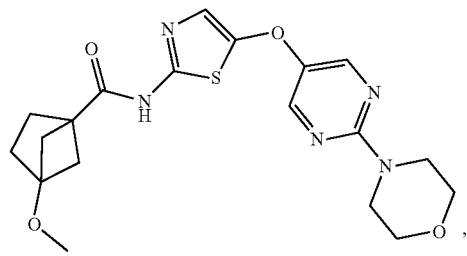
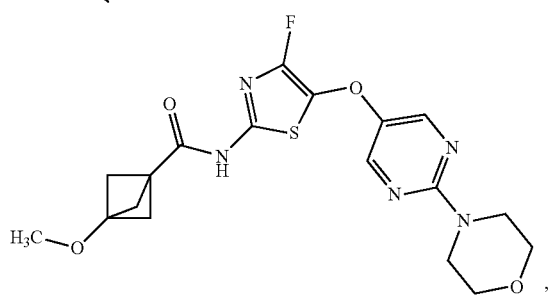
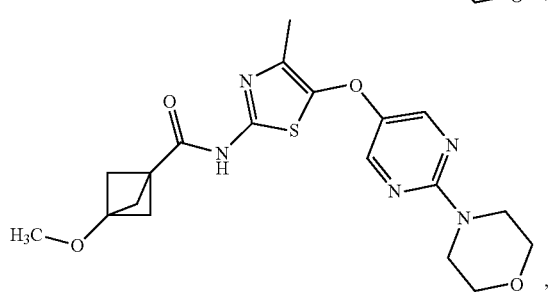
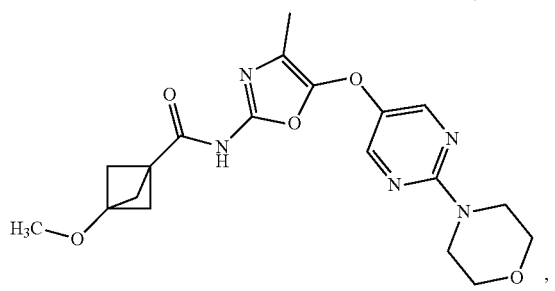
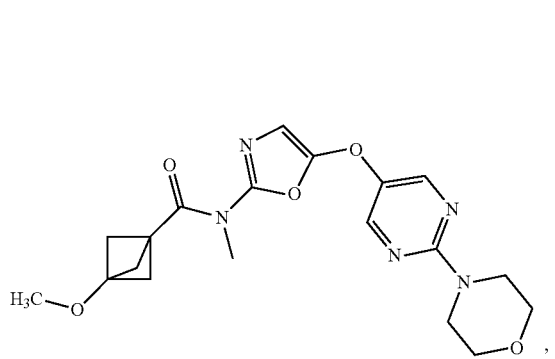
310
-continued
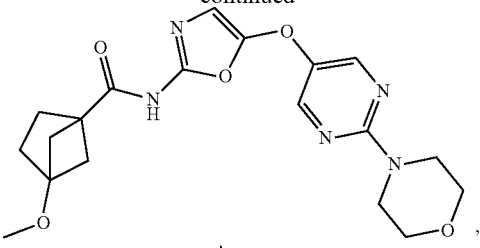
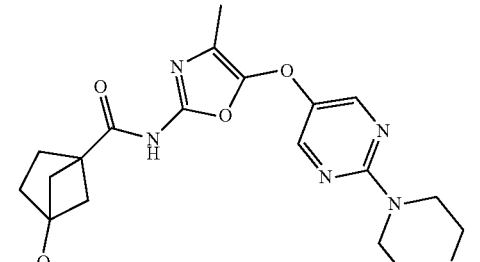
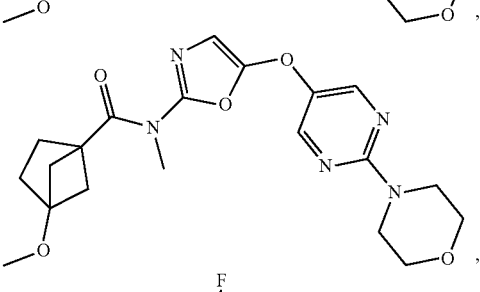
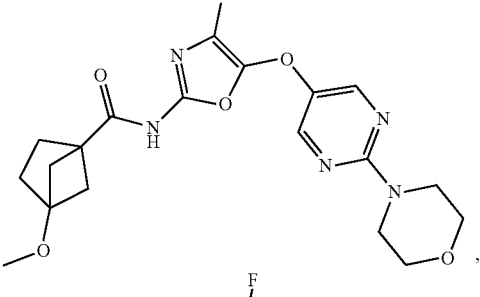
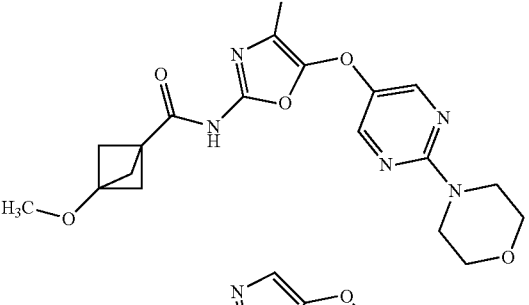
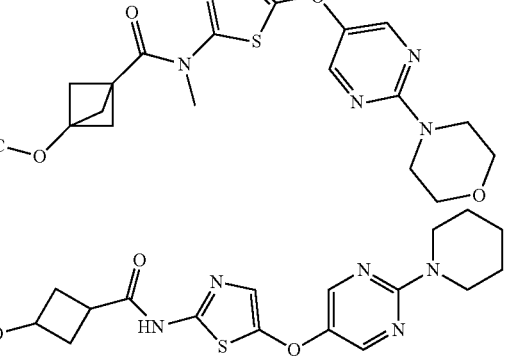

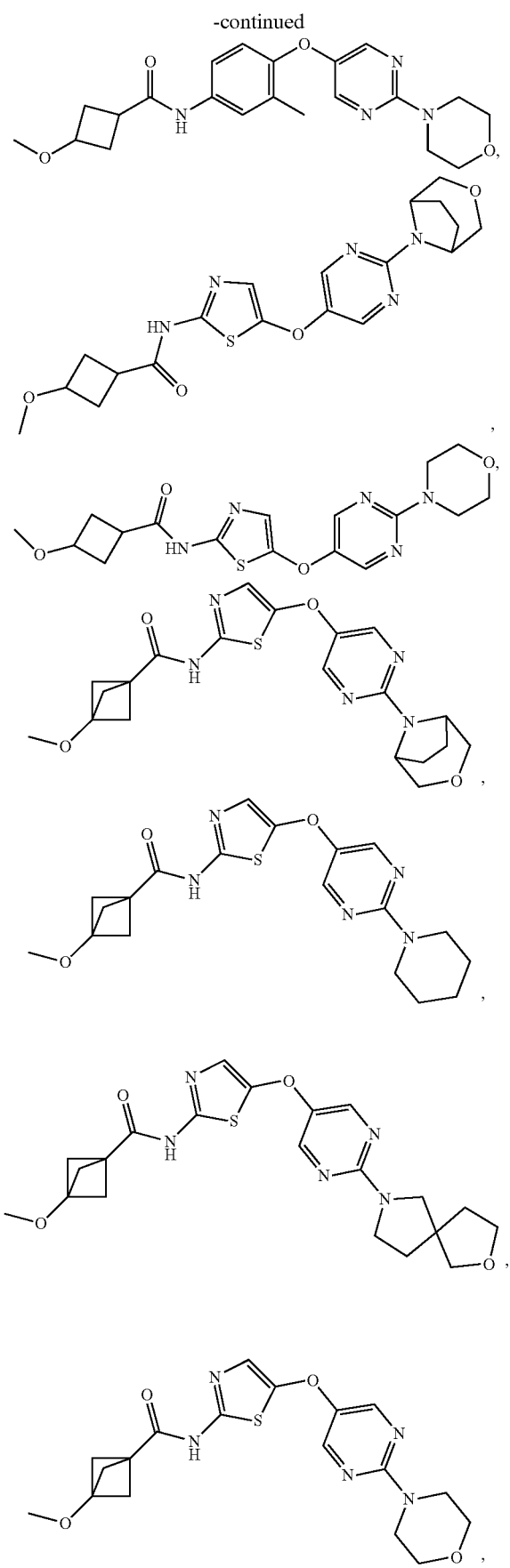

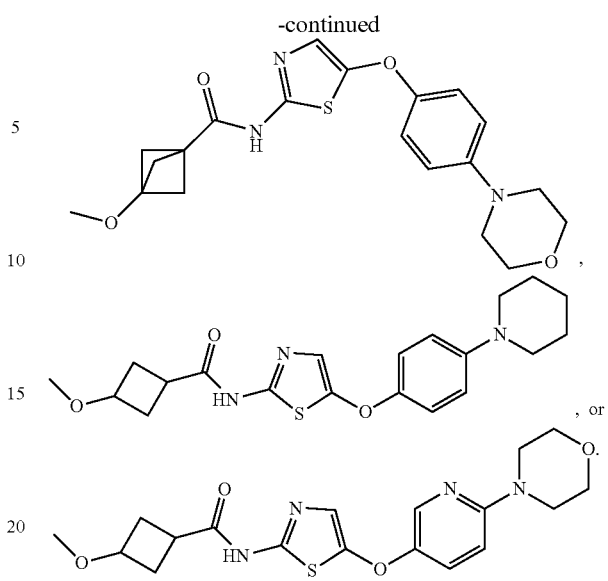

Embodiment 17: The compound of embodiment 16, wherein the compound is configured to cross the blood brain barrier (BBB) of a human or non-human subject. Embodiment 18: The compound of embodiment 17, wherein the compound has a central nervous system multiparameter optimization (CNS MPO) score greater than or equal to 4.0, a Papp score greater than 10, or an efflux ratio of the compound is less than 2.0.

Embodiment 19: A composition comprising the compound according to any one of embodiments 12-18.

Embodiment 20: A method of preventing, delaying the onset of, or treating a health condition in a subject in need thereof, the method comprising the steps of: identifying the subject presenting with the health condition and administering to the subject a therapeutically effective dose of compound RGN6024.

Embodiment 21: The method of embodiment 20, wherein the subject is a human or a non-human animal. Embodiment 22: The method of embodiment 20 or embodiment 21, wherein the non-human subject is a livestock, a companion animal, a lab animal, or a zoological, a wild animal, reptile, fish or bird.

Embodiment 23: The method of any one of embodiments 20-22, wherein the health condition comprises one or more cancers. Embodiment 24: The method of any one of embodiments 20-22, wherein the health condition comprises brain cancer, breast cancer, skin cancer, metastatic cancer, pancreatic cancer, lung cancer, kidney cancer, liver cancer, bladder cancer, bone sarcoma, ovarian cancer, rectal cancer, blood cancer, gastrointestinal cancer, medulloblastoma, or any combination thereof. Embodiment 25: The method of any one of embodiments 20-22, wherein the health condition comprises brain cancer or a cancer capable of metastasizing to the brain, glioblastoma, high grade glioma, non-cell lung cancer (NSCLC) before or after metastasizing to the brain, Ewing sarcoma, melanoma, a vascularized cancer, or any combination thereof. Embodiment 26: The method of any one of embodiments 20-22, wherein the health condition comprises a non-neoplastic condition, gout, familial Mediterranean fever, nail fungus, vascular disease, or any combination thereof.

Embodiment 27: The method of any one of embodiments 20-26, further comprising administration of one or more of an anti-microbial agent, a chemotherapeutic agent, other anti-cancer therapy, or antibody or fragment thereof. Embodiment 28: The method of any one of embodiments 20-27, wherein the anti-microbial agent comprises one or more of an anti-viral, anti-fungal, anti-bacterial agent or other anti-microbial agent. Embodiment 29: The method of any one of embodiments 20-27, wherein the anti-bacterial agent comprises one or more of doxycycline or tetracycline. Embodiment 30: The method of any one of embodiments 20-27, wherein the chemotherapeutic agent comprises one or more of temozolomide, lomustine, belzutifan, cisplatin, carboplatin, nedaplatin, triplatin tetranitrate, phenanthriplatin, picoplatin, satraplatin, Doxorubicin, Melphalan, Roscovitine, Mitomycin C, Hydroxyurea, 5-Fluorouracil, AraC (cytarabine), 6-mercaptopurine, 6-thioguanine, Cisplatin, Ara-C, Etoposide, Gemcitabine, Bortezomib, Sunitinib, Sorafenib, Sodium Valproate, a HDAC Inhibitor, a DNA synthesis inhibitor, or Dacarbazine, FLT3 inhibitors, farnesyltransferase inhibitors, topoisomerase II inhibitors, P-glycoprotein modulators, hypomethylating agents, or any combination thereof. Embodiment 31: The method of any one of embodiments 20-27, wherein the anti-cancer therapy comprises one or more of chemotherapy, radiotherapy, immunotherapy, and/or surgery. Embodiment 32: The method of any one of embodiments 20-27, wherein the anti-cancer therapy comprises one or more anti-cancer therapeutic or treatment. Embodiment 33: The method of any one of embodiments 20-27, wherein the anti-cancer therapeutic or treatment is administered separately. Embodiment 34: The method of any one of embodiments 20-27, wherein the anti-microbial agent, a chemotherapeutic agent, other anti-cancer therapy, or antibody or fragment thereof, is administered before, during or after the administration of one or more compounds or compositions.

Embodiment 35: The method of embodiment 27, wherein the health condition is cancer, and the one or more anti-cancer treatments comprises administration of one or more of temozolomide, lomustine, belzutifan, or any combination thereof before, during or after administering the composition. Embodiment 36: The method of embodiment 27, wherein the health condition is NSCLC, and the one or more anti-cancer treatments comprises administration of one or more of Crizotinib, Osimertinib, or any combination thereof before, during or after administering the composition.

Embodiment 37: The method of any one of embodiments 20-26, wherein the compound is effective for preventing cancer cells from dividing, inhibiting tubulin polymerization, destabilizing microtubules, or any combination thereof.

Embodiment 38: The method of any one of embodiments 20-37, wherein the therapeutically effective amount of the compound is determined based on the disorder treated and the mechanism of delivery. Embodiment 39: The method of any one of embodiments 20-38, wherein the therapeutically effective dose in a human is in the range of about 0.5-5 mg/kg. Embodiment 40: The method of any one of embodiments 20-38, wherein the therapeutically effective dose in a mouse is in the range of about 1-25 mg/kg.

Embodiment 41: The method of any one of embodiments 20-40, wherein the route of administration is one or more of intravenous injection, oral administration, subcutaneous injection, intramuscular injection, intrasternal injection, intrathecal administration, intratumoral, intravascular, intracerebral injection, intracisternal, intracerebroventricular, intranasal or inhalation, parenteral, buccal, enteral, intraperitoneal, inhalable, infused, intramuscular, ophthalmic, intravitreal, otic, rectal, sublingual, topical, transdermal, intrapulmonary, intrauterine, vaginal, via ultrasound-mediated blood brain barrier disruption, implantable devices, infusion techniques, or nanoparticle-based delivery.

Embodiment 42: The method of any one of embodiments 20-40, wherein the compound is in the form of a tablet, pill, coated tablet or coated pill. Embodiment 43: The method of any one of embodiments 20-42, wherein the compound is administered at least once daily, every other day, every third day, twice weekly, weekly, every other week, twice monthly or monthly, every other month, every six months, or other suitable dosing regimen.

Embodiment 44: The method of any one of embodiments 20-43, wherein the compound results in an 83% drug resistant glioblastoma (LN-18) tumor growth reduction in a mouse model versus placebo with oral daily dosing at less than 25% of a toxic dose. Embodiment 45: The method of any one of embodiments 20-43, wherein the compound results in an 86% drug resistant glioblastoma (LN-18) tumor growth reduction in a mouse model versus Temozolomide (TMZ) with oral daily dosing at less than 25% of a toxic dose.

Embodiment 46: A system for using artificial intelligence (AI) to generate one or more candidate compounds, wherein the one or more candidate compounds are derived from RGN6024, incorporate RGN6024, or a combination thereof, the system comprising: a processor configured to execute computer-readable instructions; and a memory component communicatively coupled to the processor, comprising: an AI model comprising one or more neural networks, trained with a training data set comprising chemical training data, wherein training the AI model comprises feeding the training data set as input into the AI model, wherein the AI model is trained to generate the one or more candidate compounds as output; and computer-readable instructions for: inputting chemical data into the AI model, wherein the chemical data comprises data unique to RGN6024; and generating, by the AI model, the one or more candidate compounds.

Embodiment 47: A method for using artificial intelligence (AI) to generate one or more candidate compounds, wherein the one or more candidate compounds are derived from RGN6024, incorporate RGN6024, or a combination thereof, the method comprising: providing an AI model comprising one or more neural networks, trained with a training data set comprising chemical training data, wherein training the AI model comprises feeding the training data set as input into the AI model, wherein the AI model is trained to generate the one or more candidate compounds as output; inputting chemical data into the AI model, wherein the chemical data comprises data unique to RGN6024; and generating, by the AI model, the one or more candidate compounds.

Embodiment 48: A method for screening one or more of a potential drug candidate compound to determine whether it is therapeutically effective as compared to any one of the compounds disclosed herein as a reference compound, wherein the method comprises: identifying one or more of an in vitro, ex vivo or in vivo model for experimentation; contacting at least one of a cell, fluid, tissue, organ or animal with at least of one of the reference compound, the potential drug candidate compound, or a negative control compound; determining in parallel one or more drug parameter or characteristic from contacting the cell, fluid, tissue, organ, or animal with at least one of the reference compound, the potential drug candidate compound or the negative control compound; and comparing the drug parameter or characteristic of one or more of the negative control, the reference compound, or the drug candidate compound to determine whether the drug candidate compound is therapeutically effective.

Embodiment 49: The method of embodiment 48, wherein the in vitro model comprises a cell viability assay, cell cycle analysis, immunofluorescent staining assay, immunofluorescent staining of cellular beta tubulin, tubulin polymerization assay, competitive binding assay, colchicine competitive binding assay, binding site cellular assay, colchicine-binding site cellular assay, reversibility assay, kinetic solubility assay, microsomal stability assay, plasma protein binding study, cellular permeability study, or cell cycle analysis by flow cytometry. Embodiment 50: The method of embodiment 48, wherein the ex vivo model comprises an excised tumor in a chicken egg model. Embodiment 51: The method of embodiment 48, wherein the in vivo model comprises a pharmacokinetic (PK) study, brain pharmacokinetic (PK) study, maximum tolerated dose study, efficacy study, metabolite profiling in hepatocytes, survivability study, or tumor size study.

Embodiment 52: The method of any one of embodiments 48-51, wherein the drug parameter or characteristic analyzed comprises pharmacokinetics (PK), pharmacodynamics (PD), brain pharmacokinetics (brain PK), target-site binding, cell viability, cellular permeability, blood brain barrier permeability, efficacy, toxicity and safety, stability, microsomal stability, kinetic solubility, plasma protein binding, microsomal stability, or effects on cell cycle.

Embodiment 53: The method of any one of embodiments 48-52, wherein the cell contacted with the reference compound, the potential drug candidate compound, or a negative control compound comprises a primary tumor cells, cancer cell, U87 glioblastoma cells, LN-18 glioblastoma cells, HMC3 microglial cells, patient-derived GBM cells, MDR1-MDCK (multidrug-resistant-1-Mandin-Darby canine kidney) cells, human cryopreserved hepatocytes, or cells used in a patient-derived xenograft model. Embodiment 54: The method of any one of embodiments 48-52, wherein the fluid contacted with the reference compound, the potential drug candidate compound, or a negative control compound comprises plasma, cerebrospinal fluid, brain homogenate, urine, whole blood, serum, or tumor homogenate. Embodiment 55: The method of any one of embodiments 48-52, wherein the tissue contacted with the reference compound, the potential drug candidate compound, or a negative control compound comprises a brain tumor tissue, normal brain tissue, tumor tissue, or solid tumor tissue. Embodiment 56: The method of any one of embodiments 48-52, wherein the organ contacted with the reference compound, the potential drug candidate compound, or a negative control compound comprises a brain, breast, skin, lungs, liver, bones, or connective tissue. Embodiment 57: The method of any one of embodiments 48-52, wherein the animal contacted with the reference compound, the potential drug candidate compound, or a negative control compound comprises a mouse, rat, dog, monkey, rabbit, or pig.

The foregoing discussion of the disclosure has been presented for purposes of illustration and description. The foregoing is not intended to limit the disclosure to the form or forms disclosed herein. Although the description of the disclosure has included description of one or more embodiments and certain variations and modifications, other variations and modifications are within the scope of the disclosure, e.g., as can be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A compound according to formula (I-D):

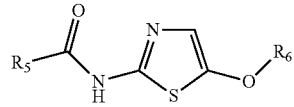

(I-D)

wherein $R_5$ is selected from:

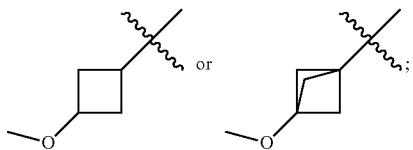

and $R_6$ is an aryl or a heteroaryl, wherein the aryl and the heteroaryl are each independently unsubstituted or are each independently substituted with one or more of an alkyl, alkenyl, alkynyl, alkoxyl, alkylsulfo, alkylamino, halogen, thiol, hydroxyl, nitro, cyano, cycloalkyl, heterocyclyl, heterocyclic alkyl, aryl, heteroaryl, cycloalkoxyl, heterocyclic alkoxyl, cycloalkylthio, or heterocyclic alkylthio.

2. The compound of claim 1, wherein $R_6$ is one of the following:

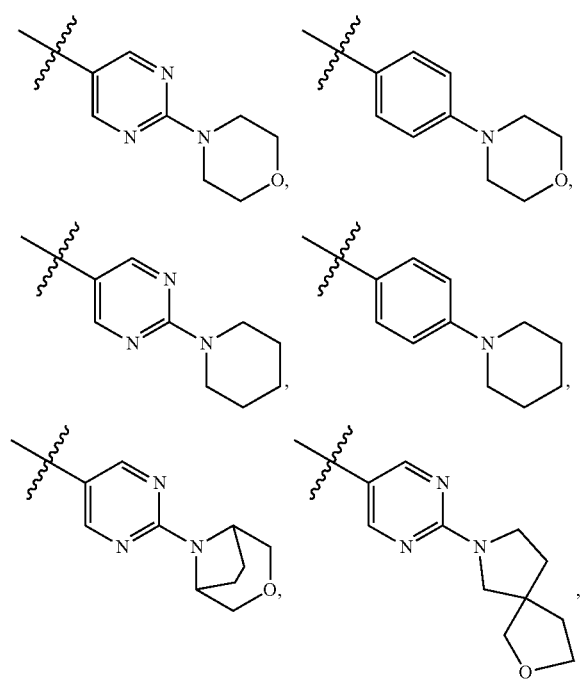

-continued

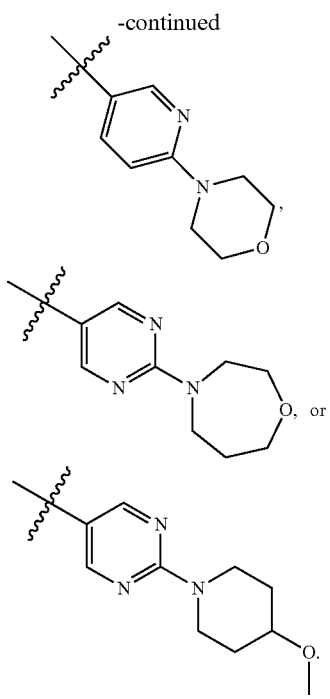

3. A composition comprising at least one compound according to formula (I-D):

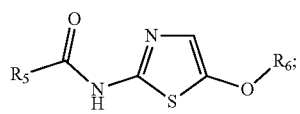
(I-D)

and
one or more of the following: a tag, an inactive moiety or a targeting moiety linked to the compound;
wherein $R_5$ is selected from:

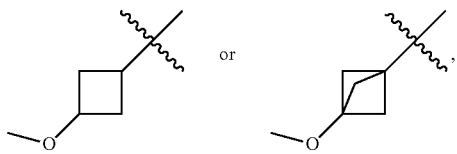

and $R_6$ is an aryl or a heteroaryl, wherein the aryl and the heteroaryl are each independently unsubstituted or are each independently substituted with one or more of an alkyl, alkenyl alkynyl, alkoxyl, alkylsulfo, alkylamino, halogen, thiol, hydroxyl, nitro, cyano, cycloalkyl, heterocyclyl, heterocyclic alkyl, aryl, heteroaryl, cycloalkoxyl, heterocyclic alkoxyl cycloalkylthio, or heterocyclic alkylthio.

4. The compound of claim 3, wherein the tag is a fluorescent tag, radioactive tag, biotin, or any combination thereof.

5. The compound of claim 3, wherein the inactive moiety is an ester, carbamate, aminoacyl ester, or any combination thereof.

6. The compound of claim 3, wherein the targeting moiety is an antibody, polyethylene glycol (PEG) conjugate, or long chain polymer, peptide sequence, or any combination thereof.

7. The compound of claim 1, wherein the compound is:

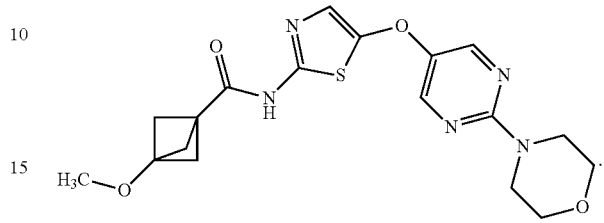
RGN6024

8. A composition comprising at least one compound according to claim 1.

9. A compound according to formula II-D:

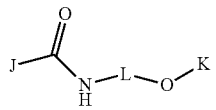
(II-D)

wherein J is:

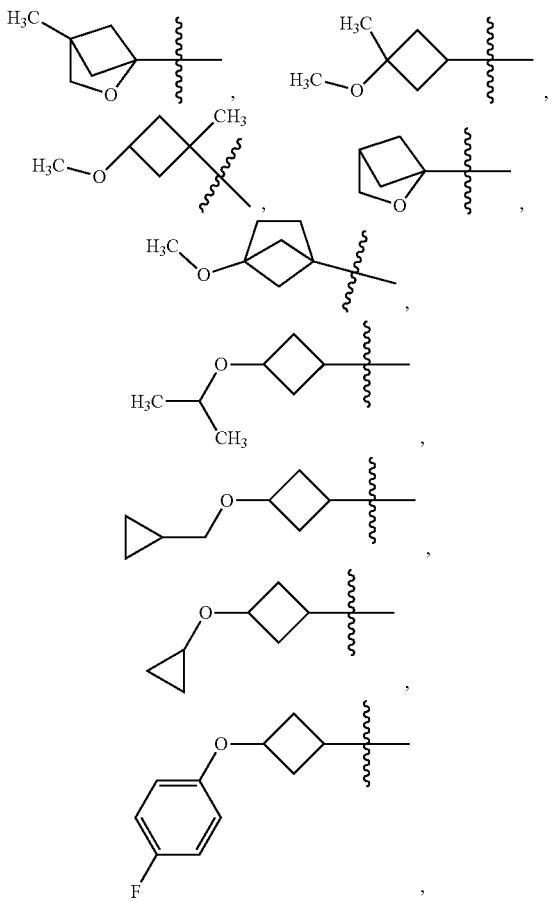

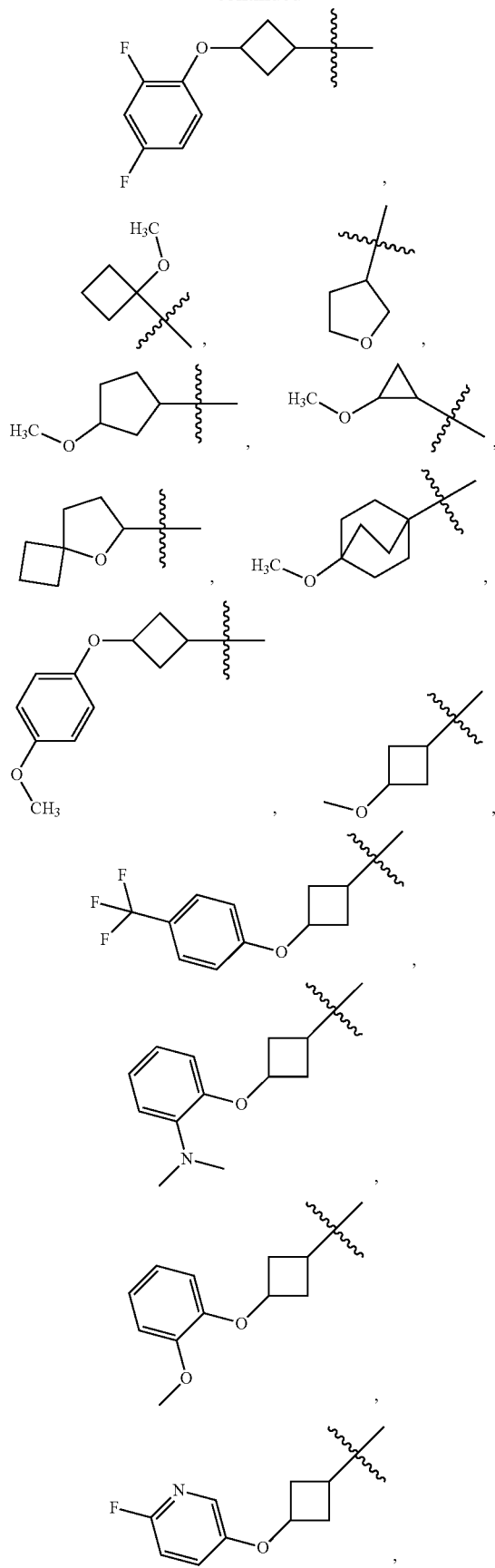
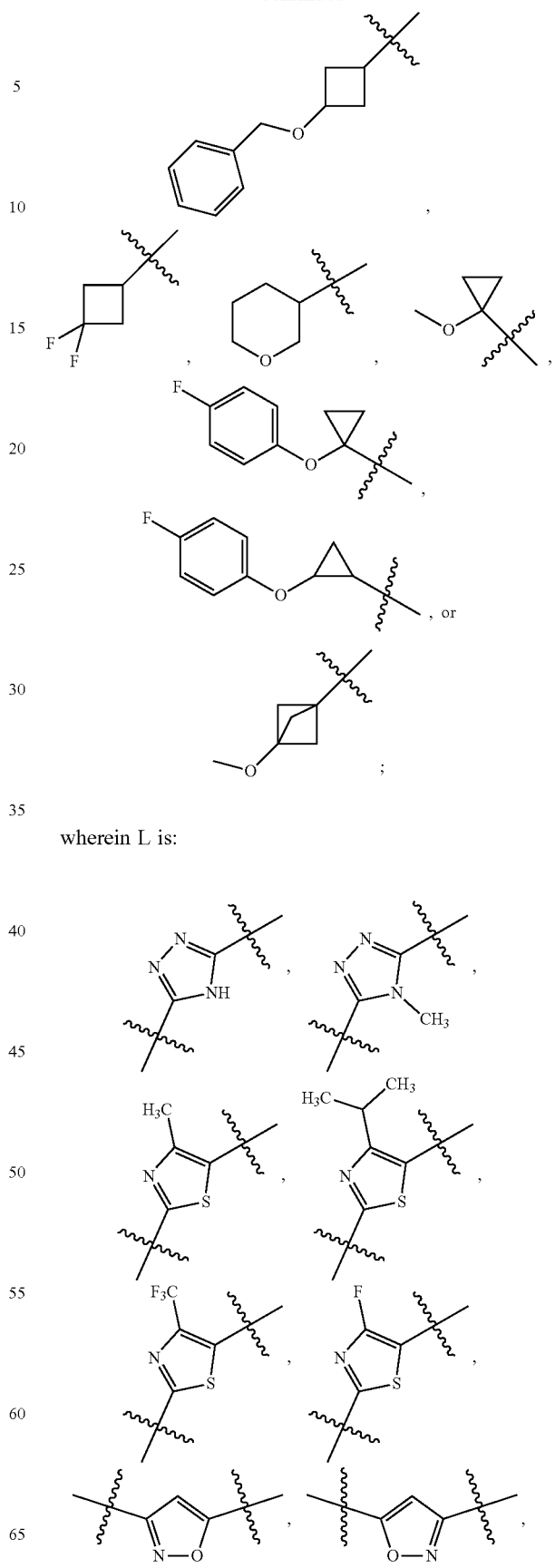
wherein L is:

-continued

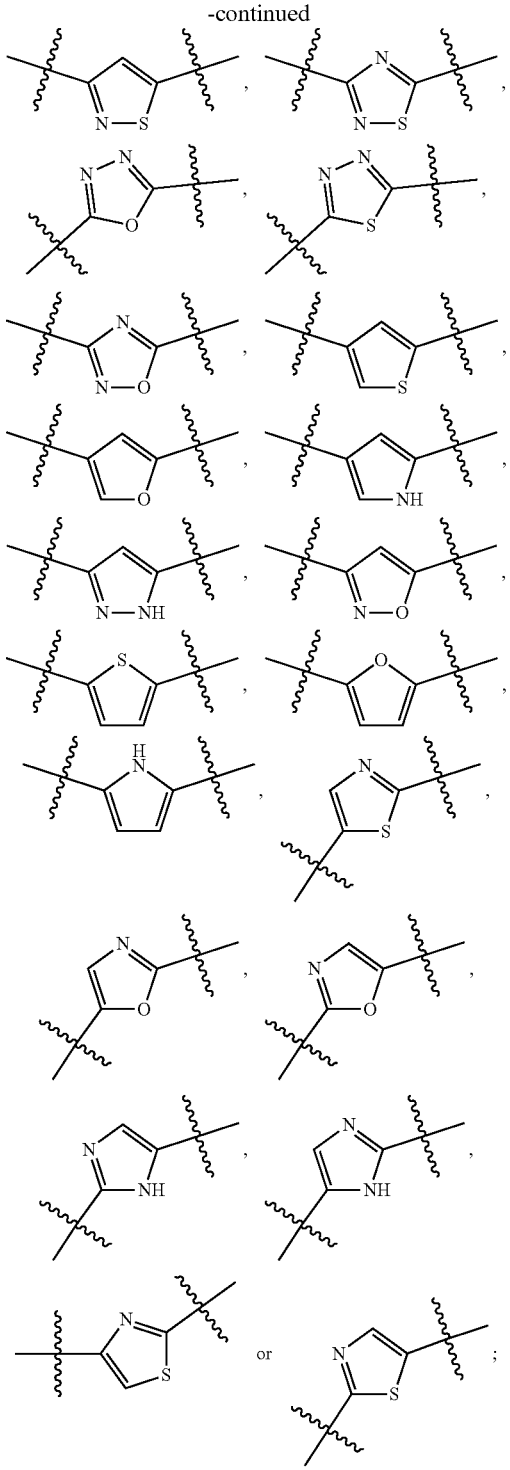

and wherein K is an aryl or a heteroaryl, wherein the aryl and the heteroaryl are each independently unsubstituted or are independently substituted with one or more groups selected from alkyl, alkenyl, alkynyl, alkoxyl, alkylsulfo, alkylamino, halogen, thiol, hydroxyl, nitro, cyano, cycloalkyl, heterocyclic alkyl, aryl, heterocyclyl, heteroaryl, cycloalkoxyl, heterocyclic alkoxyl, cycloalkylthio, and heterocyclic alkylthio.

10. The compound of claim 9, wherein K is selected from the following:

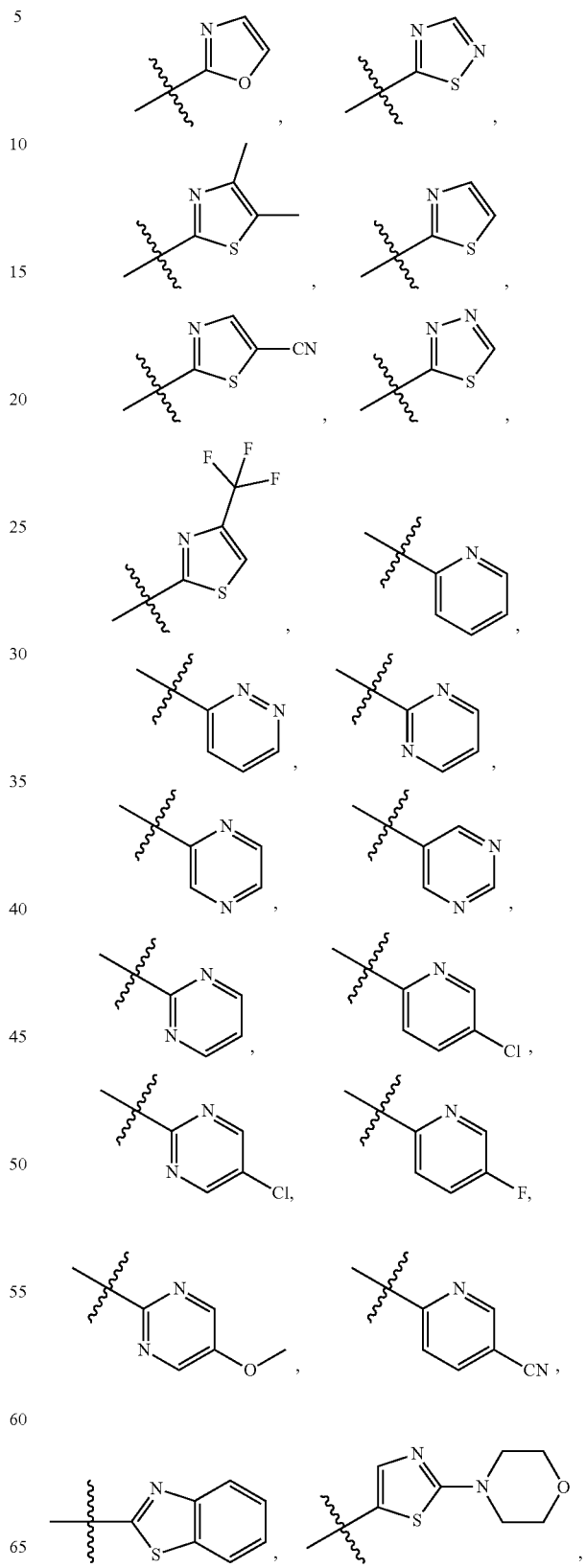

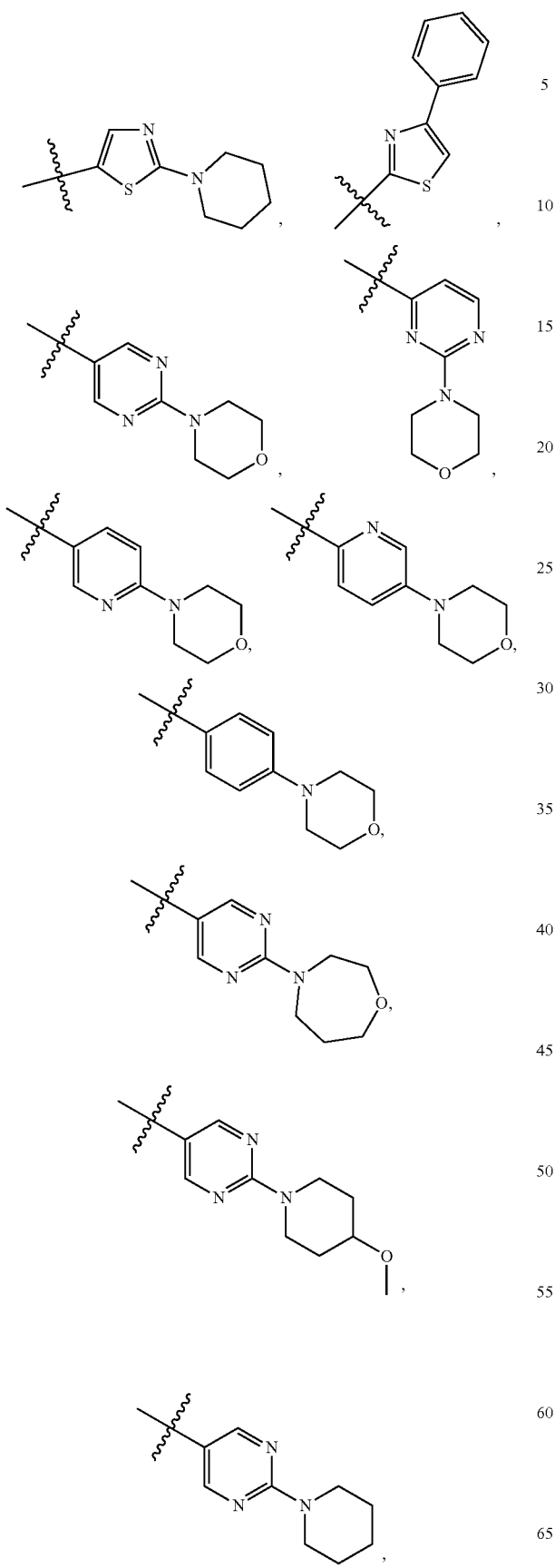
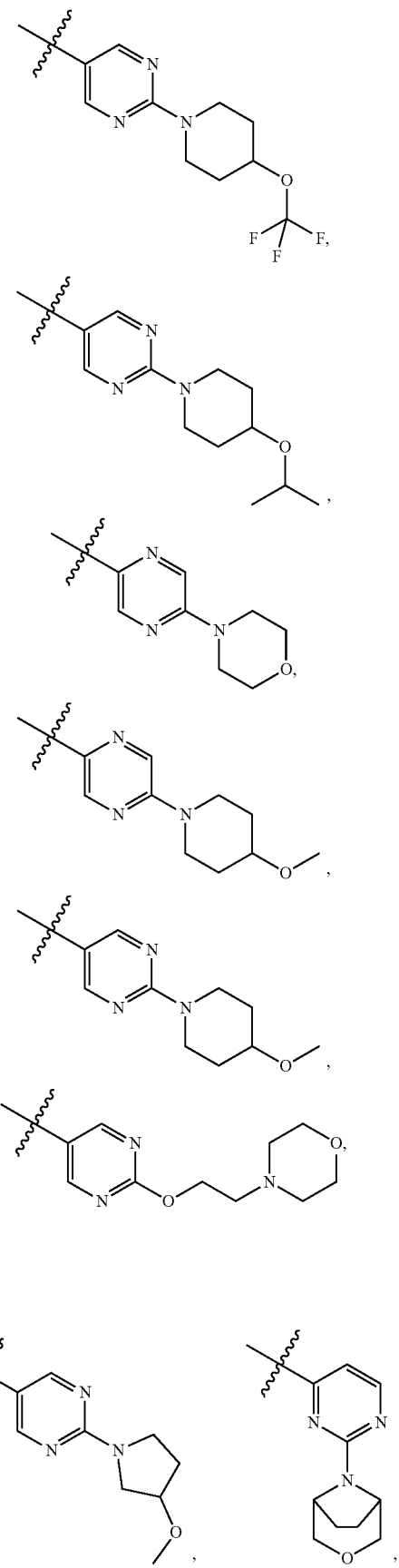

325
-continued
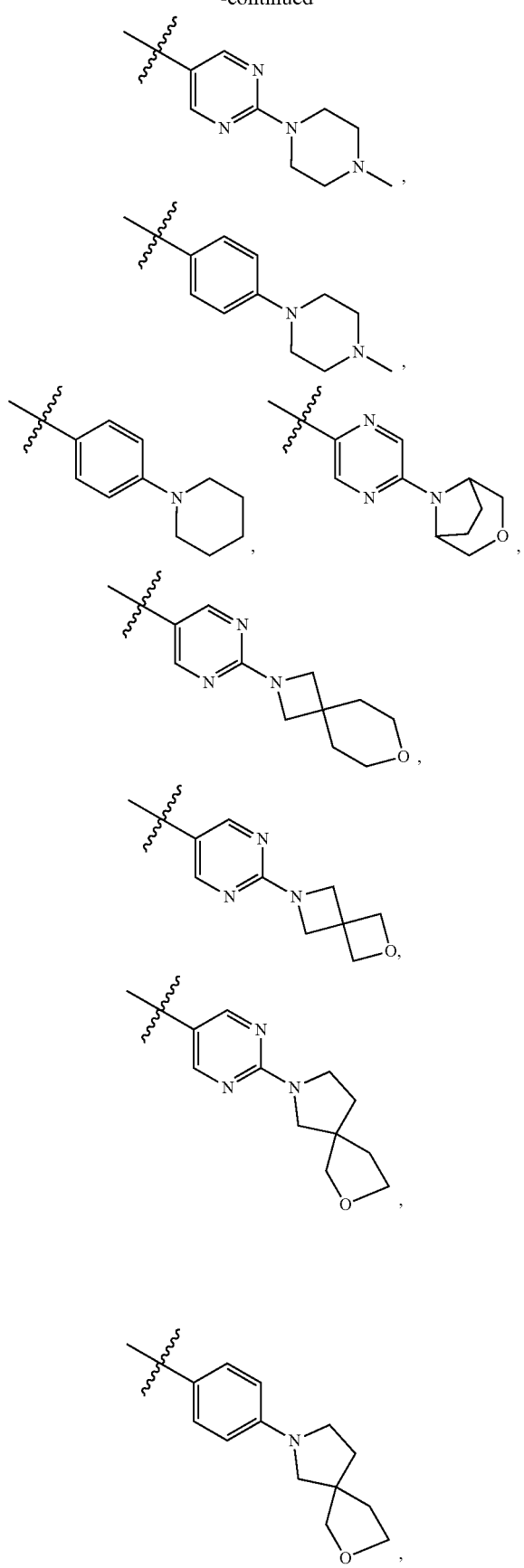
326
-continued
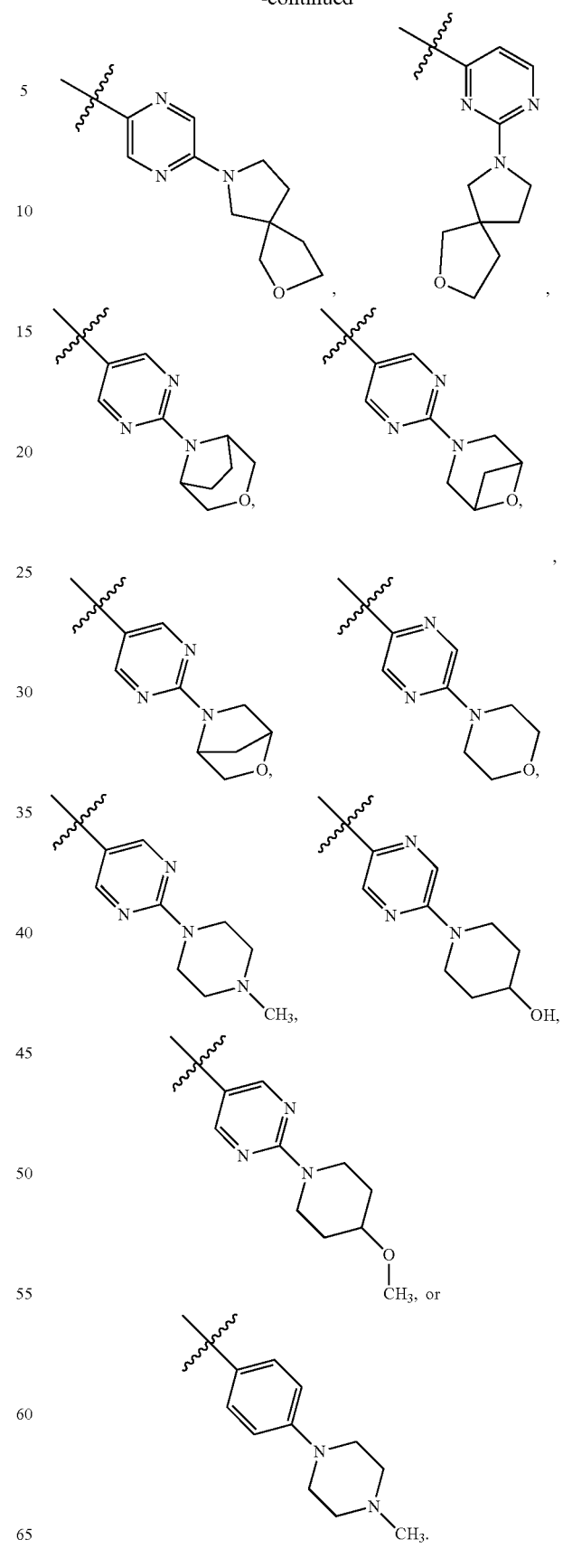

11. A composition comprising at least one compound according to claim 9.

\* \* \* \* \*